United States Patent
Kim et al.

(10) Patent No.: US 12,049,468 B2
(45) Date of Patent: Jul. 30, 2024

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Bitnari Kim, Gyeonggi-do (KR); Su-Hyun Lee, Gyeonggi-do (KR); Doo-Hyeon Moon, Gyeonggi-do (KR); Hyo-Soon Park, Gyeonggi-do (KR); Tae-Jun Han, Gyeonggi-do (KR); Sang-Hee Cho, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 654 days.

(21) Appl. No.: 16/972,962

(22) PCT Filed: May 9, 2019

(86) PCT No.: PCT/KR2019/005537
§ 371 (c)(1),
(2) Date: Dec. 7, 2020

(87) PCT Pub. No.: WO2019/235748
PCT Pub. Date: Dec. 12, 2019

(65) Prior Publication Data
US 2021/0253586 A1   Aug. 19, 2021

(30) Foreign Application Priority Data

Jun. 8, 2018 (KR) .................. 10-2018-0066283
Apr. 16, 2019 (KR) .................. 10-2019-0044358

(51) Int. Cl.
*C07D 487/06* (2006.01)
*H10K 85/60* (2023.01)
*H10K 101/00* (2023.01)

(52) U.S. Cl.
CPC ....... *C07D 487/06* (2013.01); *H10K 85/6572* (2023.02); *H10K 85/6574* (2023.02); *H10K 2101/90* (2023.02)

(58) Field of Classification Search
CPC .............. C07D 487/06; C07D 487/16; H10K 85/6572; H10K 85/6574; H10K 2101/90; H10K 50/11; H10K 85/342; H10K 2101/10; H10K 85/615; H10K 85/631; H10K 85/654; H10K 85/657
See application file for complete search history.

(56) References Cited

U.S. PATENT DOCUMENTS

| | | | |
|---|---|---|---|
| 9,997,723 B2 | 6/2018 | Kang et al. | |
| 10,636,980 B2 | 4/2020 | Moon et al. | |
| 2016/0163998 A1 | 6/2016 | Saito et al. | |
| 2018/0175306 A1* | 6/2018 | Dyatkin ................. | C09K 11/06 |
| 2019/0131542 A1 | 5/2019 | Kim et al. | |
| 2019/0221751 A1 | 7/2019 | Cho et al. | |

FOREIGN PATENT DOCUMENTS

| | | | | |
|---|---|---|---|---|
| KR | 20180022325 A | 3/2018 | | |
| WO | WO-2010114264 A2 * | 10/2010 | ........... | C07D 209/56 |
| WO | 2015037965 A1 | 3/2015 | | |
| WO | 2015099486 A1 | 7/2015 | | |
| WO | 2016080791 A1 | 5/2016 | | |
| WO | WO-2019190149 A1 * | 10/2019 | ........... | C07D 209/86 |

OTHER PUBLICATIONS

Wagner, Jakub, et al. "TADF/RTP OLED organic emitters based on concaved N-PAHs with tunable intrinsic DA electronic structure." (2022). (Year: 2022).*
Szlachcic et al., . "Organic light emitting diodes (OLED) based on helical structures containing 7-membered fused rings." Dyes and Pigments 114 (2015): 184-195. (Year: 2015).*
Notification of Preliminary Rejection from Korea Patent Office for Korean application No. 2019-0044358; Application Date: Apr. 16, 2019.

* cited by examiner

*Primary Examiner* — Dawn L Garrett
(74) *Attorney, Agent, or Firm* — G. Creston Campbell

(57) ABSTRACT

The present disclosure relates to a plurality of host materials comprising a compound represented by formula 1 and a compound represented by formula 2, and an organic electroluminescent device comprising the same. By comprising the plurality of host materials comprising a specific combination of compounds, it is possible to provide an organic electroluminescent device having long lifespan characteristics.

10 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. At present, phosphorous materials, which provide excellent luminous efficiency in realizing panels, are mainly used in organic electroluminescent devices. OLEDs having high luminous efficiency and/or long lifespan are required for long time uses and high resolution of displays.

Korean Patent Application Laying-Open No. 2018-0012709 discloses a diazadibenzo azuleno fluorene derivative. However, a use as one of a plurality of host materials is not specifically disclosed, and performances of OLED devices still need to be improved.

DISCLOSURE OF THE INVENTION

Problems to be Solved

The objective of the present disclosure is to provide an organic electroluminescent device having long lifespan characteristics by comprising a plurality of host materials comprising a specific combination of compounds.

Solution to Problems

The present inventors found that the objective above can be achieved by a plurality of host materials comprising at least one first host compound and at least one second host compound, wherein the first host compound is represented by the following formula 1, and the second host compound is represented by the following formula 2:

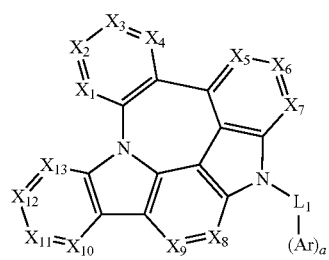

(1)

wherein $X_1$ to $X_{13}$ each independently represent N or $CR_1$;

$L_1$ represents a single bond, a substituted or unsubstituted (C6-C30)arylene, a substituted or unsubstituted (C3-C30)cycloalkylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to an adjacent substituent to form a ring;

$R_1$ represents $-L_1-(Ar)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to an adjacent substituent to form a ring;

$R_5$ to $R_9$ each independently represent a substituted or unsubstituted (C1-C30)alkyl, a substituted or unsubstituted (C6-C30)aryl, or a substituted or unsubstituted (3- to 30-membered)heteroaryl;

a represents an integer of 1 to 3, where if a is an integer of 2 or more, each of Ar may be the same or different;

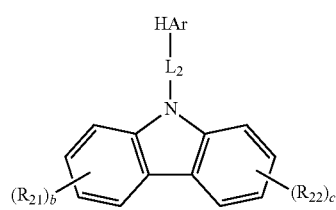

(2)

wherein

HAr represents a substituted or unsubstituted (3- to 30-membered)heteroaryl;

$L_2$ represents a single bond, a substituted or unsubstituted (C6-C30)arylene, or a substituted or unsubstituted (3- to 30-membered)heteroarylene;

$R_{21}$ and $R_{22}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to an adjacent substituent to form a ring, with a proviso that at least one of two adjacent $R_{21}$'s or two adjacent $R_{22}$'s are linked to each other to form a ring; and b represents an integer of 1 to 4, c represents an integer of 1 to 6, where if b and c are an integer of 2 or more, each of $R_{21}$ and each of $R_{22}$ may be the same or different.

Effects of the Invention

By comprising the plurality of host materials of the present disclosure, an organic electroluminescent device having long lifespan characteristics is provided, and a display device or a lighting device using the organic electroluminescent device can be manufactured.

EMBODIMENTS OF THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (a host material or a dopant material), an electron buffer material, a hole blocking material, an electron transport material, or an electron injection material.

The term "a plurality of host materials" in the present disclosure means a host material comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host materials of the present disclosure may be a combination of at least two host materials, and selectively, conventional materials comprised in organic electroluminescent materials may be additionally comprised. The at least two compounds comprised in the plurality of host materials of the present disclosure may be comprised together in one light-emitting layer, or may be each comprised in separate light-emitting layers by a method known in the field. For example, the at least two compounds may be mixture-evaporated or co-evaporated, or may be individually evaporated.

Hereinafter, the compounds represented by formulas 1 and 2 will be described in detail.

Herein, the term "(C1-C30)alkyl" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, iso-propyl, n-butyl, iso-butyl, tert-butyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7 ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl" or "(C6-C30)arylene" is meant to be a monocyclic or fused ring radical derived from an aromatic hydrocarbon having 6 to 30 ring backbone carbon atoms, in which the number of the ring backbone carbon atoms is preferably 6 to 20, more preferably 6 to 15. The above aryl or arylene may be partially saturated. The above aryl may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. More specifically, the above aryl may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4"-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, and a 9,9-diphenyl-4-fluorenyl group. The term "(3- to 30-membered)heteroaryl" or "(3- to 30-membered)heteroarylene" is an aryl having 3 to 30 ring backbone atoms, in which the number of the ring backbone atoms is preferably 3 to 20, more preferably 5 to 15, and including at least one, preferably 1 to 4 heteroatoms selected from the group consisting of B, N, O, S, Si, and P. The above heteroaryl or heteroarylene may be a monocyclic ring, or a fused ring condensed with at least one benzene ring; may be partially saturated; and may be one formed by linking at least one heteroaryl or aryl group to a heteroaryl group via a single bond(s). The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. More specifically, the above heteroaryl or heteroarylene may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, an azacarbazolyl-8-yl group, an azacarbazolyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. Furthermore, "halogen" includes F, Cl, Br, and I.

In addition, "ortho," "meta," and "para" signify substitution positions of two substituents. The ortho position represents a just neighboring position, and, for example, in the case of benzene, represents 1,2 positions. The meta position represents the position next to the just neighboring position, and, for example, in the case of benzene, represents 1,3 positions. The para position represents the position next to the meta position, and, for example, in the case of benzene, represents 1,4 positions.

Herein, "substituted" in the expression "substituted or unsubstituted" means that a hydrogen atom in a certain functional group is replaced with another atom or functional group, i.e., a substituent. The substituents of the substituted alkyl, the substituted cycloalkyl, the substituted cycloalkylene, the substituted cycloalkenyl, the substituted heterocycloalkyl, the substituted aryl, the substituted arylene, the substituted heteroaryl, and the substituted heteroarylene in the formulas of the present disclosure each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (3- to 7-membered)heterocycloalkyl; a (C6-C30)aryloxy; a (C6-C30)arylthio; a (3- to 30-membered)heteroaryl unsubstituted or substituted with a (C1-C30)alkyl, a (C6-C30)aryl, or a di(C6-C30)arylamino; a (C6-C30)aryl unsubstituted or substituted with a cyano, a (3- to 30-membered)heteroaryl, or a tri(C6-C30)arylsilyl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. Preferably, the substituents each independently are at least one selected from the group consisting of a (C1-C6)alkyl, a (C6-C20)aryl, and a (3- to 20-membered)heteroaryl. For example, the substituents may be methyl, phenyl, naphthyl, biphenyl, or naphthylphenyl.

In the formulas of the present disclosure, if a substituent is linked to an adjacent substituent to form a ring, the ring may be a substituted or unsubstituted, mono- or polycyclic, alicyclic or aromatic (3- to 30-membered) ring, or the combination thereof, in which the formed ring may contain at least one heteroatom selected from nitrogen, oxygen, and sulfur. For example, the fused ring may be a substituted or unsubstituted dibenzothiophene ring, a substituted or unsubstituted dibenzofurane ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl or heteroarylene may each independently contain at least one heteroatom selected from B, N, O, S, Si, and P. In addition, the heteroatom may be substituted with at least one substituent selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

In formula 1, $X_1$ to $X_{13}$ each independently represent N or $CR_1$. According to one embodiment of the present disclosure, $X_1$ to $X_{13}$ are all $CR_1$.

In formula 1, $L_1$ represents a single bond, a substituted or unsubstituted (C6-C30)arylene, a substituted or unsubstituted (C3-C30)cycloalkylene, or a substituted or unsubstituted (3- to 30-membered)heteroarylene. According to one embodiment of the present disclosure, $L_1$ represents a single bond, or a (C6-C15)arylene unsubstituted or substituted with a (C1-C6)alkyl. According to another embodiment of the present disclosure, $L_1$ represents a single bond or an unsubstituted (C6-C12)arylene. Specifically, $L_1$ may represent a single bond, a phenylene, a naphthylene, a biphenylene, a dimethylfluorenylene, etc.

In formula 1, Ar represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_5R_6$, or —$SiR_7R_8R_9$; or may be linked to an adjacent substituent to form a ring. Herein, $R_5$ to $R_9$ each independently represent a substituted or unsubstituted (C1-C30)alkyl, a substituted or unsubstituted (C6-C30)aryl, or a substituted or unsubstituted (3- to 30-membered)heteroaryl. According to one embodiment of the present disclosure, Ar represents hydrogen, a (C6-C20)aryl unsubstituted or substituted with a (C1-C6)alkyl, a (5- to 25-membered)heteroaryl unsubstituted or substituted with a (C6-C12)aryl, or —$NR_5R_6$; and $R_5$ and $R_6$ each independently represent a (C6-C20)aryl unsubstituted or substituted with a (C1-C6)alkyl, or an unsubstituted (5- to 15-membered)heteroaryl. According to another embodiment of the present disclosure, Ar represents an unsubstituted (C6-C20)aryl, an unsubstituted (5- to 20-membered)heteroaryl, or —$NR_5R_6$; and $R_5$ and $R_6$ each independently represent an unsubstituted (C6-C20)aryl. Specifically, Ar may represent hydrogen, a phenyl, a naphthyl, a biphenyl, a naphthylphenyl, a phenylnaphthyl, a terphenyl, a dimethylfluorenyl, a dimethylbenzofluorenyl, a dibenzofuranyl, a benzonaphthofuranyl, a dibenzothiophenyl, a benzonaphthothiophenyl, a carbazolyl, a phenylcarbazolyl, a benzocarbazolyl, a phenylbenzocarbazolyl, a dibenzocarbazolyl, —$NR_5R_6$, etc.; and $R_5$ and $R_6$ may each independently represent a phenyl, a naphthyl, a biphenyl, a naphthylphenyl, a dimethylfluorenyl, a dibenzofuranyl, etc.

According to one embodiment of the present disclosure, Ar may represent a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted naphthyridinyl, a substituted or unsubstituted fluorenyl, a substituted or unsubstituted benzofluorenyl, a substituted or unsubstituted diphenylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyidibenzofuranylamino.

In formula 1, $R_1$ represents -$L_1$-$(Ar)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, a substituted or unsubstituted (3- to 30-membered) heteroaryl, —$NR_5R_6$, or —$SiR_7R_8R_9$; or may be linked to an adjacent substituent to form a ring. According to one embodiment of the present disclosure, $R_1$ represents hydrogen, an unsubstituted (C6-C12)aryl, or an unsubstituted (5- to 15-membered)heteroaryl; or may be linked to an adjacent substituent to form an unsubstituted monocyclic (6- to 12-membered) aromatic ring. Specifically, $R_1$ may represent hydrogen, a phenyl, a dibenzofuranyl, a dibenzothiophenyl, etc., or may be linked to an adjacent substituent to form a benzene ring, etc.

Formula 1 may be represented by the following formula 1-1.

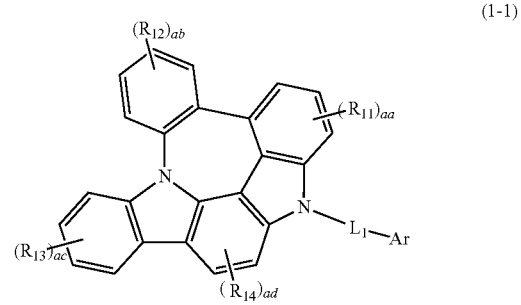

(1-1)

wherein $L_1$ represents a single bond, or a substituted or unsubstituted (C6-C30)arylene;

Ar represents hydrogen, deuterium, a substituted or unsubstituted (C6-C30)aryl, a substituted or unsubstituted (3- to 30-membered)heteroaryl, or —$NR_5R_6$;

$R_5$ and $R_6$ each independently represent a substituted or unsubstituted (C1-C30)alkyl, a substituted or unsubstituted (C6-C30)aryl, or a substituted or unsubstituted (3- to 30-membered)heteroaryl;

$R_{11}$ to $R_{14}$ each independently are identical to the definition of $R_1$ in formula 1; and aa represents an integer of 1 to 3, ab and ac each independently represent an integer of 1 to 4, ad represents 1 or 2, where if aa, ab, ac, and ad are an integer of 2 or more, each of $R_{11}$, each of $R_{12}$, each of $R_{13}$, and each of $R_{14}$ may be the same or different.

In addition, formula 1 may be represented by at least one of the following formulas 1-11 to 1-40.

-continued
1-11
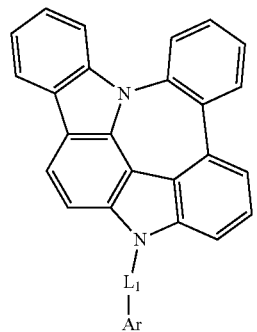
1-15
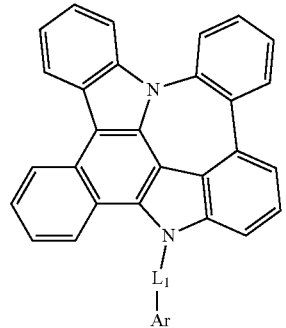
1-12
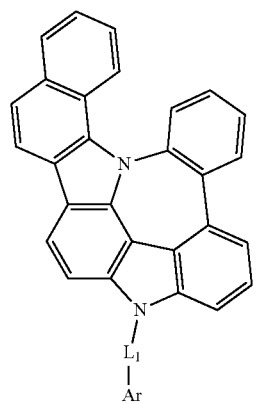
1-16
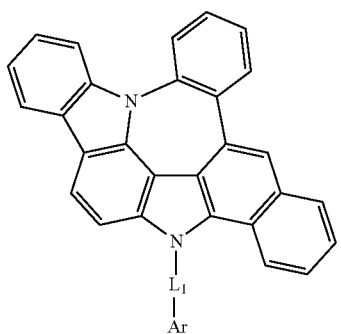
1-13
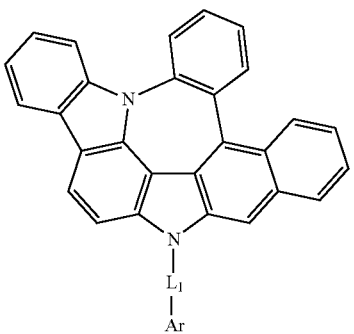
1-17
1-14
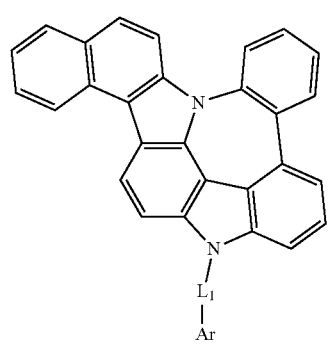
1-18
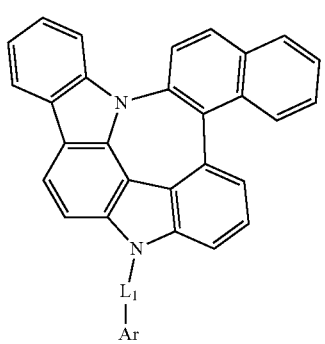

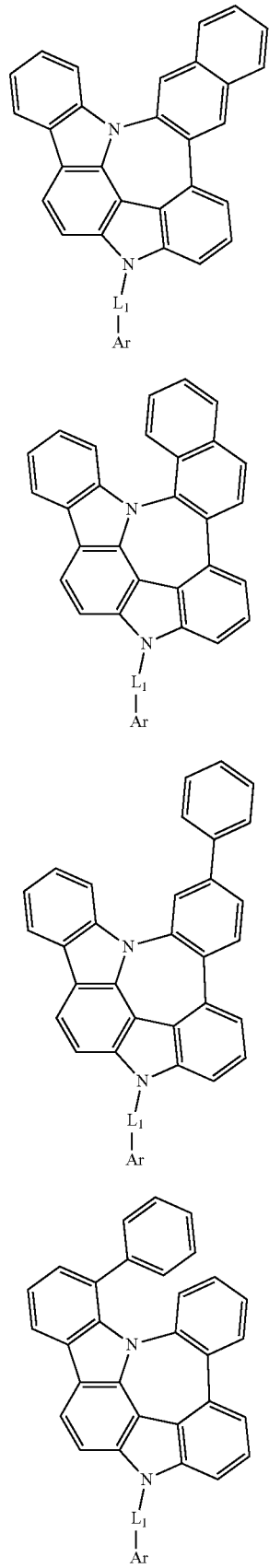
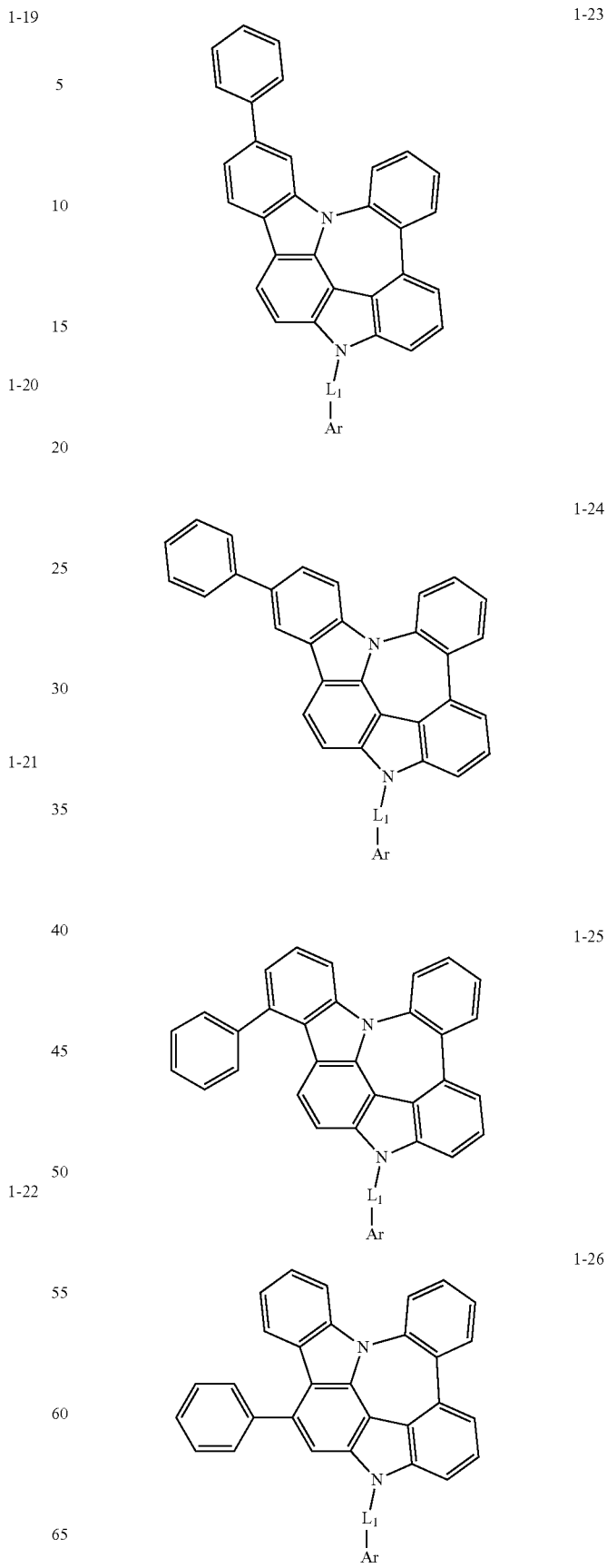

1-27
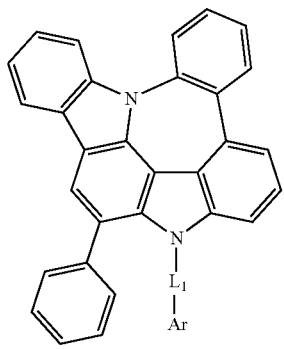
1-28
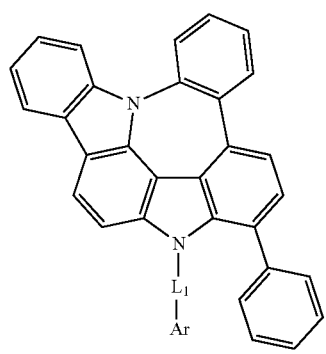
1-29
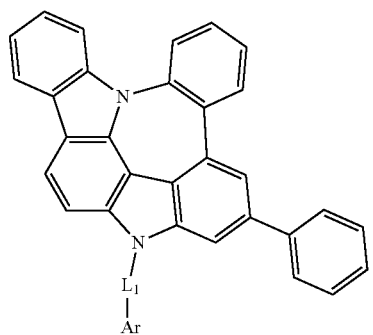
1-30
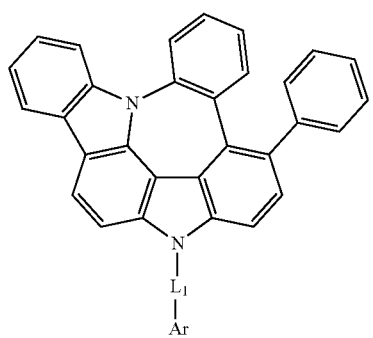
1-31
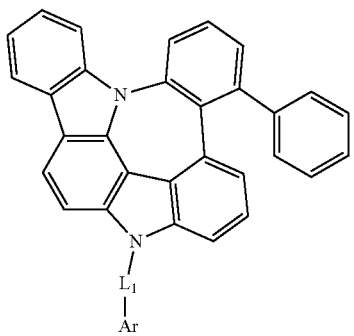
1-32
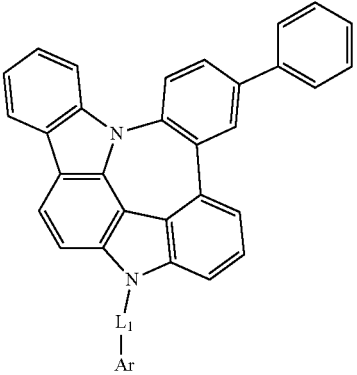
1-33
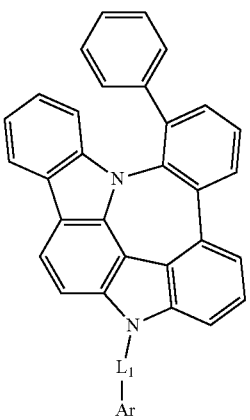
1-34
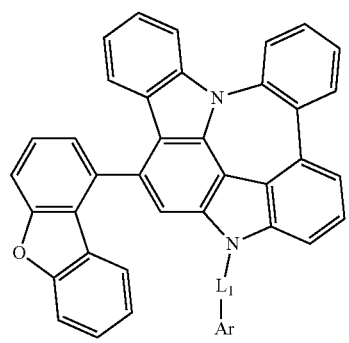

-continued
1-35
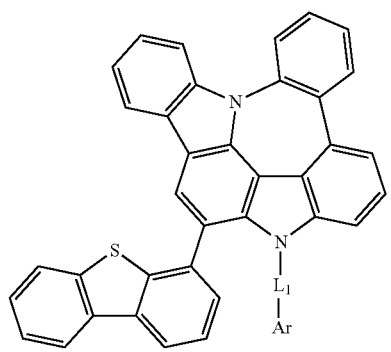
1-36
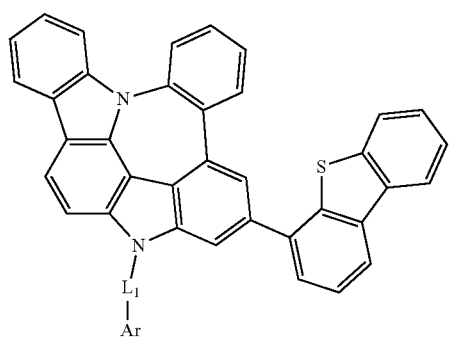
1-37
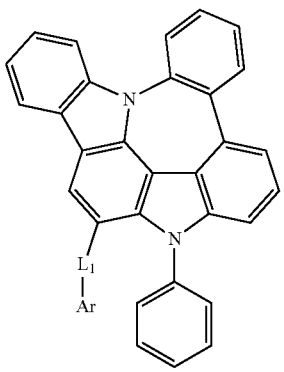
1-38
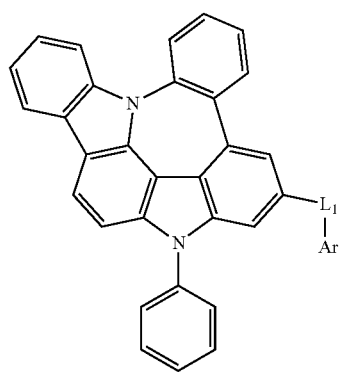
-continued
1-39
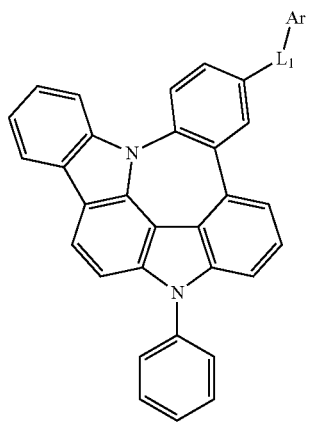
1-40
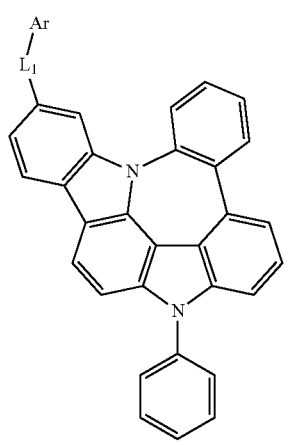
wherein
$L_1$ represents a single bond, or is represented by one of the following formulas $L_1$-1 to $L_1$-7, and
$L_1$-1
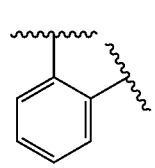
$L_1$-2
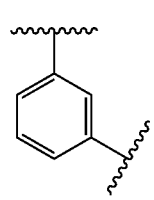
$L_1$-3
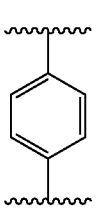

-continued
L₁-4
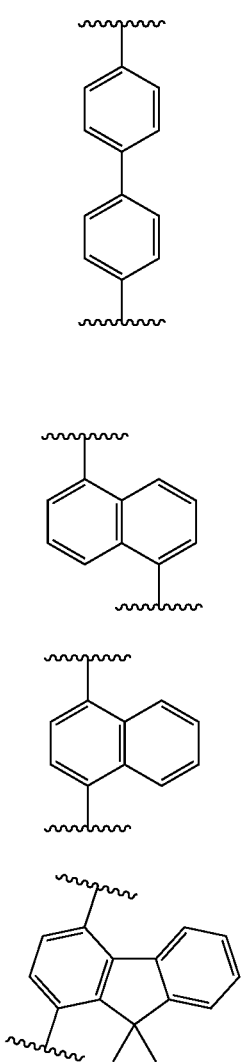
L₁-5
L₁-6
L₁-7
Ar is represented by one of the following formulas Ar-1 to Ar-121.
Ar-1
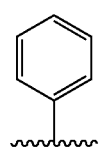
Ar-2
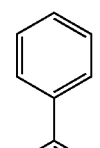
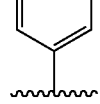
-continued
Ar-3
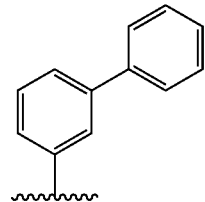
Ar-4
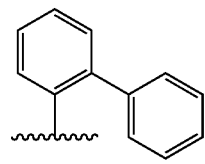
Ar-5
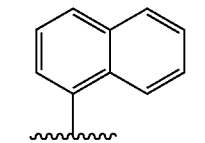
Ar-6
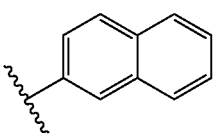
Ar-7
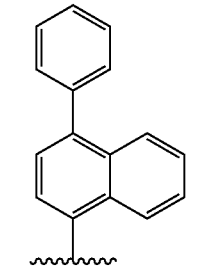
Ar-8
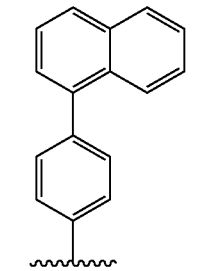
Ar-9
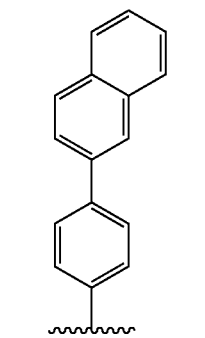

-continued
Ar-10
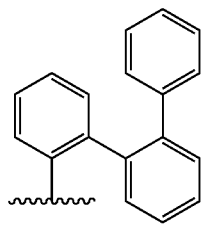
Ar-11
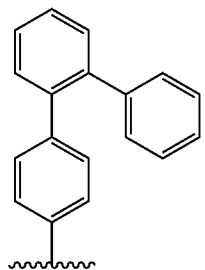
Ar-12
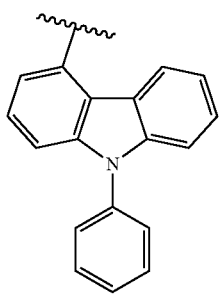
Ar-13
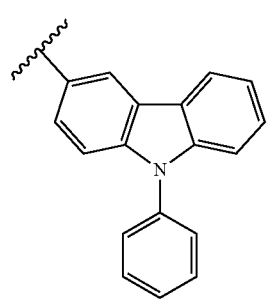
Ar-14
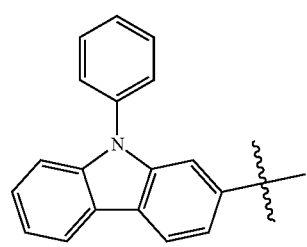
Ar-15
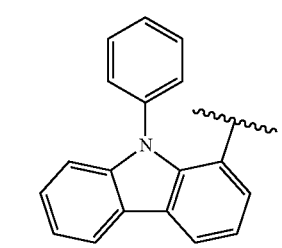
-continued
Ar-16
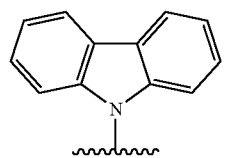
Ar-17
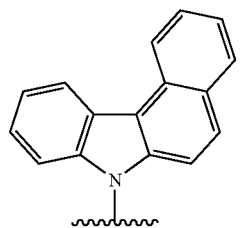
Ar-18
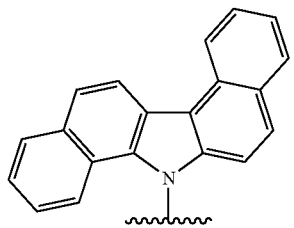
Ar-19
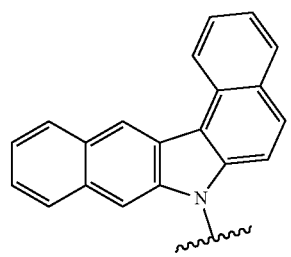
Ar-20
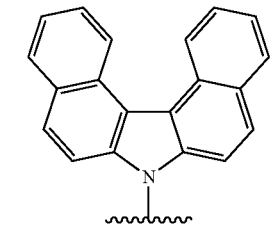
Ar-21
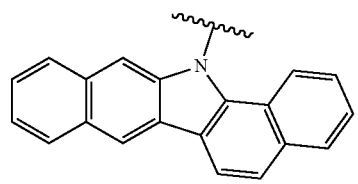
Ar-22
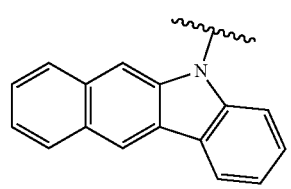

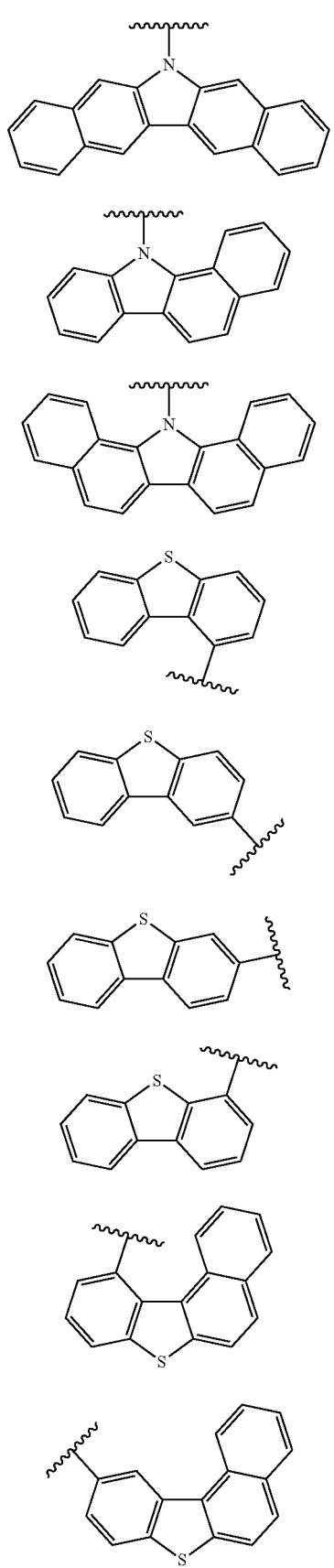
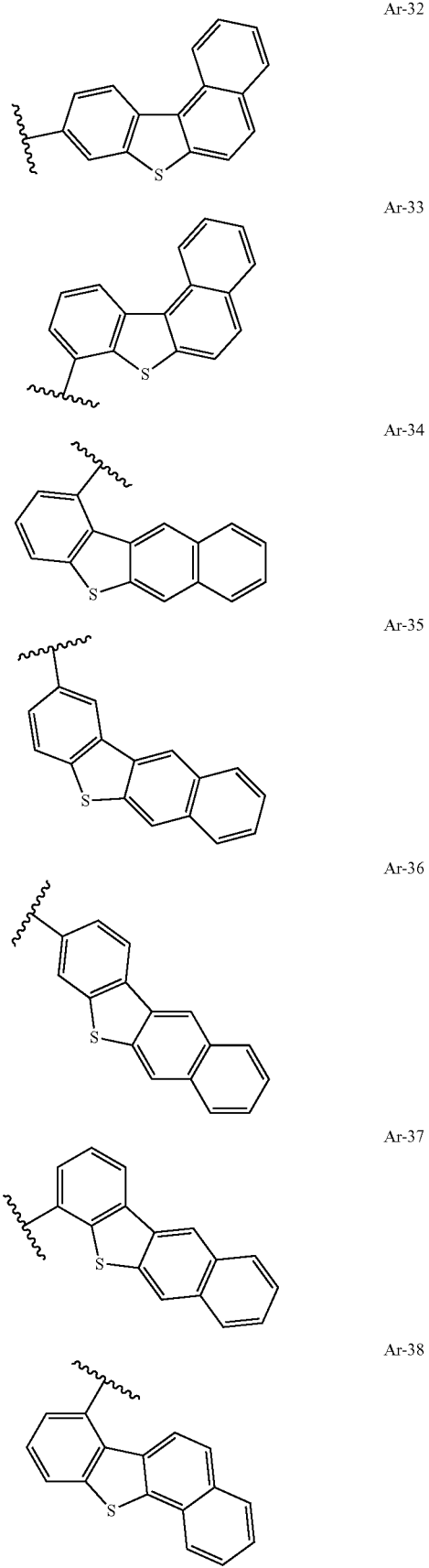

-continued
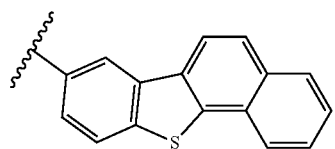
Ar-39
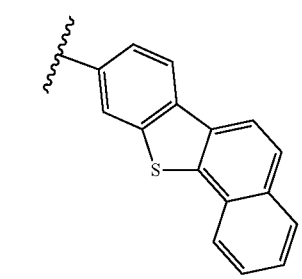
Ar-40
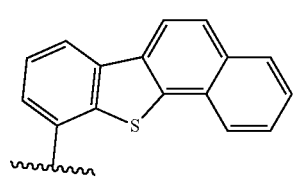
Ar-41
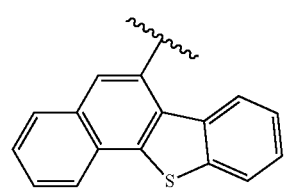
Ar-42
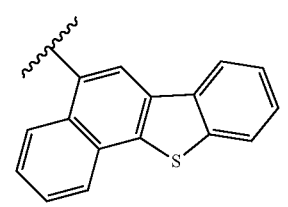
Ar-43
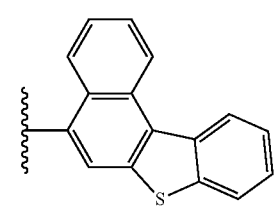
Ar-44
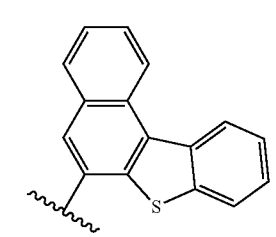
Ar-45
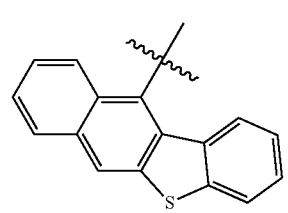
Ar-46
-continued
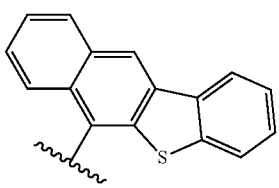
Ar-48
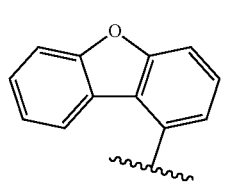
Ar-49
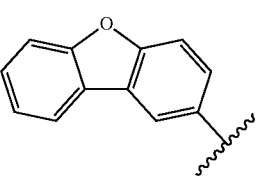
Ar-50
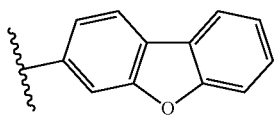
Ar-51
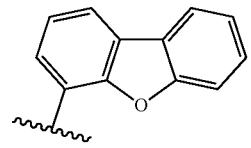
Ar-52
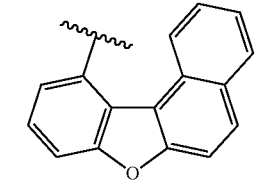
Ar-53
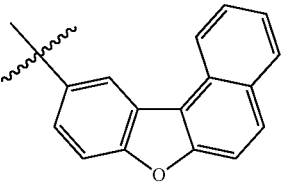
Ar-54
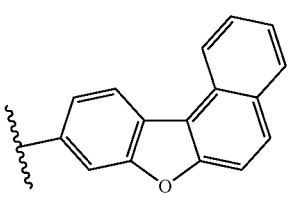
Ar-55

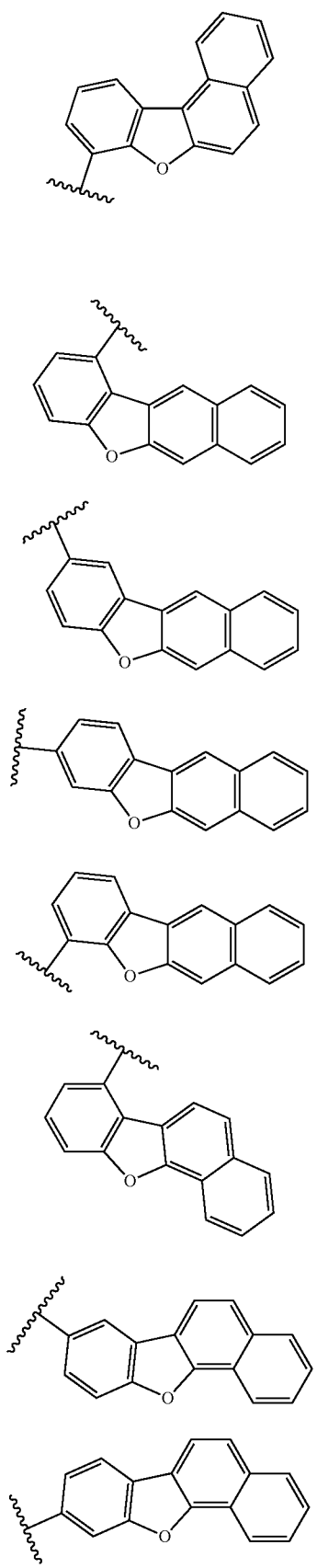

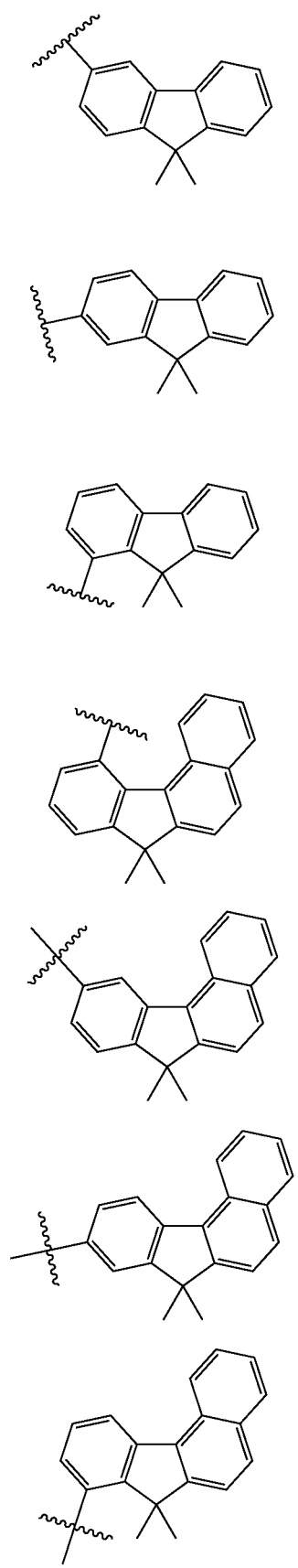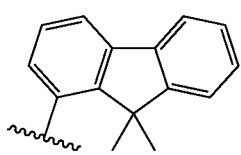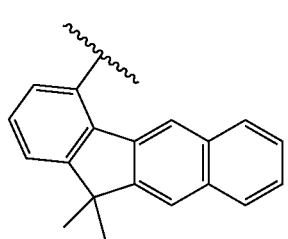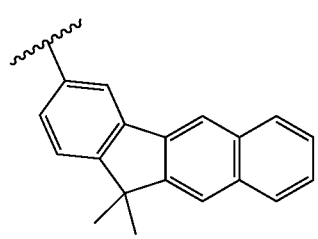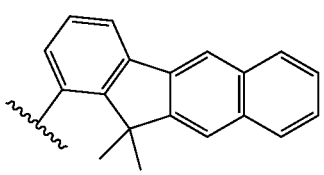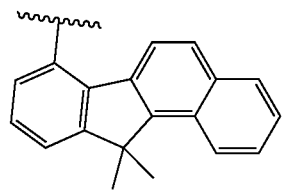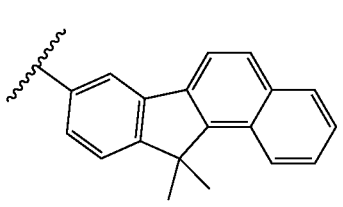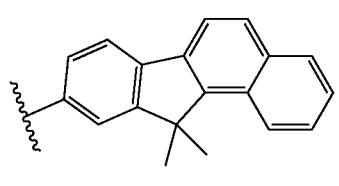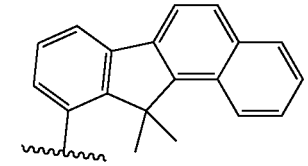

Ar-87
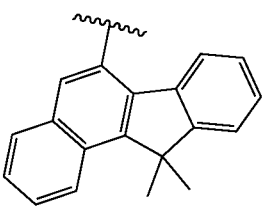
Ar-88
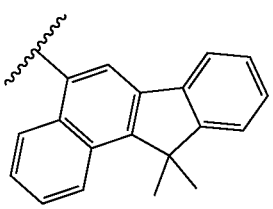
Ar-89
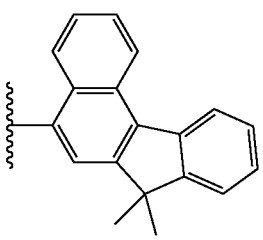
Ar-90
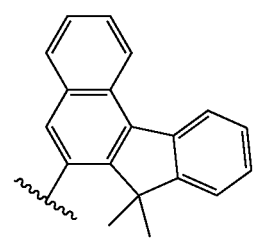
Ar-91
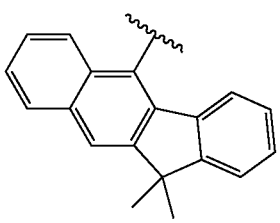
Ar-92
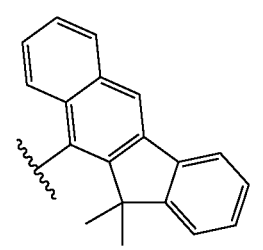
Ar-93
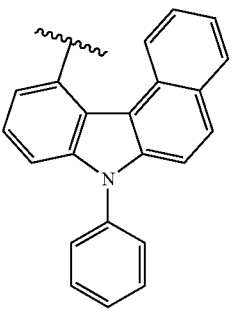
Ar-94
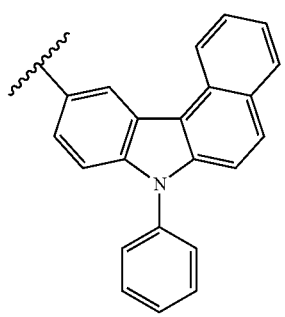
Ar-95
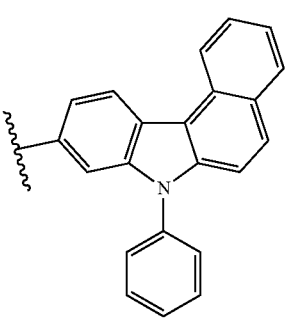
Ar-96
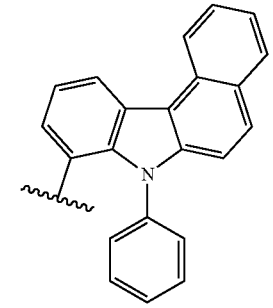
Ar-97
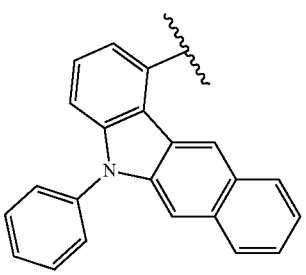

Ar-98
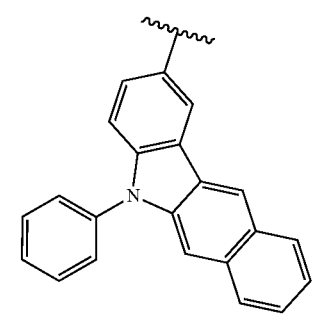
Ar-99
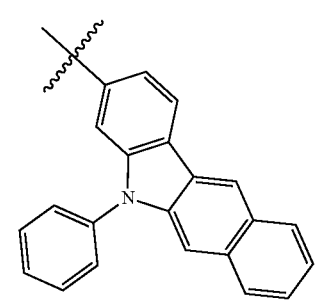
Ar-100
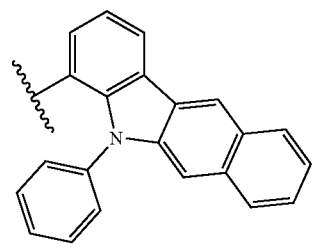
Ar-101
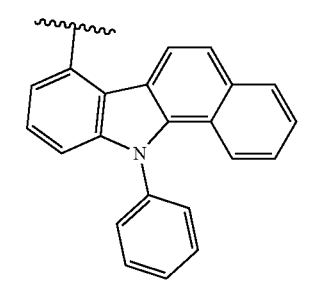
Ar-102
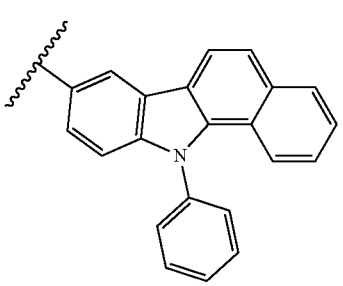
Ar-103
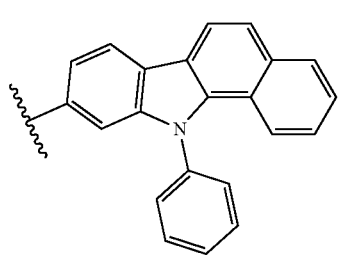
Ar-104
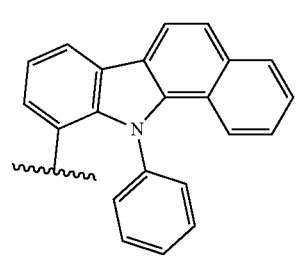
Ar-105
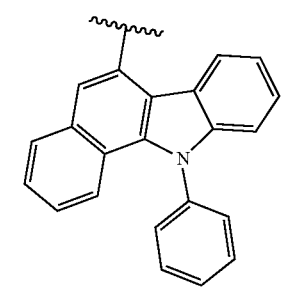
Ar-106
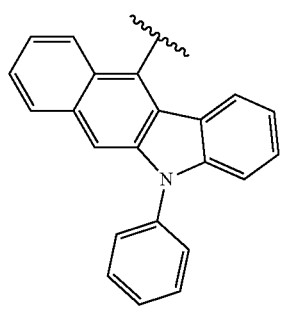
Ar-107
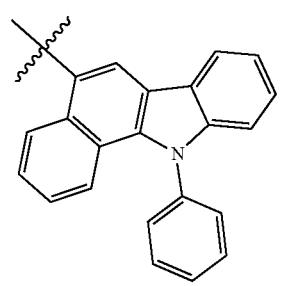

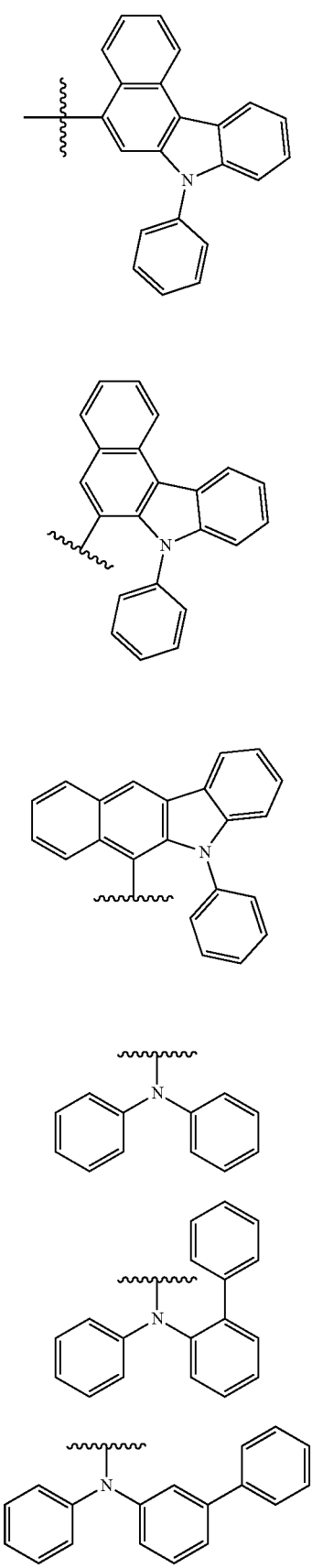
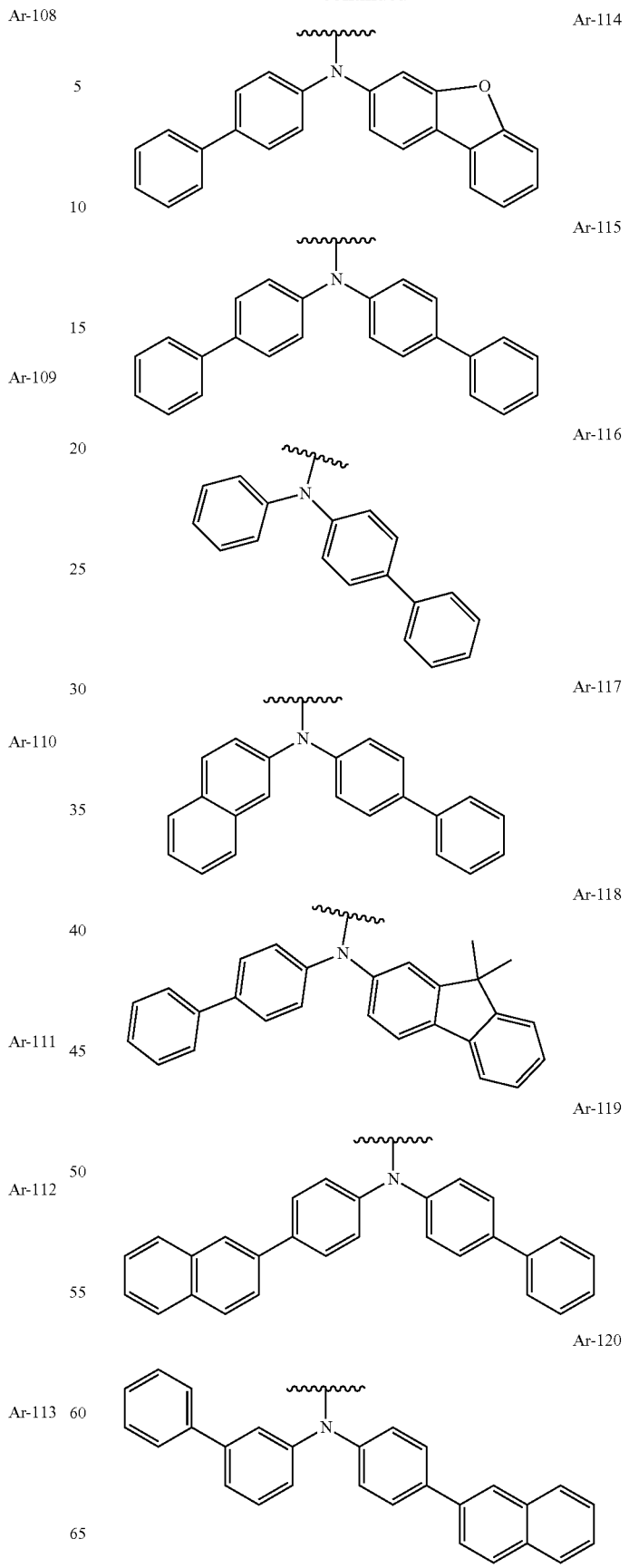

Ar-121

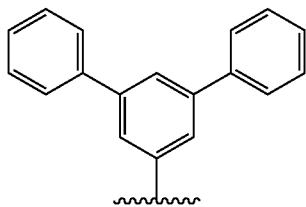

In formula 2, HAr represents a substituted or unsubstituted (3- to 30-membered)heteroaryl. According to one embodiment of the present disclosure, HAr represents a (3- to 15-membered)heteroaryl substituted with one or more (C6-C20)aryls. According to another embodiment of the present disclosure, HAr represents a (3- to 15-membered) heteroaryl substituted with one or more (C6-C12)aryls. Specifically, HAr may represent a pyridyl substituted with one or more phenyls; a pyrimidinyl substituted with one or more phenyls; a triazinyl substituted with one or more selected from phenyl, naphthyl, and biphenyl; a quinazolinyl substituted with one or more selected from phenyl, naphthyl, biphenyl, and naphthylphenyl; a quinoxalinyl substituted with one or more selected from phenyl, naphthyl, biphenyl, naphthylphenyl, etc.

According to one embodiment of the present disclosure, HAr may represent a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, or a substituted or unsubstituted benzothienopyrimidinyl.

In formula 2, $L_2$ represents a single bond, a substituted or unsubstituted (C6-C30)arylene, or a substituted or unsubstituted (3- to 30-membered)heteroarylene. According to one embodiment of the present disclosure, $L_2$ represents a single bond, or a (C6-C20)arylene unsubstituted or substituted with a (C1-C6)alkyl. According to another embodiment of the present disclosure, $L_2$ represents a single bond or a (C6-C15)arylene unsubstituted or substituted with a (C1-C6)alkyl. Specifically, $L_2$ may represent a single bond, a phenylene, a naphthylene, a biphenylene, a dimethylfluorenylene, a dimethylbenzofluorenylene, etc.

In formula 2, $R_{21}$ and $R_{22}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_5R_6$, or —$SiR_7R_8R_9$; or may be linked to an adjacent substituent to form a ring, with a proviso that at least one of two adjacent $R_{21}$'s or two adjacent $R_{22}$'s are linked to each other to form a ring. According to one embodiment of the present disclosure, $R_{21}$ and $R_{22}$ each independently represent hydrogen, or an unsubstituted (C6-C12)aryl, or two adjacent $R_{21}$'s or two adjacent $R_{22}$'s are linked to each other to form a polycyclic aromatic ring. Specifically, $R_{21}$ and $R_{22}$ may each independently represent hydrogen, a phenyl, etc., or two adjacent $R_{21}$'s or two adjacent $R_{22}$'s are linked to each other to form a benzene ring, an indole ring substituted with a phenyl, a benzoindole ring substituted with one or more selected from a phenyl and a biphenyl, a benzofuran ring, a benzothiophene ring, etc.

Formula 2 may be represented by at least one of the following formulas 2-1 to 2-6.

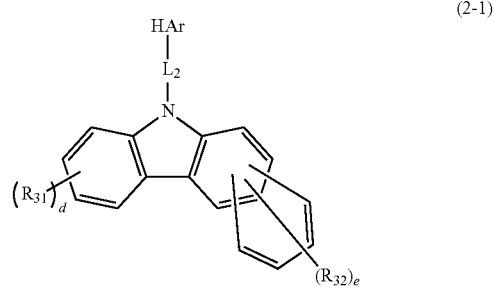

(2-1)

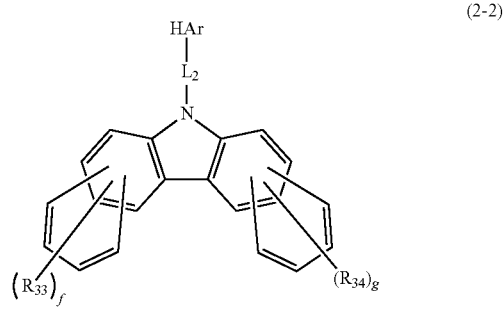

(2-2)

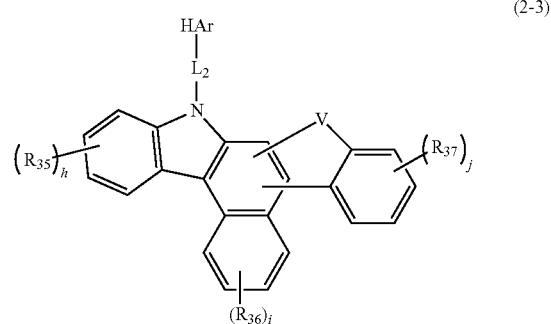

(2-3)

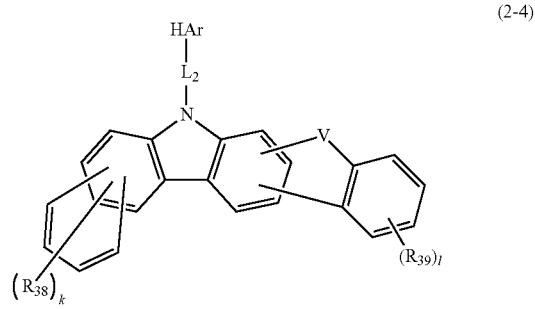

(2-4)

-continued

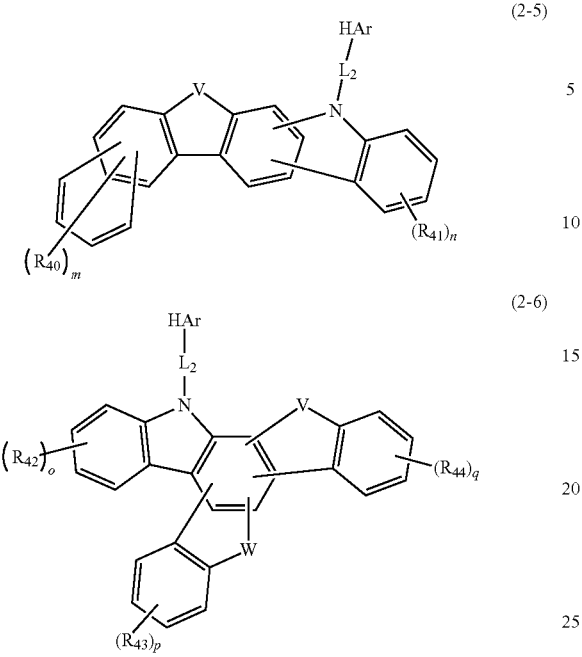

(2-5)

(2-6)

wherein

HAr and L₂ are as defined in formula 2;

$R_{31}$ to $R_{44}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —NR₅R₆, or —SiR₇R₈R₉; or may be linked to an adjacent substituent to form a ring;

V and W each independently represent NR₁₆, O, or S;

R₁₆ represents a substituted or unsubstituted (C6-C30) aryl, or a substituted or unsubstituted (3- to 30-membered)heteroaryl; and d, h, i, j, l, n, o, p, and q each independently represent an integer of 1 to 4, e, f, g, k, and m each independently represent an integer of 1 to 6, where if d to q are an integer of 2 or more, each of R₃₁ to each of R₄₄ may be the same or different.

In addition, formula 2 may be represented by at least one of the following formulas 2-11 to 2-38.

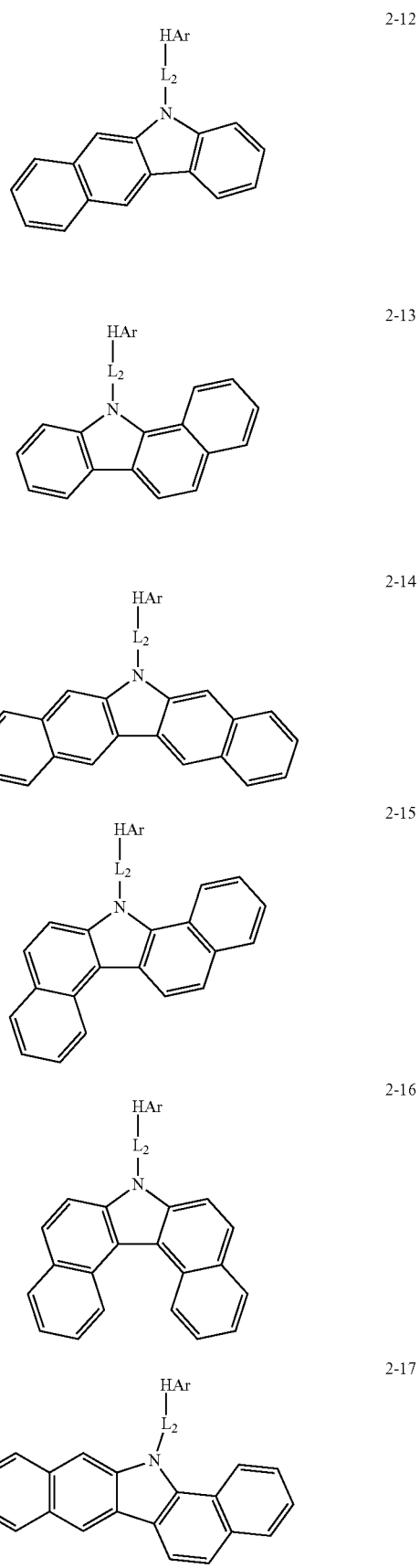

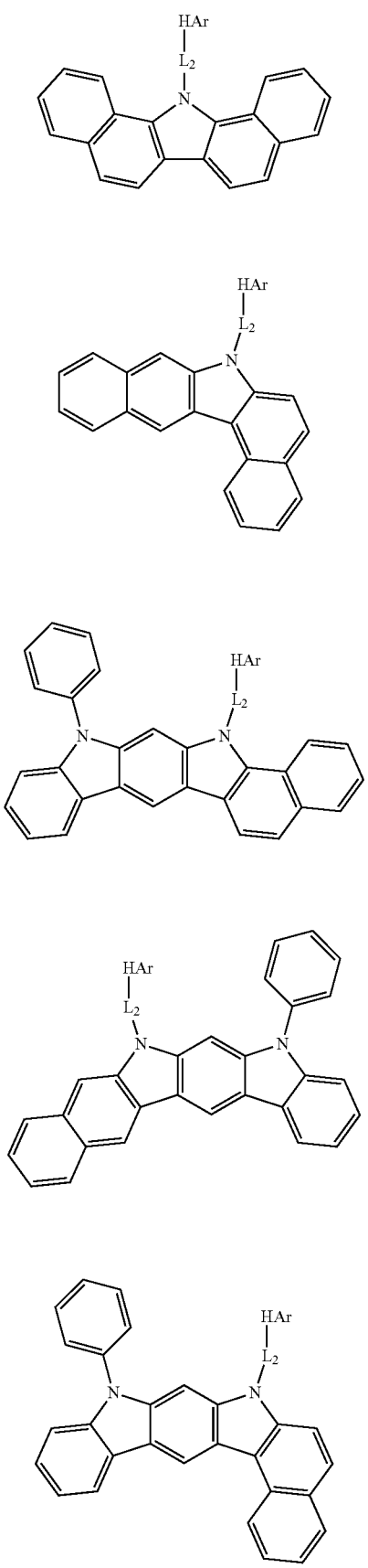
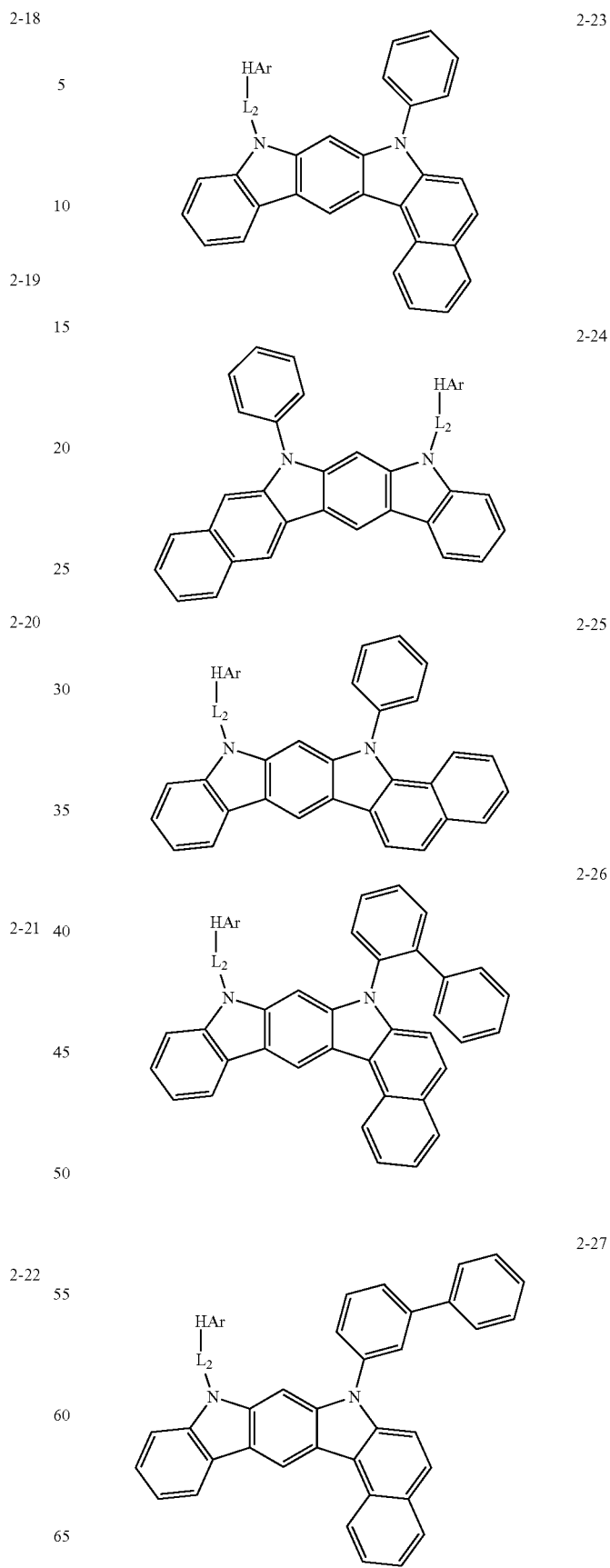

-continued
2-28
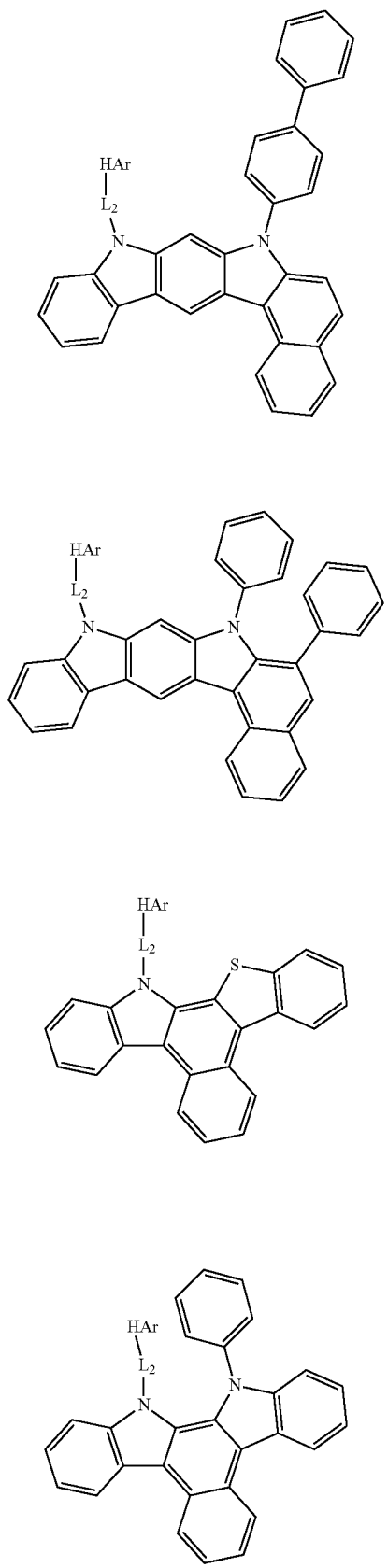
2-29
2-30
2-31
2-32
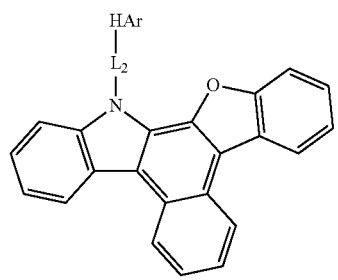
2-33
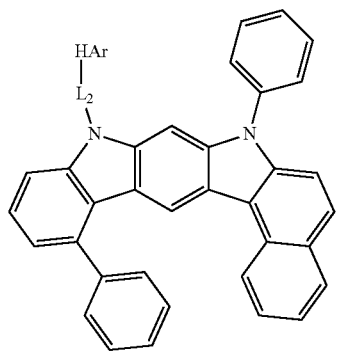
2-34
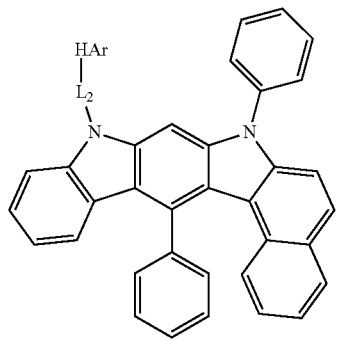
2-35
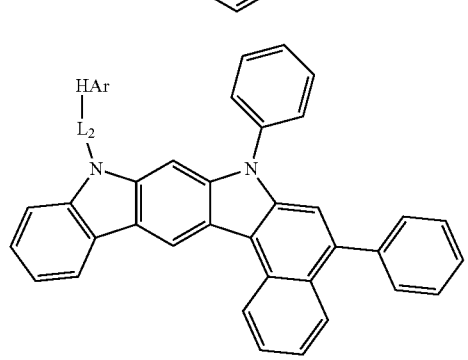
2-36
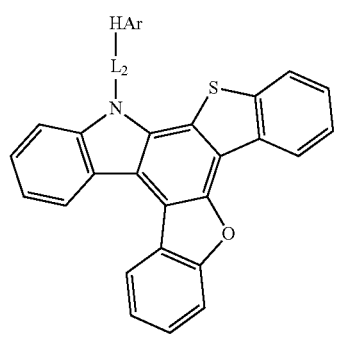

2-37
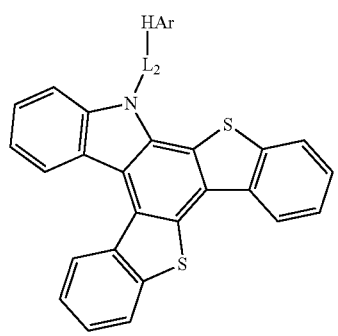
2-38
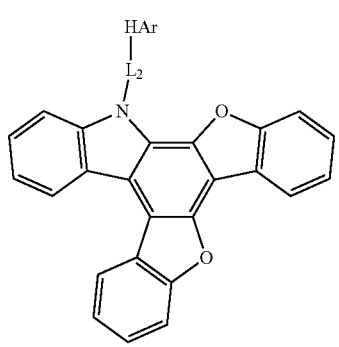
wherein
HAr is represented by one of the following formulas 2-40 to 2-58, and
2-40
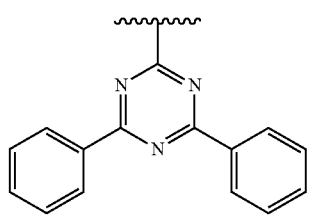
2-41
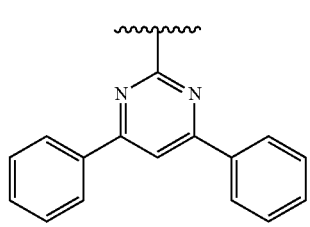
2-42
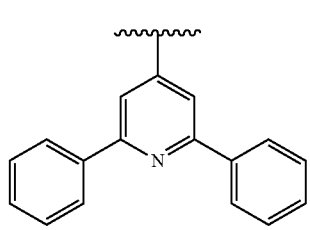
2-43
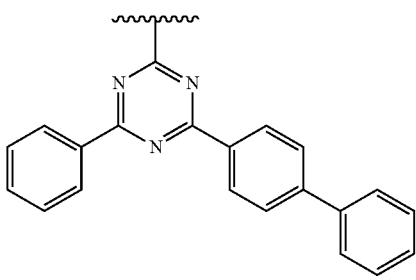
2-44
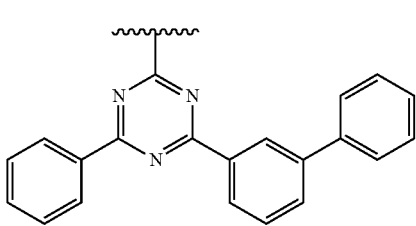
2-45
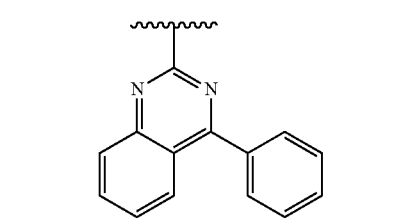
2-46
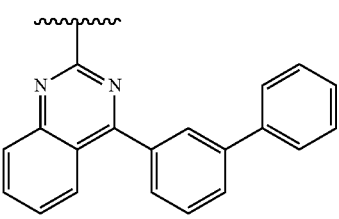
2-47
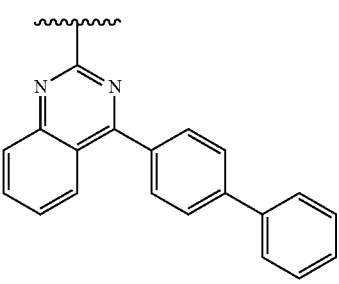
2-48
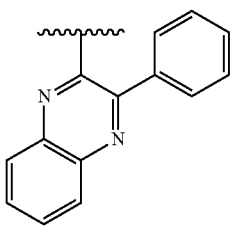

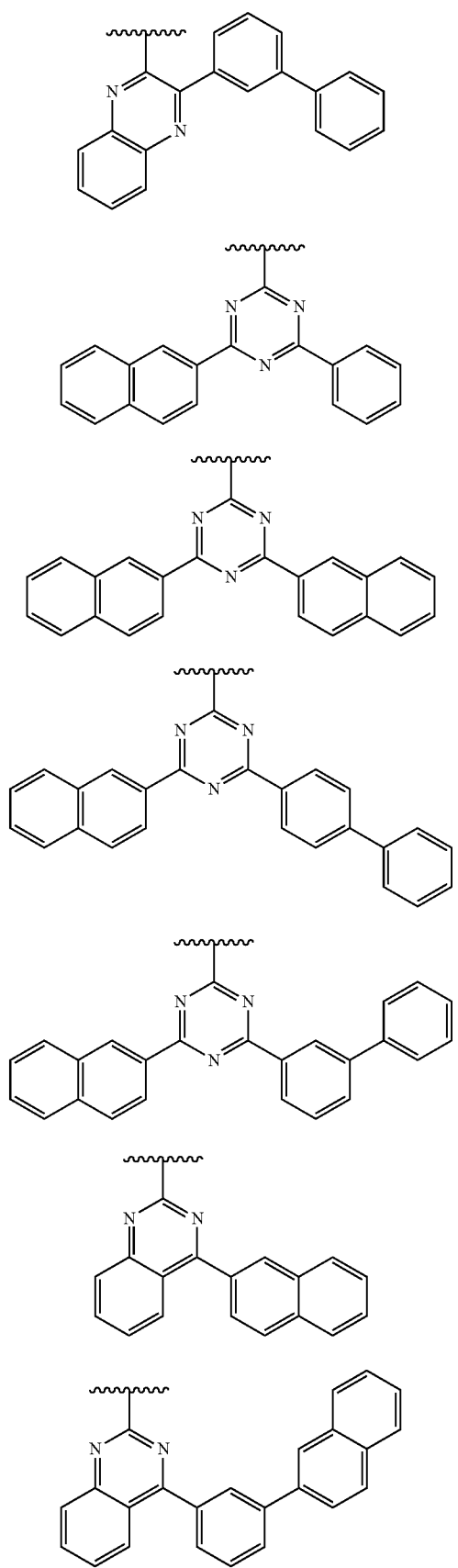
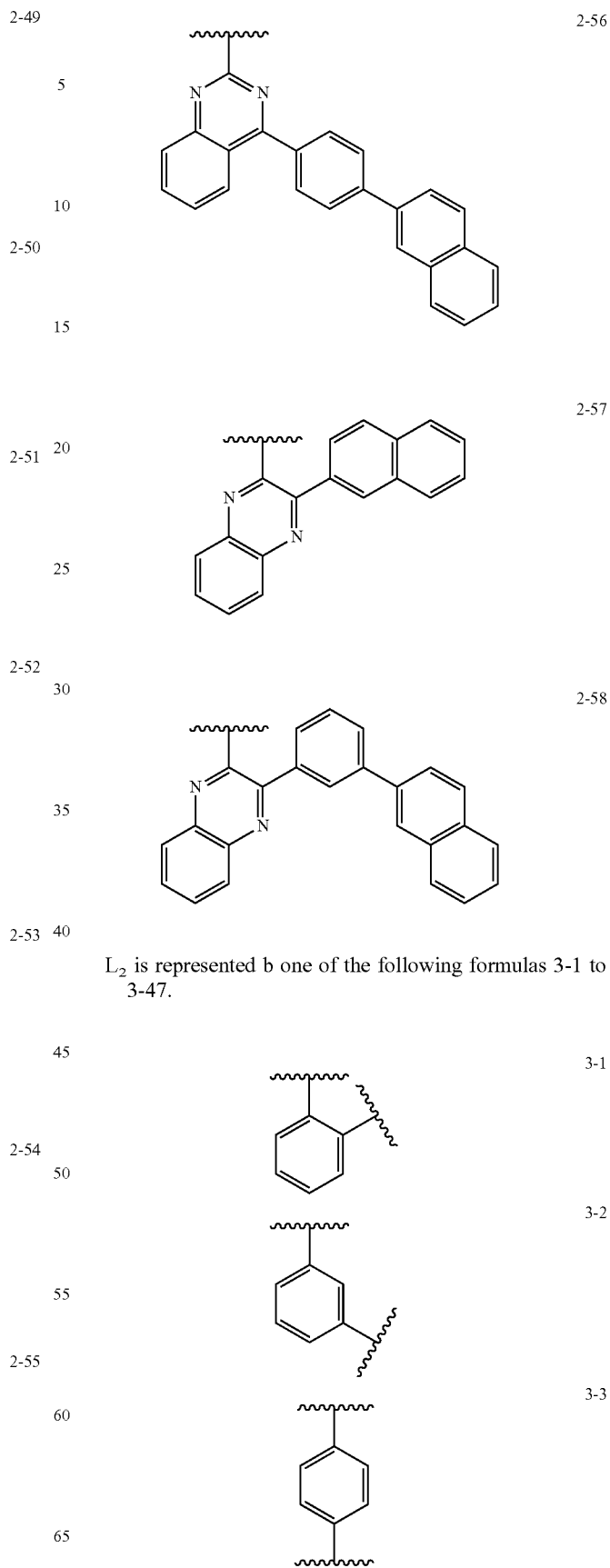
$L_2$ is represented b one of the following formulas 3-1 to 3-47.

-continued
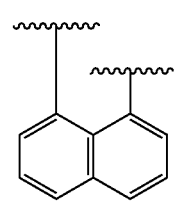
3-4
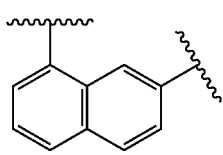
3-5
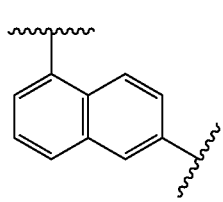
3-6
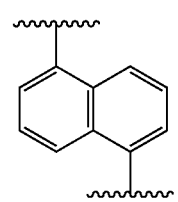
3-7
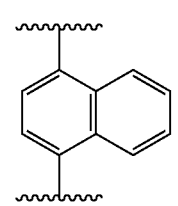
3-8
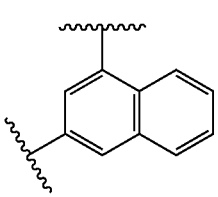
3-9
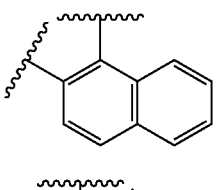
3-10
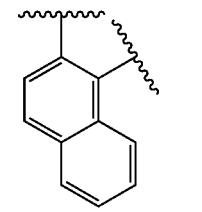
3-11
-continued
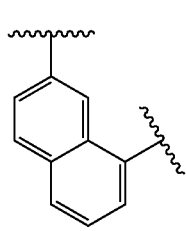
3-12
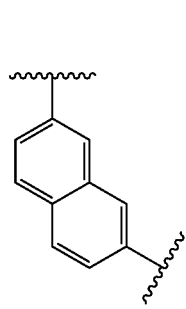
3-13
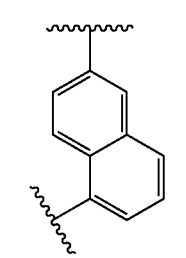
3-14
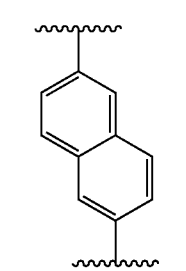
3-15
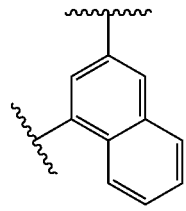
3-16
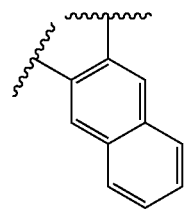
3-17

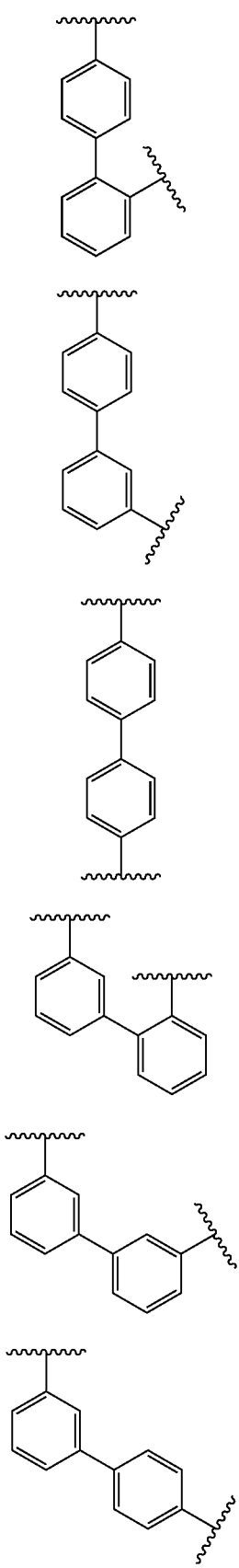
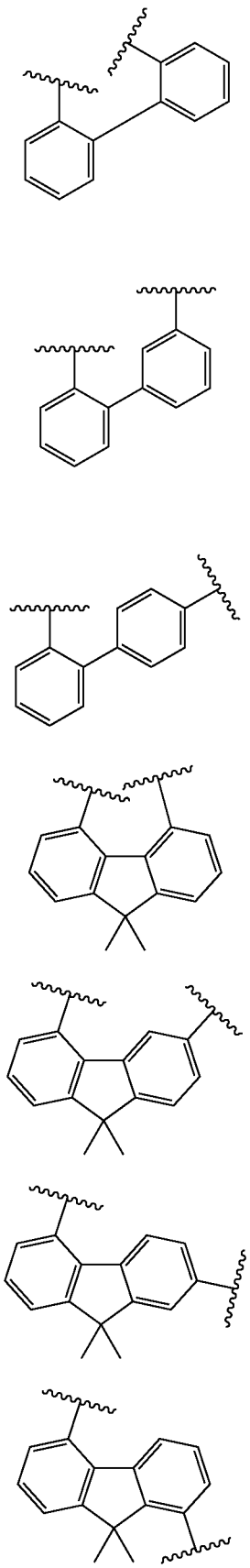

-continued
3-31 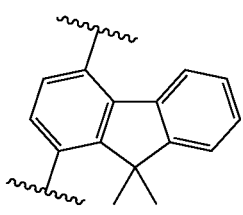
3-32 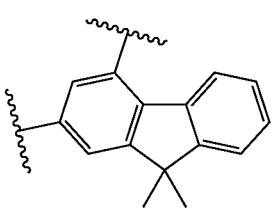
3-33 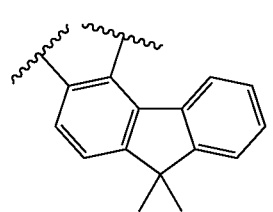
3-34 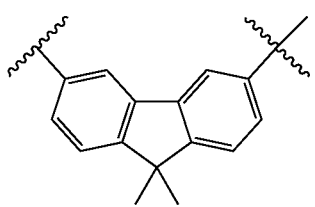
3-35 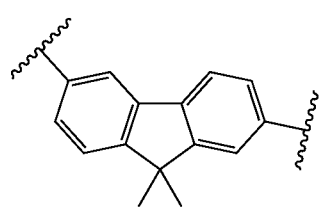
3-36 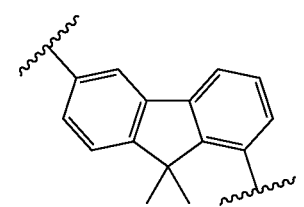
3-37 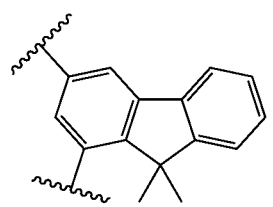
-continued
3-38 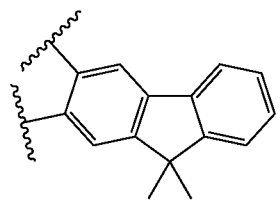
3-39 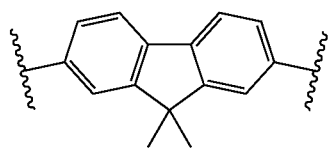
3-40 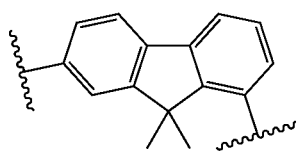
3-41 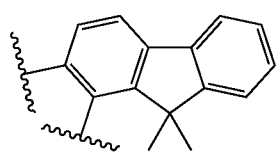
3-42 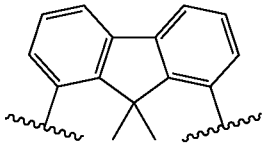
3-43 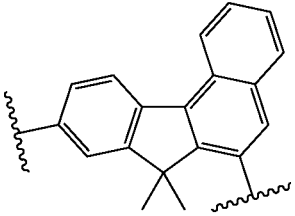
3-44 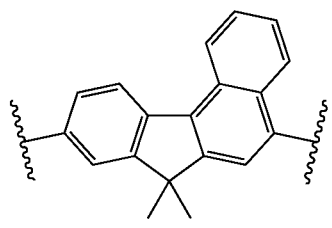
3-45 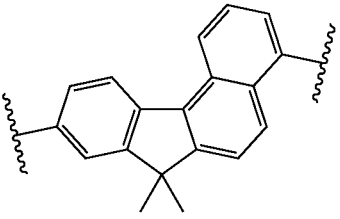

-continued 3-46

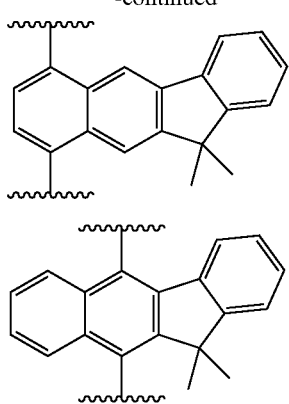

3-47

The compound represented by formula 1 includes the following compounds, but is not limited thereto.

| Compound | Formula | $L_1$ | Ar | Compound | Formula | $L_1$ | Ar |
|---|---|---|---|---|---|---|---|
| C1-1 | 1-11 | $L_1$-1 | Ar-1 | C1-2 | 1-11 | $L_1$-1 | Ar-2 |
| C1-3 | 1-11 | $L_1$-2 | Ar-2 | C1-4 | 1-11 | $L_1$-2 | Ar-4 |
| C1-5 | 1-11 | $L_1$-2 | Ar-26 | C1-6 | 1-11 | $L_1$-2 | Ar-49 |
| C1-7 | 1-11 | $L_1$-2 | Ar-71 | C1-8 | 1-11 | $L_1$-2 | Ar-115 |
| C1-9 | 1-11 | $L_1$-2 | Ar-27 | C1-10 | 1-11 | $L_1$-2 | Ar-51 |
| C1-11 | 1-11 | $L_1$-2 | Ar-28 | C1-12 | 1-11 | $L_1$-2 | Ar-52 |
| C1-13 | 1-11 | $L_1$-2 | Ar-29 | C1-14 | 1-11 | $L_1$-2 | Ar-53 |
| C1-15 | 1-11 | $L_1$-2 | Ar-33 | C1-16 | 1-11 | $L_1$-2 | Ar-54 |
| C1-17 | 1-11 | $L_1$-2 | Ar-50 | C1-18 | 1-11 | $L_1$-2 | Ar-55 |
| C1-19 | 1-11 | $L_1$-2 | Ar-56 | C1-20 | 1-11 | $L_1$-3 | Ar-119 |
| C1-21 | 1-11 | $L_1$-3 | Ar-2 | C1-22 | 1-11 | $L_1$-3 | Ar-4 |
| C1-23 | 1-11 | $L_1$-3 | Ar-26 | C1-24 | 1-11 | $L_1$-3 | Ar-49 |
| C1-25 | 1-11 | $L_1$-3 | Ar-71 | C1-26 | 1-11 | $L_1$-3 | Ar-116 |
| C1-27 | 1-12 | $L_1$-1 | Ar-1 | C1-28 | 1-12 | $L_1$-2 | Ar-4 |
| C1-29 | 1-12 | $L_1$-2 | Ar-49 | C1-30 | 1-12 | $L_1$-3 | Ar-116 |
| C1-31 | 1-13 | $L_1$-1 | Ar-1 | C1-32 | 1-13 | $L_1$-2 | Ar-4 |
| C1-33 | 1-13 | $L_1$-2 | Ar-49 | C1-34 | 1-13 | $L_1$-3 | Ar-116 |
| C1-35 | 1-14 | $L_1$-1 | Ar-1 | C1-36 | 1-14 | $L_1$-2 | Ar-4 |
| C1-37 | 1-14 | $L_1$-2 | Ar-49 | C1-38 | 1-14 | $L_1$-3 | Ar-116 |
| C1-39 | 1-15 | $L_1$-1 | Ar-1 | C1-40 | 1-15 | $L_1$-2 | Ar-4 |
| C1-41 | 1-15 | $L_1$-2 | Ar-49 | C1-42 | 1-15 | $L_1$-3 | Ar-116 |
| C1-43 | 1-16 | $L_1$-1 | Ar-1 | C1-44 | 1-16 | $L_1$-2 | Ar-4 |
| C1-45 | 1-16 | $L_1$-2 | Ar-49 | C1-46 | 1-16 | $L_1$-3 | Ar-116 |
| C1-47 | 1-17 | $L_1$-1 | Ar-1 | C1-48 | 1-17 | $L_1$-2 | Ar-4 |
| C1-49 | 1-17 | $L_1$-2 | Ar-49 | C1-50 | 1-17 | $L_1$-3 | Ar-116 |
| C1-51 | 1-18 | $L_1$-1 | Ar-1 | C1-52 | 1-18 | $L_1$-2 | Ar-4 |
| C1-53 | 1-18 | $L_1$-2 | Ar-49 | C1-54 | 1-18 | $L_1$-3 | Ar-116 |
| C1-55 | 1-19 | $L_1$-1 | Ar-1 | C1-56 | 1-19 | $L_1$-2 | Ar-4 |
| C1-57 | 1-19 | $L_1$-2 | Ar-49 | C1-58 | 1-19 | $L_1$-3 | Ar-116 |
| C1-59 | 1-20 | $L_1$-1 | Ar-1 | C1-60 | 1-20 | $L_1$-2 | Ar-4 |
| C1-61 | 1-20 | $L_1$-2 | Ar-49 | C1-62 | 1-20 | $L_1$-3 | Ar-116 |
| C1-63 | 1-21 | $L_1$-1 | Ar-1 | C1-64 | 1-21 | $L_1$-2 | Ar-4 |
| C1-65 | 1-21 | $L_1$-2 | Ar-49 | C1-66 | 1-21 | $L_1$-3 | Ar-116 |
| C1-67 | 1-22 | $L_1$-1 | Ar-1 | C1-68 | 1-22 | $L_1$-2 | Ar-4 |
| C1-69 | 1-22 | $L_1$-2 | Ar-49 | C1-70 | 1-22 | $L_1$-3 | Ar-116 |
| C1-71 | 1-23 | $L_1$-1 | Ar-1 | C1-72 | 1-23 | $L_1$-2 | Ar-4 |
| C1-73 | 1-23 | $L_1$-2 | Ar-49 | C1-74 | 1-23 | $L_1$-3 | Ar-116 |
| C1-75 | 1-24 | $L_1$-1 | Ar-1 | C1-76 | 1-24 | $L_1$-2 | Ar-4 |
| C1-77 | 1-24 | $L_1$-2 | Ar-49 | C1-78 | 1-24 | $L_1$-3 | Ar-116 |
| C1-79 | 1-25 | $L_1$-1 | Ar-1 | C1-80 | 1-25 | $L_1$-2 | Ar-4 |
| C1-81 | 1-25 | $L_1$-2 | Ar-49 | C1-82 | 1-25 | $L_1$-3 | Ar-116 |
| C1-83 | 1-26 | $L_1$-1 | Ar-1 | C1-84 | 1-26 | $L_1$-2 | Ar-4 |
| C1-85 | 1-26 | $L_1$-2 | Ar-49 | C1-86 | 1-26 | $L_1$-3 | Ar-116 |
| C1-87 | 1-27 | $L_1$-1 | Ar-1 | C1-88 | 1-27 | $L_1$-2 | Ar-4 |
| C1-89 | 1-27 | $L_1$-2 | Ar-49 | C1-90 | 1-27 | $L_1$-3 | Ar-116 |
| C1-91 | 1-28 | $L_1$-1 | Ar-1 | C1-92 | 1-28 | $L_1$-2 | Ar-4 |
| C1-93 | 1-28 | $L_1$-2 | Ar-49 | C1-94 | 1-28 | $L_1$-3 | Ar-116 |
| C1-95 | 1-29 | $L_1$-1 | Ar-1 | C1-96 | 1-29 | $L_1$-2 | Ar-4 |
| C1-97 | 1-29 | $L_1$-2 | Ar-49 | C1-98 | 1-29 | $L_1$-3 | Ar-116 |
| C1-99 | 1-30 | $L_1$-1 | Ar-1 | C1-100 | 1-30 | $L_1$-2 | Ar-4 |
| C1-101 | 1-30 | $L_1$-2 | Ar-49 | C1-102 | 1-30 | $L_1$-3 | Ar-116 |
| C1-103 | 1-31 | $L_1$-1 | Ar-1 | C1-104 | 1-31 | $L_1$-2 | Ar-4 |
| C1-105 | 1-31 | $L_1$-2 | Ar-49 | C1-106 | 1-31 | $L_1$-3 | Ar-116 |

-continued

| Compound | Formula | $L_1$ | Ar | Compound | Formula | $L_1$ | Ar |
|---|---|---|---|---|---|---|---|
| C1-107 | 1-32 | $L_1$-1 | Ar-1 | C1-108 | 1-32 | $L_1$-2 | Ar-4 |
| C1-109 | 1-32 | $L_1$-2 | Ar-49 | C1-110 | 1-32 | $L_1$-3 | Ar-116 |
| C1-111 | 1-33 | $L_1$-1 | Ar-1 | C1-112 | 1-33 | $L_1$-2 | Ar-4 |
| C1-113 | 1-33 | $L_1$-2 | Ar-49 | C1-114 | 1-33 | $L_1$-3 | Ar-116 |
| C1-115 | 1-34 | $L_1$-1 | Ar-1 | C1-116 | 1-34 | $L_1$-2 | Ar-4 |
| C1-117 | 1-34 | $L_1$-2 | Ar-49 | C1-118 | 1-34 | $L_1$-3 | Ar-116 |
| C1-119 | 1-35 | $L_1$-1 | Ar-1 | C1-120 | 1-35 | $L_1$-2 | Ar-4 |
| C1-121 | 1-35 | $L_1$-2 | Ar-49 | C1-122 | 1-35 | $L_1$-3 | Ar-116 |
| C1-123 | 1-36 | $L_1$-1 | Ar-1 | C1-124 | 1-36 | $L_1$-2 | Ar-4 |
| C1-125 | 1-36 | $L_1$-2 | Ar-49 | C1-126 | 1-36 | $L_1$-3 | Ar-116 |
| C1-127 | 1-37 | $L_1$-1 | Ar-1 | C1-128 | 1-37 | $L_1$-2 | Ar-4 |
| C1-129 | 1-37 | $L_1$-2 | Ar-49 | C1-130 | 1-37 | $L_1$-3 | Ar-116 |
| C1-131 | 1-38 | $L_1$-1 | Ar-1 | C1-132 | 1-38 | $L_1$-2 | Ar-4 |
| C1-133 | 1-38 | $L_1$-2 | Ar-49 | C1-134 | 1-38 | $L_1$-3 | Ar-116 |
| C1-135 | 1-39 | $L_1$-1 | Ar-1 | C1-136 | 1-39 | $L_1$-2 | Ar-4 |
| C1-137 | 1-39 | $L_1$-2 | Ar-49 | C1-138 | 1-39 | $L_1$-3 | Ar-116 |
| C1-139 | 1-40 | $L_1$-1 | Ar-1 | C1-140 | 1-40 | $L_1$-2 | Ar-4 |
| C1-141 | 1-40 | $L_1$-2 | Ar-49 | C1-142 | 1-40 | $L_1$-3 | Ar-116 |
| C1-143 | 1-11 | Single bond | Ar-2 | C1-144 | 1-11 | Single bond | Ar-50 |
| C1-145 | 1-11 | Single bond | Ar-3 | C1-146 | 1-11 | $L_1$-2 | Ar-111 |
| C1-147 | 1-11 | Single bond | Ar-51 | C1-148 | 1-11 | Single bond | Ar-121 |

The compound represented by formula 2 includes the following compounds, but is not limited thereto.

| Compound | Formula | $L_2$ | HAr | Compound | Formula | $L_2$ | HAr |
|---|---|---|---|---|---|---|---|
| C2-1 | 2-11 | 3-3 | 2-40 | C2-2 | 2-11 | 3-3 | 2-45 |
| C2-3 | 2-11 | 3-3 | 2-48 | C2-4 | 2-11 | 3-8 | 2-45 |
| C2-5 | 2-11 | 3-3 | 2-50 | C2-6 | 2-11 | 3-8 | 2-50 |
| C2-7 | 2-12 | 3-3 | 2-40 | C2-8 | 2-12 | 3-8 | 2-40 |
| C2-9 | 2-12 | 3-3 | 2-50 | C2-10 | 2-12 | 3-8 | 2-50 |
| C2-11 | 2-12 | 3-20 | 2-40 | C2-12 | 2-12 | 3-34 | 2-40 |
| C2-13 | 2-12 | 3-3 | 2-45 | C2-14 | 2-12 | 3-8 | 2-45 |
| C2-15 | 2-12 | 3-20 | 2-45 | C2-16 | 2-12 | 3-34 | 2-45 |
| C2-17 | 2-12 | 3-3 | 2-48 | C2-18 | 2-12 | 3-8 | 2-48 |
| C2-19 | 2-12 | 3-20 | 2-48 | C2-20 | 2-12 | 3-34 | 2-48 |
| C2-21 | 2-13 | 3-3 | 2-40 | C2-22 | 2-13 | 3-3 | 2-45 |
| C2-23 | 2-13 | 3-3 | 2-48 | C2-24 | 2-13 | 3-8 | 2-45 |
| 02-25 | 2-13 | 3-3 | 2-50 | C2-26 | 2-13 | 3-8 | 2-50 |
| C2-27 | 2-14 | 3-3 | 2-40 | C2-28 | 2-14 | 3-3 | 2-45 |
| C2-29 | 2-14 | 3-3 | 2-48 | C2-30 | 2-14 | 3-8 | 2-45 |
| C2-31 | 2-14 | 3-3 | 2-50 | C2-32 | 2-14 | 3-8 | 2-50 |
| C2-33 | 2-15 | 3-3 | 2-40 | C2-34 | 2-15 | 3-3 | 2-45 |
| C2-35 | 2-15 | 3-3 | 2-48 | C2-36 | 2-15 | 3-8 | 2-45 |
| C2-37 | 2-15 | 3-3 | 2-50 | C2-38 | 2-15 | 3-8 | 2-50 |
| C2-39 | 2-16 | 3-3 | 2-40 | C2-40 | 2-16 | 3-8 | 2-40 |
| C2-41 | 2-16 | 3-20 | 2-40 | C2-42 | 2-16 | 3-34 | 2-40 |
| C2-43 | 2-16 | 3-3 | 2-45 | C2-44 | 2-16 | 3-8 | 2-45 |
| C2-45 | 2-16 | 3-3 | 2-50 | C2-46 | 2-16 | 3-8 | 2-50 |
| C2-47 | 2-16 | 3-20 | 2-45 | C2-48 | 2-16 | 3-34 | 2-45 |
| C2-49 | 2-16 | 3-3 | 2-48 | C2-50 | 2-16 | 3-8 | 2-48 |
| C2-51 | 2-16 | 3-20 | 2-48 | C2-52 | 2-16 | 3-34 | 2-48 |
| C2-53 | 2-17 | 3-3 | 2-40 | C2-54 | 2-17 | 3-3 | 2-45 |
| C2-55 | 2-17 | 3-3 | 2-48 | C2-56 | 2-17 | 3-8 | 2-45 |
| C2-57 | 2-17 | 3-3 | 2-50 | C2-58 | 2-17 | 3-8 | 2-50 |
| C2-59 | 2-18 | 3-3 | 2-40 | C2-60 | 2-18 | 3-3 | 2-45 |
| C2-61 | 2-18 | 3-3 | 2-48 | C2-62 | 2-18 | 3-8 | 2-45 |
| C2-63 | 2-18 | 3-3 | 2-50 | C2-64 | 2-18 | 3-8 | 2-50 |
| C2-65 | 2-19 | 3-3 | 2-40 | C2-66 | 2-19 | 3-3 | 2-45 |
| C2-67 | 2-19 | 3-3 | 2-48 | C2-68 | 2-19 | 3-8 | 2-45 |
| C2-69 | 2-19 | 3-3 | 2-50 | C2-70 | 2-19 | 3-8 | 2-50 |
| C2-71 | 2-20 | 3-3 | 2-40 | C2-72 | 2-20 | 3-3 | 2-45 |
| C2-73 | 2-20 | 3-3 | 2-48 | C2-74 | 2-20 | 3-8 | 2-45 |
| C2-75 | 2-20 | 3-3 | 2-50 | C2-76 | 2-20 | 3-8 | 2-50 |
| C2-77 | 2-21 | 3-3 | 2-40 | C2-78 | 2-21 | 3-3 | 2-45 |
| C2-79 | 2-21 | 3-3 | 2-48 | C2-80 | 2-21 | 3-8 | 2-45 |
| C2-81 | 2-21 | 3-3 | 2-50 | C2-82 | 2-21 | 3-8 | 2-50 |
| C2-83 | 2-22 | 3-3 | 2-40 | C2-84 | 2-22 | 3-3 | 2-45 |
| C2-85 | 2-22 | 3-3 | 2-48 | C2-86 | 2-22 | 3-8 | 2-45 |
| C2-87 | 2-22 | 3-3 | 2-50 | C2-88 | 2-22 | 3-8 | 2-50 |
| C2-89 | 2-23 | 3-3 | 2-40 | C2-90 | 2-23 | 3-8 | 2-40 |

-continued

| Compound | Formula | L$_2$ | HAr | Compound | Formula | L$_2$ | HAr |
|---|---|---|---|---|---|---|---|
| C2-91 | 2-23 | 3-20 | 2-40 | C2-92 | 2-23 | 3-34 | 2-40 |
| C2-93 | 2-23 | 3-3 | 2-50 | C2-94 | 2-23 | 3-8 | 2-50 |
| C2-95 | 2-23 | 3-3 | 2-45 | C2-96 | 2-23 | 3-8 | 2-45 |
| C2-97 | 2-23 | 3-20 | 2-45 | C2-98 | 2-23 | 3-34 | 2-45 |
| C2-99 | 2-23 | 3-3 | 2-48 | C2-100 | 2-23 | 3-8 | 2-48 |
| C2-101 | 2-23 | 3-20 | 2-48 | C2-102 | 2-23 | 3-34 | 2-48 |
| C2-103 | 2-24 | 3-3 | 2-40 | C2-104 | 2-24 | 3-3 | 2-45 |
| C2-105 | 2-24 | 3-3 | 2-48 | C2-106 | 2-24 | 3-8 | 2-45 |
| C2-107 | 2-24 | 3-3 | 2-50 | C2-108 | 2-24 | 3-8 | 2-50 |
| C2-109 | 2-25 | 3-3 | 2-40 | C2-110 | 2-25 | 3-3 | 2-45 |
| C2-111 | 2-25 | 3-3 | 2-48 | C2-112 | 2-25 | 3-8 | 2-45 |
| C2-113 | 2-25 | 3-3 | 2-50 | C2-114 | 2-25 | 3-8 | 2-50 |
| C2-115 | 2-26 | 3-3 | 2-40 | C2-116 | 2-26 | 3-3 | 2-45 |
| C2-117 | 2-26 | 3-3 | 2-48 | C2-118 | 2-26 | 3-8 | 2-45 |
| C2-119 | 2-26 | 3-3 | 2-50 | C2-120 | 2-26 | 3-8 | 2-50 |
| C2-121 | 2-27 | 3-3 | 2-40 | C2-122 | 2-27 | 3-3 | 2-45 |
| C2-123 | 2-27 | 3-3 | 2-48 | C2-124 | 2-27 | 3-8 | 2-45 |
| C2-125 | 2-27 | 3-3 | 2-50 | C2-126 | 2-27 | 3-8 | 2-50 |
| C2-127 | 2-28 | 3-3 | 2-40 | C2-128 | 2-28 | 3-3 | 2-45 |
| C2-129 | 2-28 | 3-3 | 2-48 | C2-130 | 2-28 | 3-8 | 2-45 |
| C2-131 | 2-28 | 3-3 | 2-50 | C2-132 | 2-28 | 3-8 | 2-50 |
| C2-133 | 2-29 | 3-3 | 2-40 | C2-134 | 2-29 | 3-3 | 2-45 |
| C2-135 | 2-29 | 3-3 | 2-48 | C2-136 | 2-29 | 3-8 | 2-45 |
| C2-137 | 2-29 | 3-3 | 2-50 | C2-138 | 2-29 | 3-8 | 2-50 |
| C2-139 | 2-30 | 3-3 | 2-40 | C2-140 | 2-30 | 3-8 | 2-40 |
| C2-141 | 2-30 | 3-20 | 2-40 | C2-142 | 2-30 | 3-34 | 2-40 |
| C2-143 | 2-30 | 3-3 | 2-50 | C2-144 | 2-30 | 3-8 | 2-50 |
| C2-145 | 2-30 | 3-3 | 2-45 | C2-146 | 2-30 | 3-8 | 2-45 |
| C2-147 | 2-30 | 3-20 | 2-45 | C2-148 | 2-30 | 3-34 | 2-45 |
| C2-149 | 2-30 | 3-3 | 2-48 | C2-150 | 2-30 | 3-8 | 2-48 |
| C2-151 | 2-30 | 3-20 | 2-48 | C2-152 | 2-30 | 3-34 | 2-48 |
| C2-153 | 2-31 | 3-3 | 2-40 | C2-154 | 2-31 | 3-3 | 2-45 |
| C2-155 | 2-31 | 3-3 | 2-48 | C2-156 | 2-31 | 3-8 | 2-45 |
| C2-157 | 2-31 | 3-3 | 2-50 | C2-158 | 2-31 | 3-8 | 2-50 |
| C2-159 | 2-32 | 3-3 | 2-40 | C2-160 | 2-32 | 3-3 | 2-45 |
| C2-161 | 2-32 | 3-3 | 2-48 | C2-162 | 2-32 | 3-8 | 2-45 |
| C2-163 | 2-32 | 3-3 | 2-50 | C2-164 | 2-32 | 3-8 | 2-50 |
| C2-165 | 2-33 | 3-3 | 2-40 | C2-166 | 2-33 | 3-3 | 2-45 |
| C2-167 | 2-33 | 3-3 | 2-48 | C2-168 | 2-33 | 3-8 | 2-45 |
| C2-169 | 2-33 | 3-3 | 2-50 | C2-170 | 2-33 | 3-8 | 2-50 |
| C2-171 | 2-34 | 3-3 | 2-40 | C2-172 | 2-34 | 3-3 | 2-45 |
| C2-173 | 2-34 | 3-3 | 2-48 | C2-174 | 2-34 | 3-8 | 2-45 |
| C2-175 | 2-34 | 3-3 | 2-50 | C2-176 | 2-34 | 3-8 | 2-50 |
| C2-177 | 2-35 | 3-3 | 2-40 | C2-178 | 2-35 | 3-3 | 2-45 |
| C2-179 | 2-35 | 3-3 | 2-48 | C2-180 | 2-35 | 3-8 | 2-45 |
| C2-181 | 2-35 | 3-3 | 2-50 | C2-182 | 2-35 | 3-8 | 2-50 |
| C2-183 | 2-36 | 3-3 | 2-40 | C2-184 | 2-36 | 3-3 | 2-45 |
| C2-185 | 2-36 | 3-3 | 2-48 | C2-186 | 2-36 | 3-8 | 2-45 |
| C2-187 | 2-36 | 3-3 | 2-50 | C2-188 | 2-36 | 3-8 | 2-50 |
| C2-189 | 2-37 | 3-3 | 2-40 | C2-190 | 2-37 | 3-3 | 2-45 |
| C2-191 | 2-37 | 3-3 | 2-48 | C2-192 | 2-37 | 3-8 | 2-45 |
| C2-193 | 2-37 | 3-3 | 2-50 | C2-194 | 2-37 | 3-8 | 2-50 |
| C2-195 | 2-38 | 3-3 | 2-40 | C2-196 | 2-38 | 3-3 | 2-45 |
| C2-197 | 2-38 | 3-3 | 2-48 | C2-198 | 2-38 | 3-8 | 2-45 |
| C2-199 | 2-38 | 3-3 | 2-50 | C2-200 | 2-38 | 3-8 | 2-50 |
| C2-201 | 2-12 | Single bond | 2-48 | C2-202 | 2-16 | Single bond | 2-48 |
| C2-203 | 2-23 | Single bond | 2-48 | C2-204 | 2-26 | Single bond | 2-48 |
| C2-205 | 2-30 | Single bond | 2-48 | C2-206 | 2-37 | Single bond | 2-48 |
| C2-207 | 2-11 | Single bond | 2-60 | C2-208 | 2-12 | Single bond | 2-60 |
| C2-209 | 2-16 | Single bond | 2-60 | C2-210 | 2-23 | Single bond | 2-60 |
| C2-211 | 2-30 | Single bond | 2-60 | C2-212 | 2-37 | Single bond | 2-60 |

The compound represented by formula 1 according to the present disclosure may be prepared by a synthetic method known to one skilled in the art. For example, it may be prepared by referring to Korean Patent Application Laying-Open No. 2018-0012709 (published on Feb. 6, 2018), but is not limited thereto.

The compound represented by formula 2 according to the present disclosure may be prepared by a synthetic method known to a person skilled in the art. For example, it may be prepared by referring to Korean Patent Application Laying-Open Nos. 2015-0032447 (published on Mar. 26, 2015), 2015-0077513 (published on Jul. 8, 2015), and 2015-0135109 (published on Dec. 2, 2015), but is not limited thereto.

The organic electroluminescent device according to the present disclosure comprises a first electrode; a second electrode; and at least one organic layer between the first and second electrodes.

One of the first and second electrodes may be an anode, and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Herein, the second electrode may be a transflective electrode or a reflective electrode, and may be a top emission, bottom emission, or both-sides emission type according to the material used. In addition, the hole injection layer may be further doped with a p-dopant, and the electron injection layer may be further doped with an n-dopant.

The organic electroluminescent device according to the present disclosure comprises an anode, a cathode, and at least one light-emitting layer between the anode and the cathode, wherein at least one layer of the light-emitting layers comprises the compound represented by formula 1 and the compound represented by formula 2.

The light-emitting layer comprises a host and a dopant, and the host comprises the plurality of host materials. The compound represented by formula 1 may be comprised as a first host compound of the plurality of host materials and the compound represented by formula 2 may be comprised as a second host compound of the plurality of host materials. Herein, the weight ratio of the first host compound to the second host compound is in the range of 1:99 to 99:1.

The light-emitting layer is a layer from which light is emitted, and can be a single layer or a multi-layer of which two or more layers are stacked. In the plurality of host materials according to the present disclosure, the first and second host materials may both be comprised in one layer or may be respectively comprised in different light-emitting layers. According to one embodiment of the present disclosure, the doping concentration of the dopant compound with respect to the host compound of the light-emitting layer may be less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. In one embodiment of the present disclosure, the organic electroluminescent device of the present disclosure may further comprise an amine-based compound, in addition to the plurality of host materials of the present disclosure, as at least one of a hole injection material, a hole transport material, a hole auxiliary material, a light-emitting material, a light-emitting auxiliary material, and an electron blocking material. In addition, in one embodiment of the present disclosure, the organic electroluminescent device of the present disclosure may further comprise an azine-based compound, in addition to the plurality of host materials of the present disclosure, as at least one of an electron transport material, an electron injection material, an electron buffer material, and a hole blocking material.

The dopant comprised in the organic electroluminescent device according to the present disclosure may be at least one phosphorescent or fluorescent dopant, and preferably phosphorescent dopant. The phosphorescent dopant material applied to the organic electroluminescent device of the present disclosure is not particularly limited, but may be selected from metallated complex compounds of iridium (Ir), osmium (Os), copper (Cu), and platinum (Pt), preferably selected from ortho-metallated complex compounds of iridium (Ir), osmium (Os), copper (Cu), and platinum (Pt), and more preferably ortho-metallated iridium complex compounds.

The dopant comprised in the organic electroluminescent device of the present disclosure may include the compound represented by the following formula 101, but is not limited thereto.

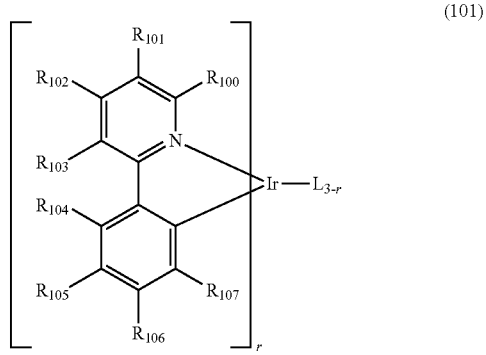

(101)

In formula 101, L is selected from the following structures 1 and 2:

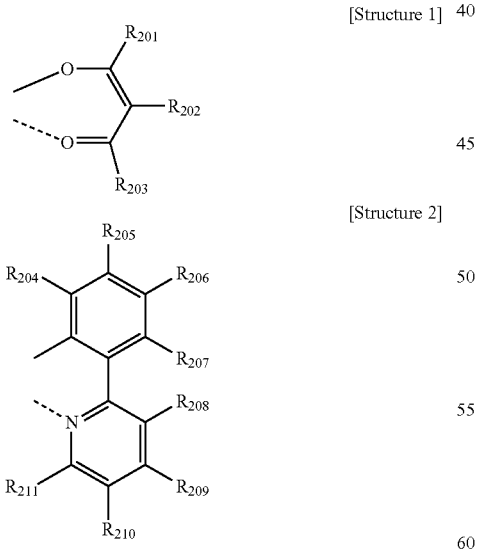

[Structure 1]

[Structure 2]

$R_{100}$ to $R_{103}$ each independently represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a substituted or unsubstituted fused ring, e.g., together with pyridine, a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline ring;

$R_{104}$ to $R_{107}$ each independently represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a substituted or unsubstituted fused ring, e.g., together with benzene, a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine ring;

$R_{201}$ to $R_{211}$ each independently represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; or may be linked to an adjacent substituent to form a substituted or unsubstituted fused ring; and r represents an integer of 1 to 3.

The specific examples of the dopant compound are as follows, but are not limited thereto.

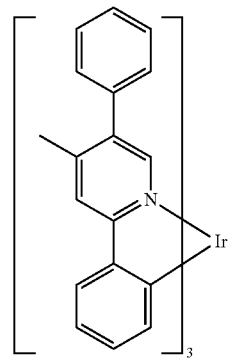

D-1

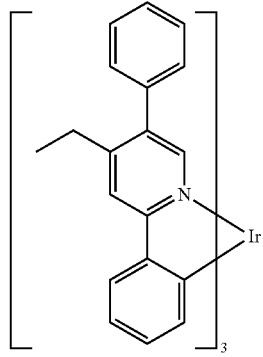

D-2

D-3
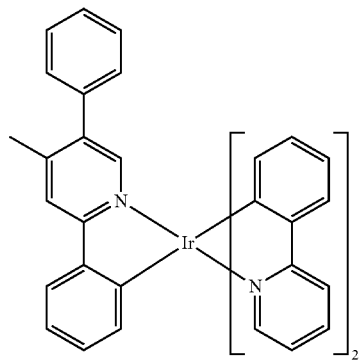
D-4
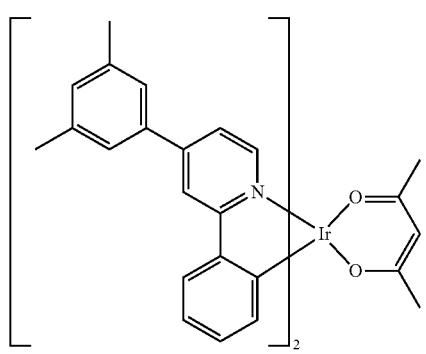
D-5
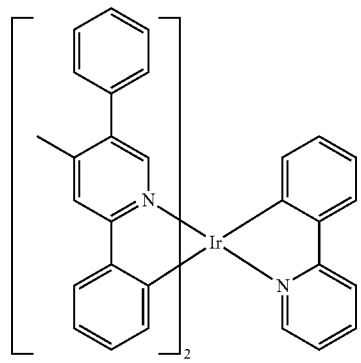
D-6
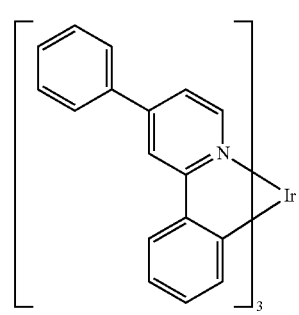
D-7
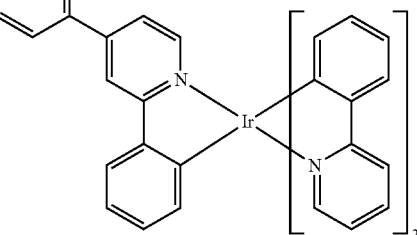
D-8
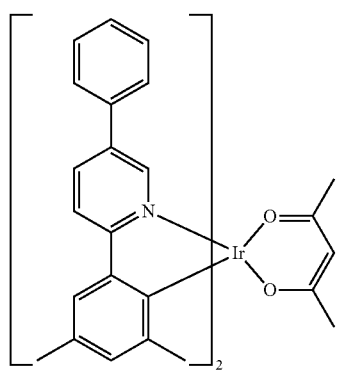
D-9
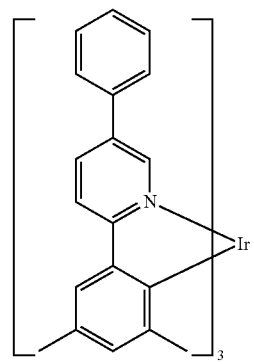
D-10
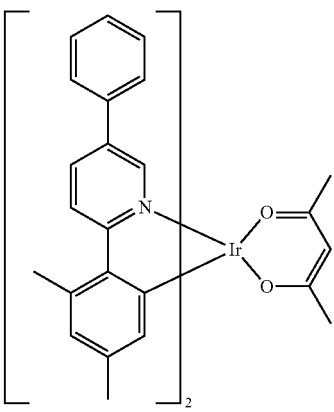

D-11
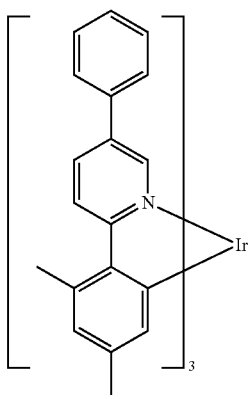
D-12
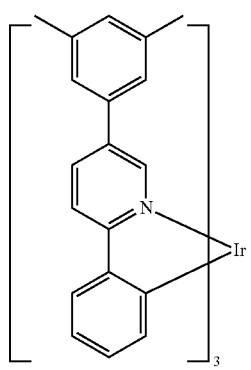
D-13
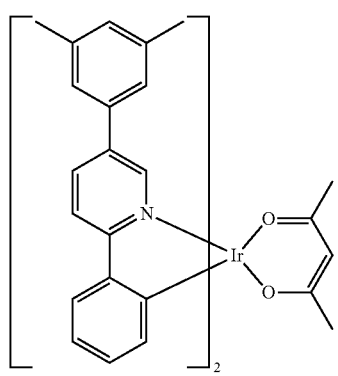
D-14
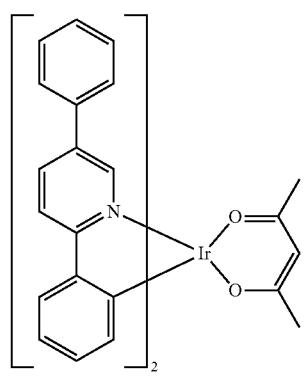
D-15
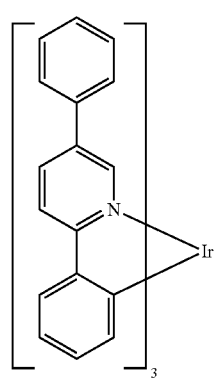
D-16
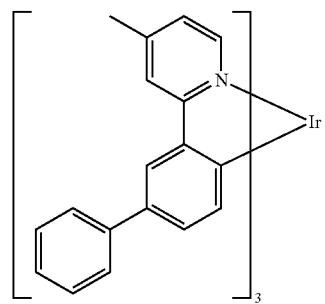
D-17
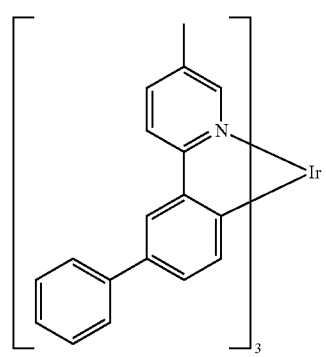
D-18
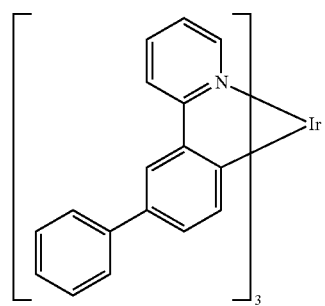

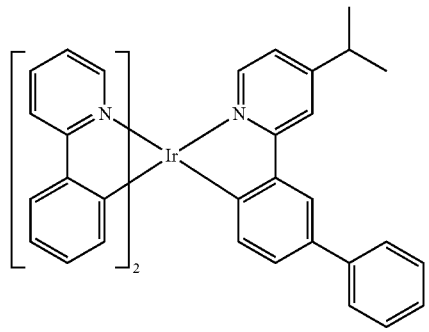
D-19
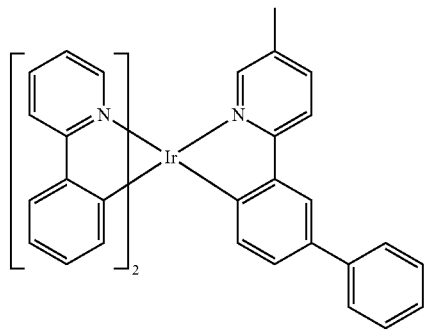
D-23
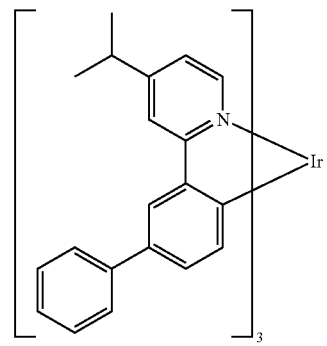
D-20
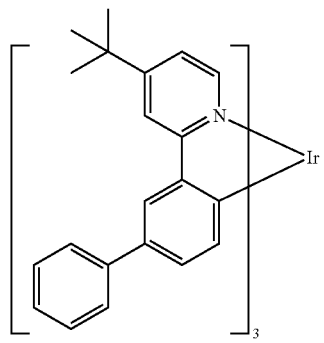
D-24
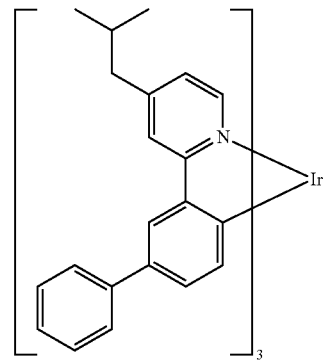
D-21
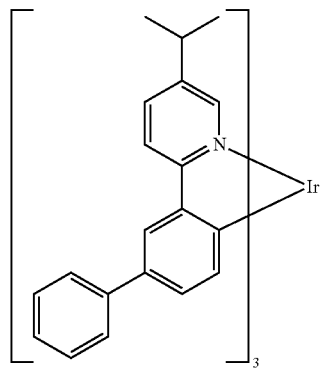
D-25
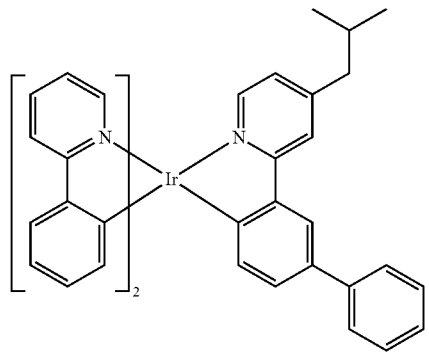
D-22
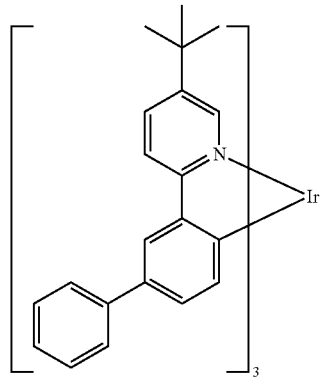
D-26

-continued
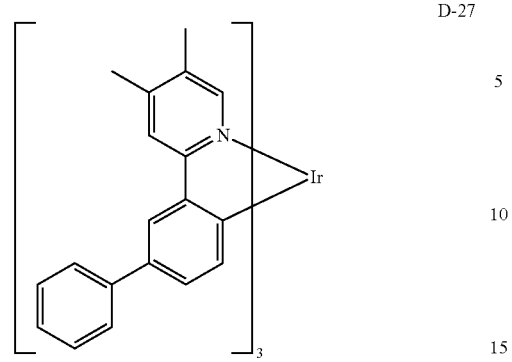
D-27
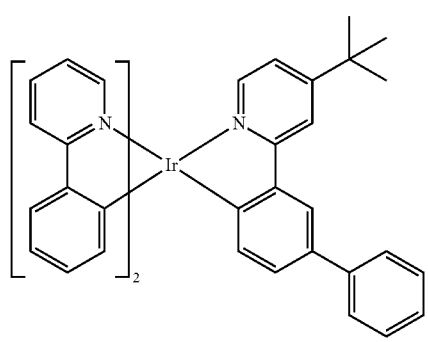
D-28
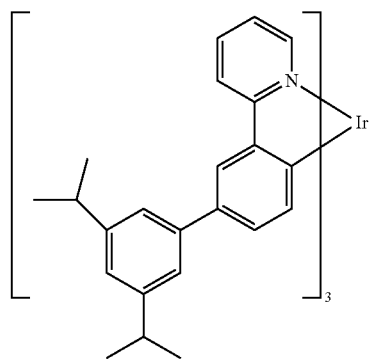
D-29
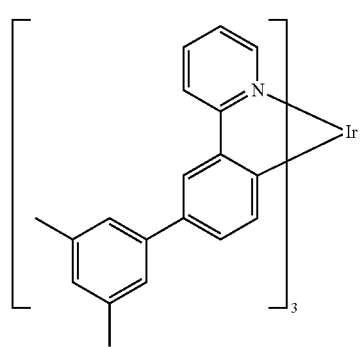
D-30
-continued
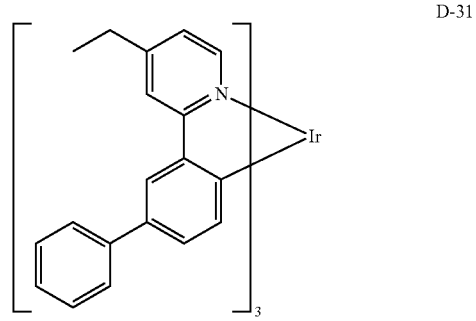
D-31
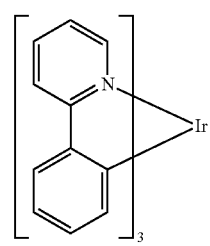
D-32
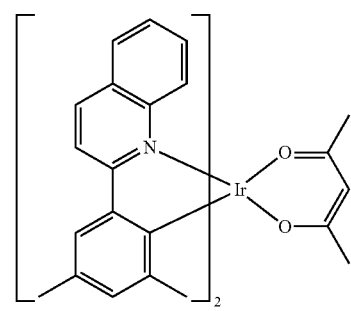
D-33
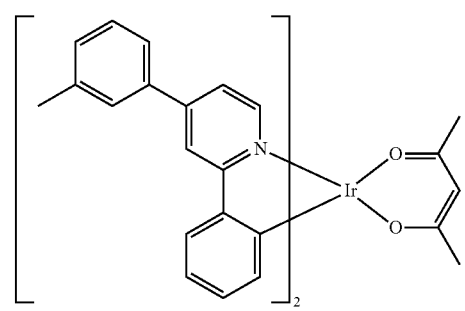
D-34
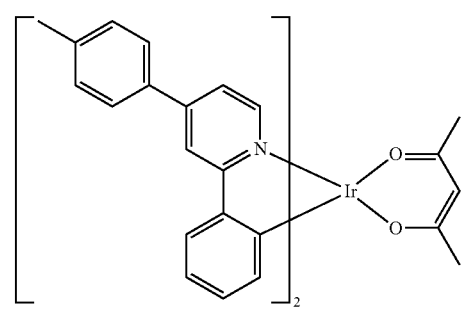
D-35

-continued
D-36
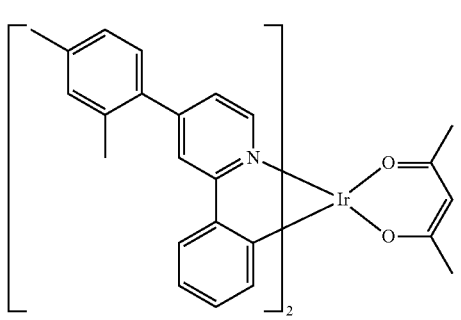
D-37
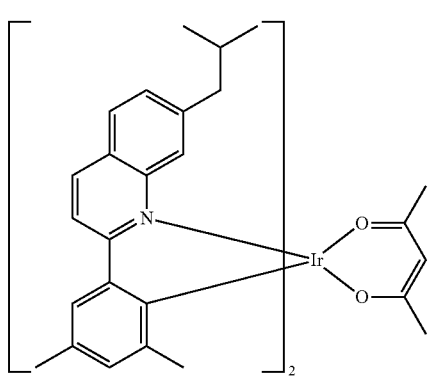
D-38
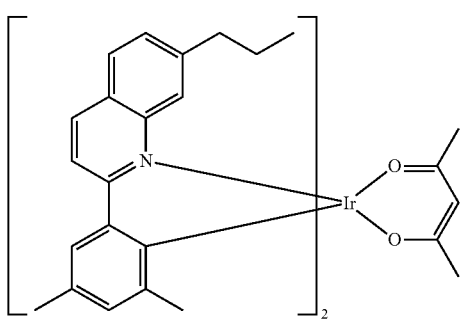
D-39
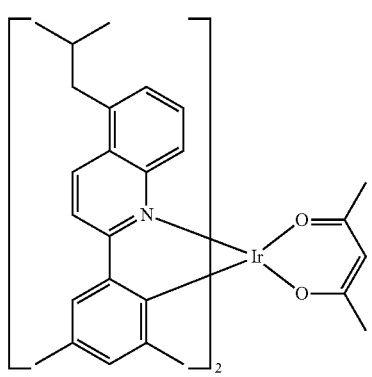
-continued
D-40
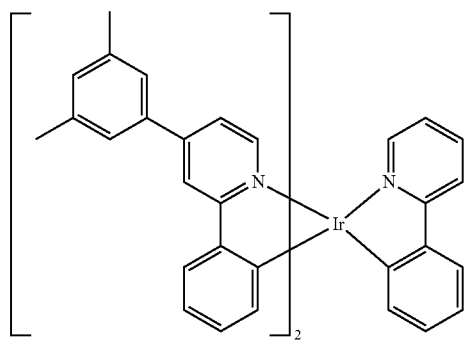
D-41
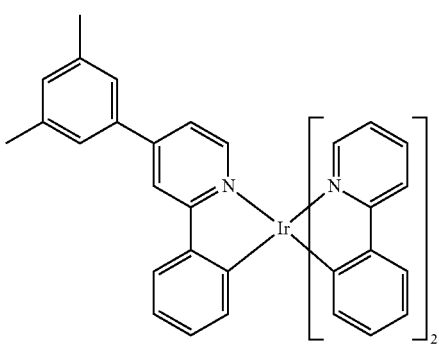
D-42
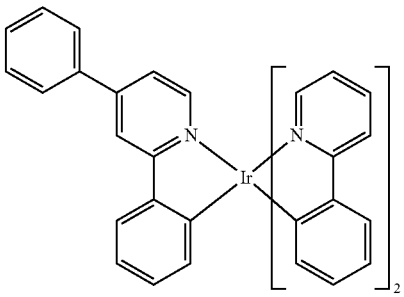
D-43
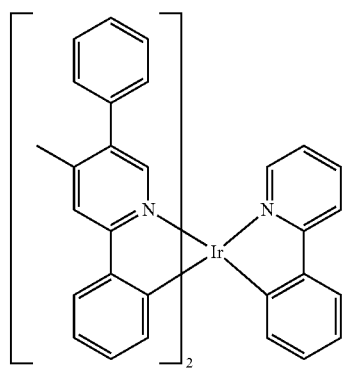

D-44 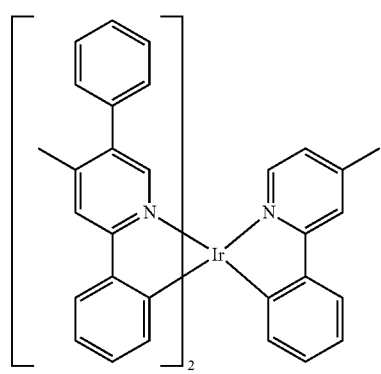
D-45 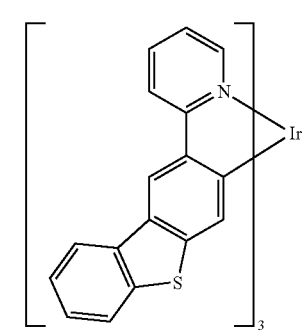
D-46 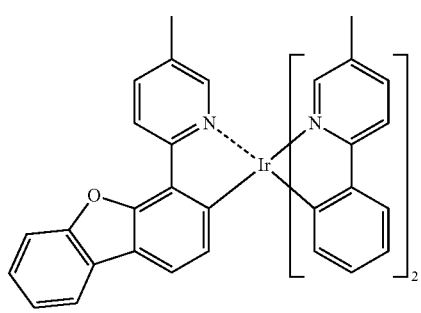
D-47 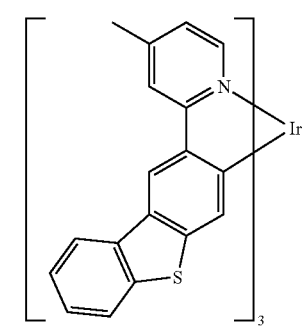
D-48 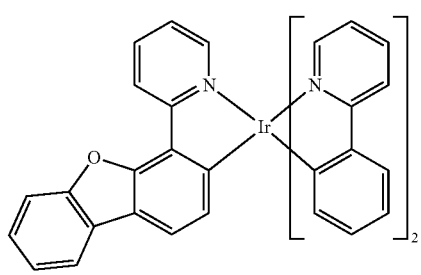
D-49 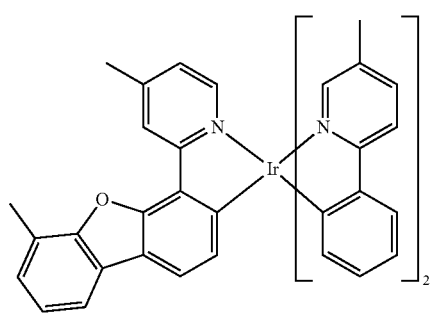
D-50 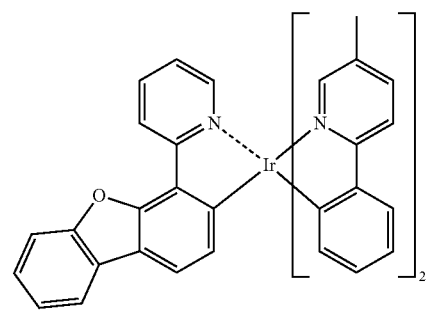
D-51 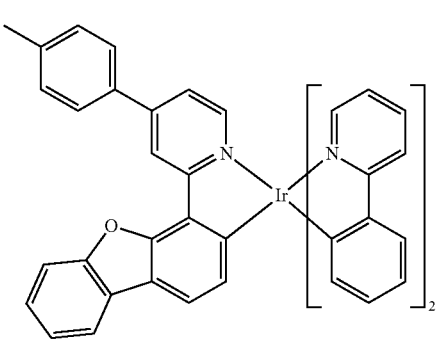
D-52 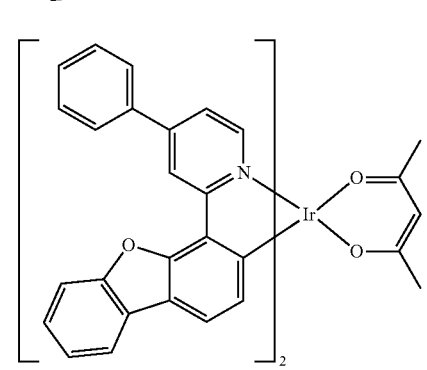
D-53 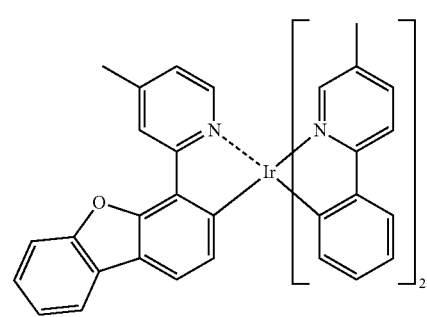

D-54
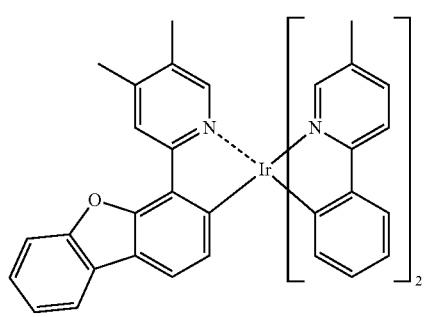
D-55
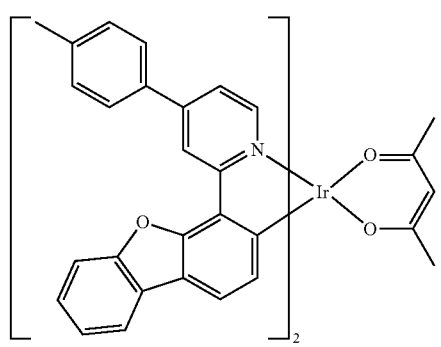
D-56
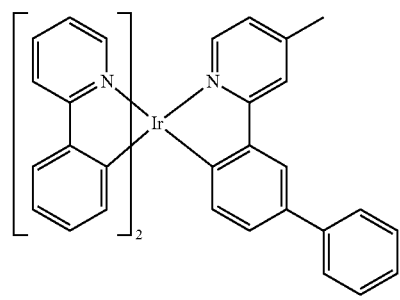
D-57
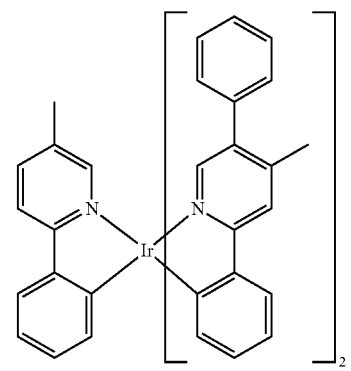
D-58
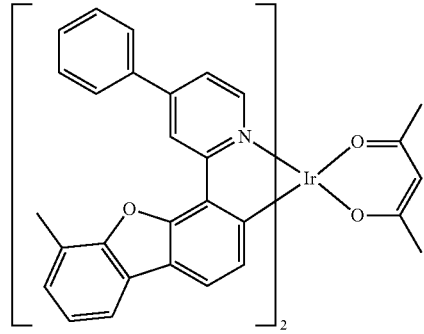
D-59
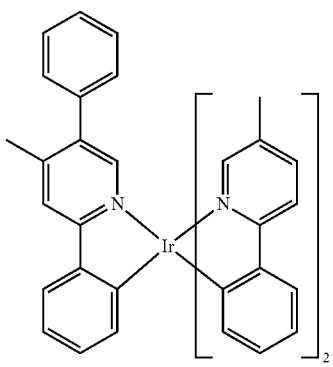
D-60
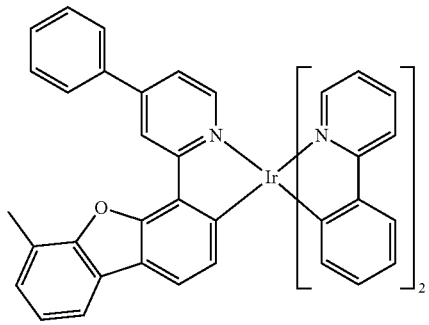
D-61
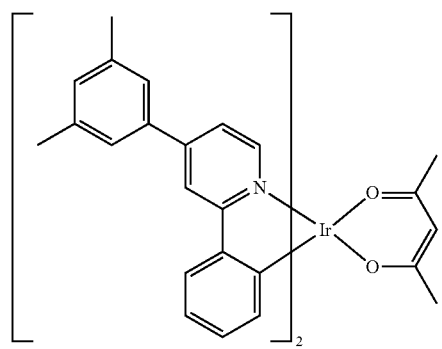

D-62
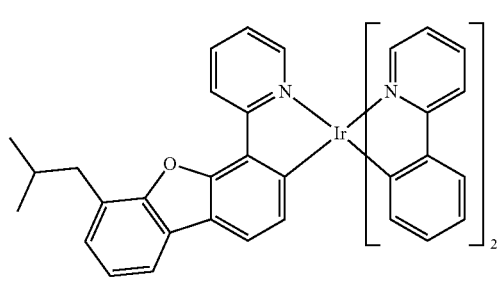
D-63
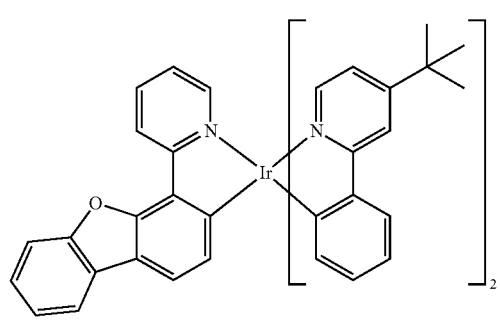
D-64
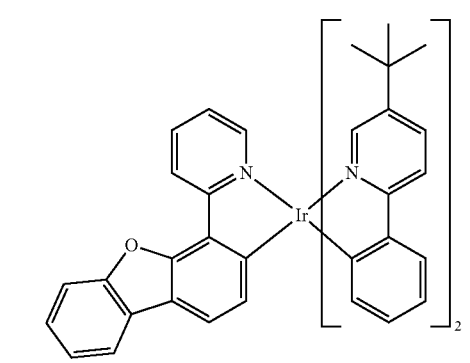
D-65
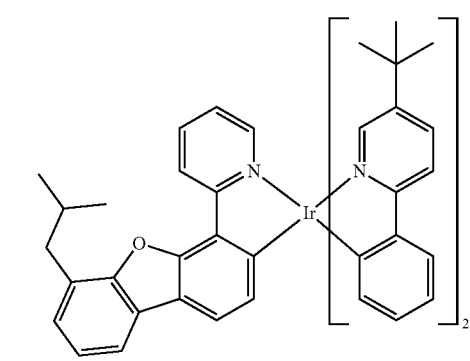
D-66
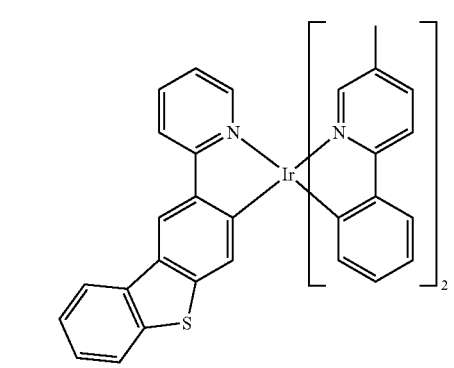
D-67
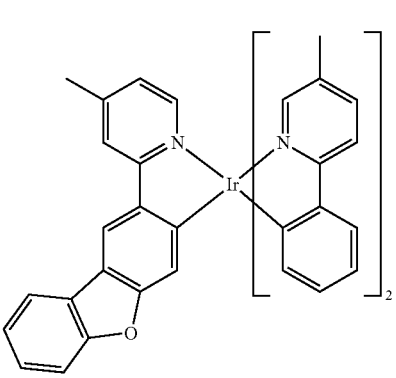
D-68
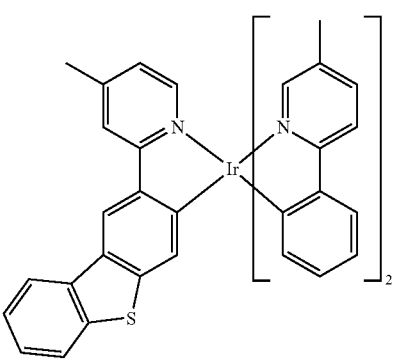
D-69
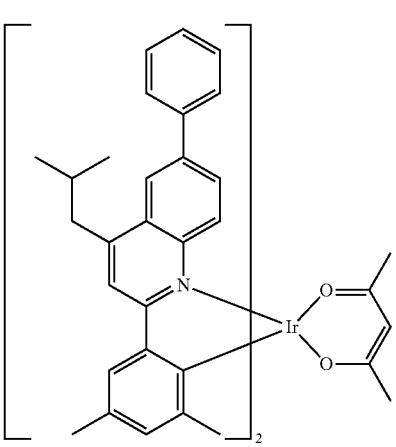
D-70
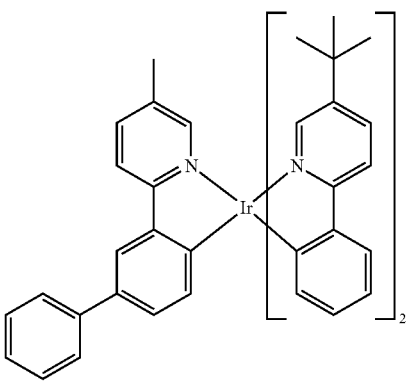

-continued
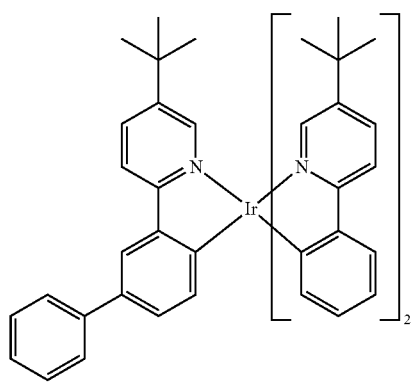
D-71
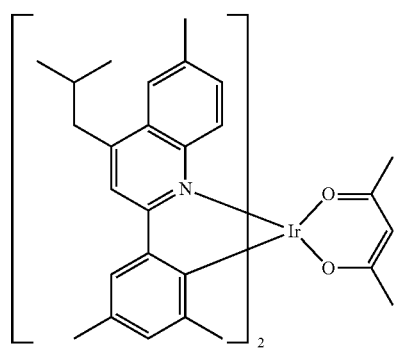
D-72
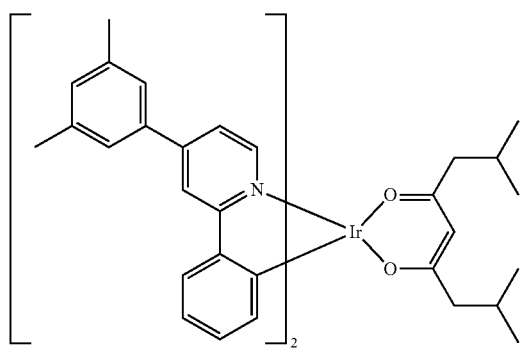
D-73
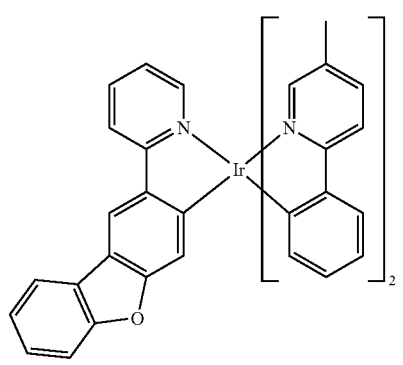
D-74
-continued
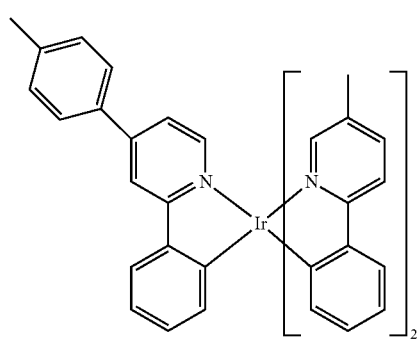
D-75
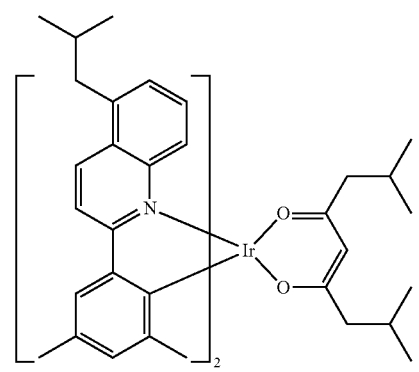
D-76
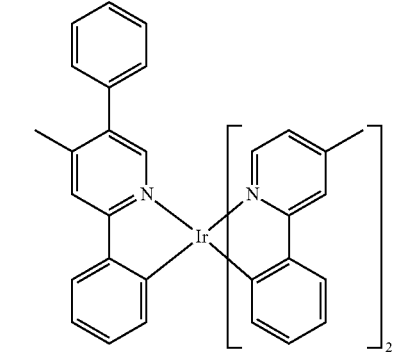
D-77
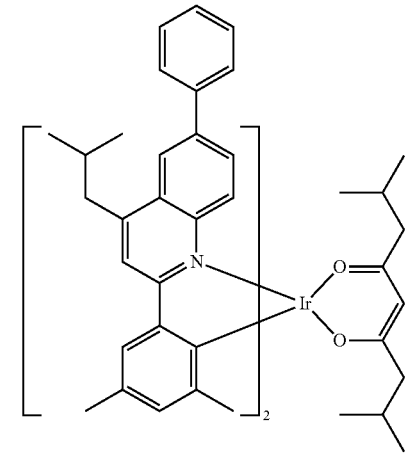
D-78

-continued
D-79
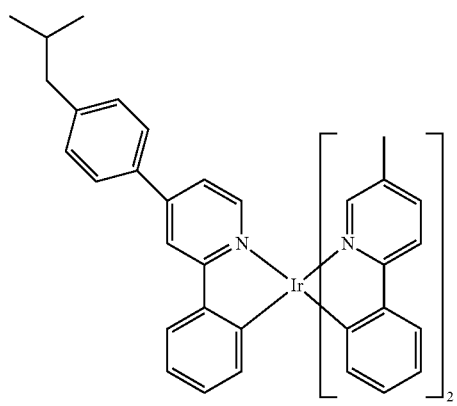
D-80
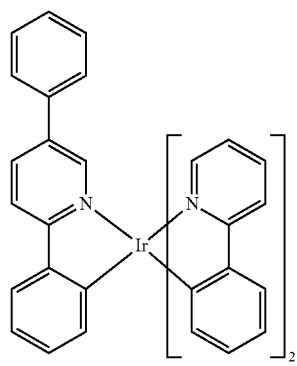
D-81
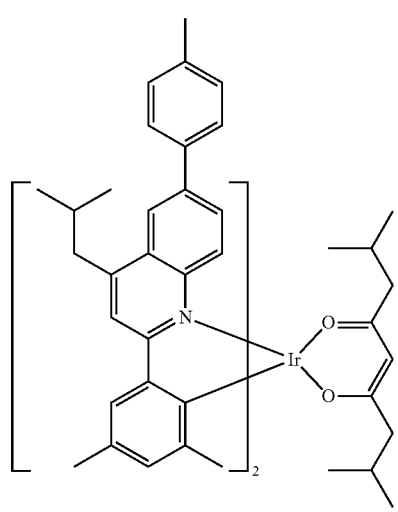
-continued
D-82
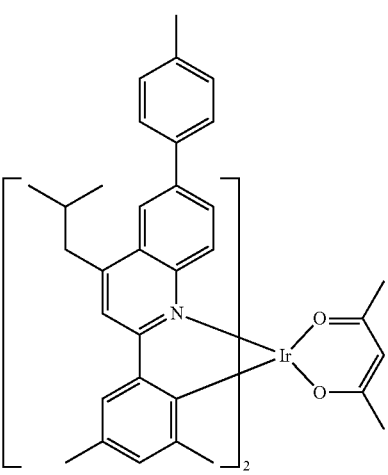
D-83
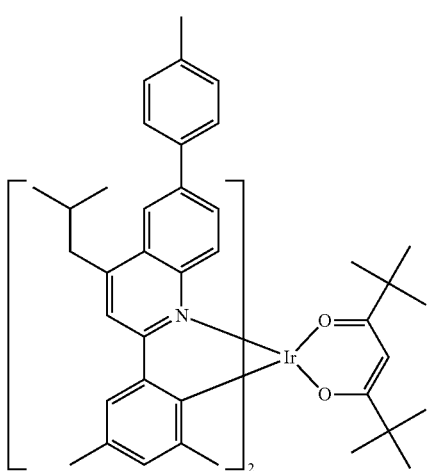
D-84
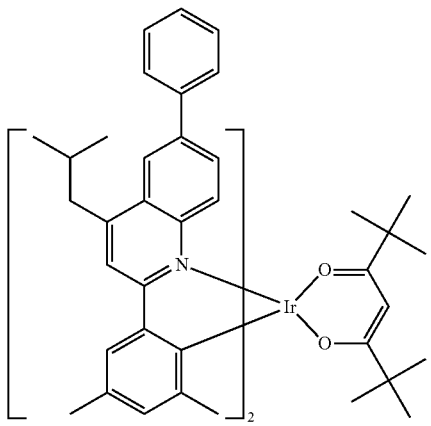

D-85
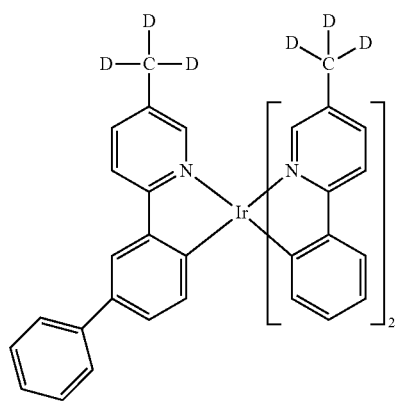
D-89
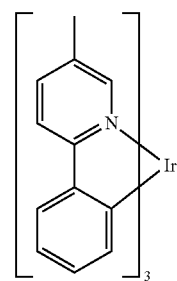
D-90
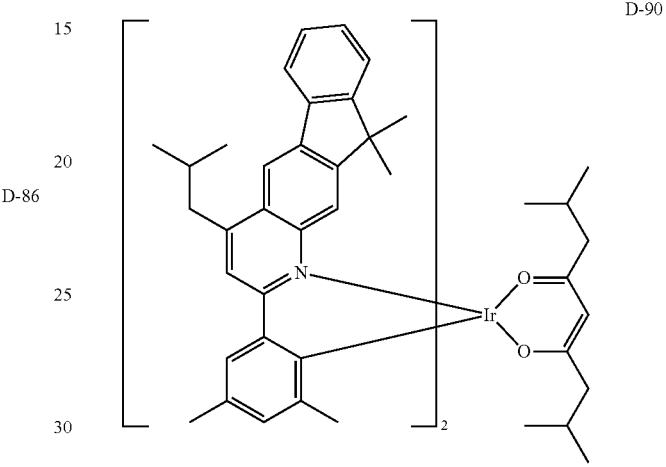
D-86
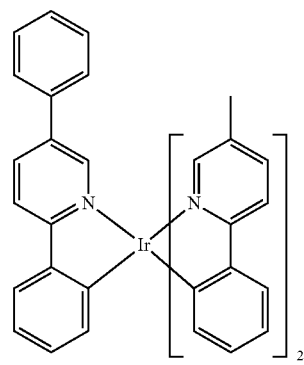
D-87
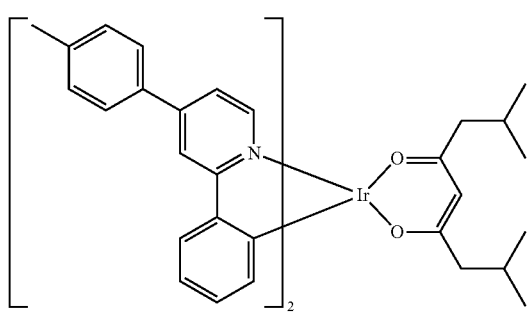
D-91
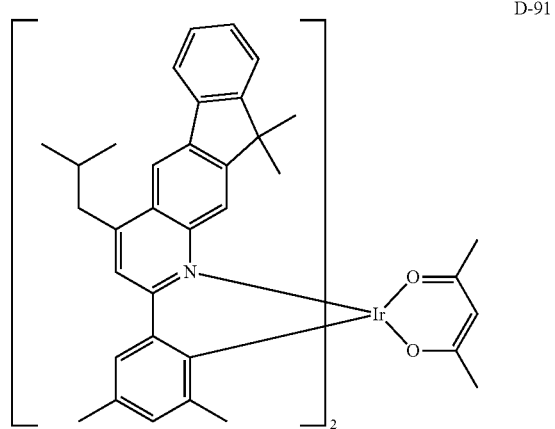
D-88
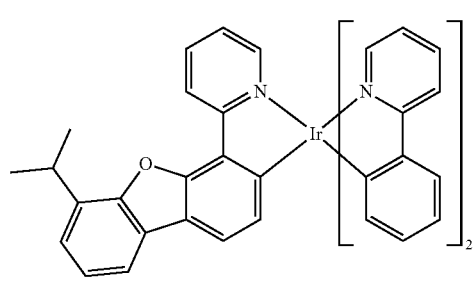
D-92
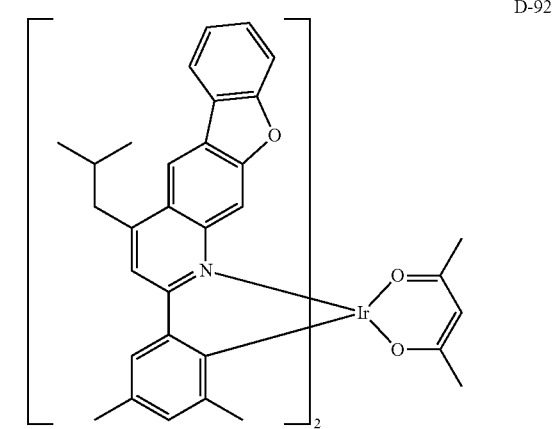

-continued
D-93
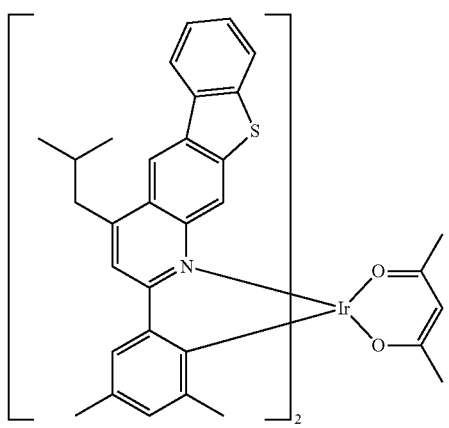
D-94
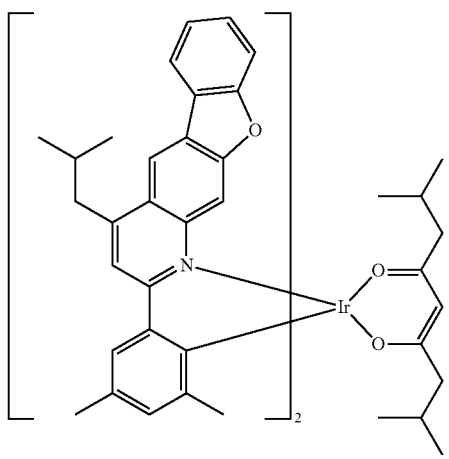
D-95
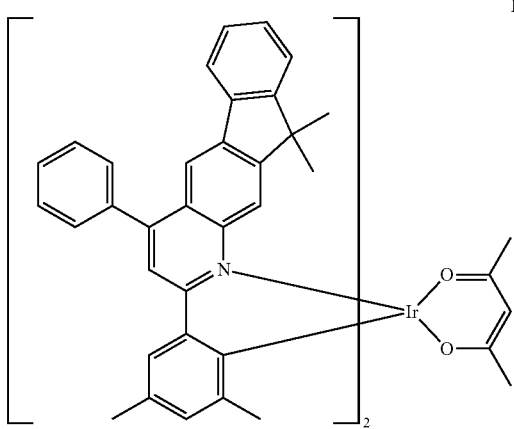
-continued
D-96
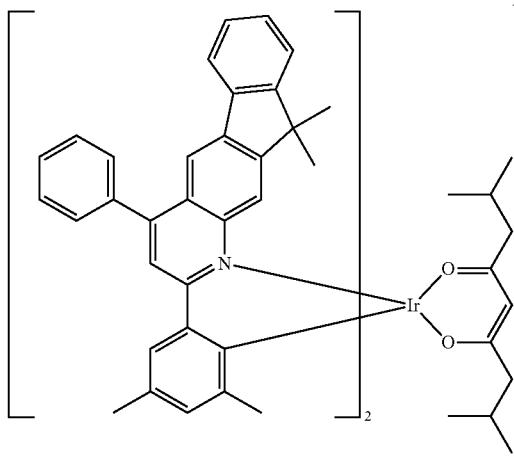
D-97
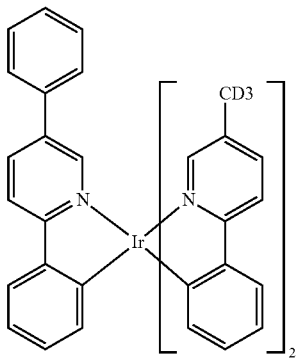
D-98
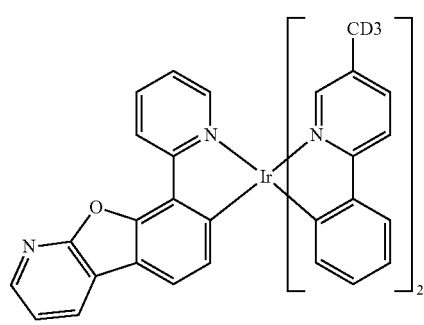
D-99
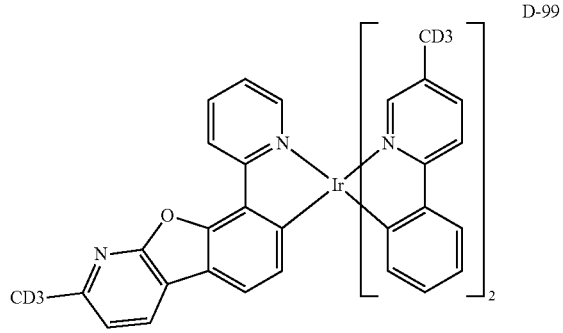

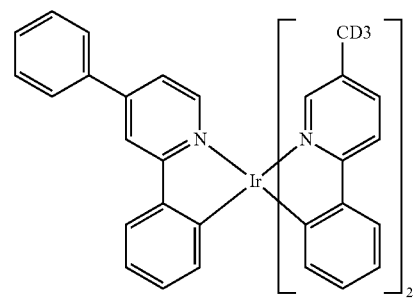
D-100
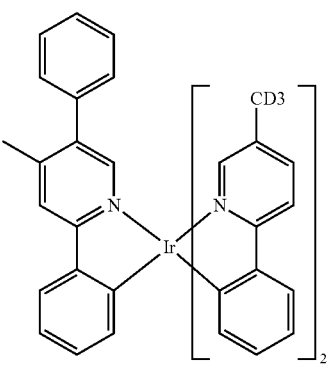
D-101
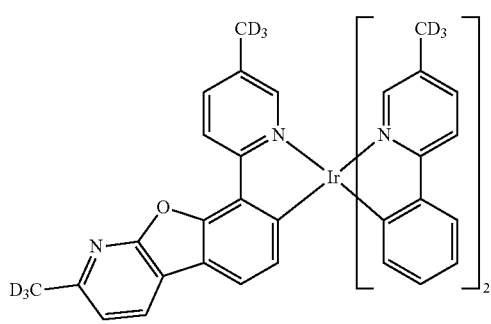
D-102
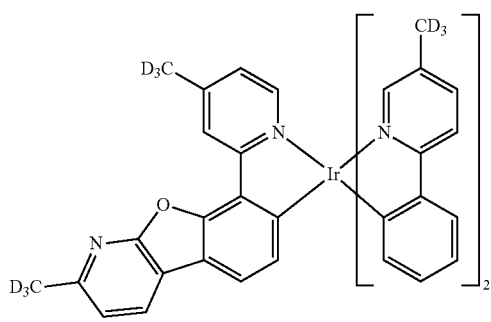
D-103
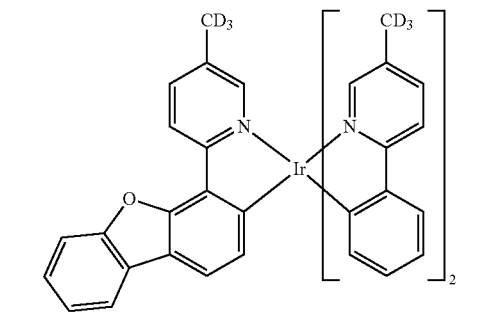
D-104
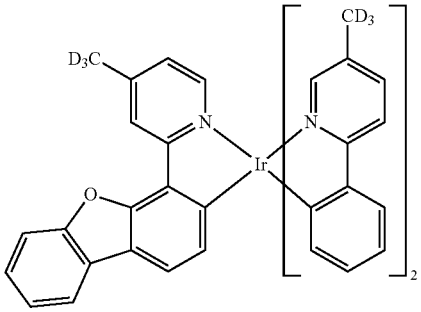
D-105
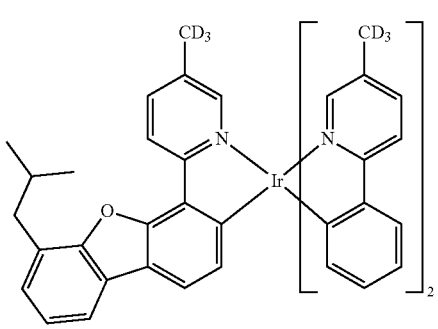
D-106
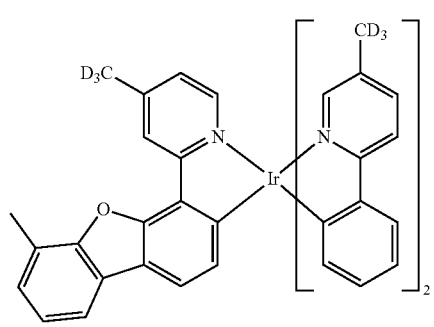
D-107
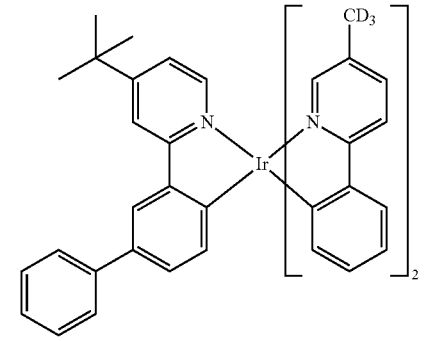
D-108

D-109
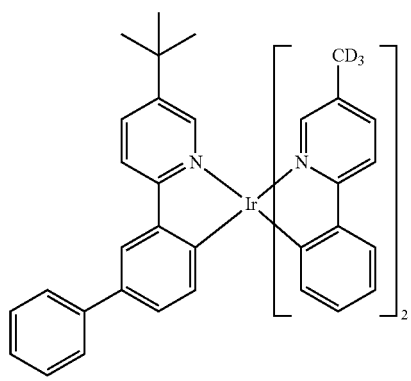
D-113
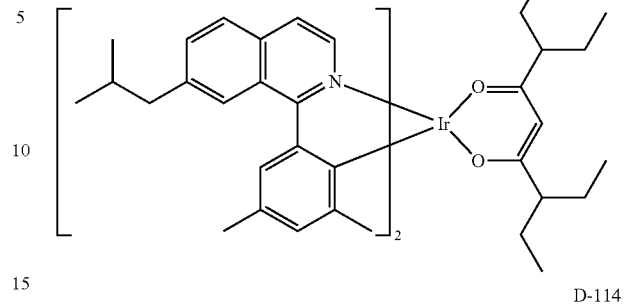
D-110
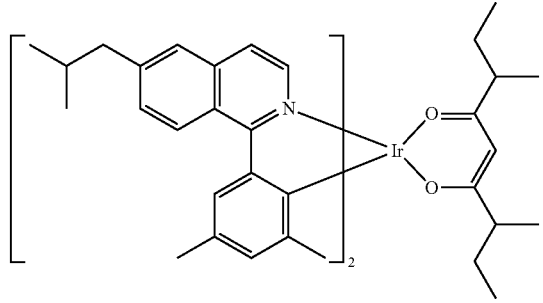
D-114
D-111
D-115
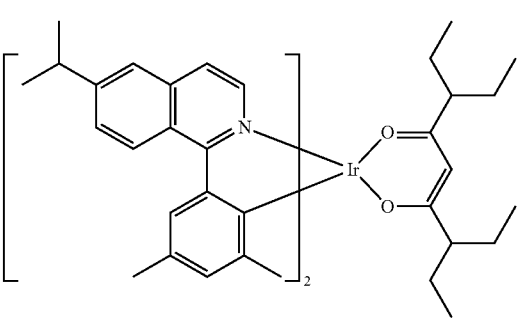
D-112
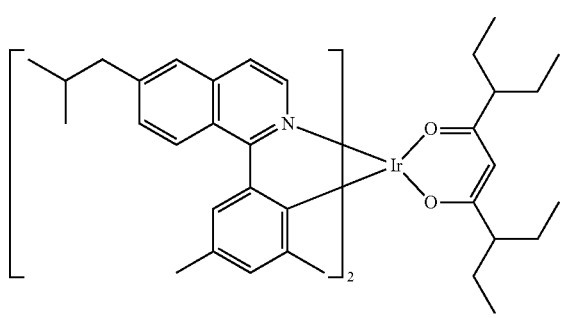
D-116
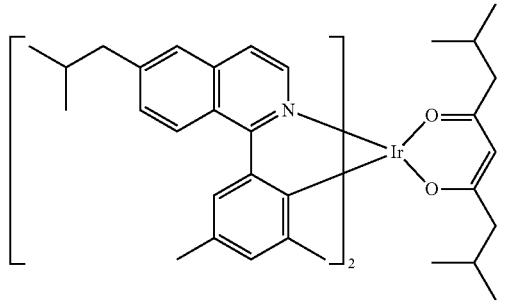
D-117
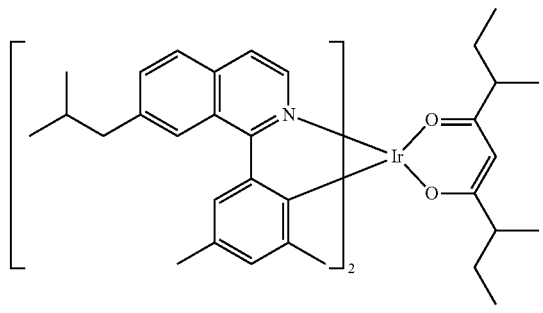

-continued

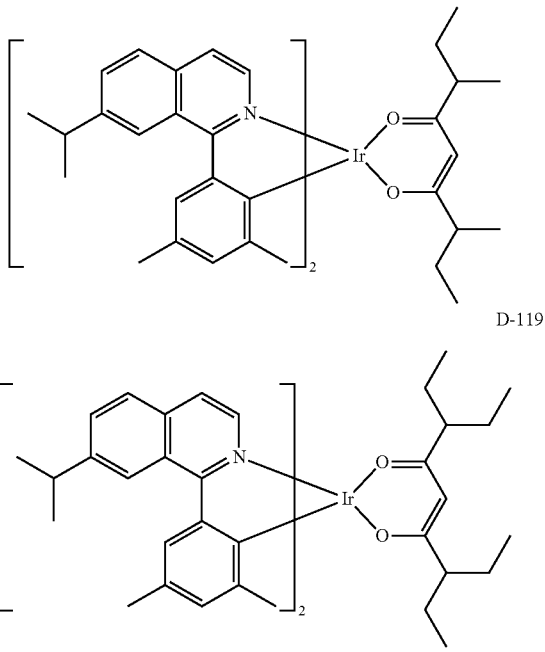

D-118

D-119

In the organic electroluminescent device of the present disclosure, between the anode and the light-emitting layer, a hole injection layer, a hole transport layer, an electron blocking layer, or a combination thereof can be used. Multiple hole injection layers can be used in order to lower the hole injection barrier (or hole injection voltage) from the anode to the hole transport layer or the electron blocking layer. Two compounds can be simultaneously used in each layer. The hole transport layer or the electron blocking layer can also be formed of multi-layers.

In addition, between the light-emitting layer and the cathode, an electron buffer layer, a hole blocking layer, an electron transport layer, an electron injection layer, or a combination thereof can be used. Multiple electron buffer layers can be used in order to control the injection of the electrons and enhance the interfacial characteristics between the light-emitting layer and the electron injection layer. Two compounds can be simultaneously used in each layer. The hole blocking layer or the electron transport layer can also be formed of multi-layers, and each layer can comprise two or more compounds.

In addition, the organic electroluminescent compound or the plurality of host materials according to the present disclosure can also be used in an organic electroluminescent device comprising a quantum dot (QD).

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a solvent in a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

In addition, the first and the second host compounds of the present disclosure may be film-formed in the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to the cell to evaporate the materials.

The present disclosure may provide a display device by using the plurality of host materials comprising the compound represented by formula 1 and the compound represented by formula 2. That is, it is possible to manufacture a display system or a lighting system by using the plurality of host materials of the present disclosure. Specifically, it is possible to produce a display system, e.g., a display system for smartphones, tablets, notebooks, PCs, TVs, or cars, or a lighting system, e.g., an outdoor or indoor lighting system, by using the plurality of host materials of the present disclosure.

Hereinafter, it is described whether the luminous efficiency and/or lifespan characteristics of the OLED device can be improved by comprising the plurality of host materials of the present disclosure. However, the following examples are for explaining the performance of the OLED device comprising the plurality of host materials according to the present disclosure in order to comprehend the present disclosure in detail, and the present disclosure is not limited to the following examples.

Device Examples 1 to 13: Production of an OLED Device Comprising the Plurality of Host Materials According to the Present Disclosure An organic light-emitting diode (OLED) device was produced comprising the plurality of host materials according to the present disclosure. A transparent electrode indium tin oxide (ITO) thin film (10 Ω/sq) on a glass substrate for an OLED device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. The second hole transport material listed in Table 1 below was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. The first and second host compounds shown in Table 1 below were introduced into two cells of the vacuum vapor depositing apparatus as a host, and compound D-39 was introduced into another cell. The two host materials were evaporated at a rate of 1:1 and the dopant material was simultaneously evaporated at a different rate and these were deposited in a doping amount of 3 wt % based on the total amount of the host and dopant to form a light-emitting layer having a thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced.

The time taken for the luminance to decrease from 100% to 90% at constant current at a luminance of 5,000 nit (lifespan; T90), of the OLEDs produced above is provided in Table 1 below.

TABLE 1

|  | Second Hole Transport Material | First Host Material | Second Host Material | Lifespan (T90, hr) |
|---|---|---|---|---|
| Device Example 1 | HT-2 | C1-4 | C2-8 | 893 |
| Device Example 2 | HT-3 | C1-4 | C2-8 | 1164 |
| Device Example 3 | HT-2 | C1-22 | C2-8 | 650 |
| Device Example 4 | HT-2 | C1-6 | C2-8 | 511 |
| Device Example 5 | HT-2 | C1-26 | C2-8 | 877 |
| Device Example 6 | HT-4 | C1-4 | C2-8 | 662 |
| Device Example 7 | HT-2 | C1-4:02-8(1:1)* | | 1025 |
| Device Example 8 | HT-2 | C1-143 | C2-8 | 1681 |
| Device Example 9 | HT-2 | C1-144 | C2-8 | 1272 |
| Device Example 10 | HT-2 | C1-145 | C2-8 | 635 |
| Device Example 11 | HT-2 | C1-146 | C2-8 | 675 |
| Device Example 12 | HT-2 | C1-147 | C2-8 | 1800 |
| Device Example 13 | HT-2 | C1-148 | C2-8 | 727 |

*In Device Example 7, the first and second host materials were pre-mixed in a ratio of 1:1 and evaporated.

Comparative Examples 1 and 2: Production of an OLED Device Comprising a Conventional Compound as a Host An OLED device was produced in the same manner as in Device Example 1, except that the material listed in Table 2 below was introduced as the second hole transport material and the single compound listed in Table 2 below was used as the host.

The time taken for the luminance to decrease from 100% to 90% at constant current at a luminance of 5,000 nit (lifespan; T90), of the OLEDs produced above is provided in Table 2 below.

TABLE 2

|  | Second Hole Transport Material | Host Material | Lifespan (T90, hr) |
|---|---|---|---|
| Comparative Example 1 | HT-4 | A | 351 |
| Comparative Example 2 | HT-2 | C2-8 | 157 |

From Tables 1 and 2, it is confirmed that an organic electroluminescent device comprising the compounds represented by the formulas 1 and 2 of the present disclosure as a plurality of host materials has much improved lifespan characteristics compared to an organic electroluminescent device comprising a single conventional organic electroluminescent compound.

The compounds used in the Device Examples and the Comparative Examples are shown in Table 3 below.

TABLE 3

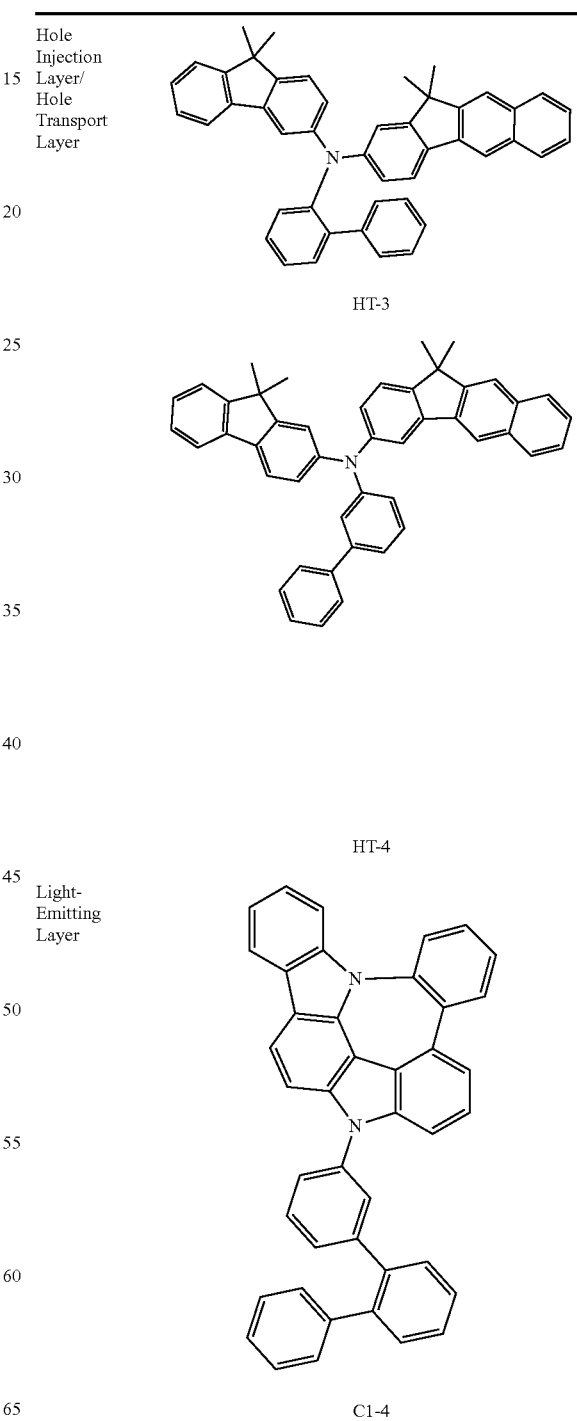

Hole Injection Layer/ Hole Transport Layer

HT-3

HT-4

Light-Emitting Layer

C1-4

TABLE 3-continued
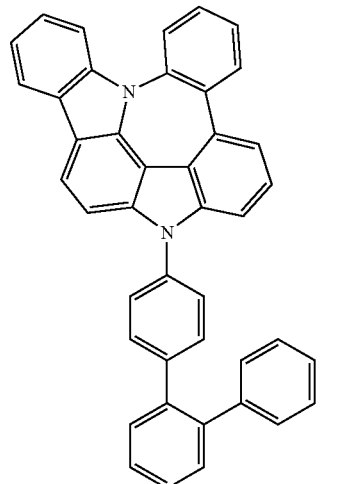 [SMILES: c1ccc(-c2ccccc2-c2ccc(-n3c4cccc5c6ccccc6n6c7ccccc7c7ccc3c(c54)c76)cc2)cc1]
C1-22
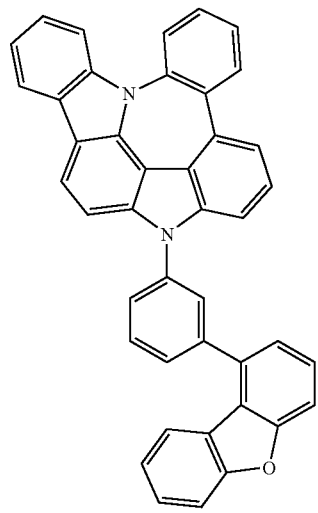 [SMILES: c1cc(-c2cccc3oc4ccccc4c23)cc(-n2c3cccc4c5ccccc5n5c6ccccc6c6ccc2c(c43)c65)c1]
C1-6
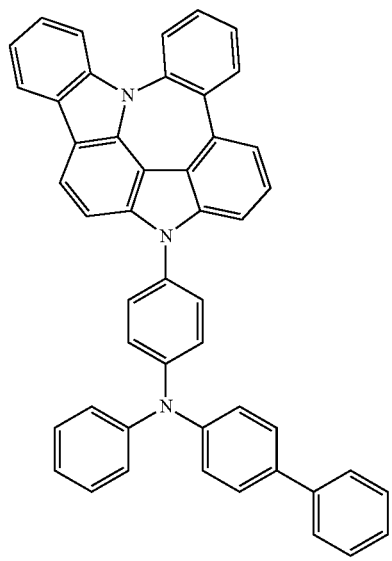 [SMILES: c1ccc(-c2ccc(N(c3ccccc3)c3ccc(-n4c5cccc6c7ccccc7n7c8ccccc8c8ccc4c(c65)c87)cc3)cc2)cc1]
TABLE 3-continued
C1-26
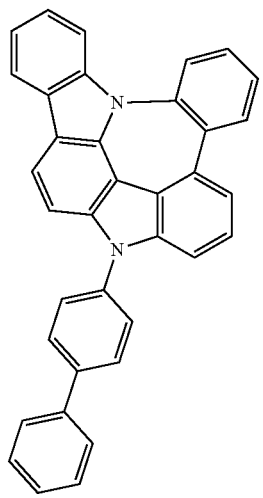 [SMILES: c1ccc(-c2ccc(-n3c4cccc5c6ccccc6n6c7ccccc7c7ccc3c(c54)c76)cc2)cc1]
C1-143
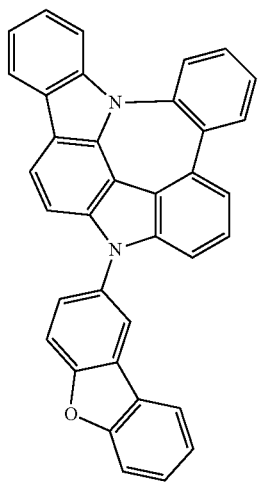 [SMILES: c1ccc2c(c1)oc1ccc(-n3c4cccc5c6ccccc6n6c7ccccc7c7ccc3c(c54)c76)cc12]
C1-144
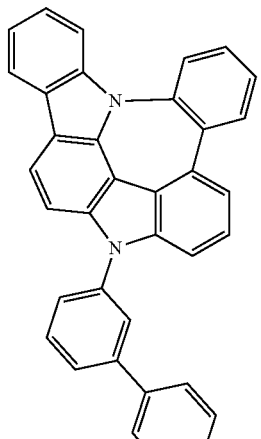
C1-145

TABLE 3-continued
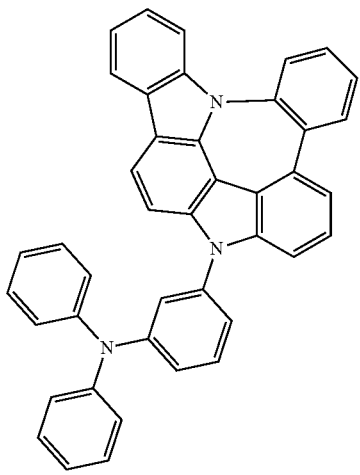 [SMILES: c1ccc(N(c2ccccc2)c2cccc(-n3c4cccc5c6ccccc6n6c7ccccc7c7ccc3c(c54)c76)c2)cc1]
C1-146
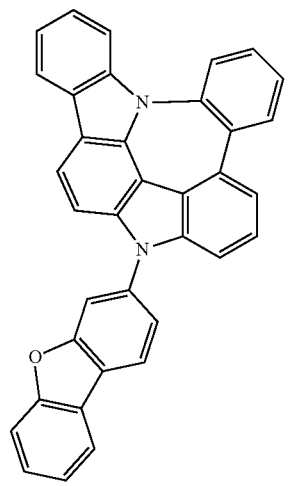 [SMILES: c1ccc2c(c1)oc1cc(-n3c4cccc5c6ccccc6n6c7ccccc7c7ccc3c(c54)c76)ccc12]
C1-147
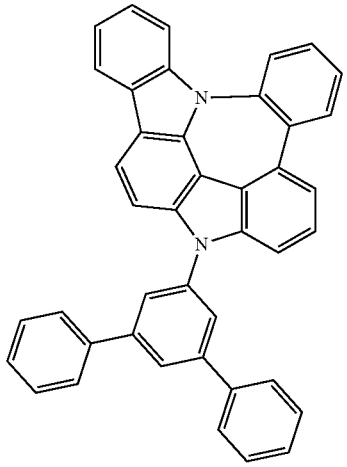 [SMILES: c1ccc(-c2cc(-c3ccccc3)cc(-n3c4cccc5c6ccccc6n6c7ccccc7c7ccc3c(c54)c76)c2)cc1]
C1-148
TABLE 3-continued
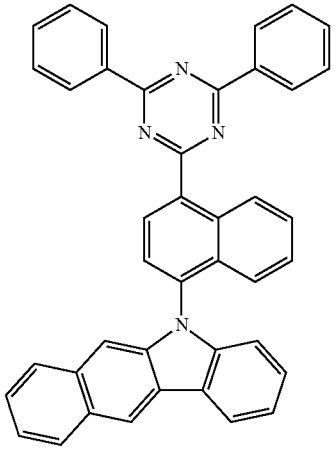 [SMILES: c1ccc(-c2nc(-c3ccccc3)nc(-c3ccc(-n4c5ccccc5c5cc6ccccc6cc54)c4ccccc34)n2)cc1]
C2-8
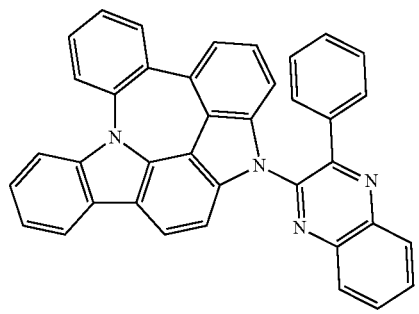 [SMILES: c1ccc(-c2nc3ccccc3nc2-n2c3cccc4c5ccccc5n5c6ccccc6c6ccc2c(c43)c65)cc1]
A
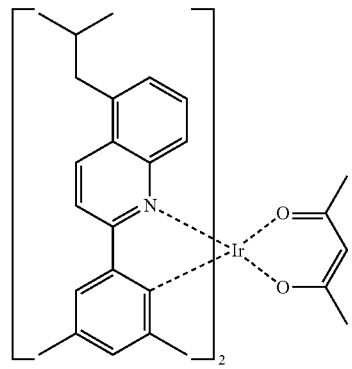
D-39
Electron Transport Layer/ Electron Injection Layer
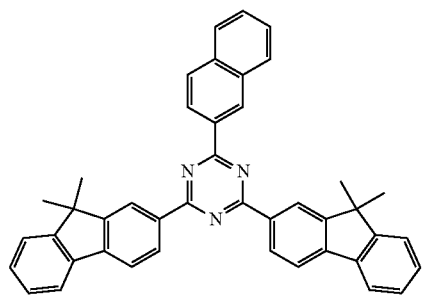 [SMILES: CC1(C)c2ccccc2-c2ccc(-c3nc(-c4ccc5c(c4)C(C)(C)c4ccccc4-5)nc(-c4ccc5ccccc5c4)n3)cc21]
ET-1

TABLE 3-continued

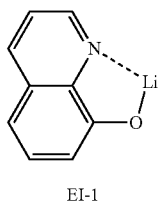

EI-1

The invention claimed is:

1. A plurality of host materials comprising at least one first host compound and at least one second host compound, wherein the first host compound is represented by the following formula 1, and the second host compound is represented by the following formula 2:

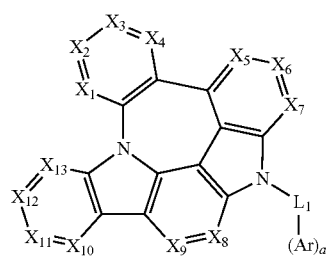

(1)

wherein $X_1$ to $X_{13}$ each independently represent N or $CR_1$;

$L_1$ represents a single bond, a substituted or unsubstituted (C6-C30)arylene, a substituted or unsubstituted (C3-C30)cycloalkylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to an adjacent substituent to form a ring;

$R_1$ represents $-L_1-(Ar)_a$, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to one pair selected from $X_1$ and $X_2$, $X_2$ and $X_3$, $X_3$ and $X_4$, $X_5$ and $X_6$, $X_6$ and $X_7$, $X_8$ and $X_9$, $X_{10}$ and $X_{11}$, $X_{11}$ and $X_{12}$, and $X_{12}$ and $X_{13}$, as a pair of an adjacent substituent to form a ring;

$R_5$ to $R_9$ each independently represent a substituted or unsubstituted (C1-C30)alkyl, a substituted or unsubstituted (C6-C30)aryl, or a substituted or unsubstituted (3- to 30-membered)heteroaryl;

a represents an integer of 1 to 3, where if a is an integer of 2 or more, each of Ar may be the same or different;

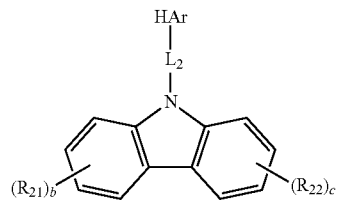

(2)

wherein

HAr represents a substituted or unsubstituted (3- to 30-membered)heteroaryl;

$L_2$ represents a single bond, a substituted or unsubstituted (C6-C30)arylene, or a substituted or unsubstituted (3- to 30-membered)heteroarylene;

$R_{21}$ and $R_{22}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_5R_6$, or $-SiR_7R_8R_9$; or may be linked to an adjacent substituent to form a ring, with a proviso that at least one of two adjacent $R_{21}$'s or two adjacent $R_{22}$'s are linked to each other to form a ring; and b represents an integer of 1 to 4, c represents an integer of 1 to 6, where if b and c are an integer of 2 or more, each of $R_{21}$ and each of $R_{22}$ may be the same or different.

2. The plurality of host materials according to claim 1, wherein formula 1 is represented by the following formula 1-1:

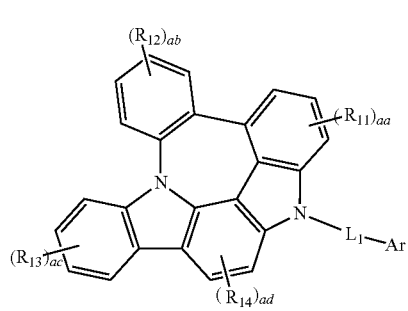

(1-1)

wherein $L_1$ represents a single bond, or a substituted or unsubstituted (C6-C30)arylene;

Ar represents hydrogen, deuterium, a substituted or unsubstituted (C6-C30)aryl, a substituted or unsubstituted (3- to 30-membered)heteroaryl, or $-NR_5R_6$;

$R_5$ and $R_6$ each independently represent a substituted or unsubstituted (C1-C30)alkyl, a substituted or unsubstituted (C6-C30)aryl, or a substituted or unsubstituted (3- to 30-membered)heteroaryl;

$R_{11}$ to $R_{14}$ each independently are identical to the definition of $R_1$ in claim 1; and aa represents an integer of 1 to 3, ab and ac each independently represent an integer of 1 to 4, ad represents 1 or 2, where if aa, ab, ac, and ad are an integer of 2 or more, each of $R_{11}$, each of $R_{12}$, each of $R_{13}$, and each of $R_{14}$ may be the same or different.

3. The plurality of host materials according to claim 1, wherein in formula 1, Ar represents a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted naphthyridinyl, a substituted or unsubstituted fluorenyl, a substituted or unsubstituted benzofluorenyl, a substituted or unsubstituted diphenylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyldibenzofuranylamino.

4. The plurality of host materials according to claim 1, wherein formula 2 is represented by at least one of the following formulas 2-1 to 2-6:

(2-1)
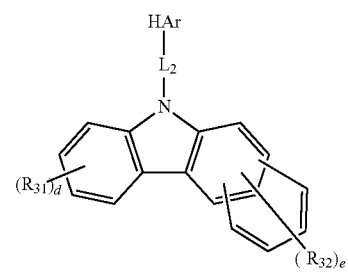

(2-2)
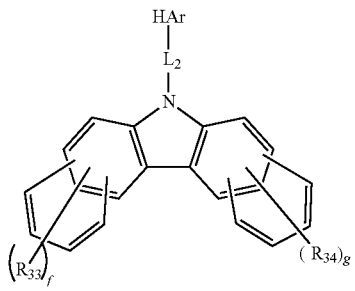

(2-3)
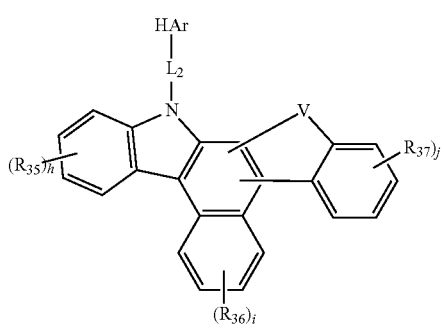

(2-4)
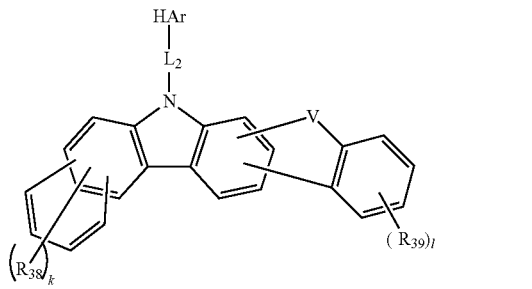

(2-5)
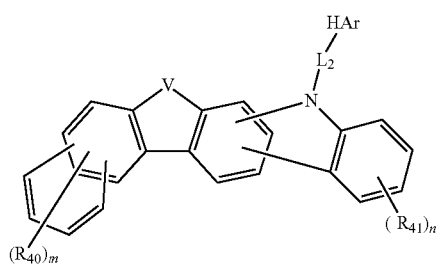

(2-6)
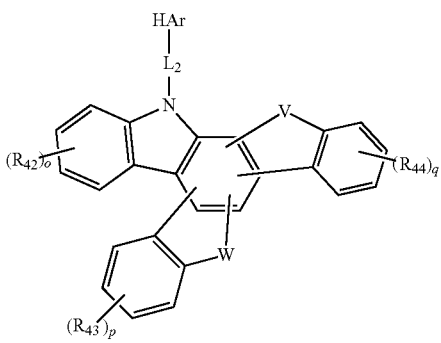

wherein

HAr and $L_2$ are as defined in claim 1;

$R_{31}$ to $R_{44}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_5R_6$, or —$SiR_7R_8R_9$; or may be linked to an adjacent substituent to form a ring;

V and W each independently represent $NR_{16}$, O, or S;

$R_{16}$ represents a substituted or unsubstituted (C6-C30) aryl, or a substituted or unsubstituted (3- to 30-membered)heteroaryl; and d, h, i, j, l, n, o, p, and q each independently represent an integer of 1 to 4, e, f, g, k, and m each independently represent an integer of 1 to 6, where if d to q are an integer of 2 or more, each of $R_{31}$ to each of $R_{44}$ may be the same or different.

5. The plurality of host materials according to claim 1, wherein in formula 2, HAr represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, or a substituted or unsubstituted benzothienopyrimidinyl.

6. The plurality of host materials according to claim 1, wherein formula 1 is represented by at least one of the following formulas 1-11 to 1-40:

1-11
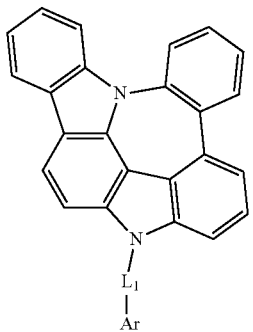

1-12
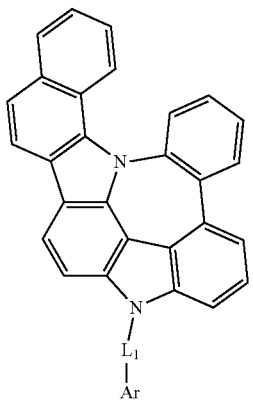

1-13
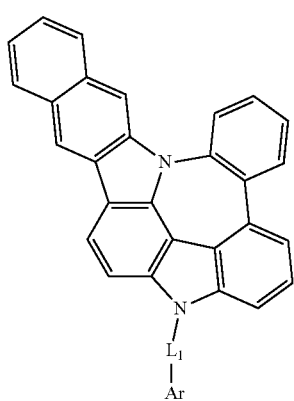

1-14
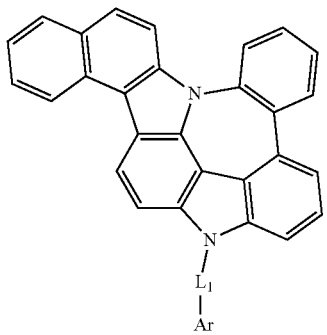

1-15
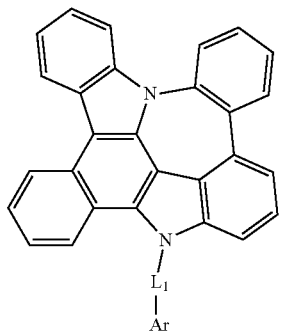

1-16
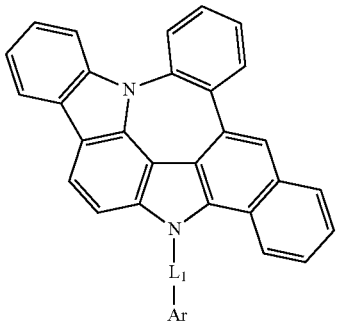

1-17
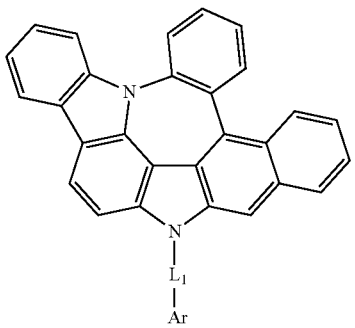

1-18
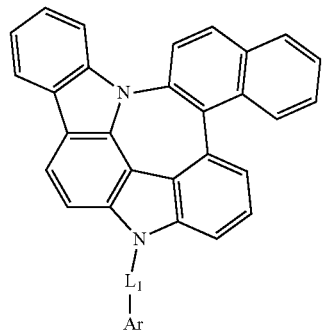
1-19
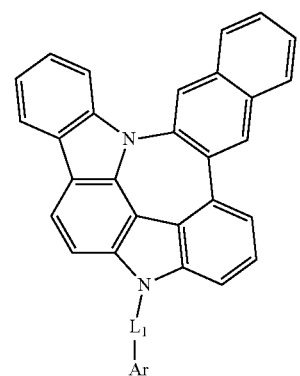
1-20
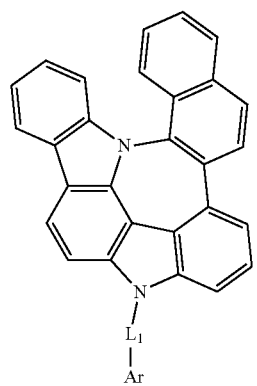
1-21
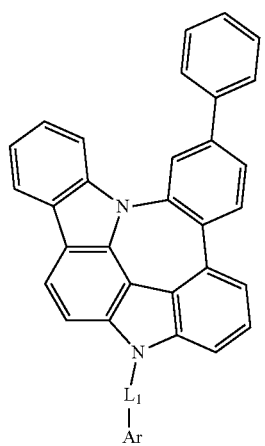
1-22
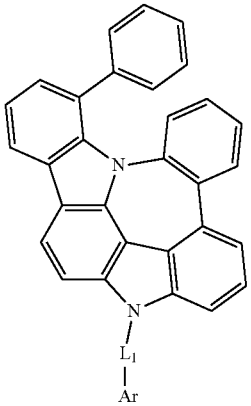
1-23
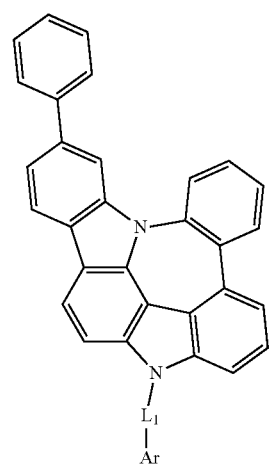
1-24
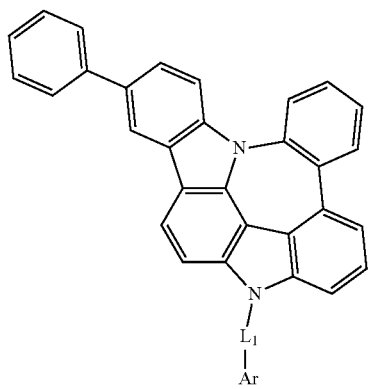
1-25
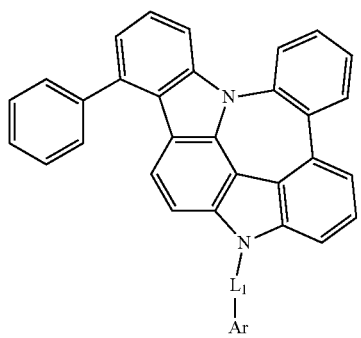

-continued
1-26
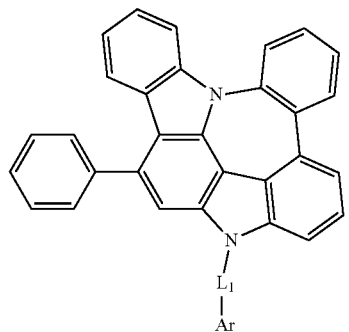
1-27
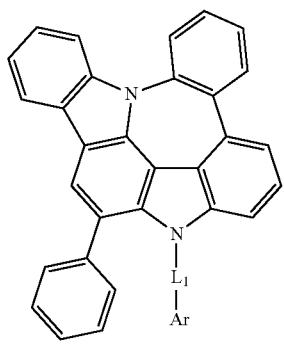
1-28
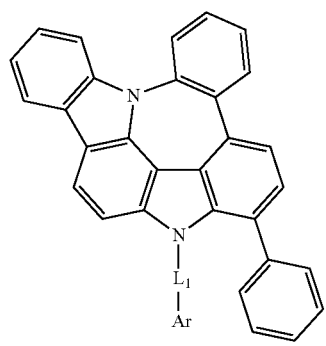
1-29
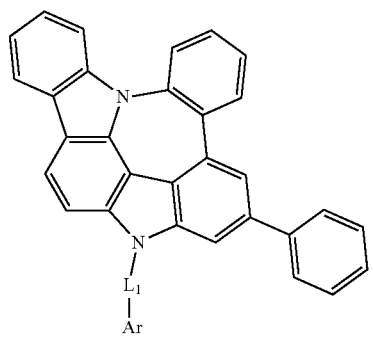
-continued
1-30
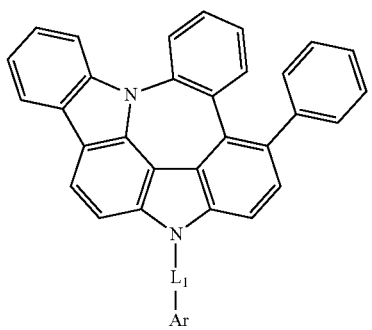
1-31
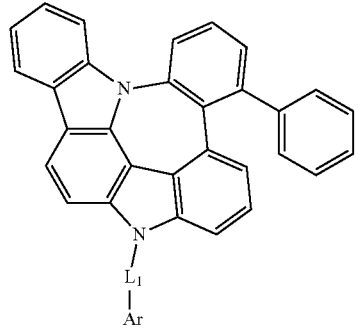
1-32
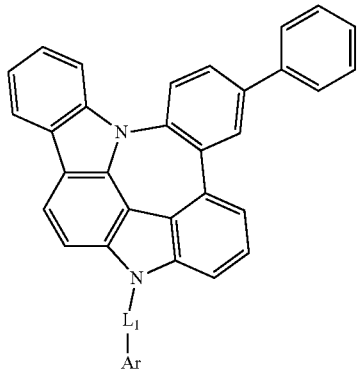
1-33
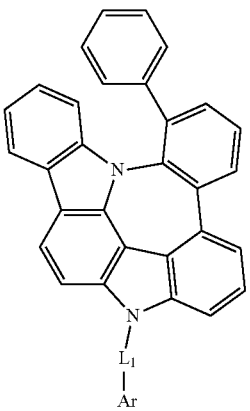

1-34
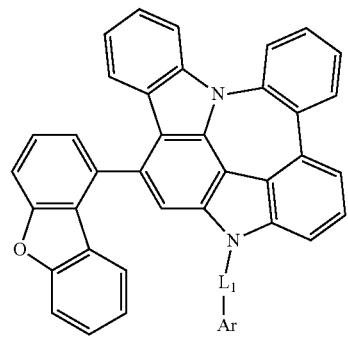
1-35
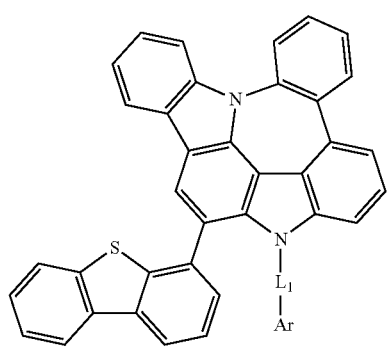
1-36
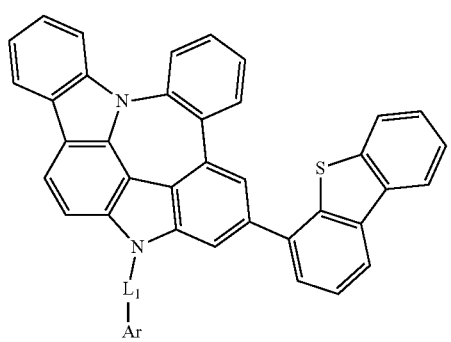
1-37
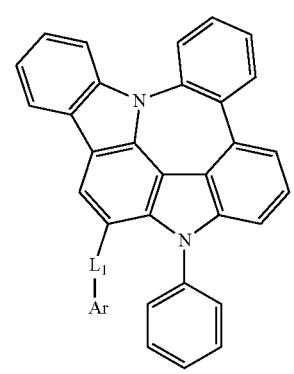
1-38
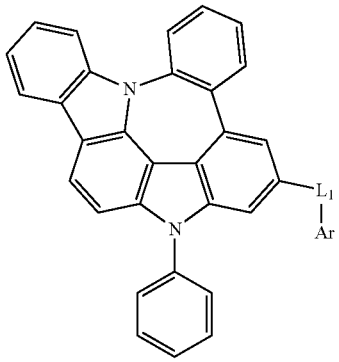
1-39
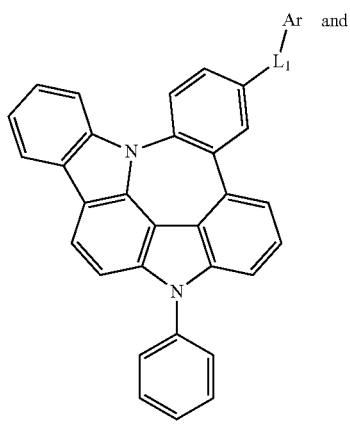
1-40
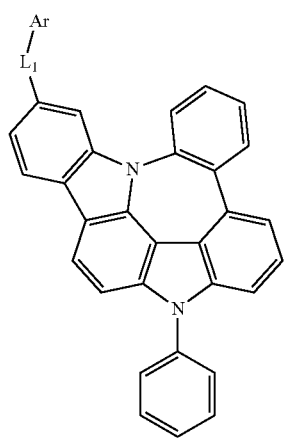
wherein
L₁ represents a single bond, or is represented by one of the following formulas L₁-1 to L₁-7, and
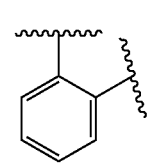
L₁-1

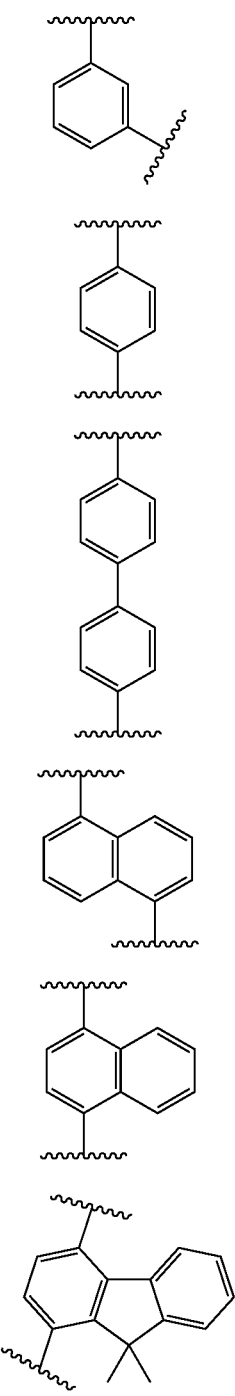
Ar is represented by one of the following formulas Ar-1 to Ar-121:
L₁-2
L₁-3
L₁-4
L₁-5
L₁-6
L₁-7
Ar-1
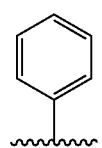
Ar-2
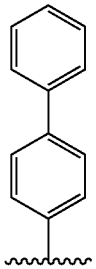
Ar-3
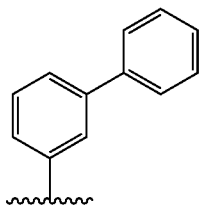
Ar-4
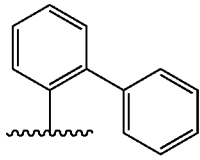
Ar-5
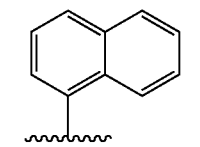
Ar-6
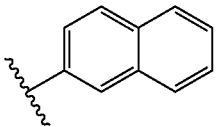
Ar-7
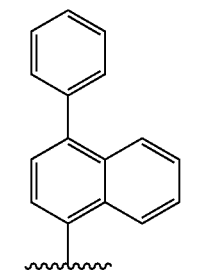
Ar-8
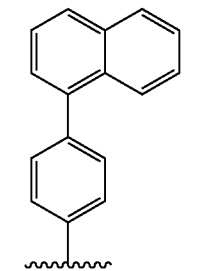

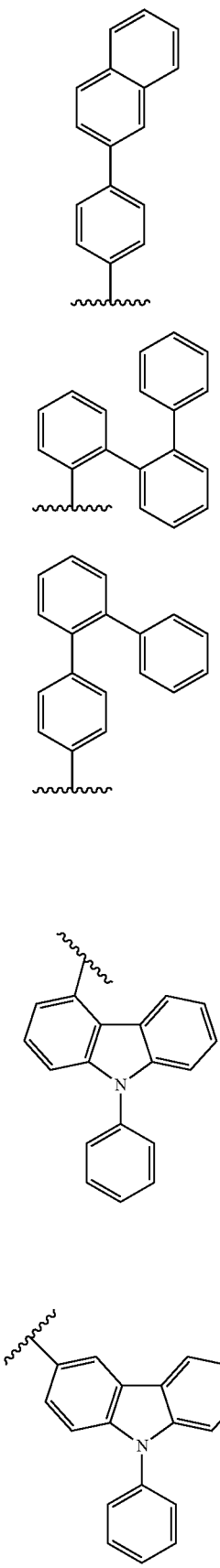

Ar-21 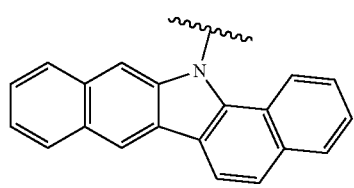
Ar-22 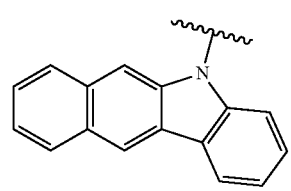
Ar-23 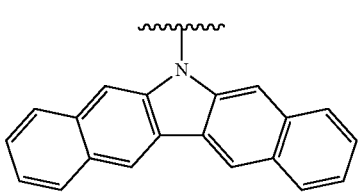
Ar-24 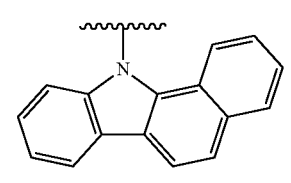
Ar-25 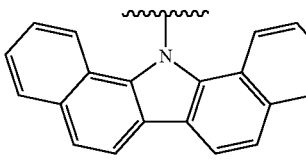
Ar-26 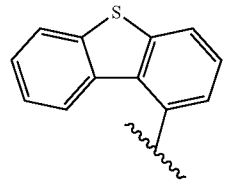
Ar-27 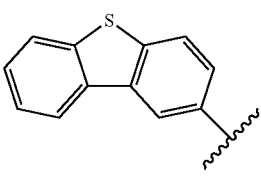
Ar-28 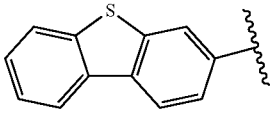
Ar-29 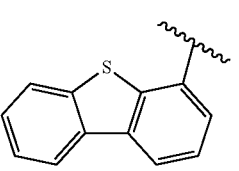
Ar-30 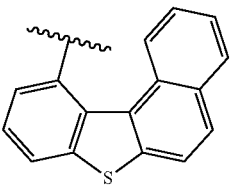
Ar-31 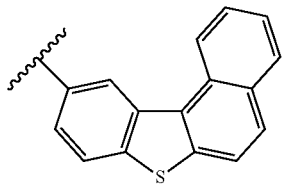
Ar-32 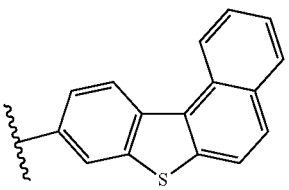
Ar-33 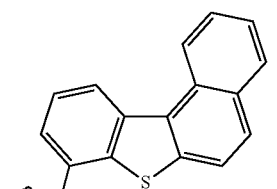
Ar-34 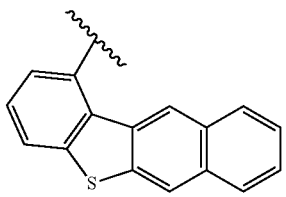
Ar-35 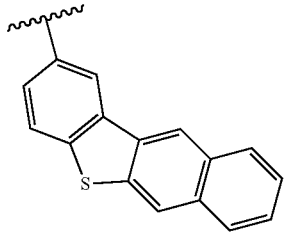
Ar-36 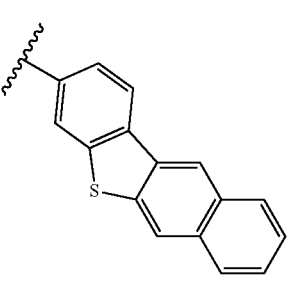

Ar-37
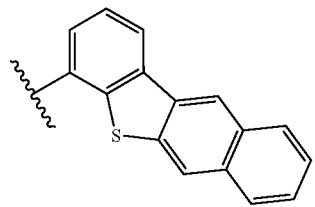
Ar-38
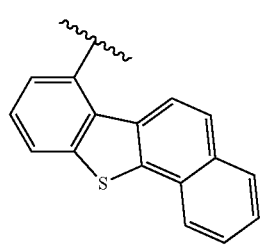
Ar-39
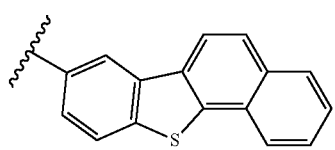
Ar-40
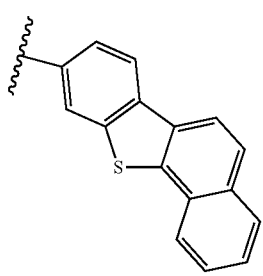
Ar-41
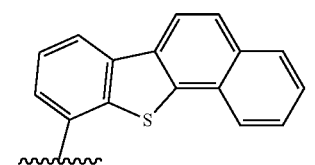
Ar-42
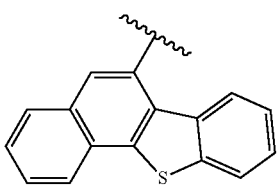
Ar-43
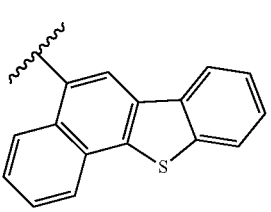
Ar-44
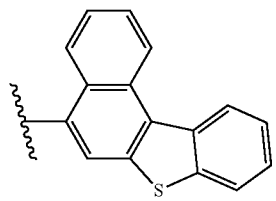
Ar-45
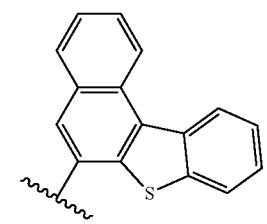
Ar-46
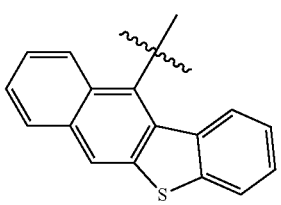
Ar-48
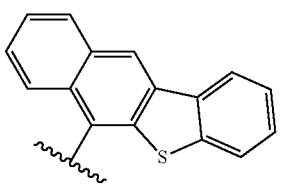
Ar-49
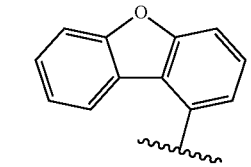
Ar-50
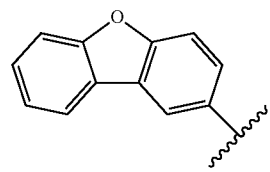
Ar-51
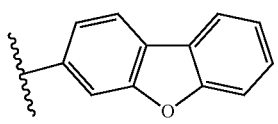
Ar-52
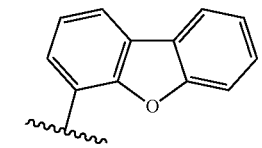

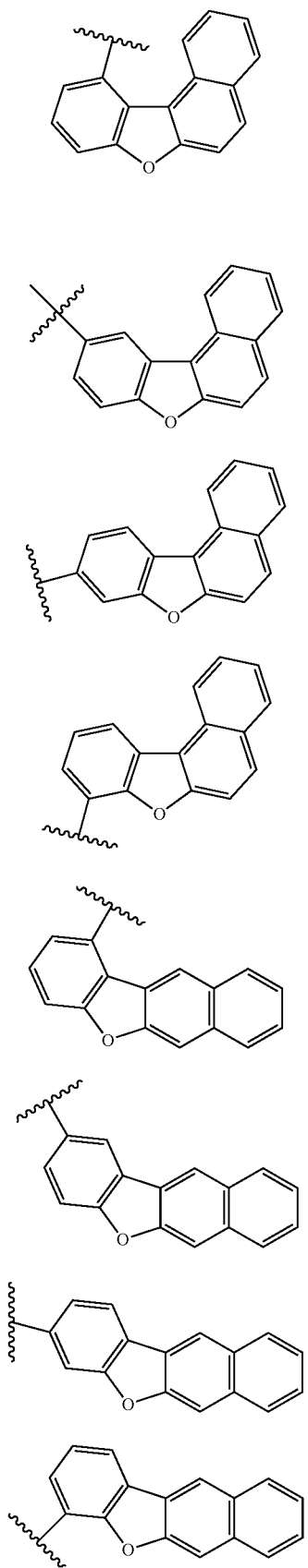
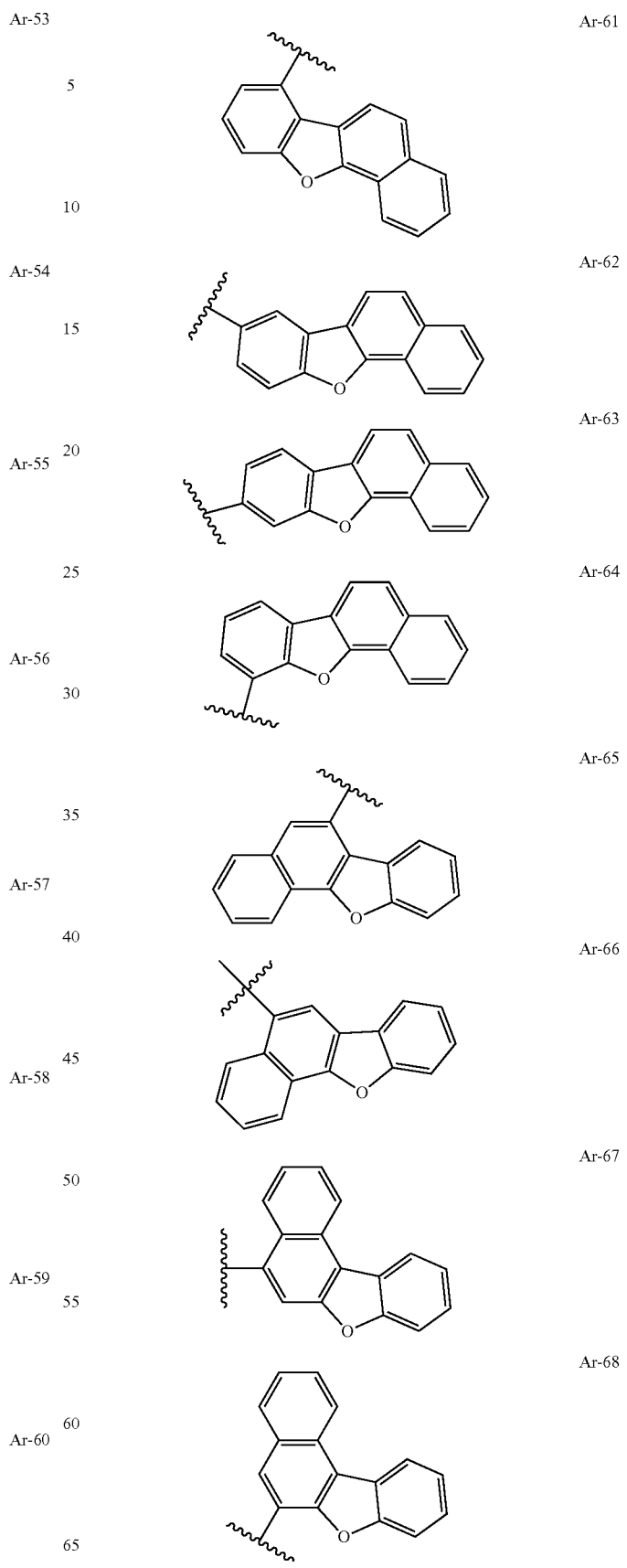

Ar-69 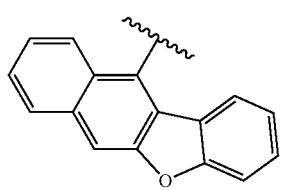
Ar-70 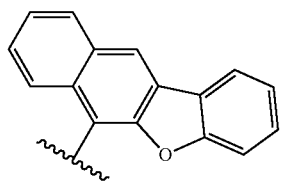
Ar-71 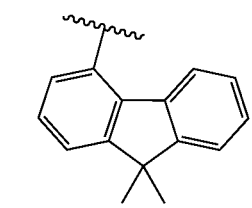
Ar-72 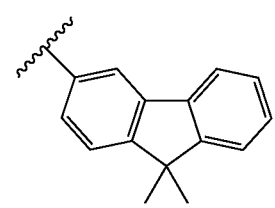
Ar-73 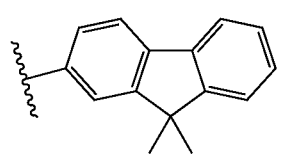
Ar-74 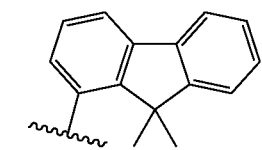
Ar-75 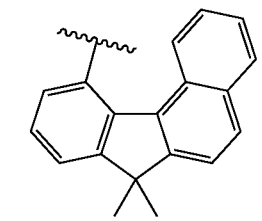
Ar-76 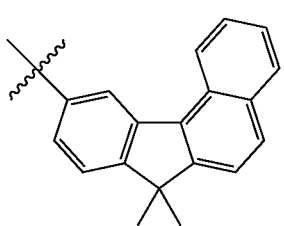
Ar-77 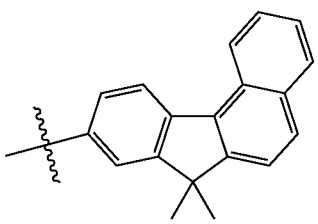
Ar-78 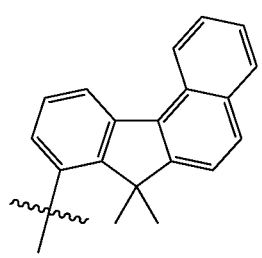
Ar-79 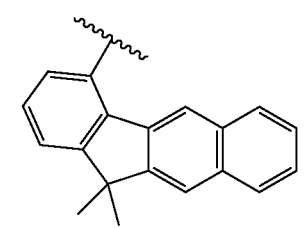
Ar-80 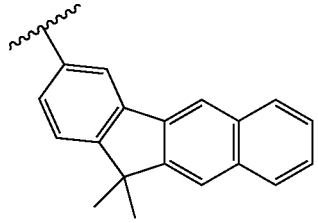
Ar-81 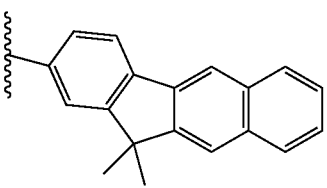
Ar-82 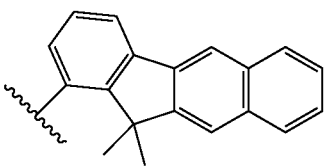
Ar-83 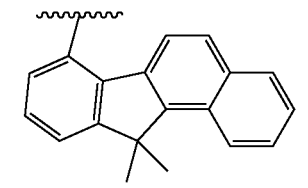

-continued
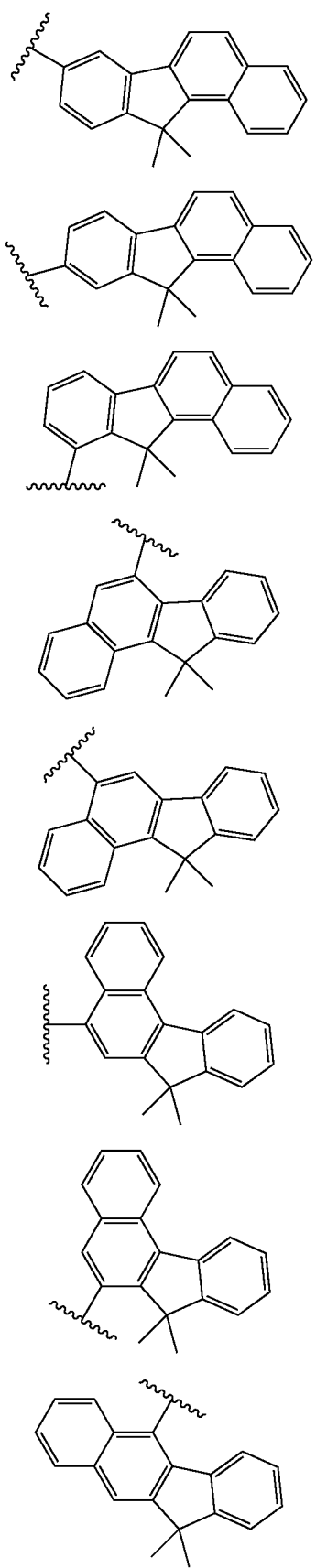
Ar-84
Ar-85
Ar-86
Ar-87
Ar-88
Ar-89
Ar-90
Ar-91
-continued
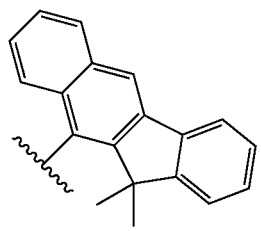
Ar-92
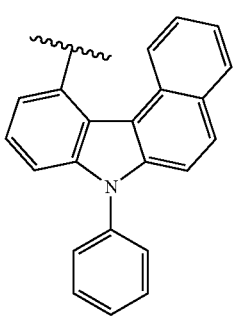
Ar-93
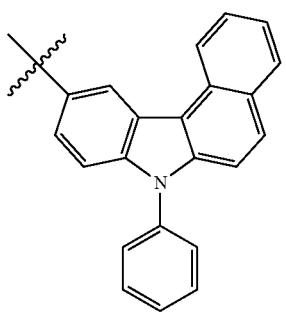
Ar-94
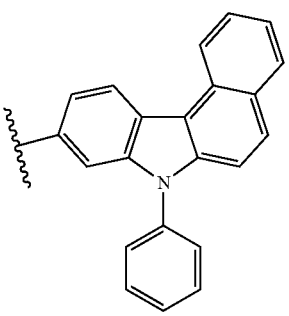
Ar-95
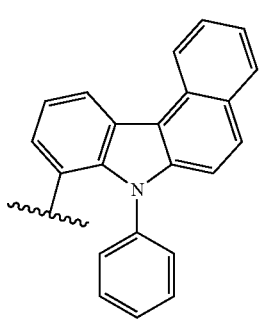
Ar-96

Ar-97
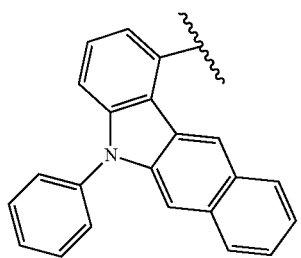
Ar-98
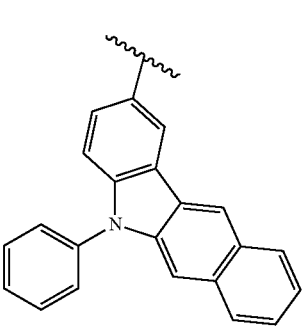
Ar-99
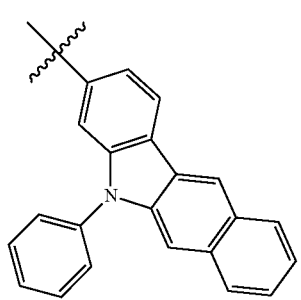
Ar-100
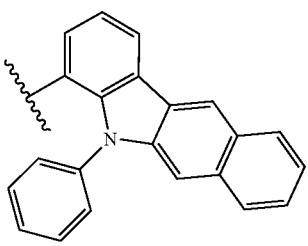
Ar-101
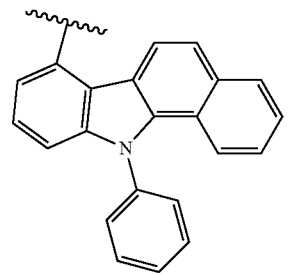
Ar-102
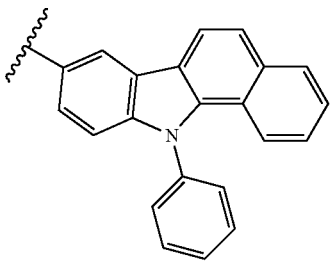
Ar-103
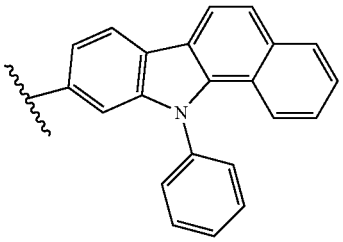
Ar-104
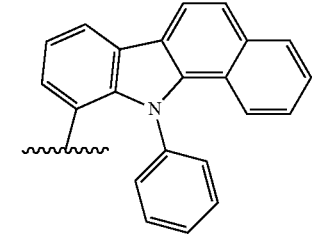
Ar-105
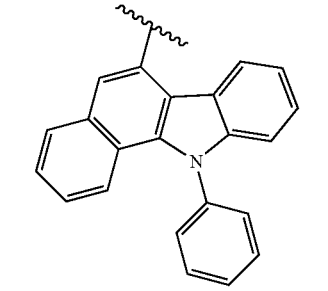
Ar-106
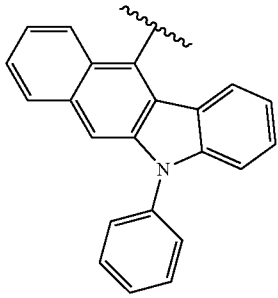
Ar-107
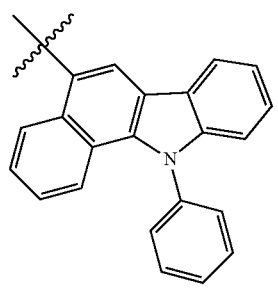

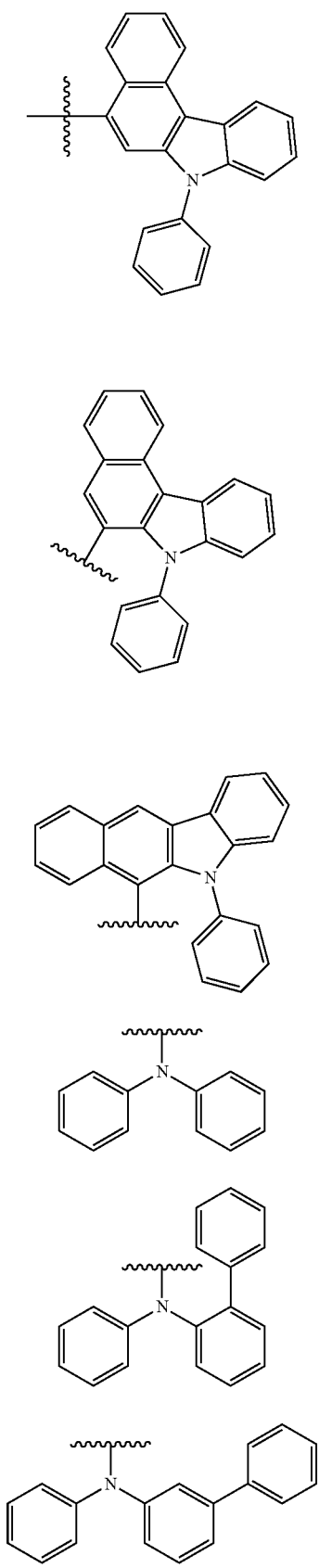
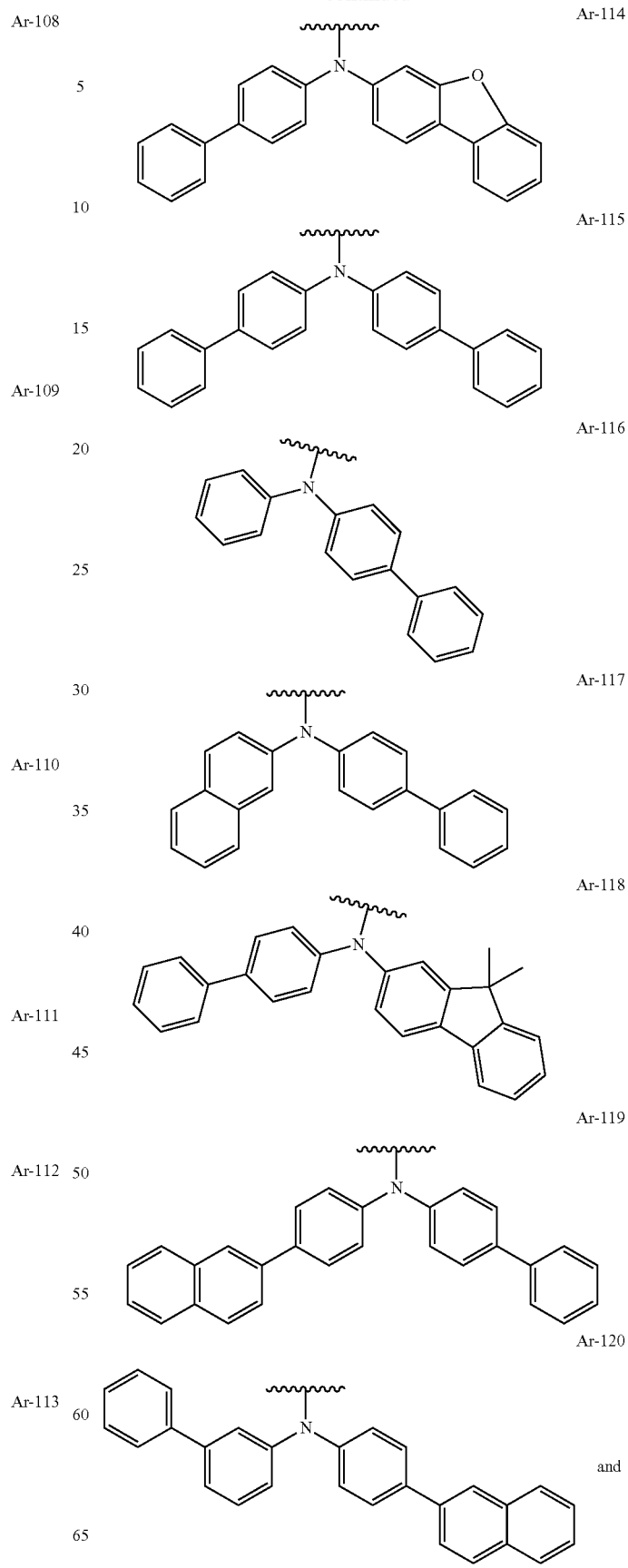

Ar-121
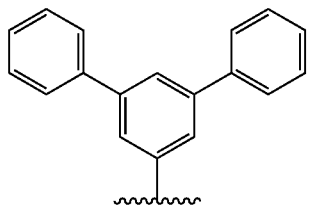
7. The plurality of host materials according to claim 1, wherein formula 2 is represented by at least one of the following formulas 2-11 to 2-38:
2-11
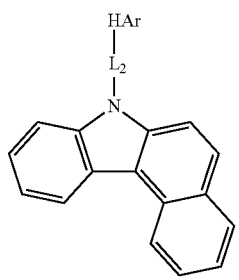
2-12
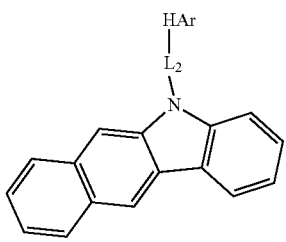
2-13
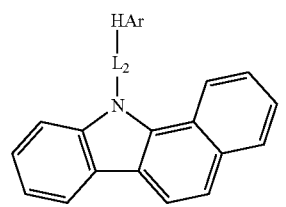
2-14
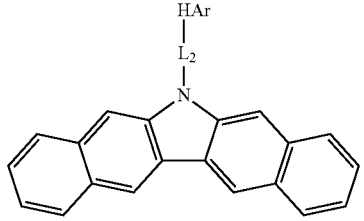
2-15
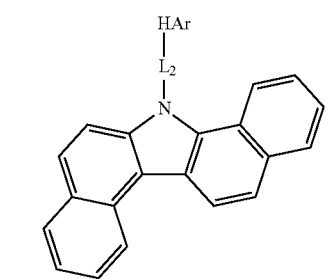
2-16
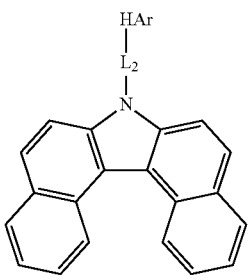
2-17
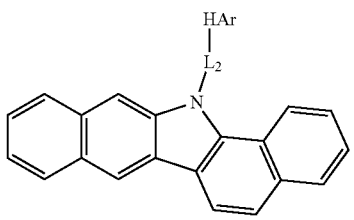
2-18
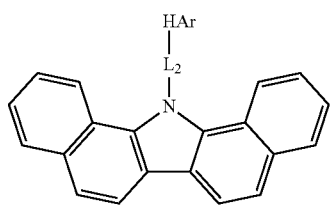
2-19
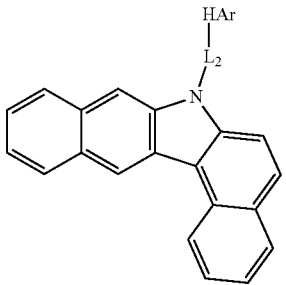
2-20
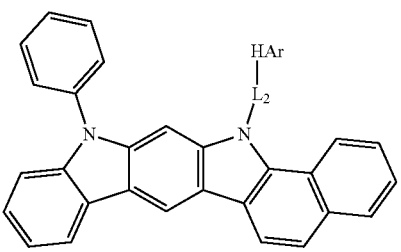
2-21
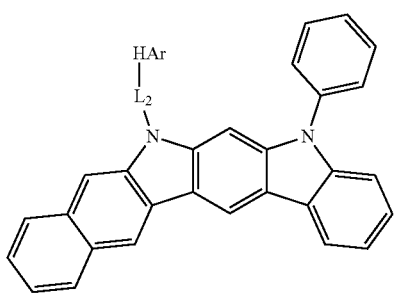

2-22
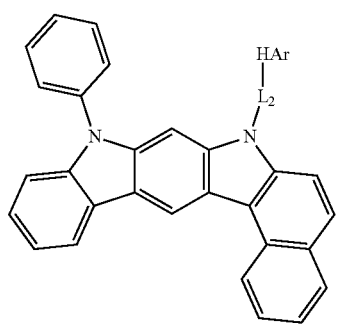
2-23
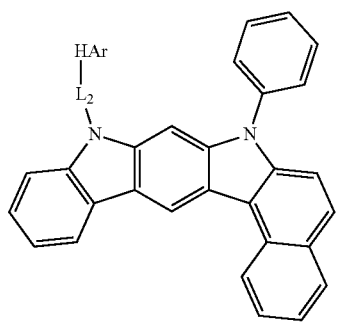
2-24
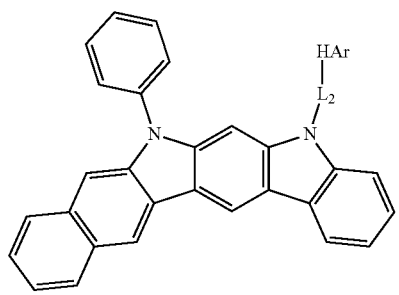
2-25
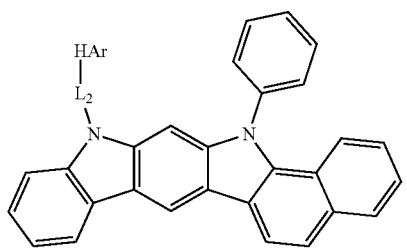
2-26
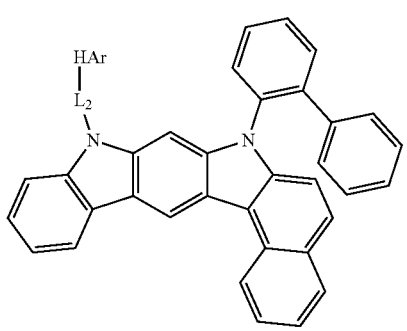
2-27
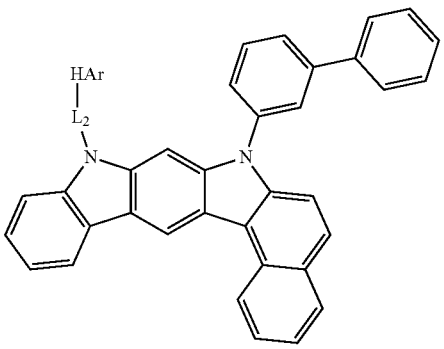
2-28
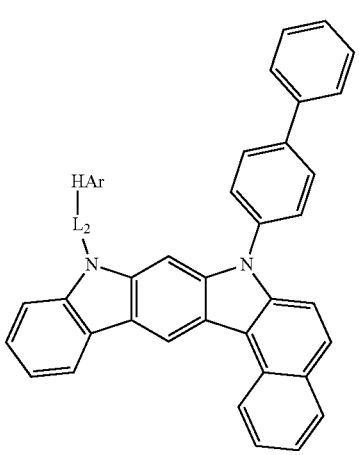
2-29
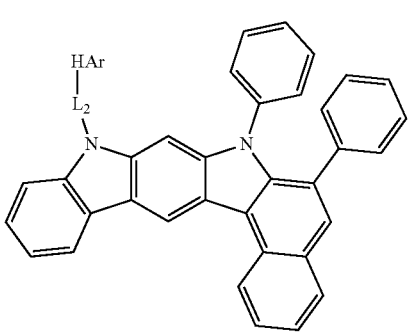
2-30
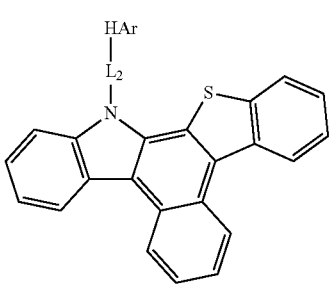

-continued
2-31
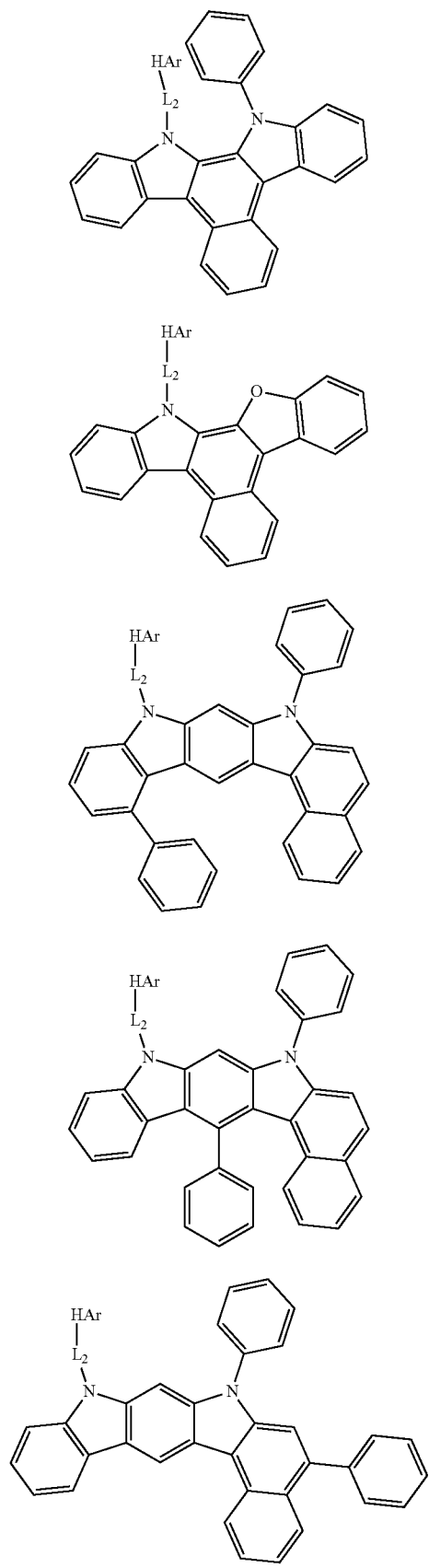
2-32
2-33
2-34
2-35
-continued
2-36
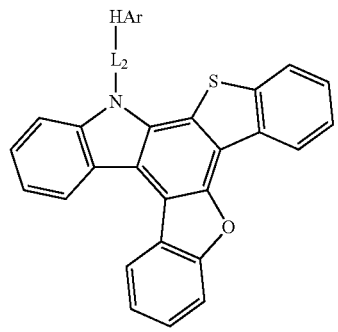
2-37
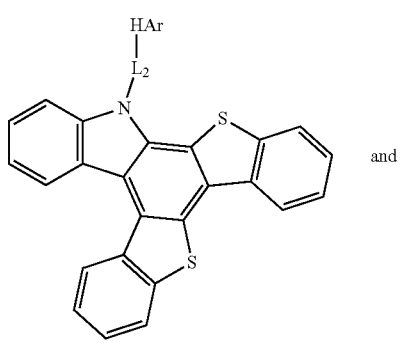
and
2-38
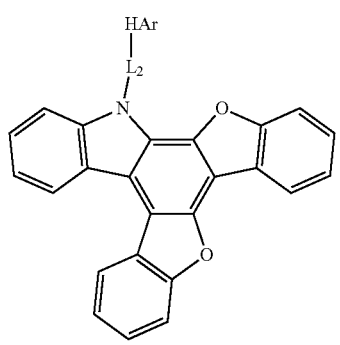
wherein
HAr is represented by one of the following formulas 2-40 to 2-58, and
2-40
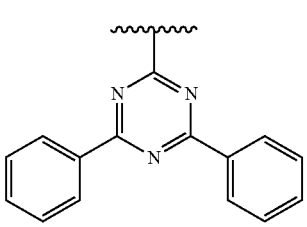
2-41
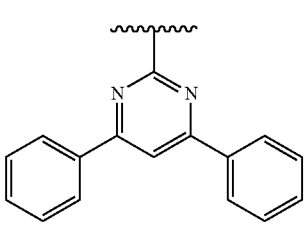

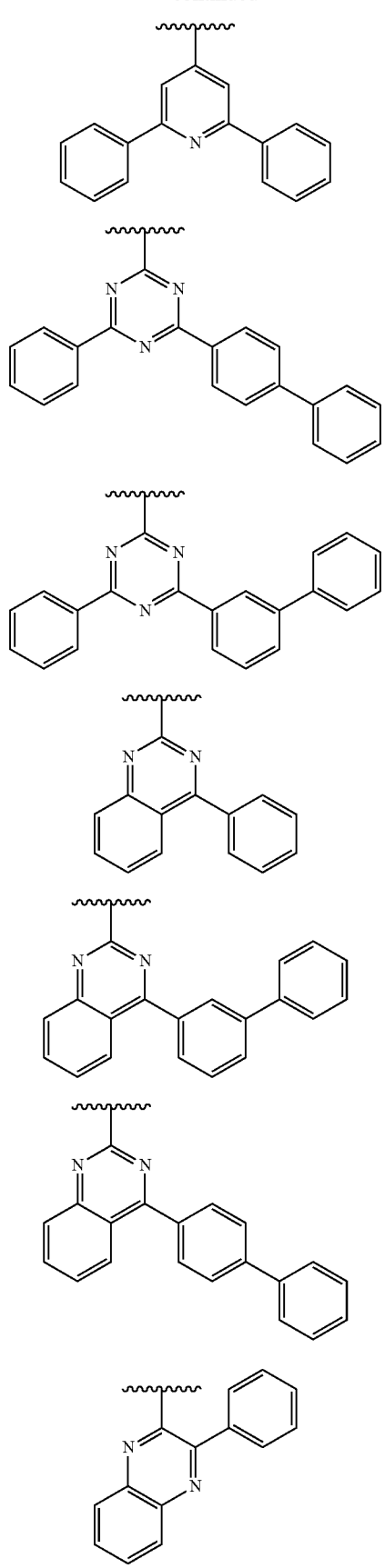
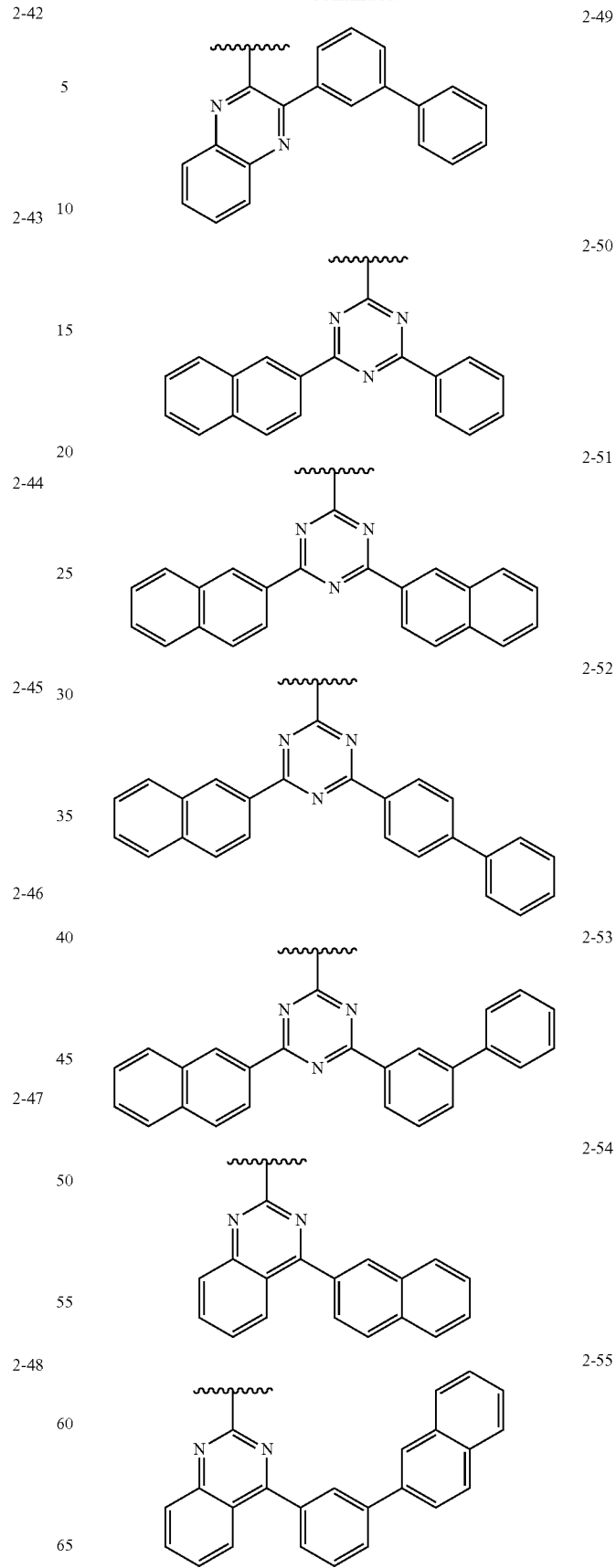

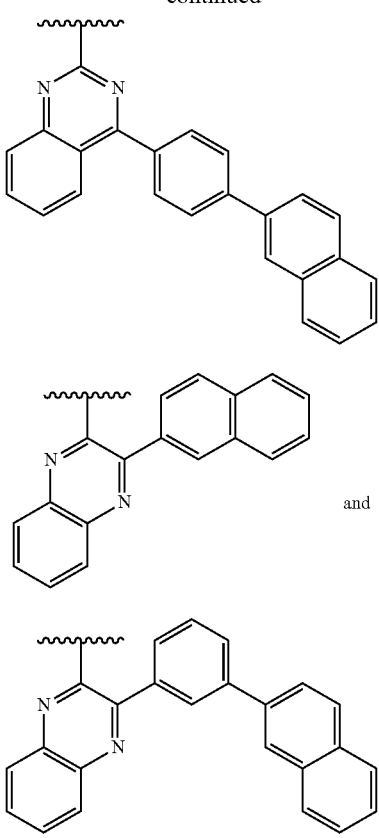
2-56
2-57
and
2-58
$L_2$ is represented by one of the following formulas 3-1 to 3-47:
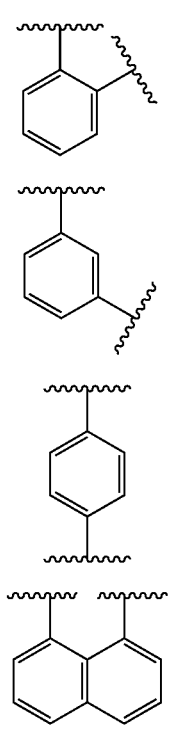
3-1
3-2
3-3
3-4
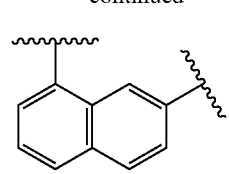
3-5
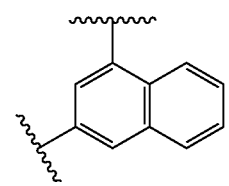
3-6
3-7
3-8
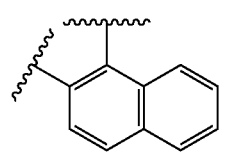
3-9
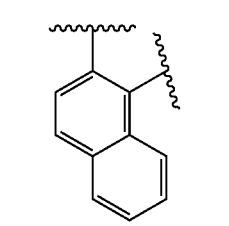
3-10
3-11
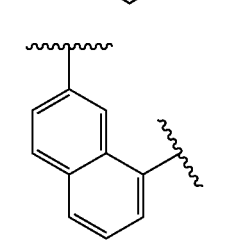
3-12

3-13
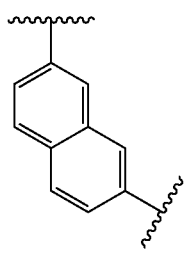
3-14
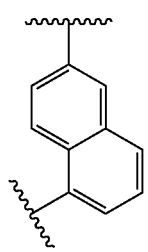
3-15
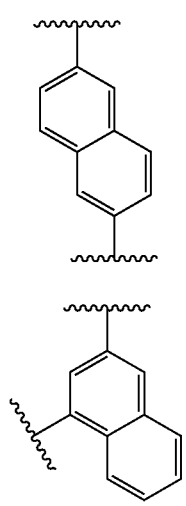
3-16
3-17
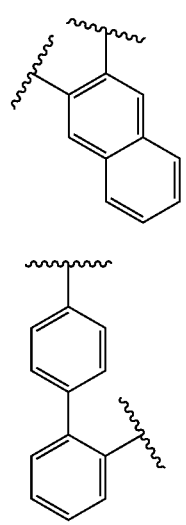
3-18
3-19
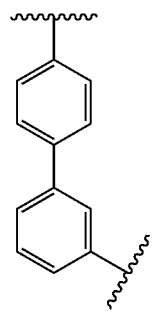
3-20
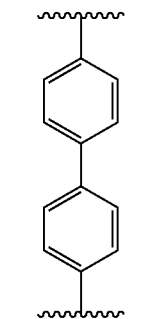
3-21
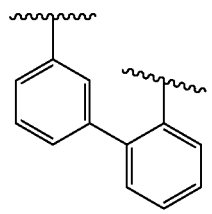
3-22
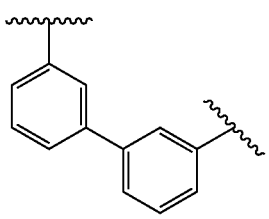
3-23
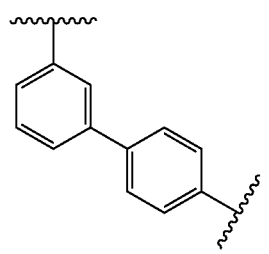
3-24
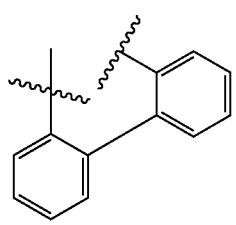

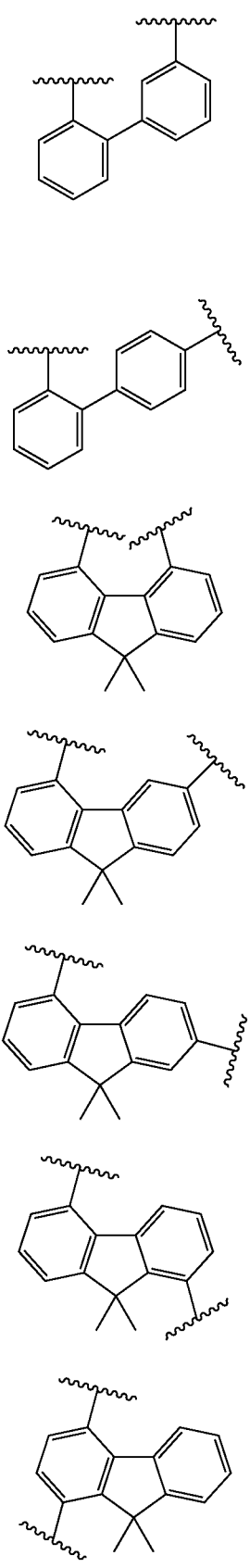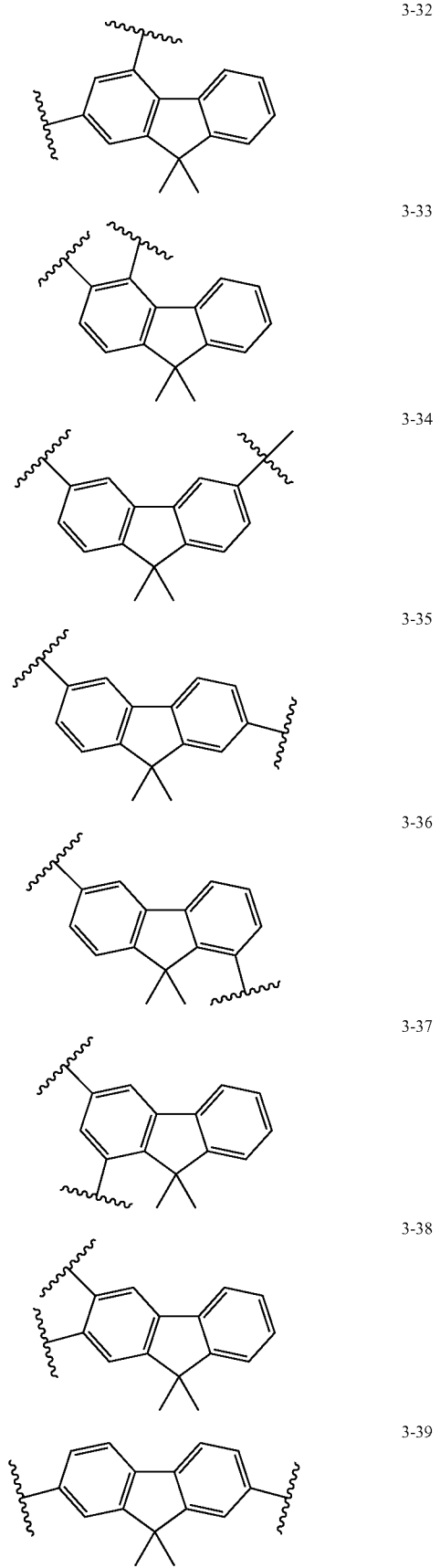

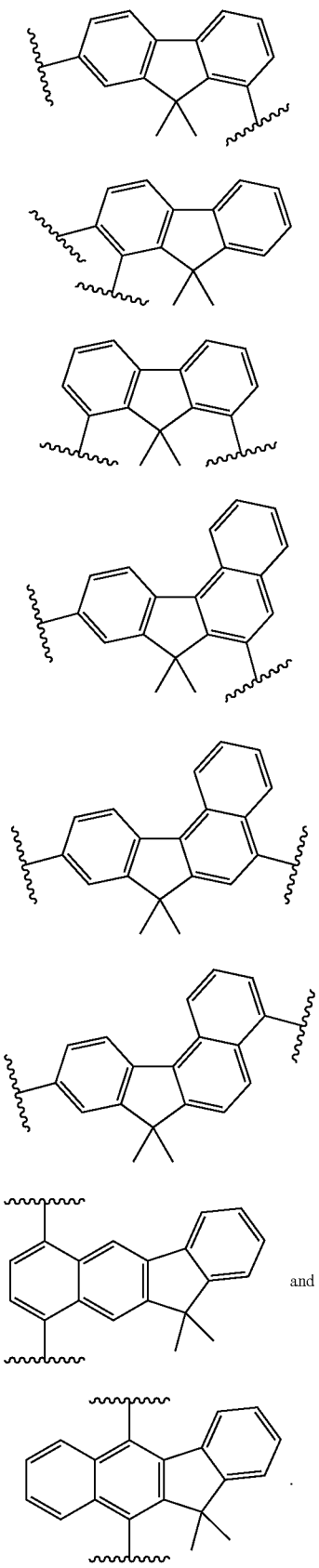
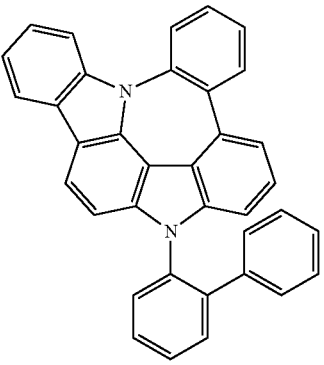
8. The plurality of host materials according to claim 1, wherein the compound represented by formula 1 is selected from the following compounds:
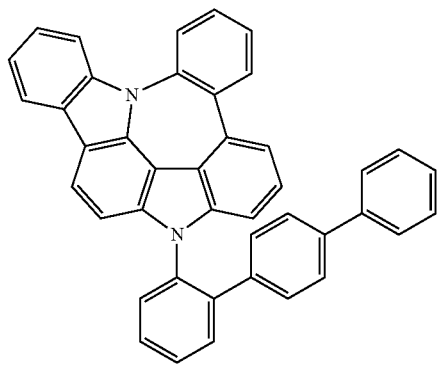
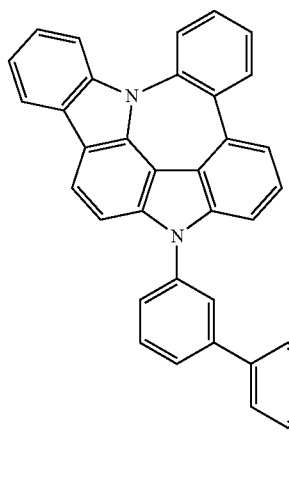

C1-4
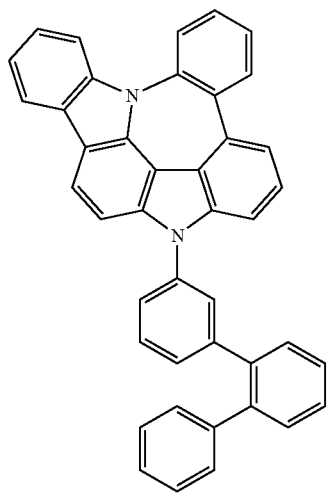
C1-5
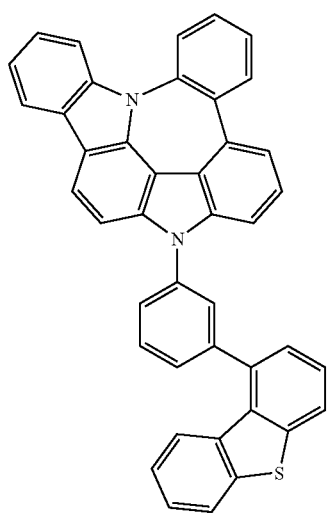
C1-6
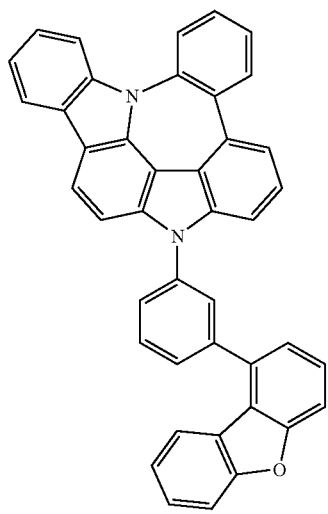
C1-7
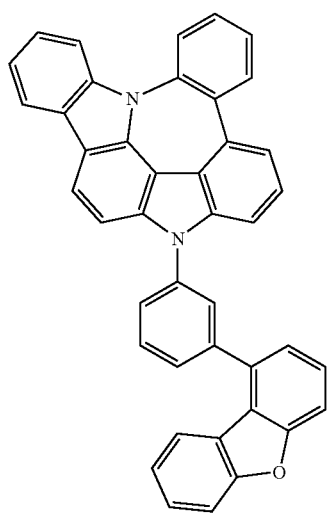
C1-8

C1-9
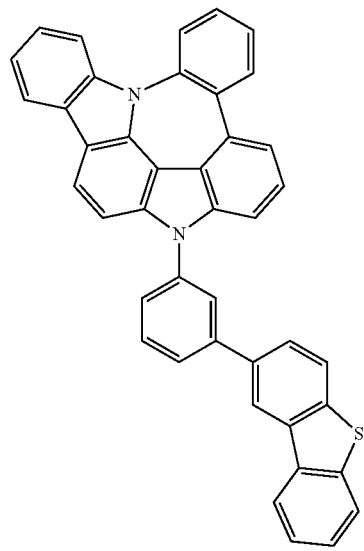
C1-10
C1-11
C1-12
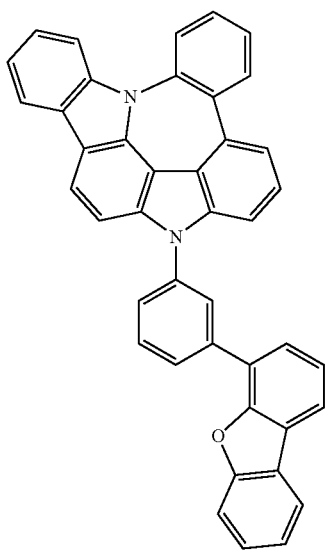
C1-13
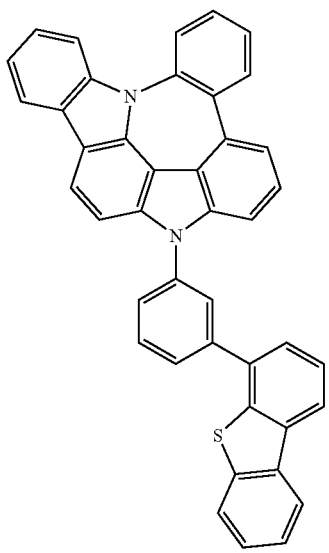
C1-14
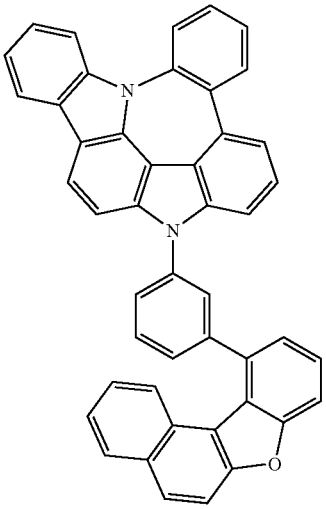

C1-15
C1-18
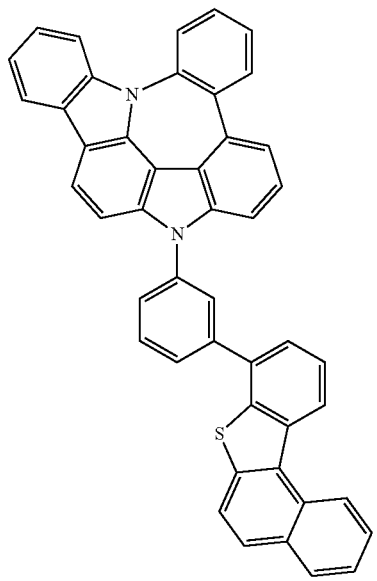
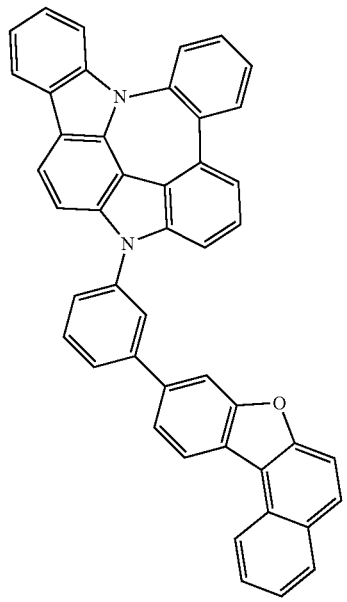
C1-16
C1-17
C1-19
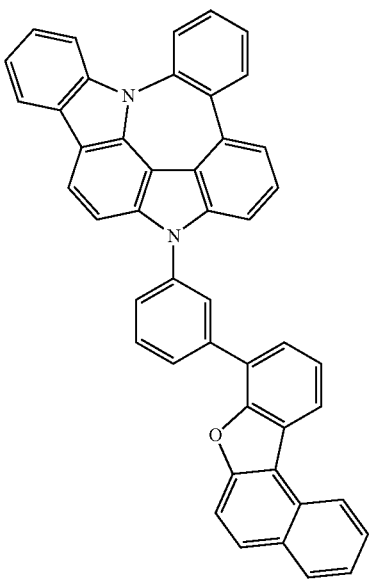

C1-20
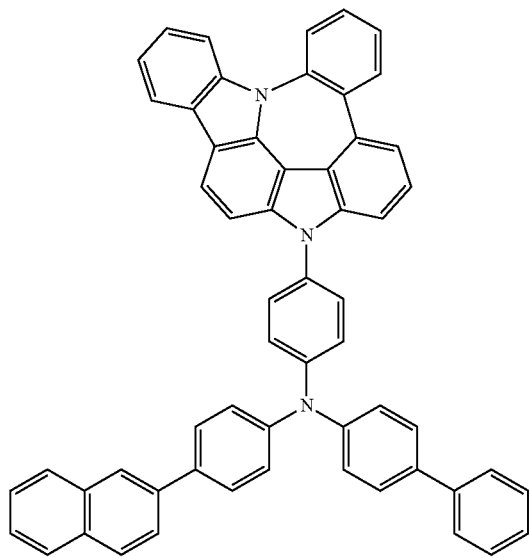
C1-21
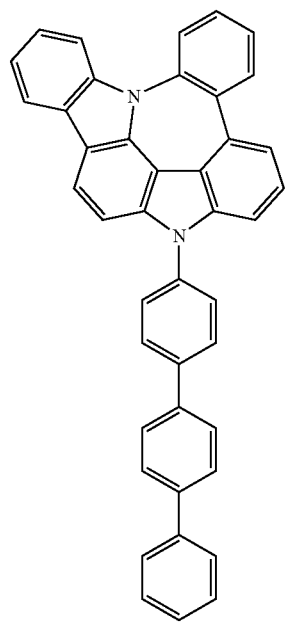
C1-22
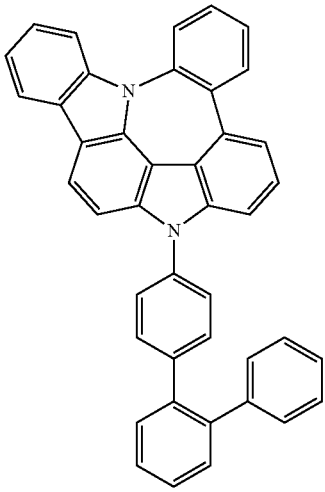
C1-23
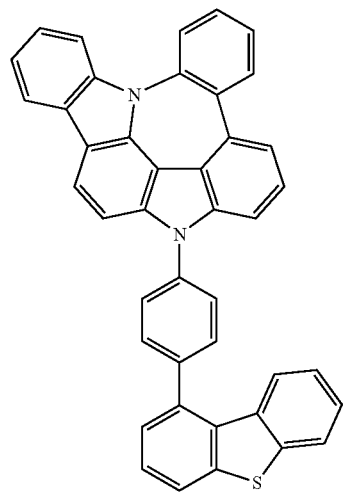
C1-24
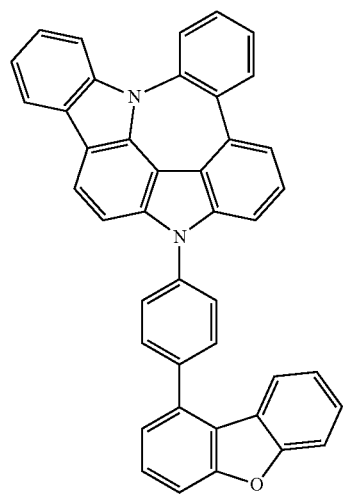

C1-25
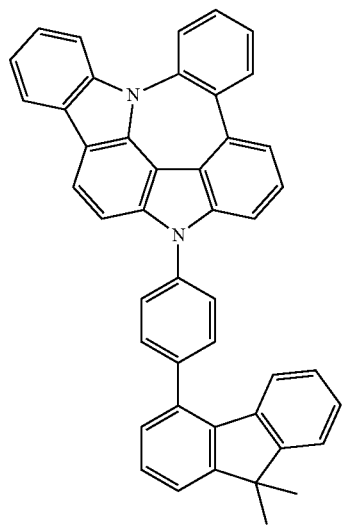
C1-26
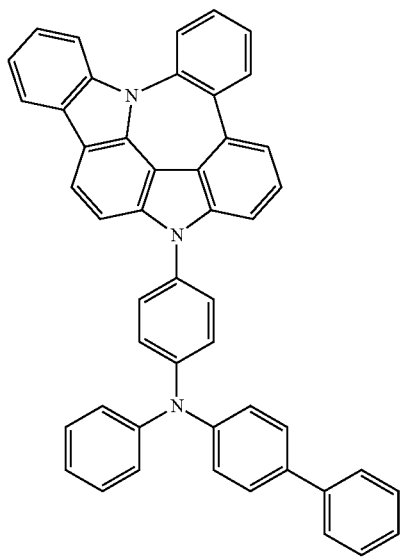
C1-27
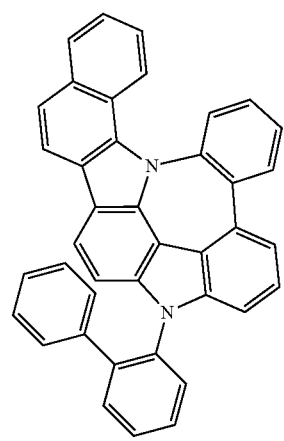
C1-28
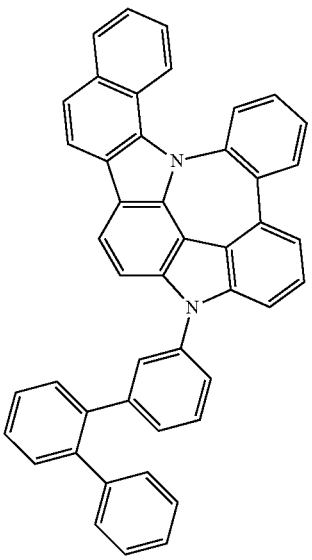
C1-29
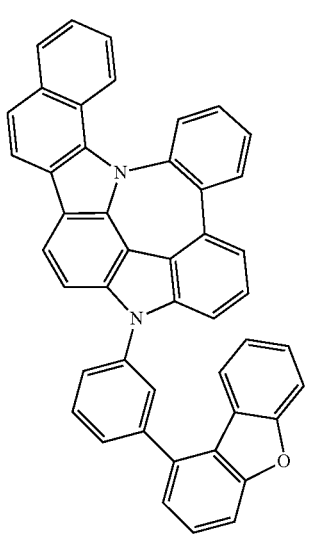

C1-30
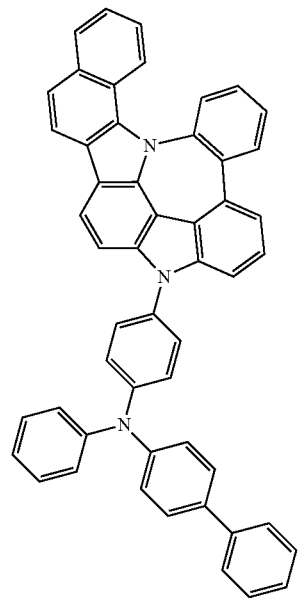
C1-31
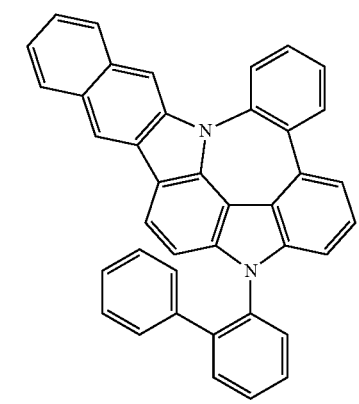
C1-32
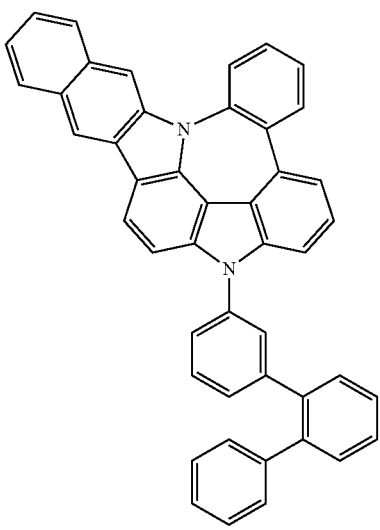
C1-33
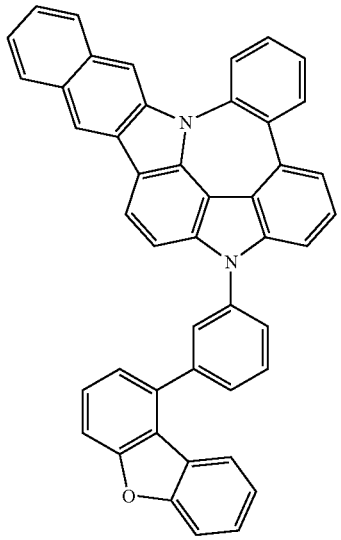
C1-34
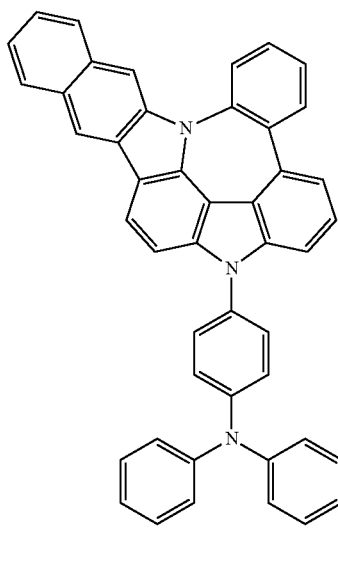
C1-35
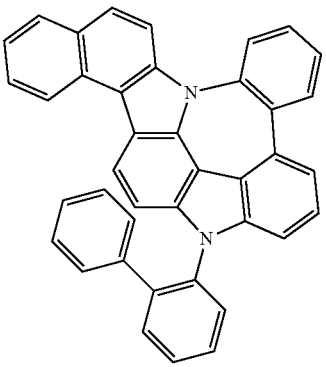

C1-36
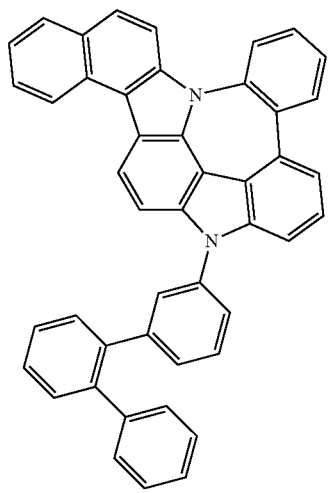
C1-37
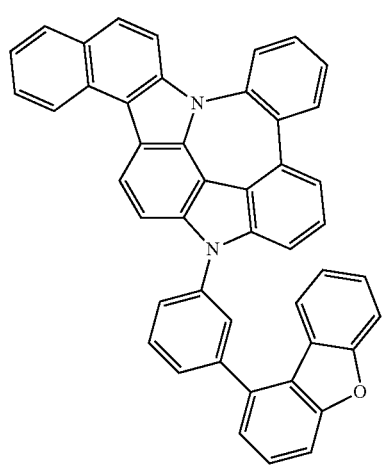
C1-38
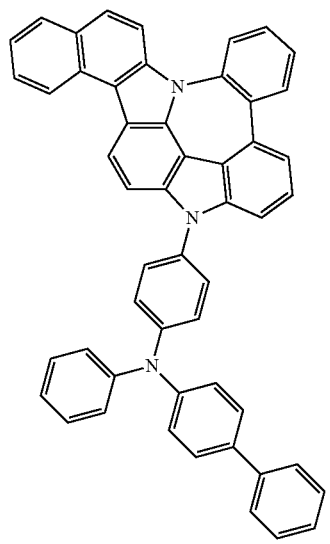
C1-39
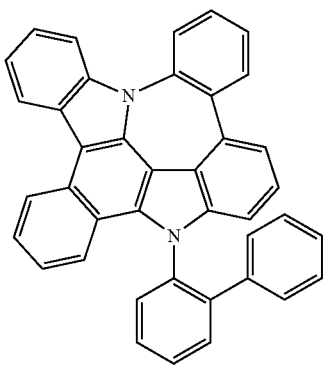
C1-40
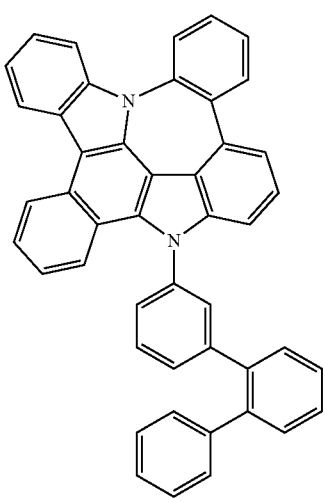
C1-41
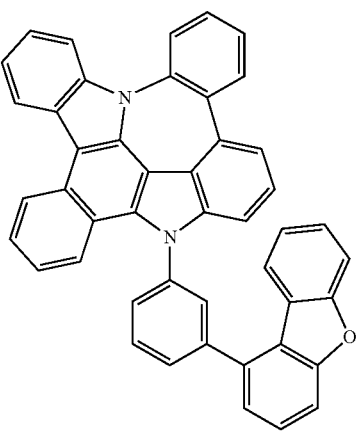

C1-42
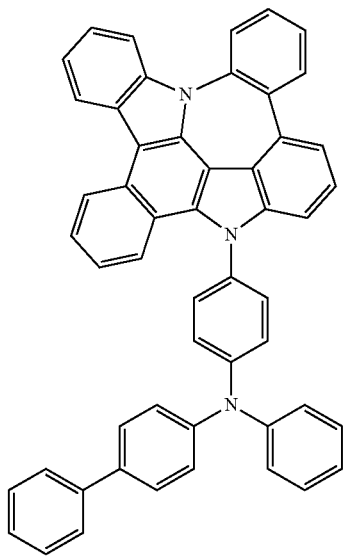
C1-43
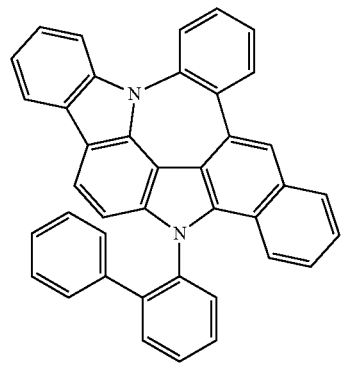
C1-44
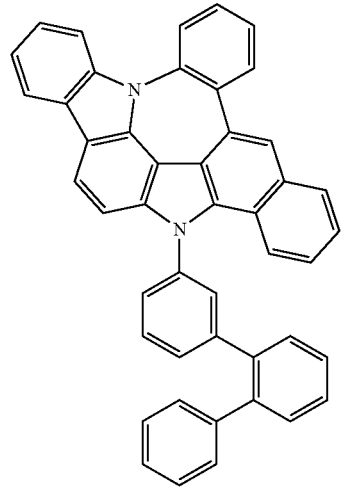
C1-45
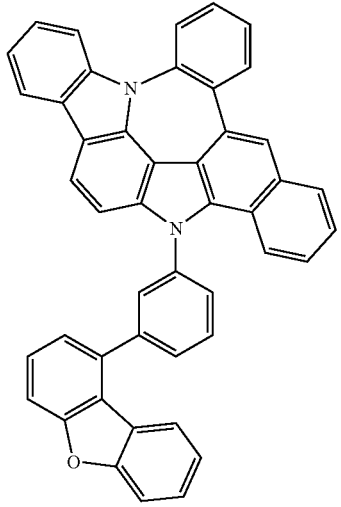
C1-46
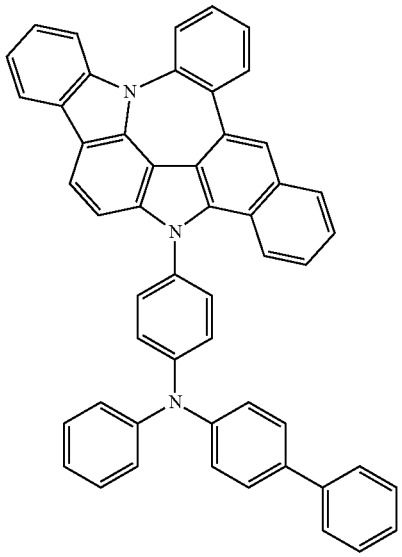
C1-47
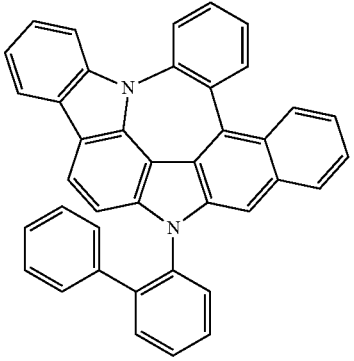

C1-48
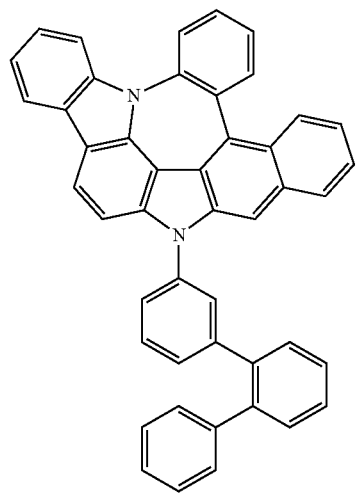
C1-49
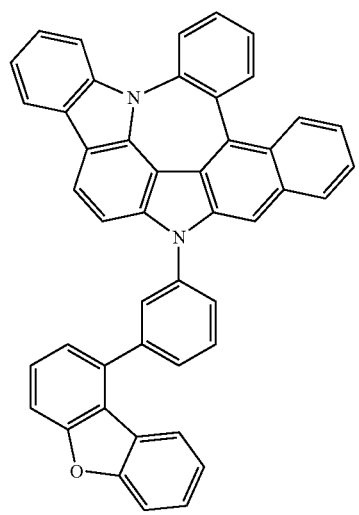
C1-50
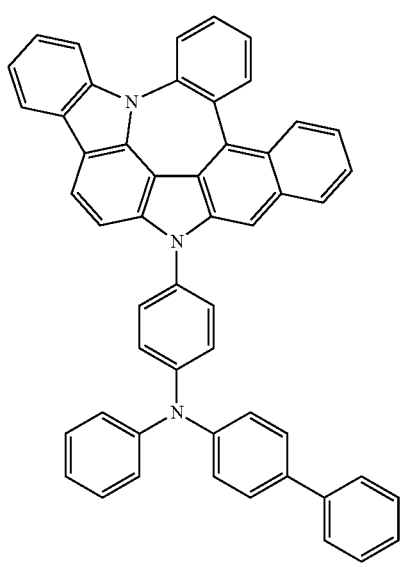
C1-51
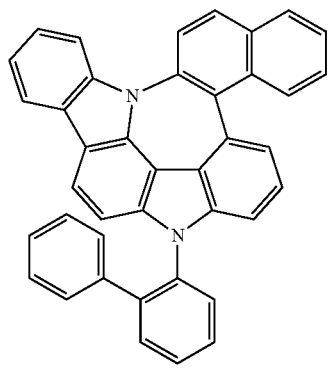
C1-52
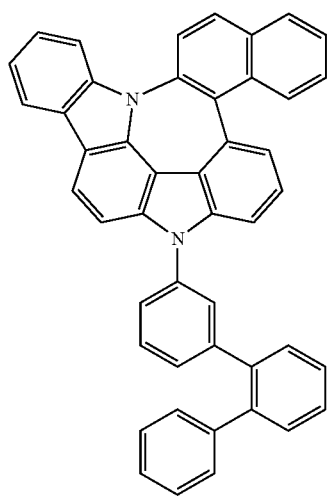
C1-53
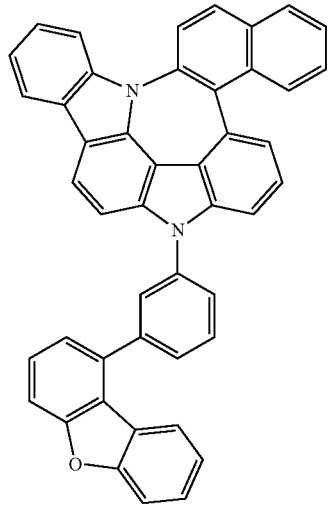

C1-54
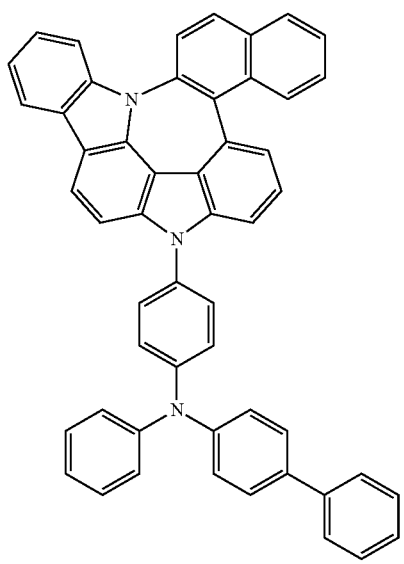
C1-55
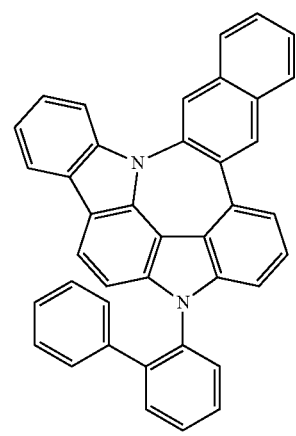
C1-56
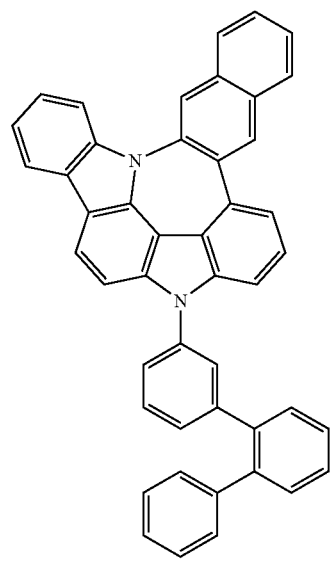
C1-57
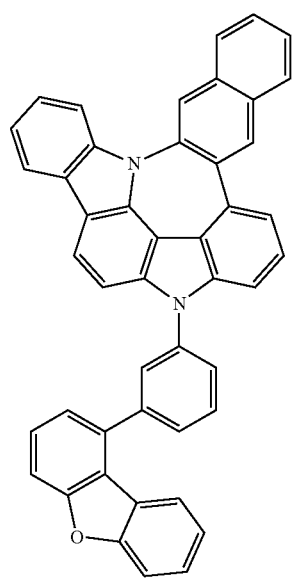
C1-58
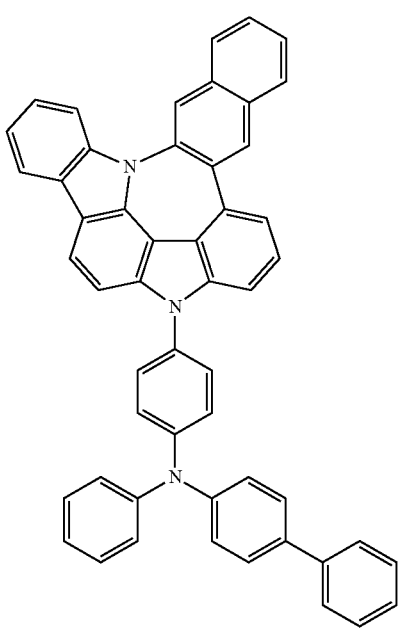
C1-59
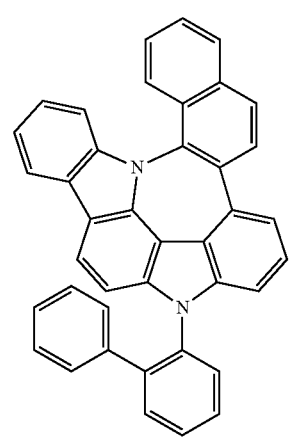

C1-60
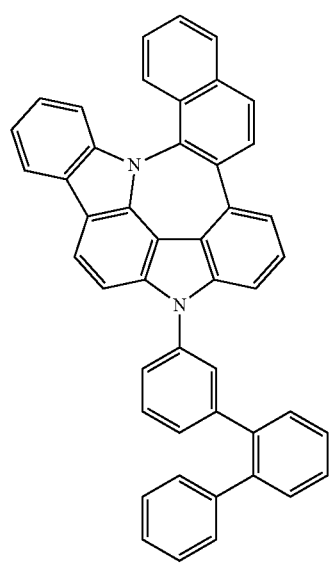
C1-62
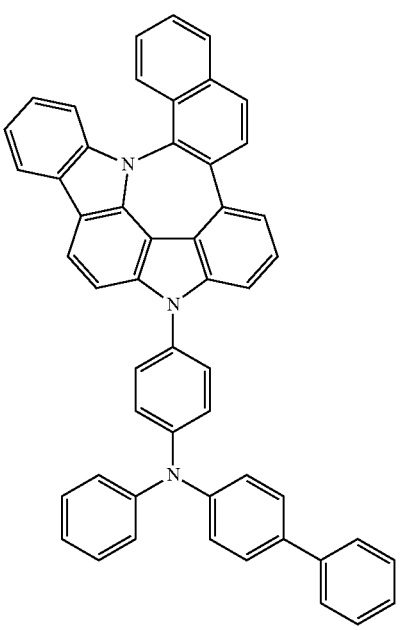
C1-61
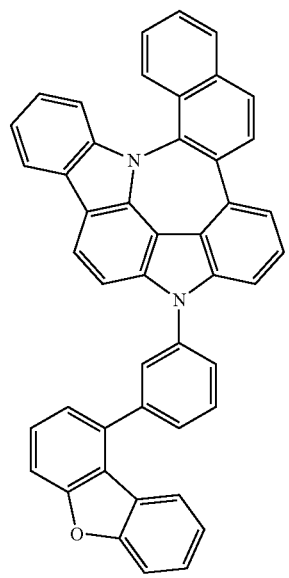
C1-63
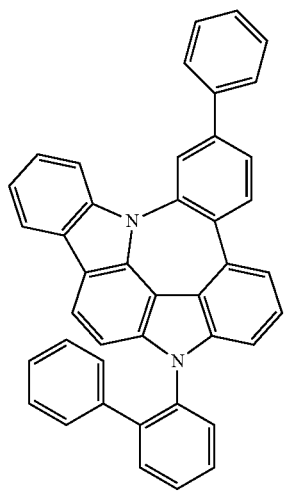

C1-64
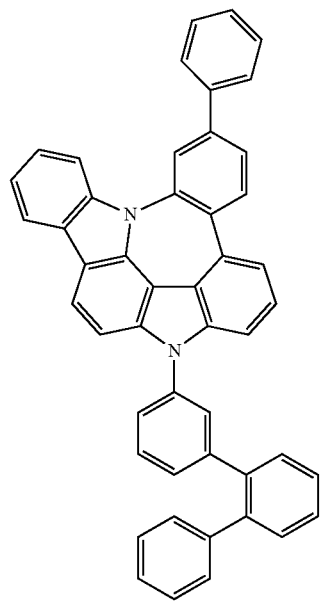
C1-65
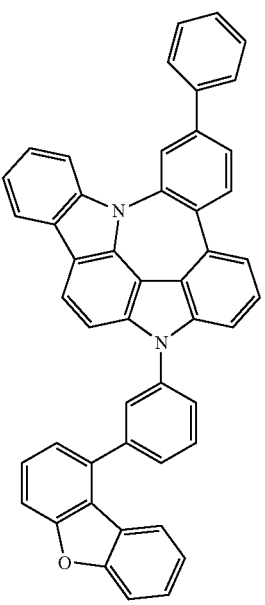
C1-66
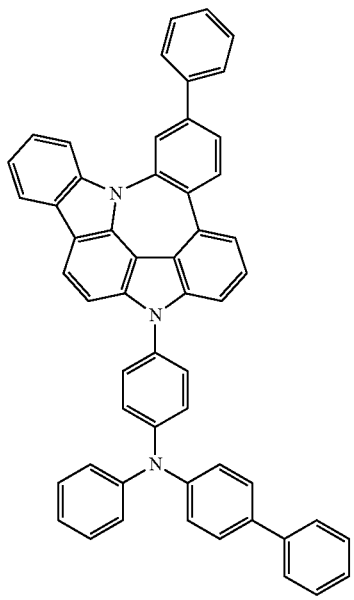
C1-67
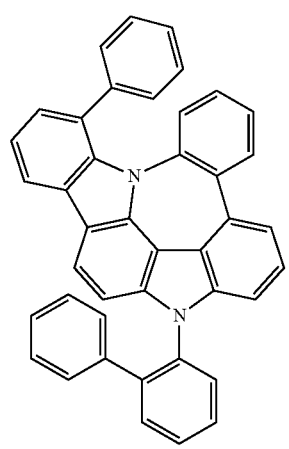
C1-68
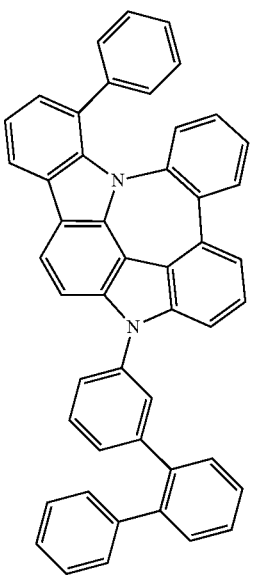

C1-69
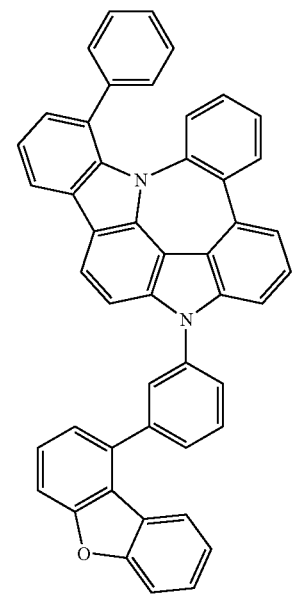
C1-70
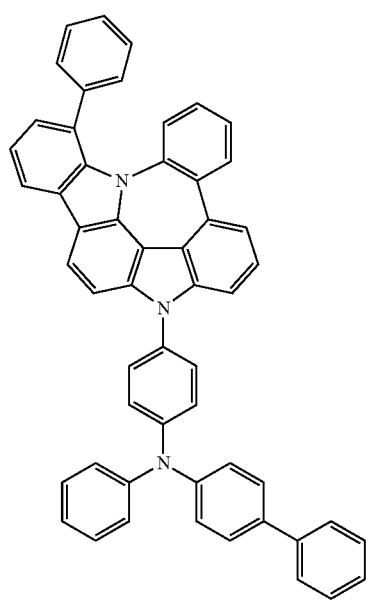
C1-71
C1-72
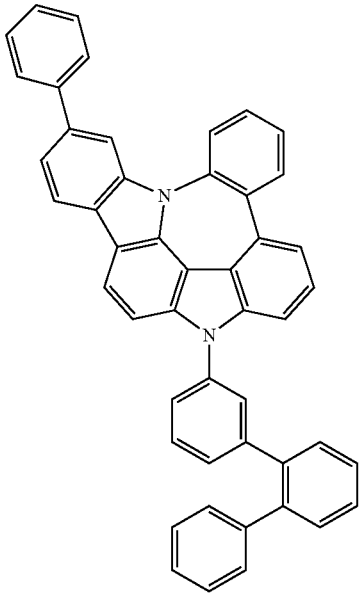
C1-73
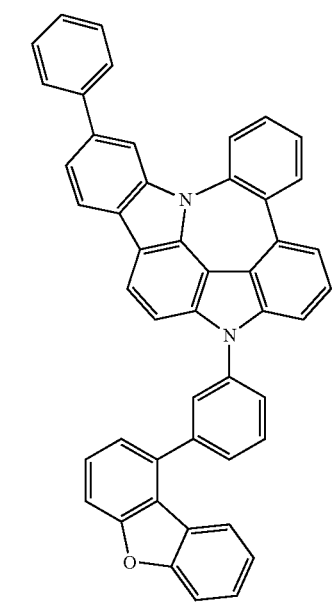

C1-74
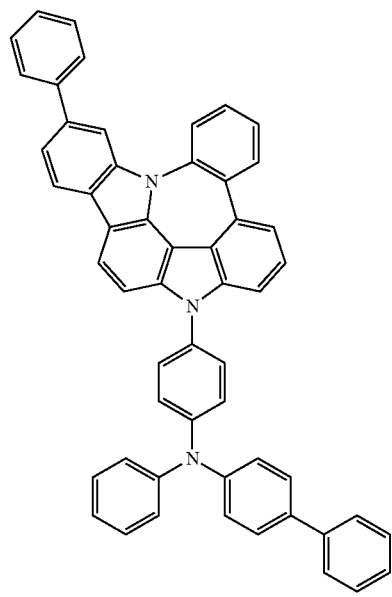
C1-75
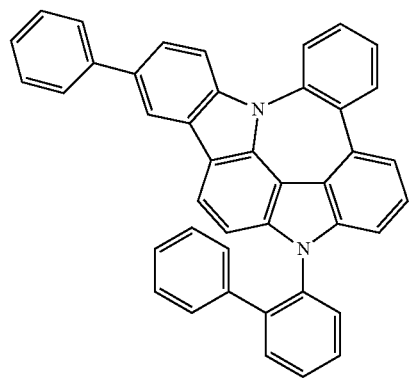
C1-76
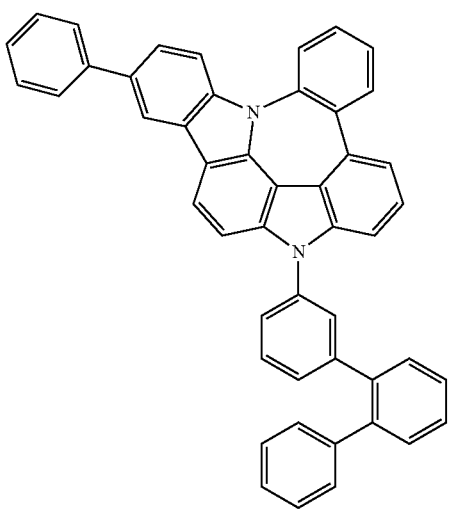
C1-77
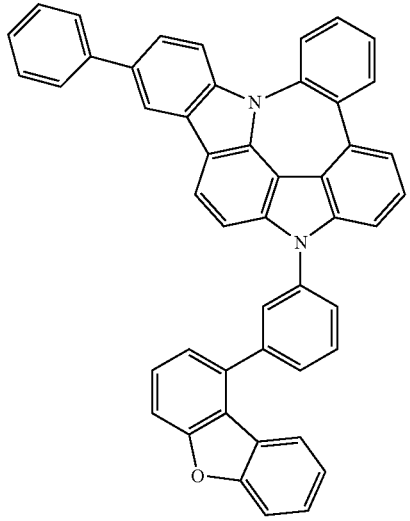
C1-78
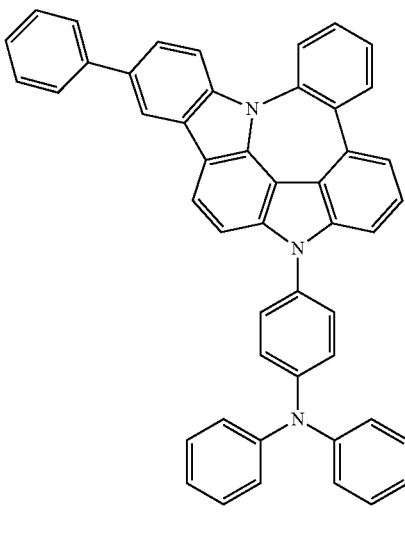
C1-79
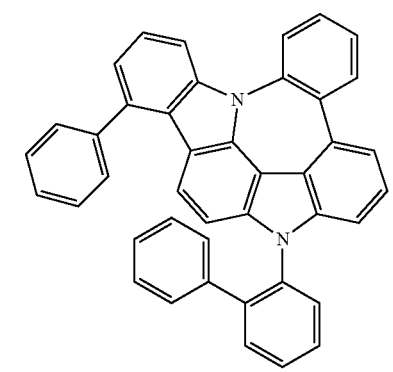

C1-80
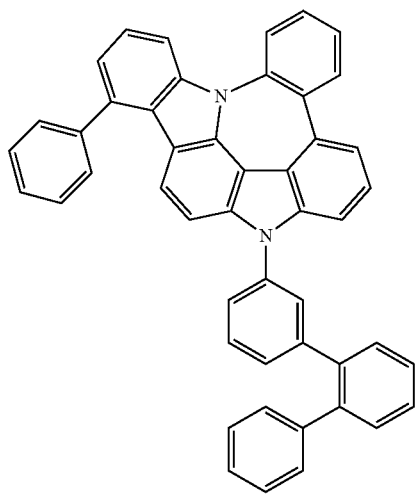
C1-81
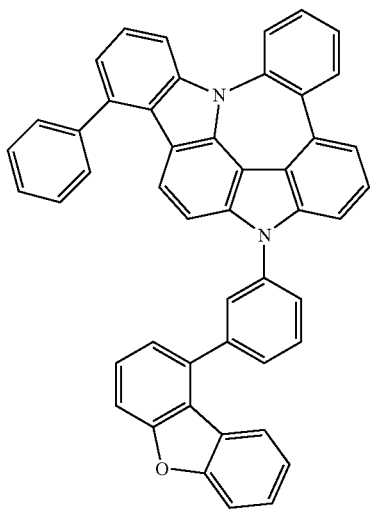
C1-82
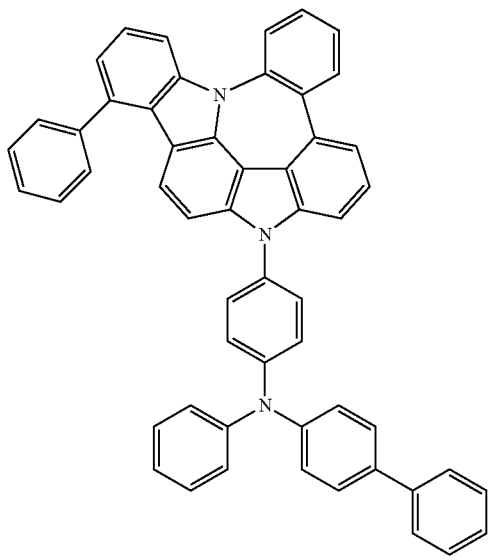
C1-83
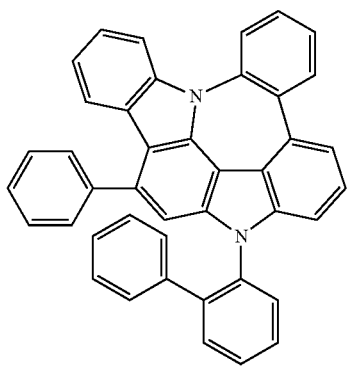
C1-84
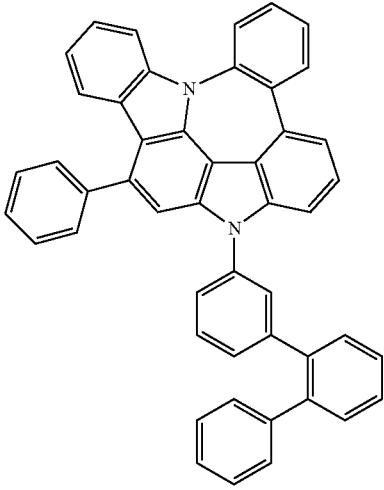
C1-85
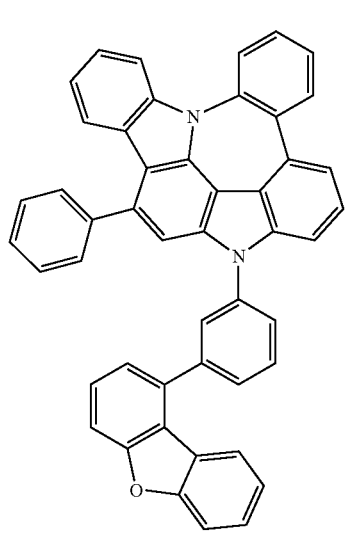

C1-86
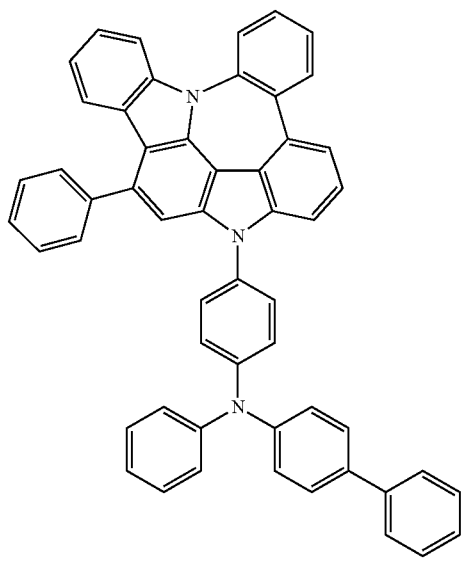
C1-87
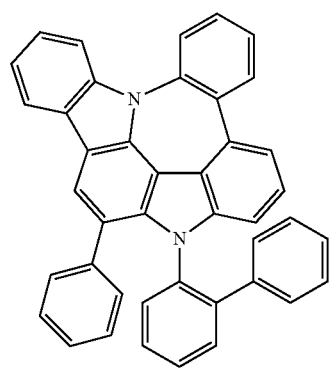
C1-88
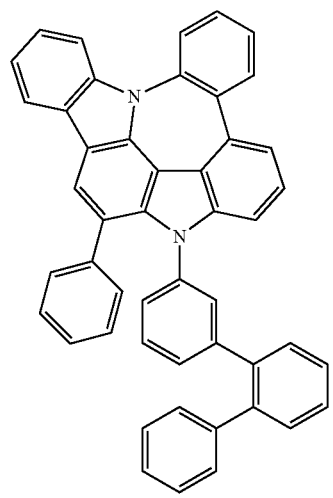
C1-89
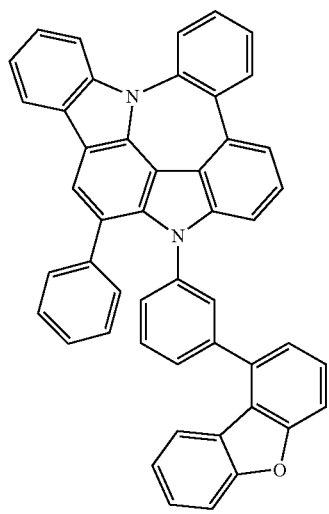
C1-90
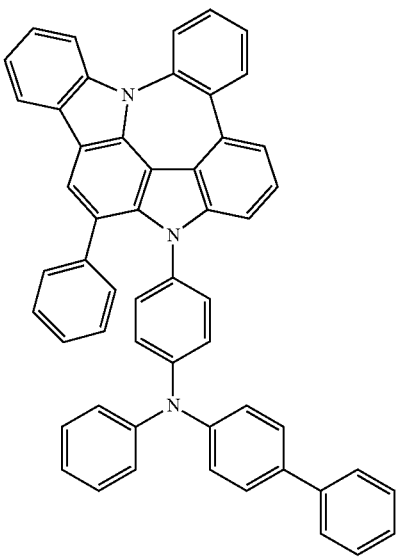
C1-91
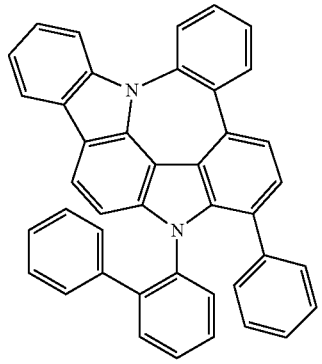

-continued
C1-92
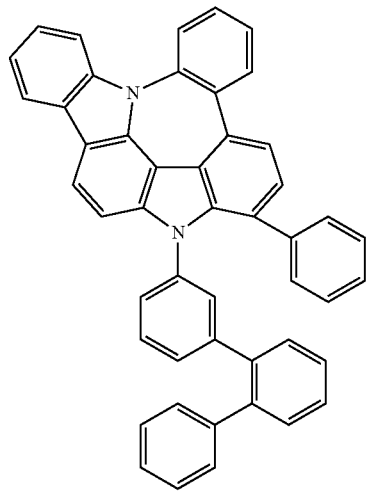
C1-93
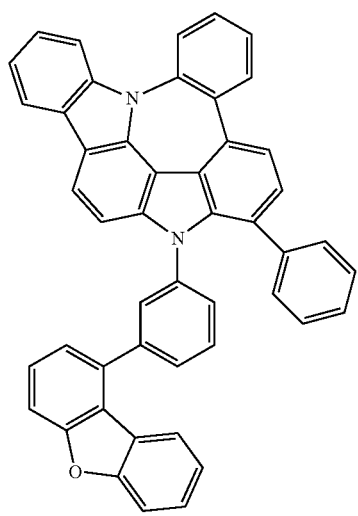
C1-94
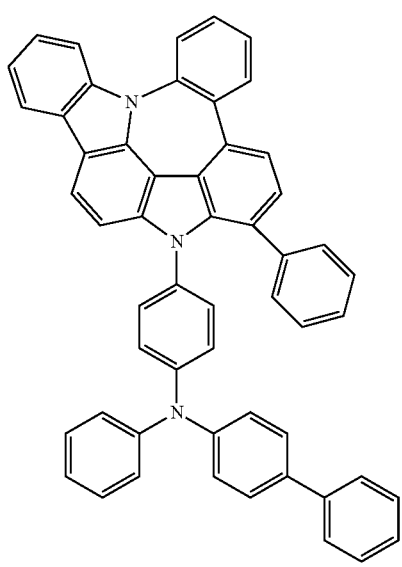
-continued
C1-95
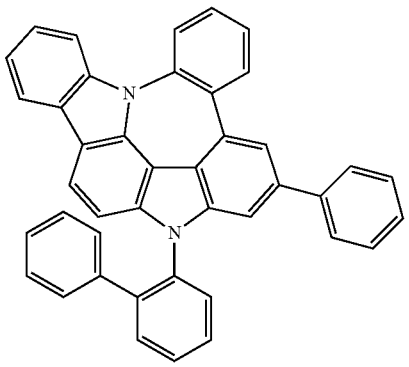
C1-96
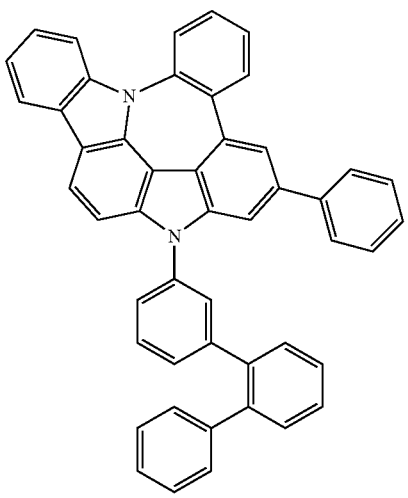
C1-97
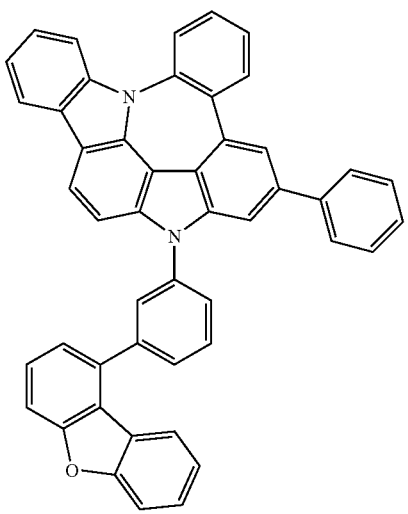

C1-98
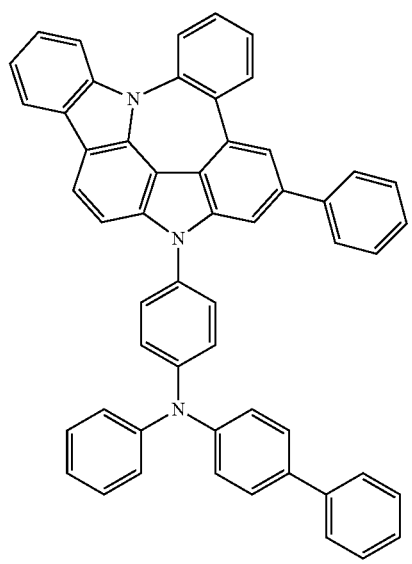
C1-101
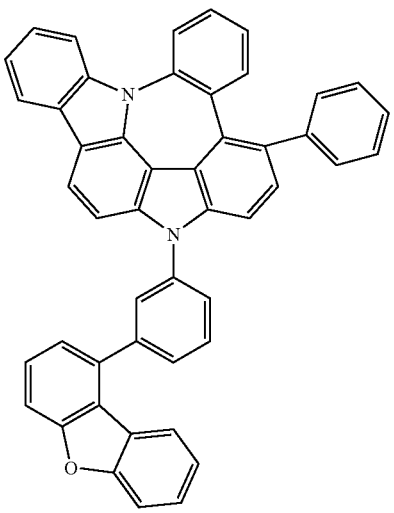
C1-99
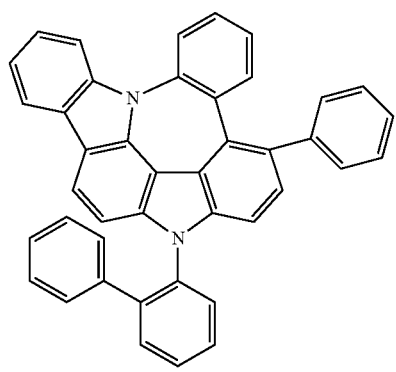
C1-102
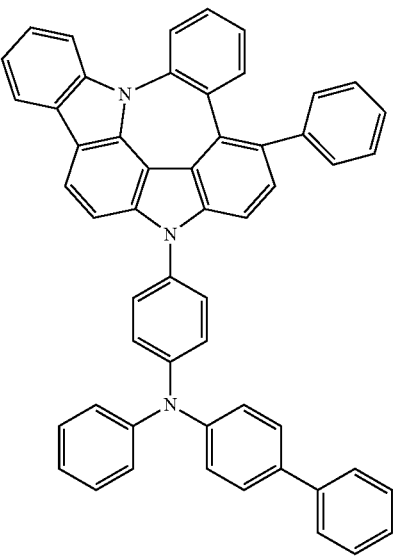
C1-100
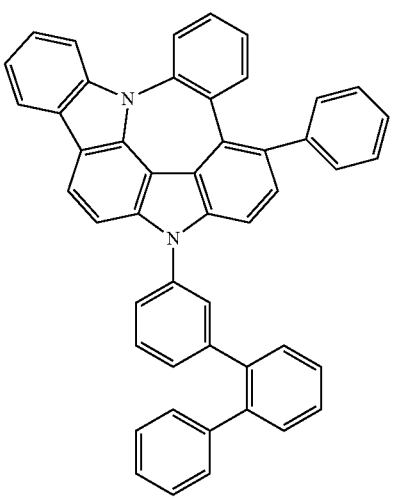
C1-103
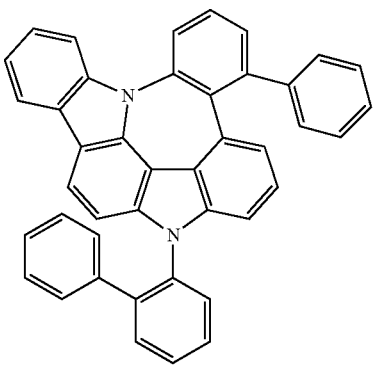

C1-104
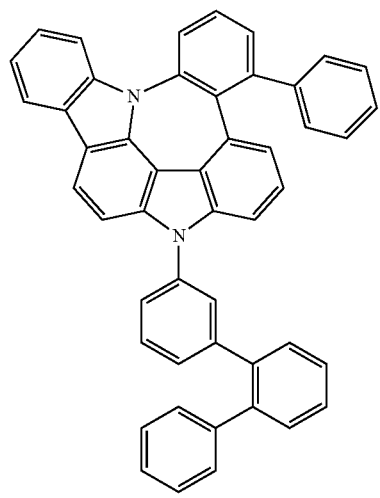
C1-105
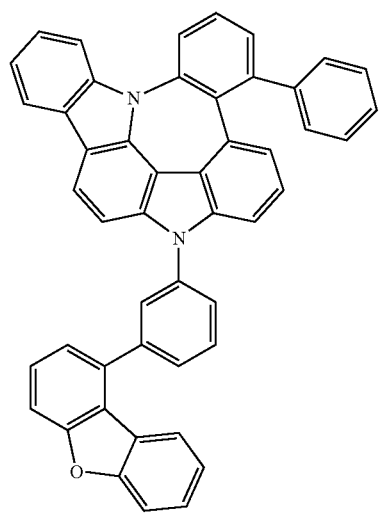
C1-106
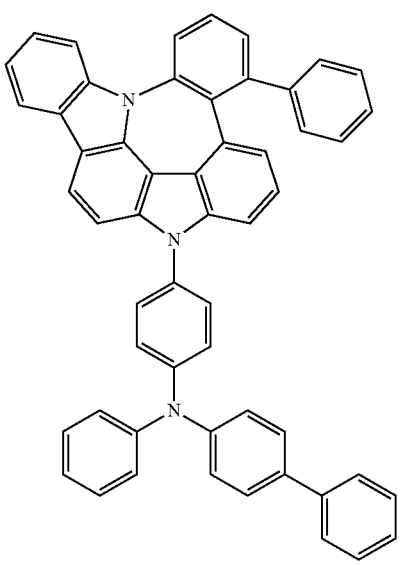
C1-107
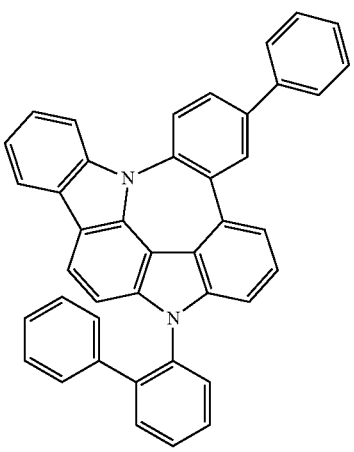
C1-108
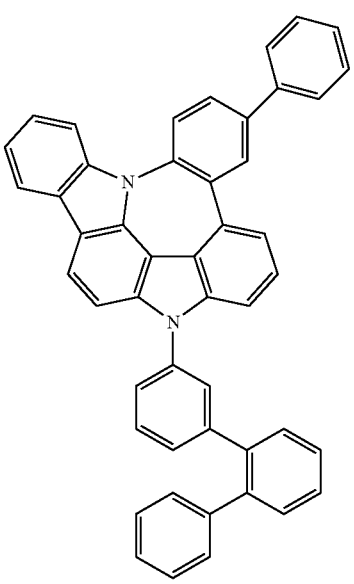
C1-109
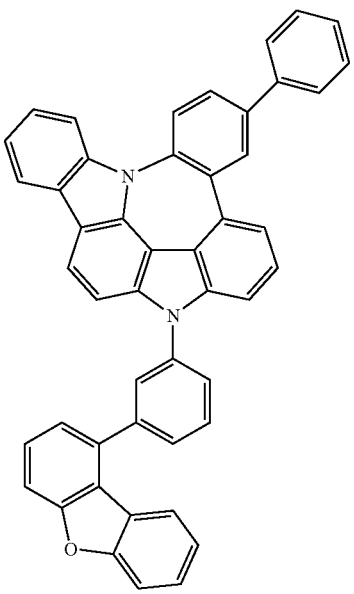

-continued
C1-110
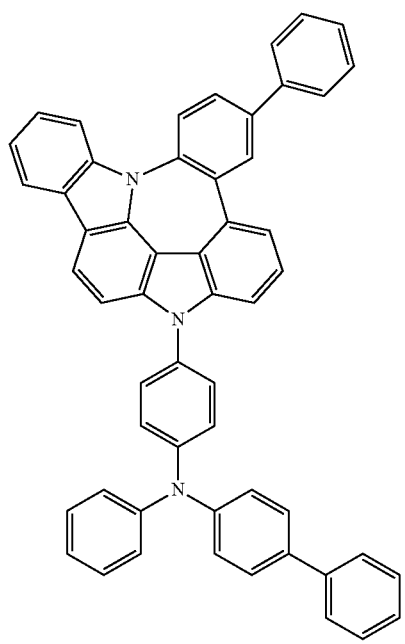
C1-111
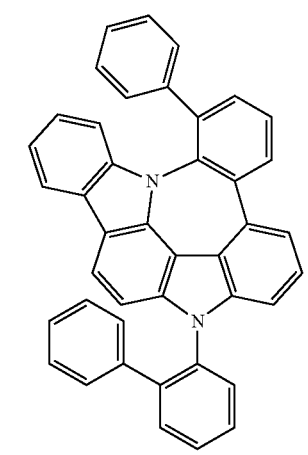
C1-112
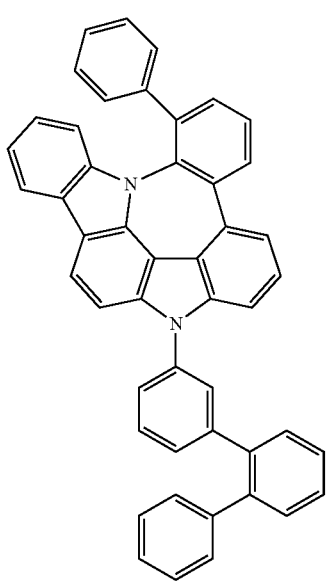
-continued
C1-113
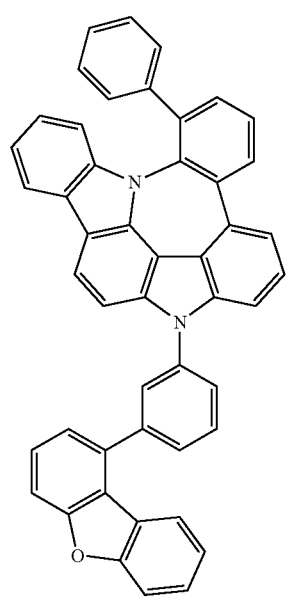
C1-114
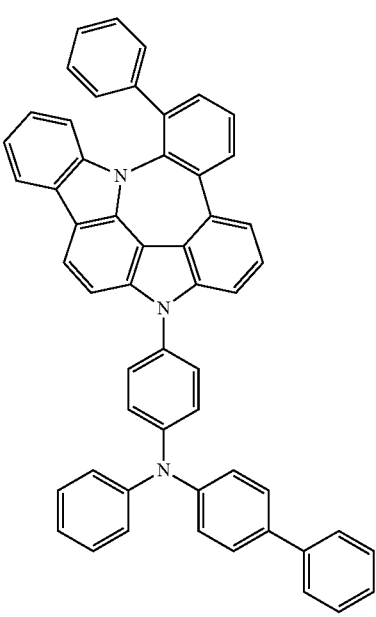
C1-115
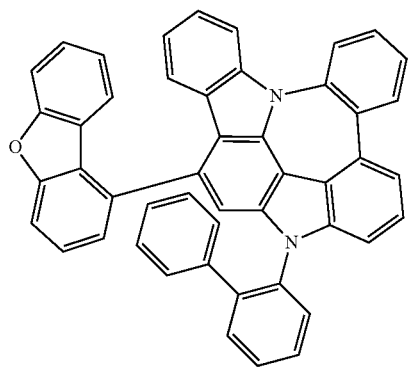

C1-116
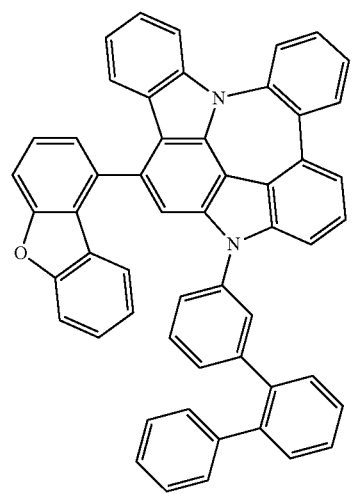
C1-117
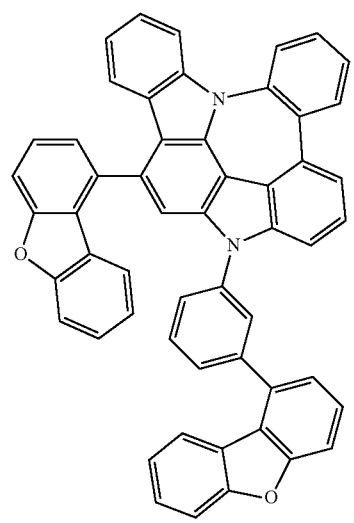
C1-118
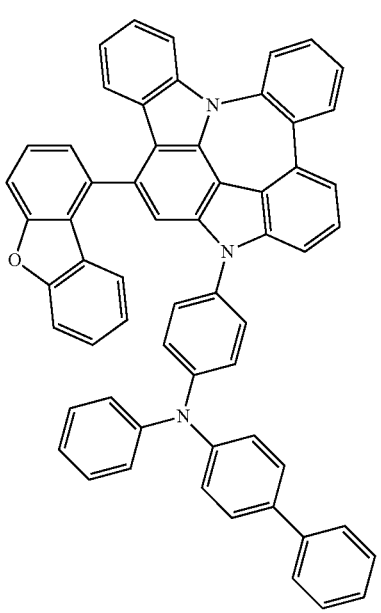
C1-119
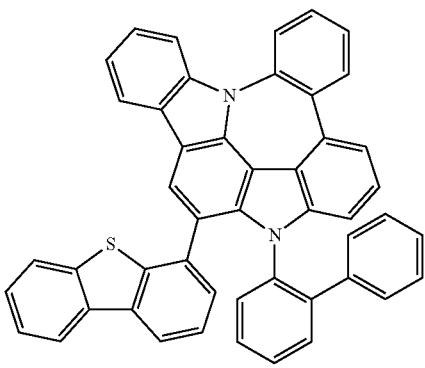
C1-120
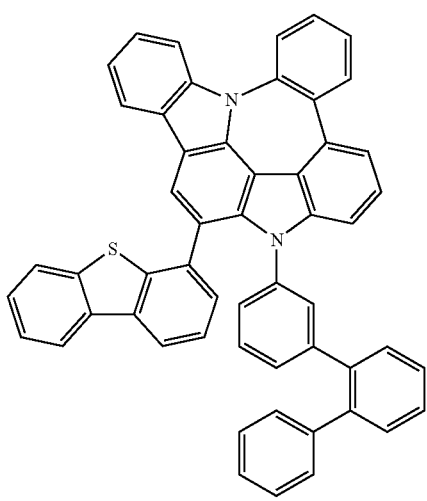
C1-121
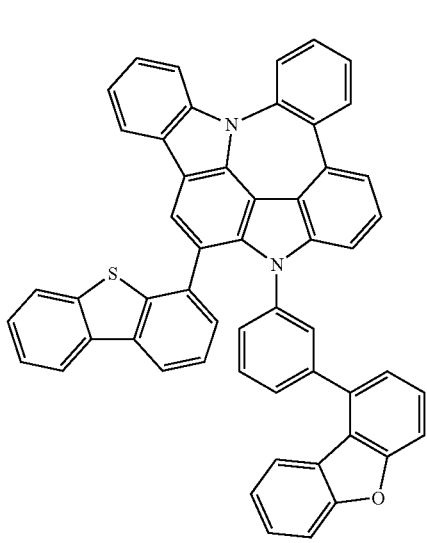

C1-122
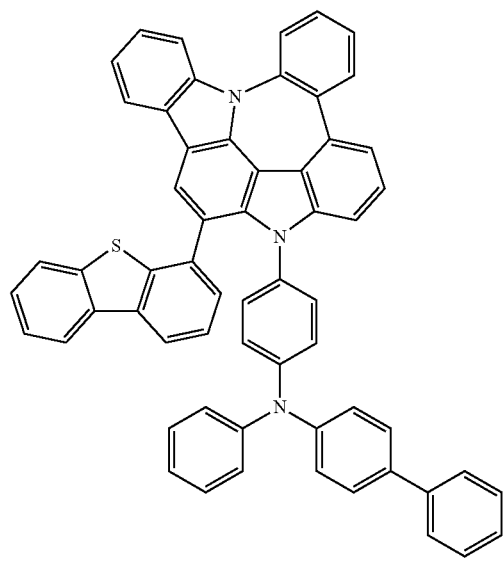
C1-123
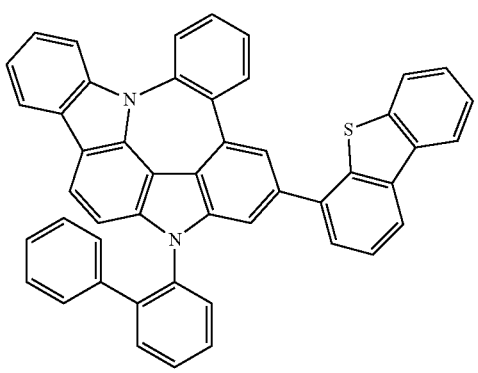
C1-124
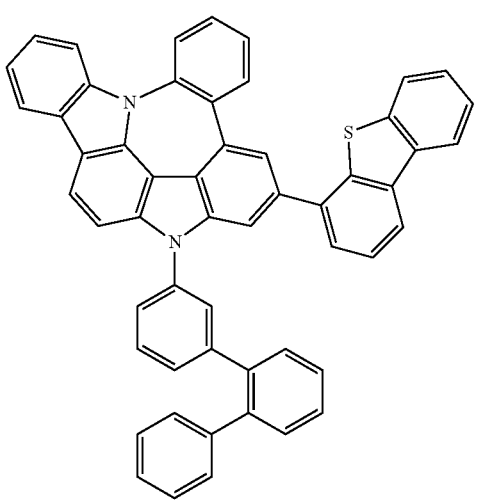
C1-125
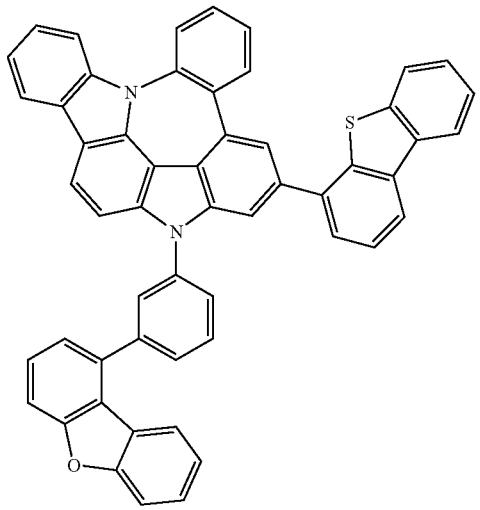
C1-126
C1-127
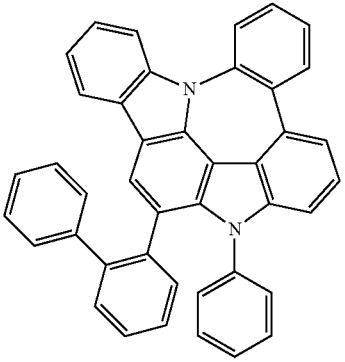

C1-128
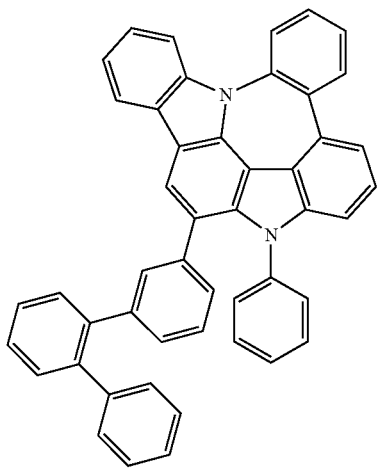
C1-129
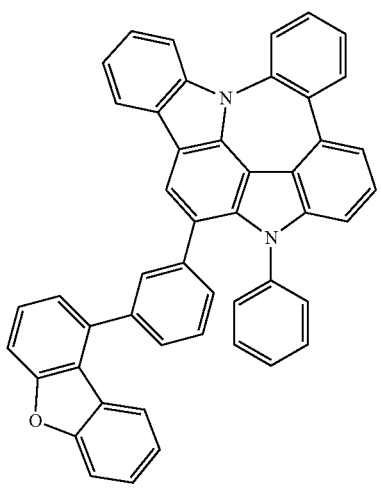
C1-130
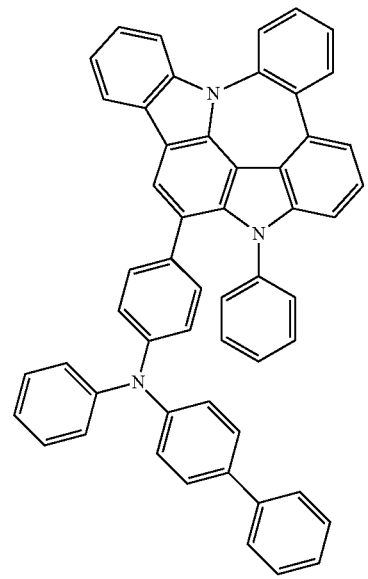
C1-131
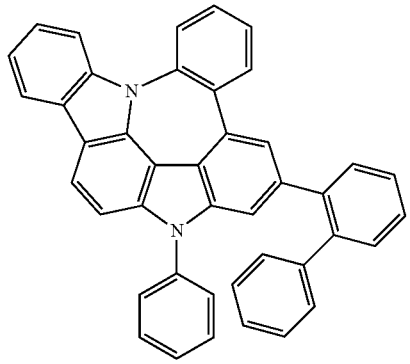
C1-132
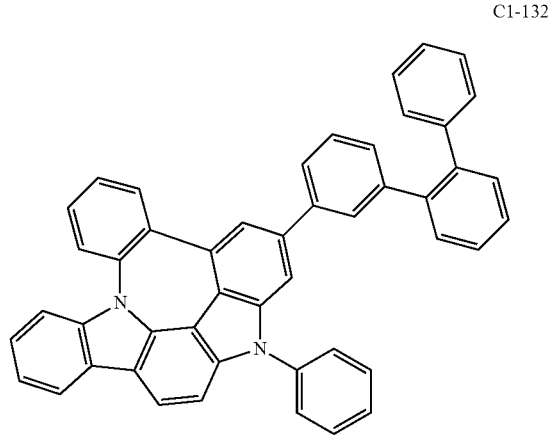
C1-133
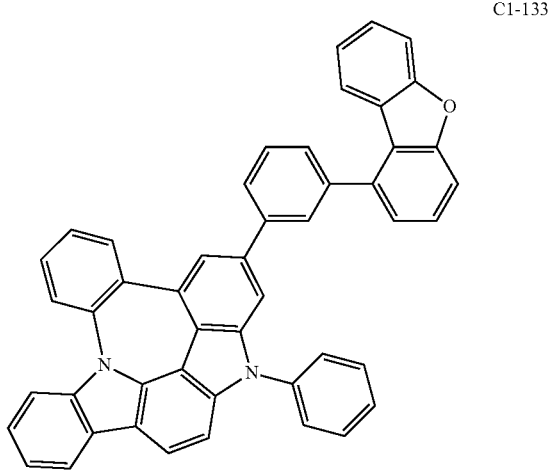

C1-134
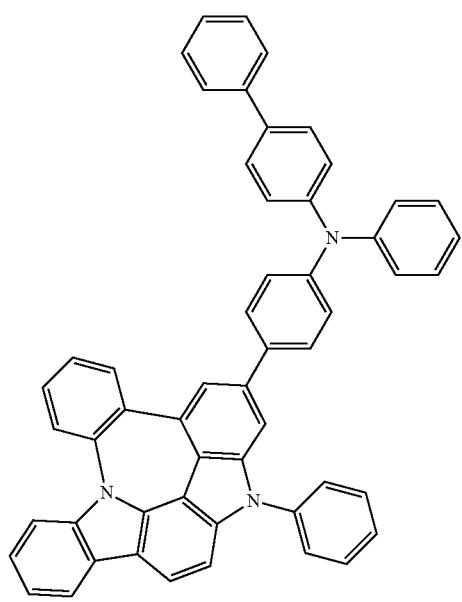
C1-135
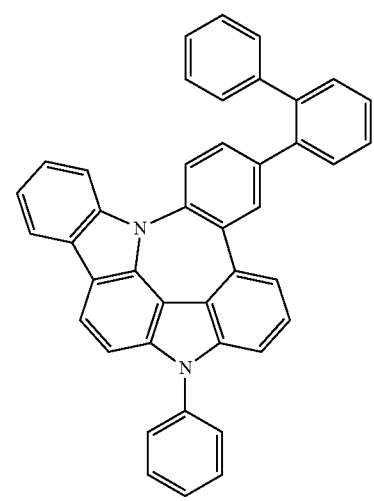
C1-136
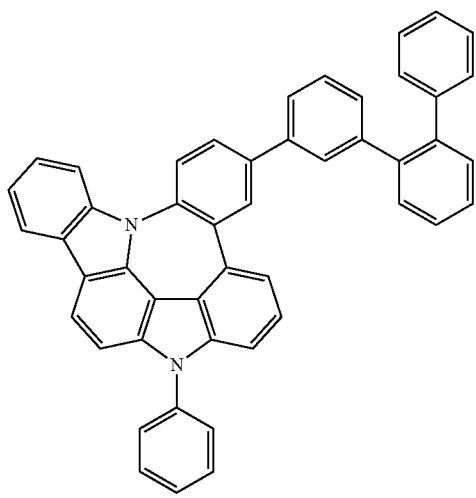
C1-137
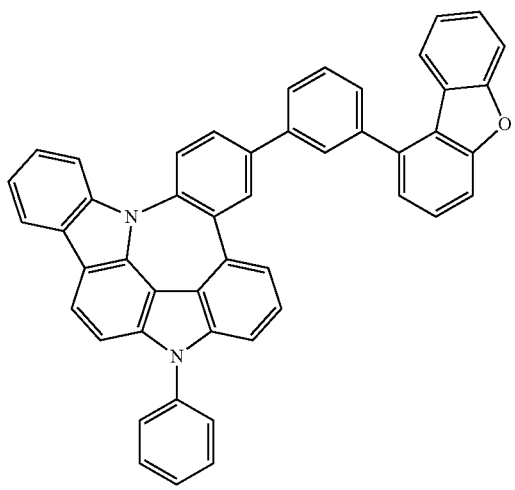
C1-138
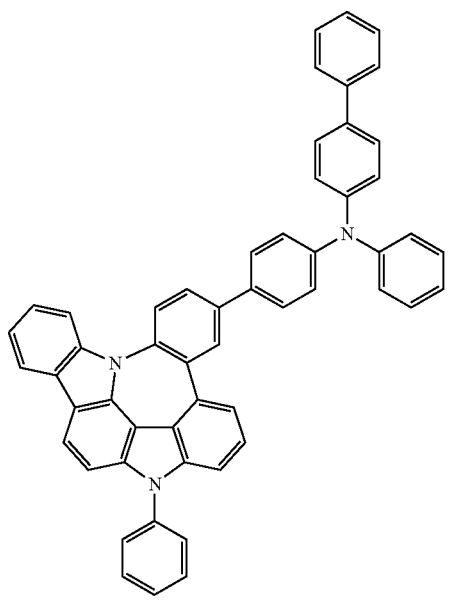
C1-139
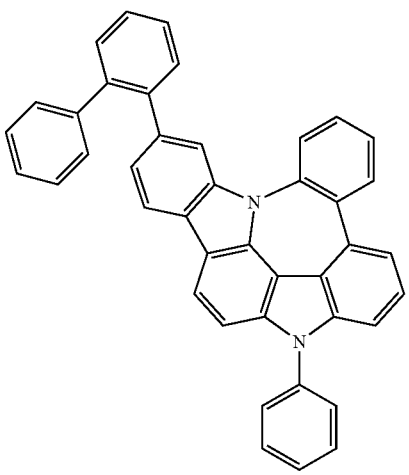

-continued
C1-140
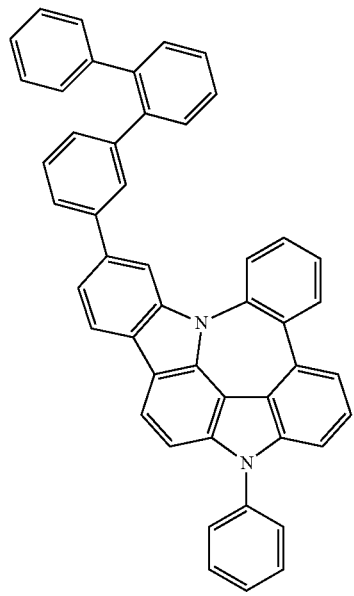
C1-141
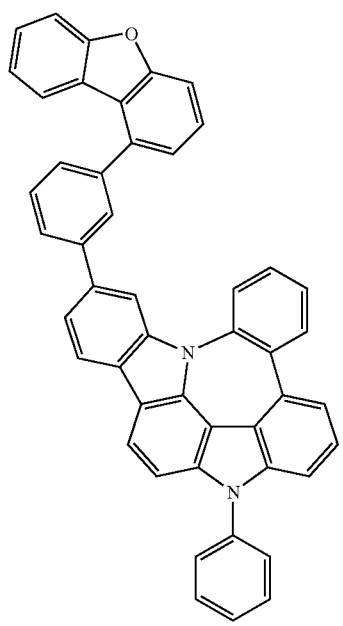
-continued
C1-142
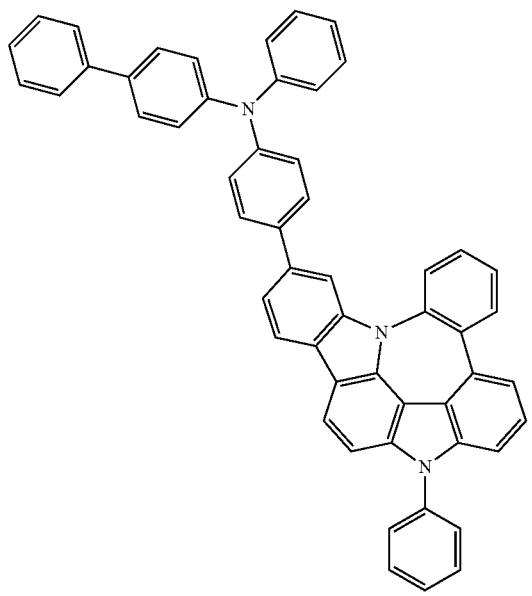
C1-143
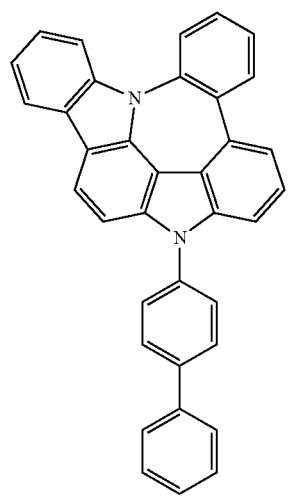
C1-144
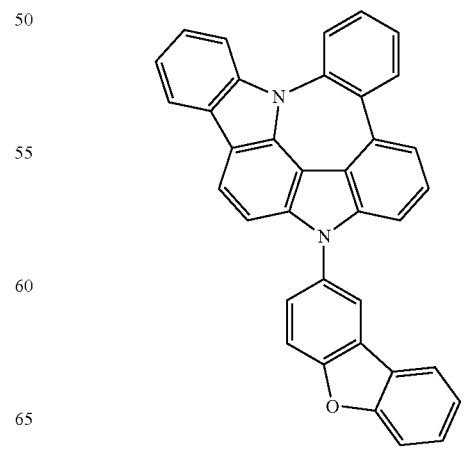

C1-145
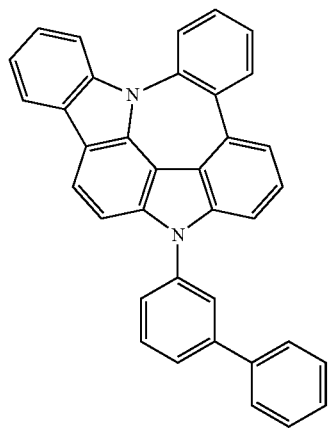
C1-146
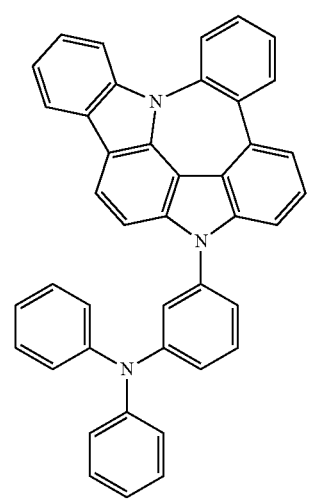
C1-147
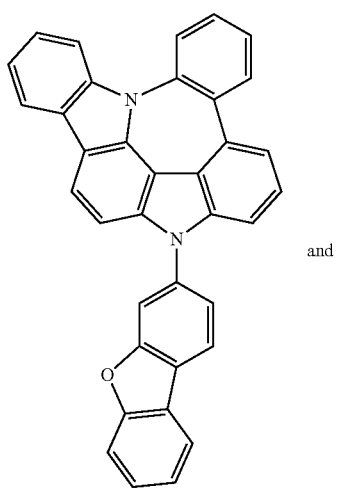
and
C1-148
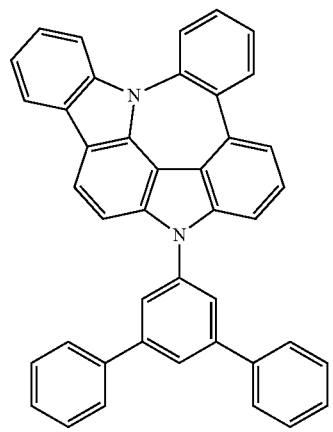
9. The plurality of host materials according to claim 1, wherein the compound represented by formula 2 is selected from the following compounds:
C2-1
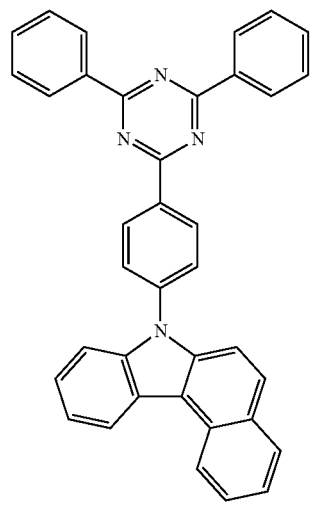
C2-2
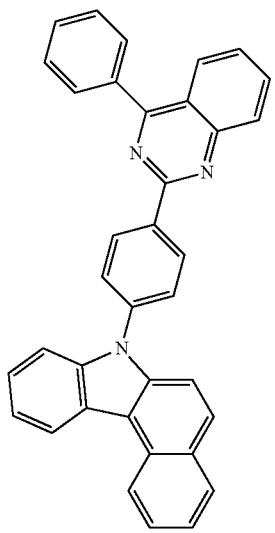

-continued
C2-3
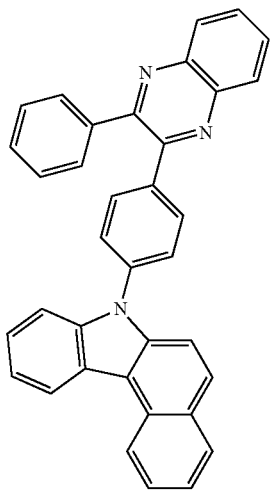
C2-4
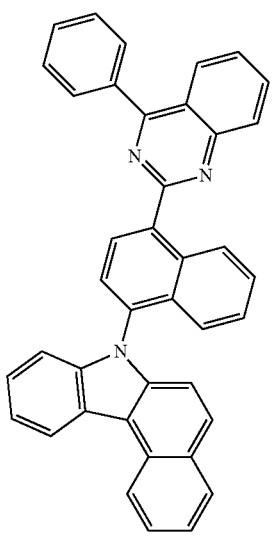
C2-5
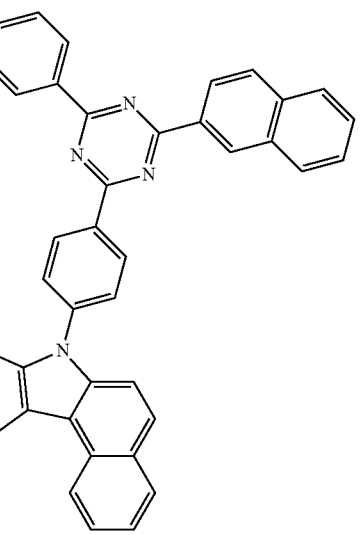
-continued
C2-6
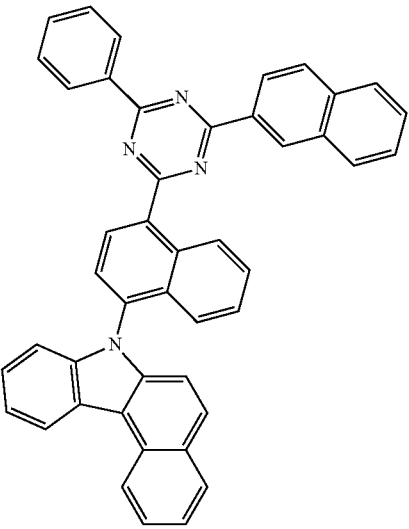
C2-7
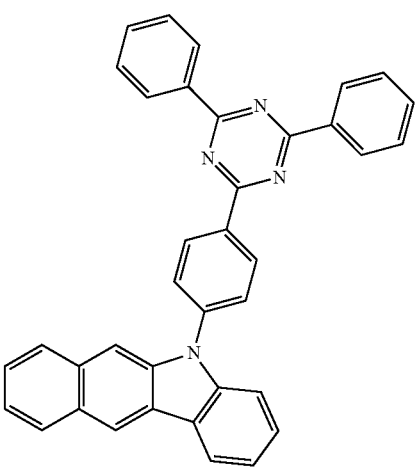
C2-8
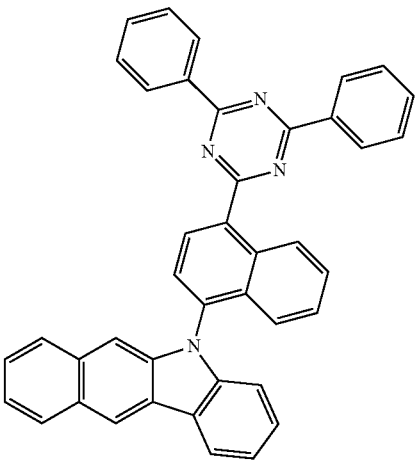

C2-9
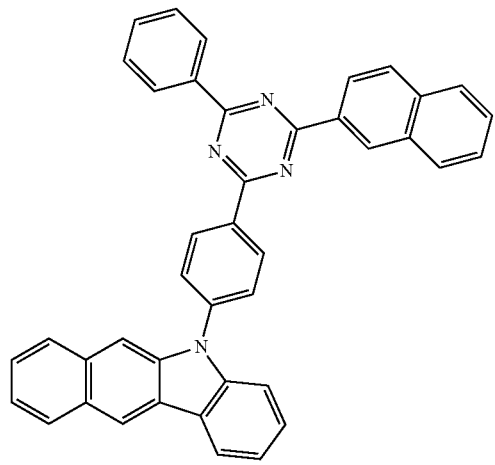
C2-10
C2-11
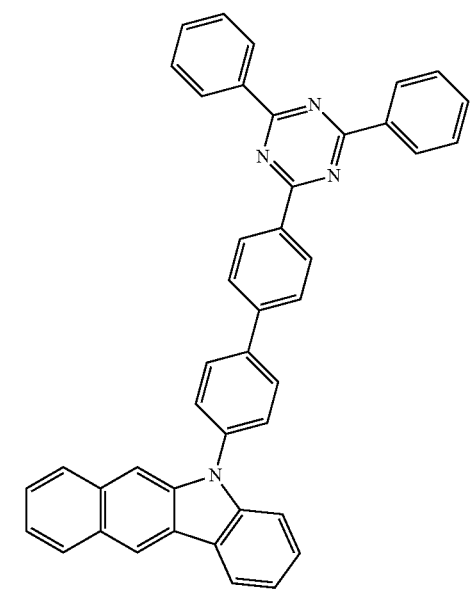
C2-12
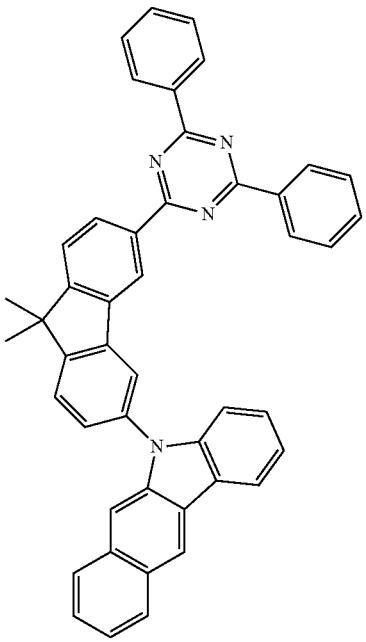
C2-13
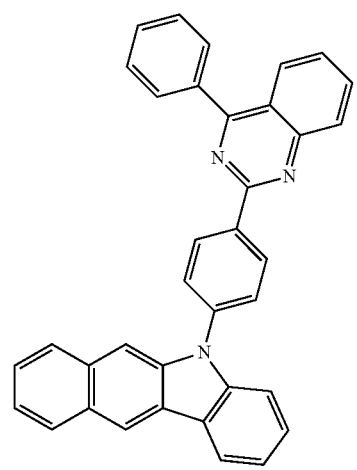
C2-14
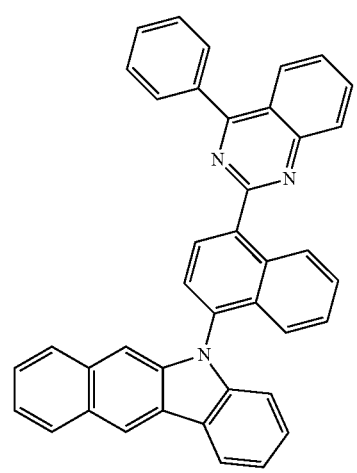

-continued
C2-15
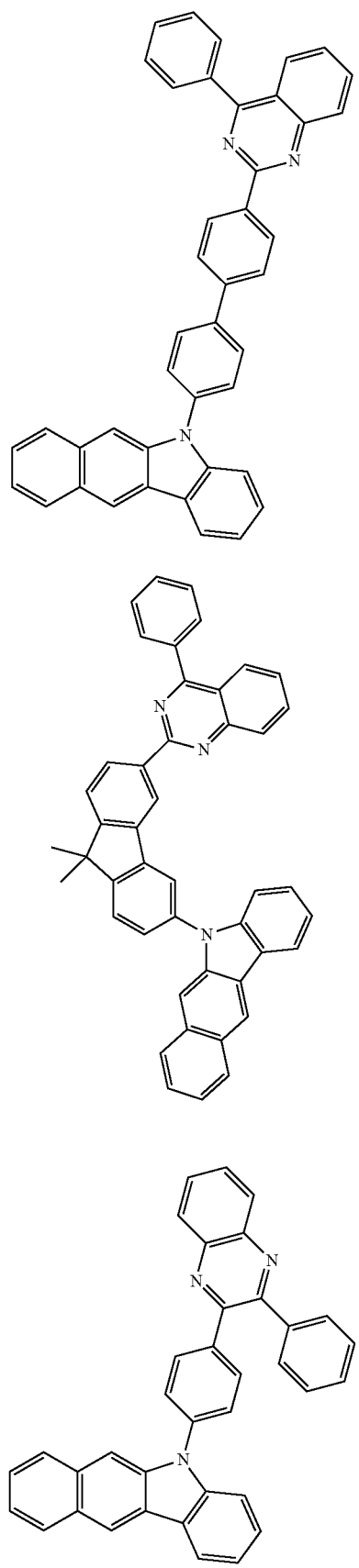
C2-16
C2-17
-continued
C2-18
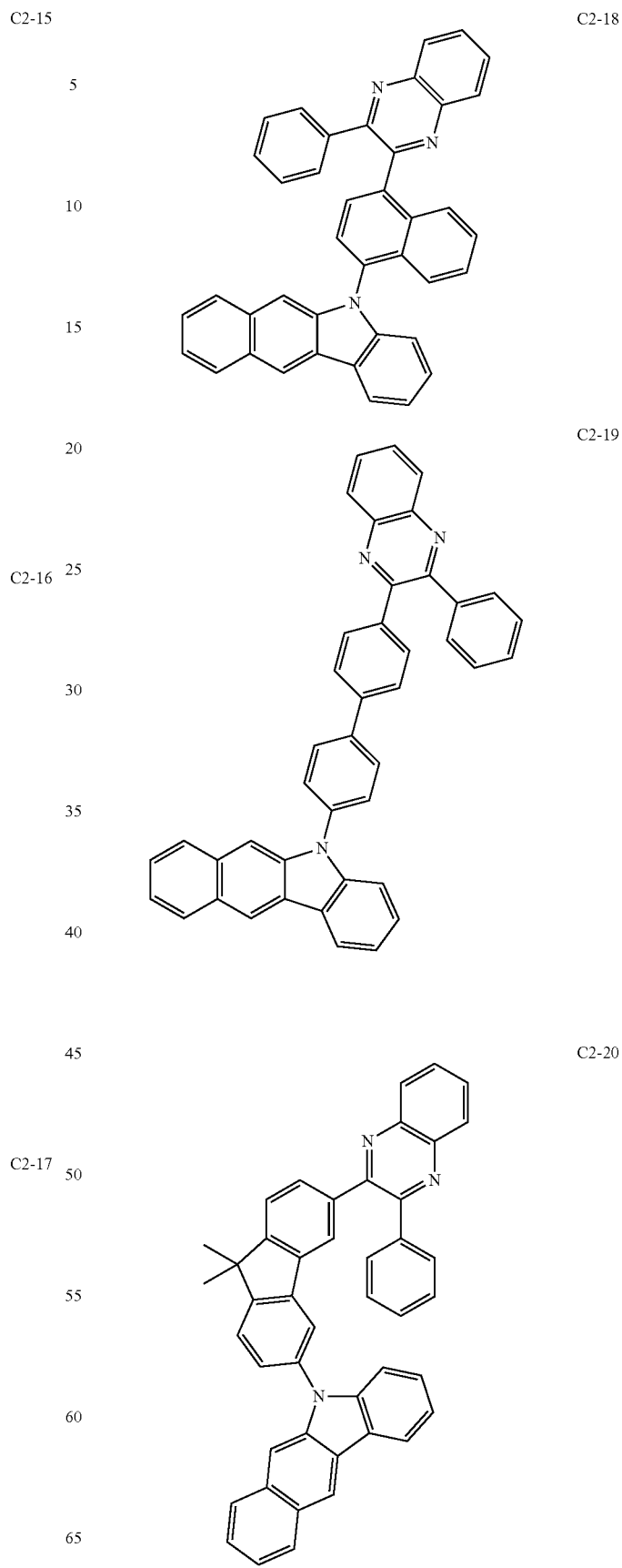
C2-19
C2-20

-continued
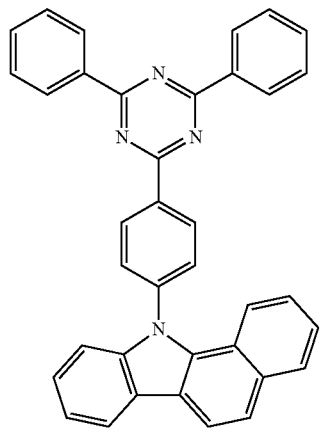
C2-21
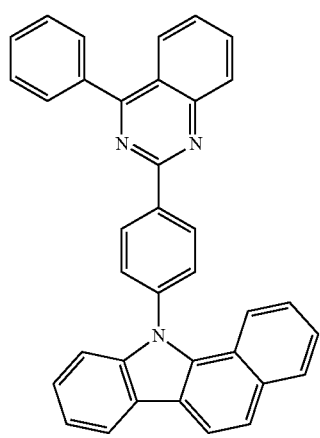
C2-22
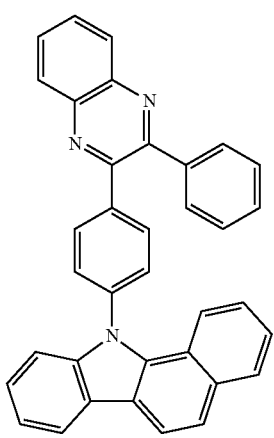
C2-23
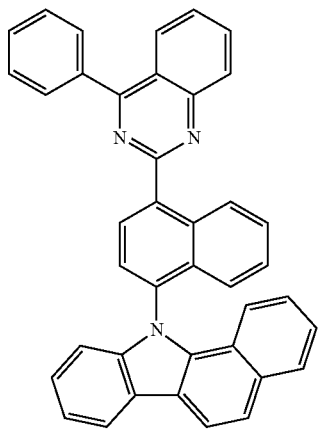
C2-24
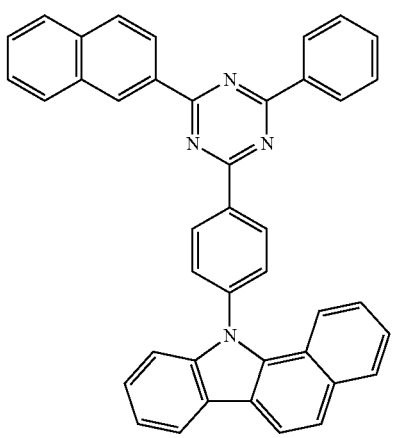
C2-25
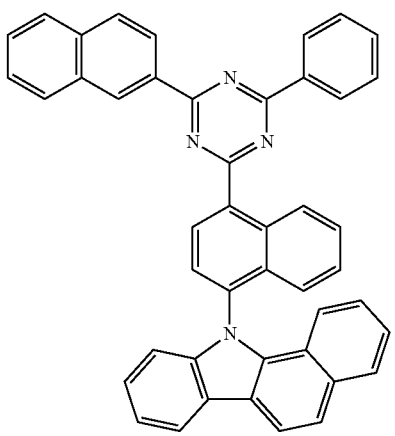
C2-26

-continued
C2-27
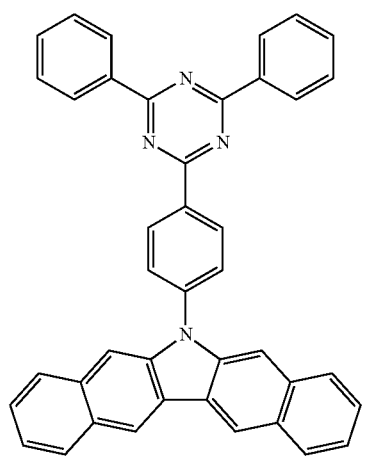
C2-28
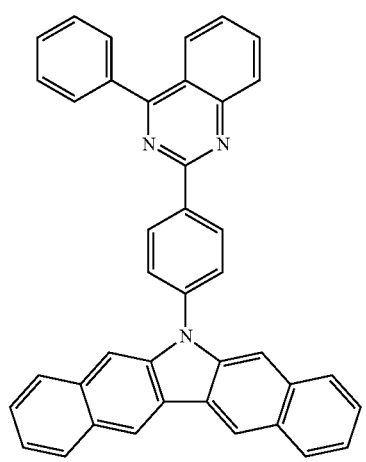
C2-29
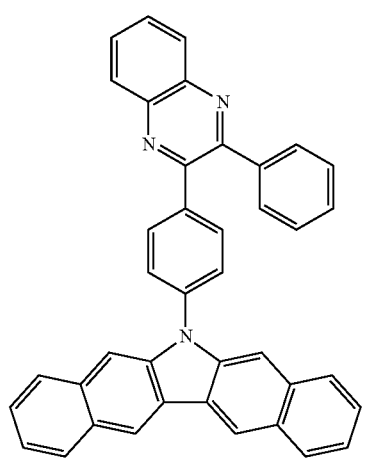
-continued
C2-30
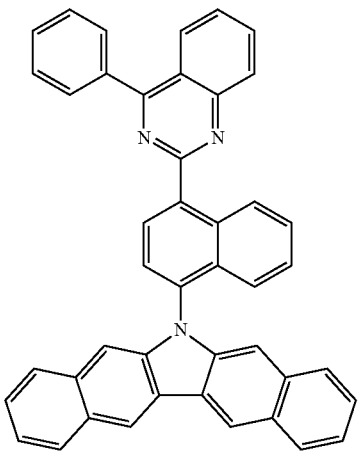
C2-31
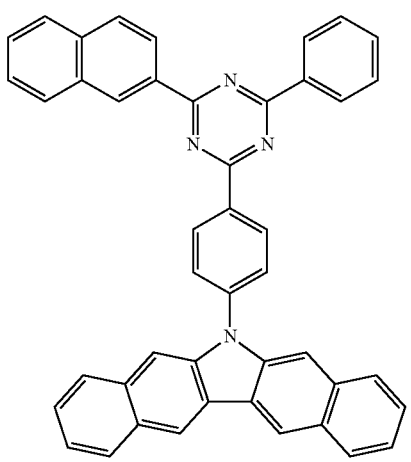
C2-32
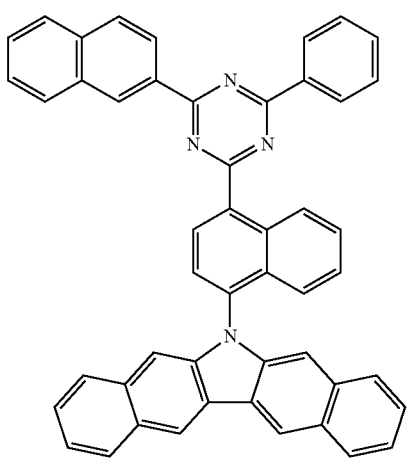

C2-33
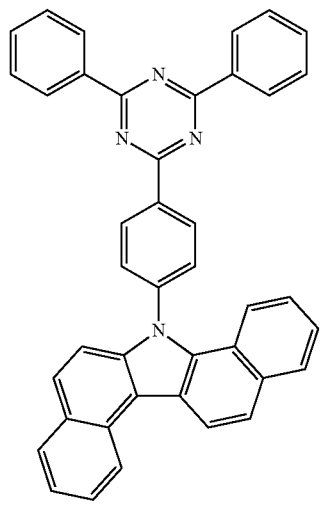
C2-34
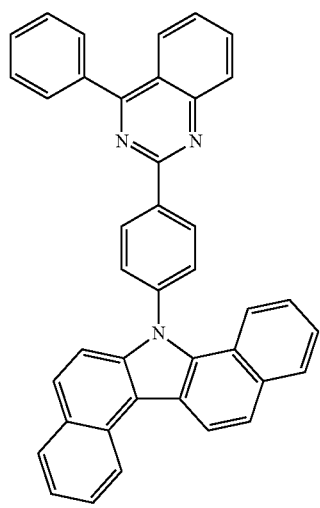
C2-35
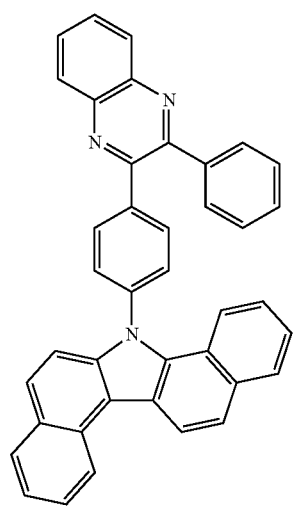
C2-36
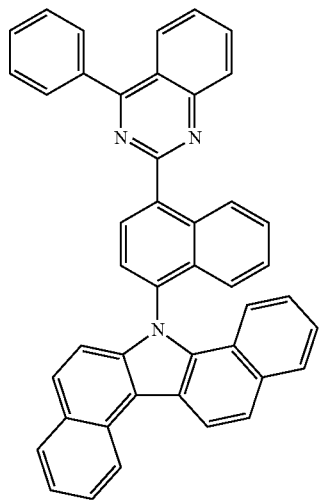
C2-37
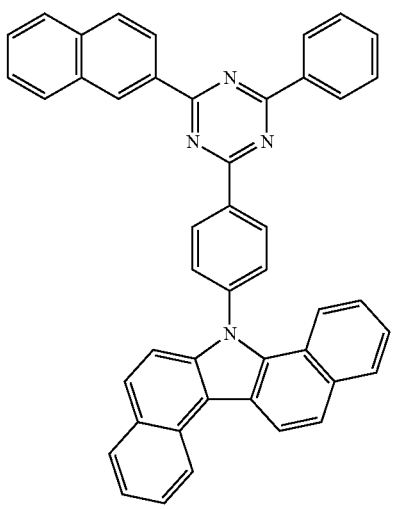
C2-38
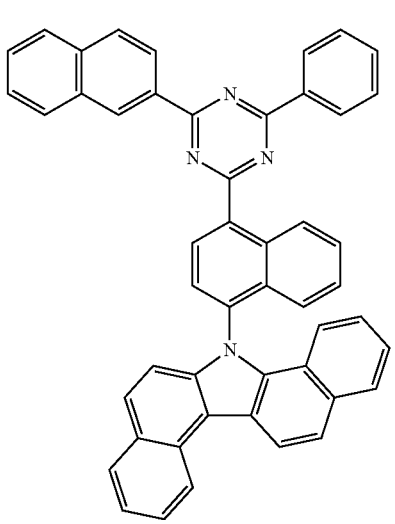

C2-39
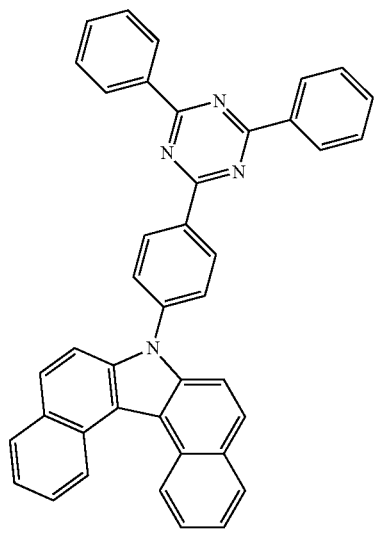
C2-41
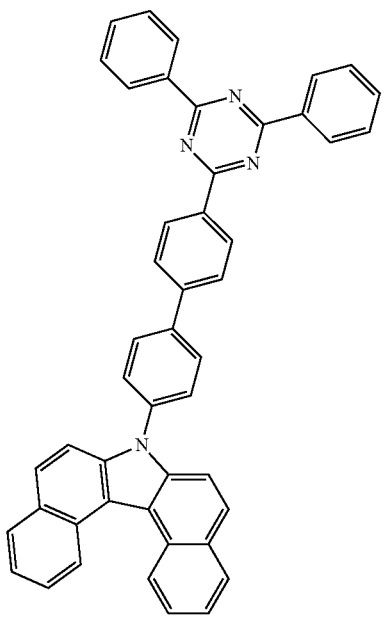
C2-40
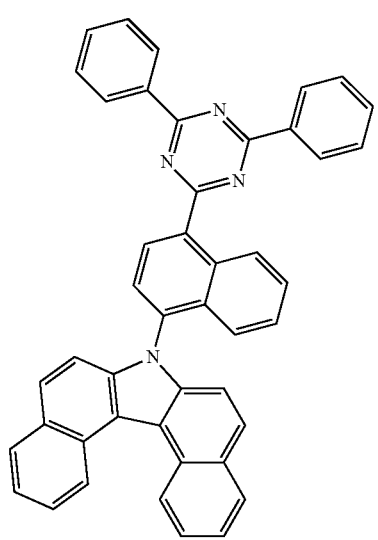
C2-42
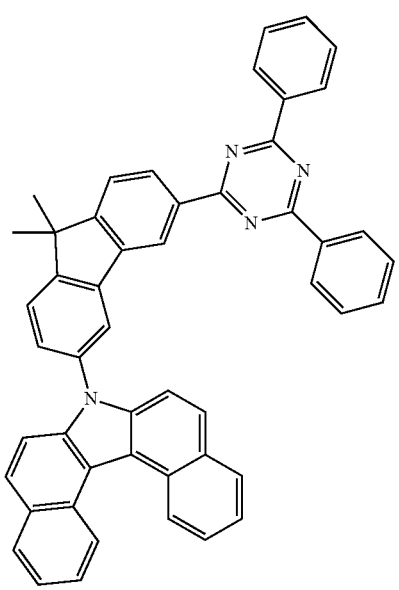

C2-43
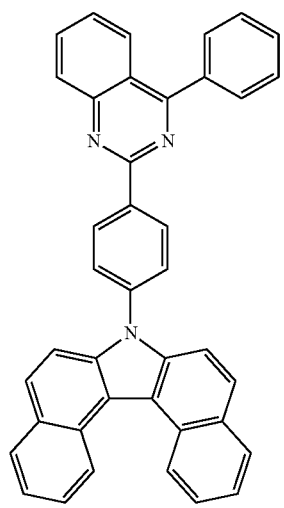
C2-44
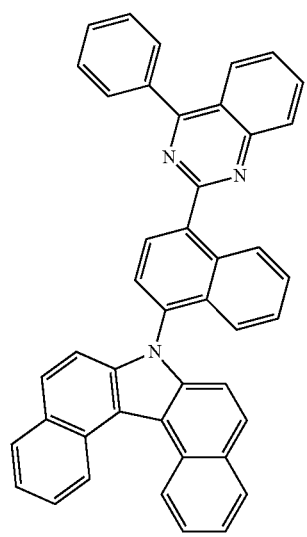
C2-45
C2-46
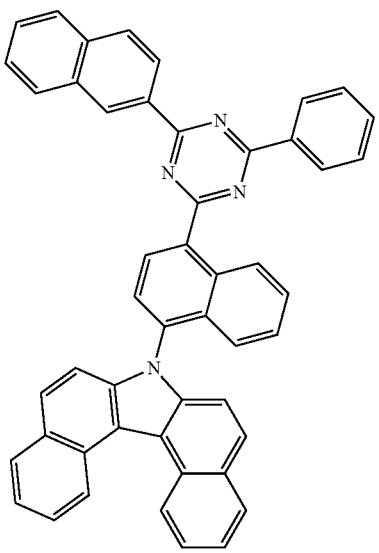
C2-47
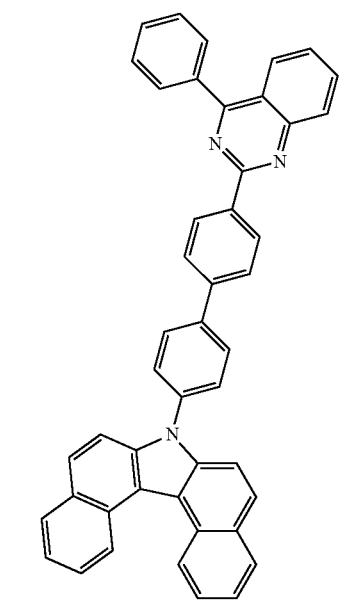

C2-48
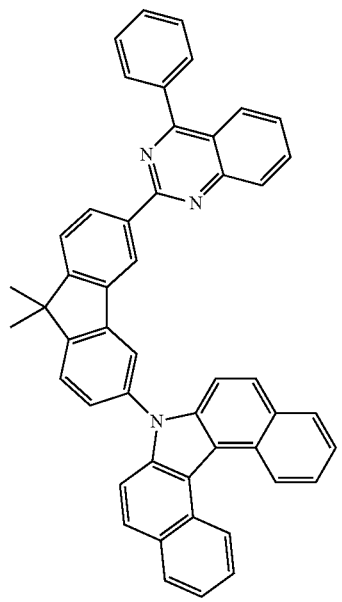
C2-49
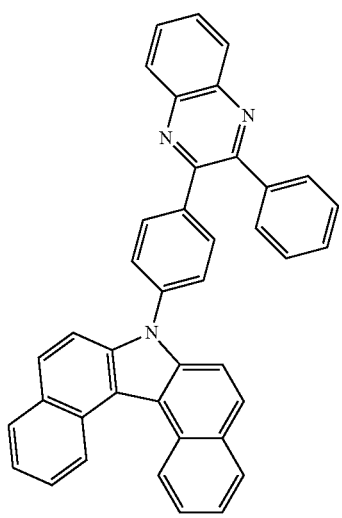
C2-50
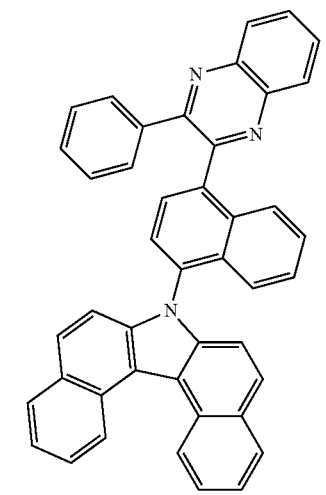
C2-51
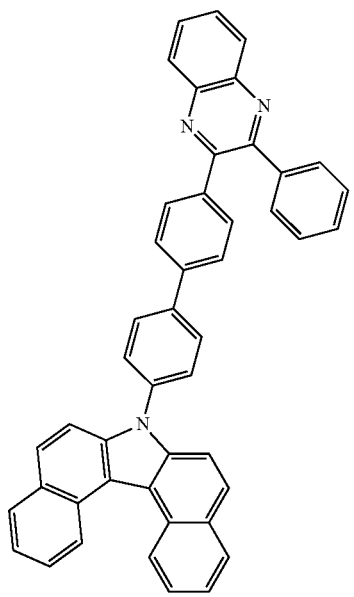
C2-52
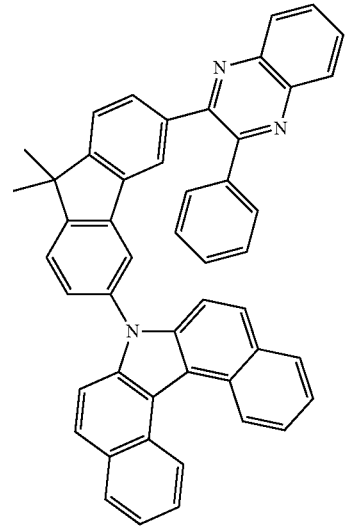
C2-53
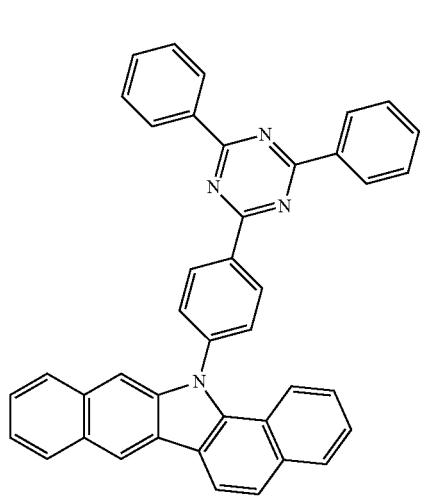

-continued
C2-54
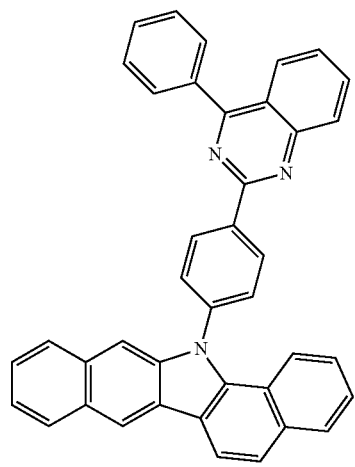
C2-55
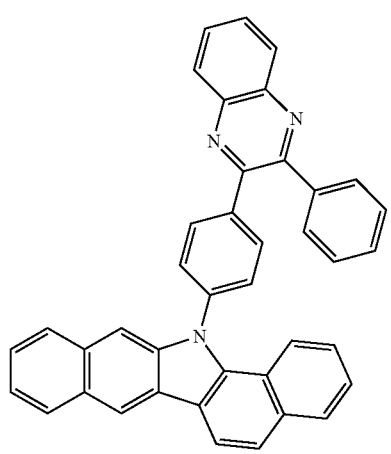
C2-56
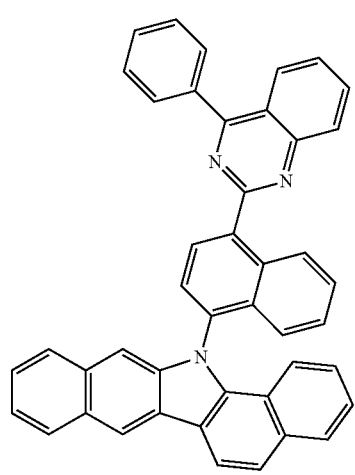
-continued
C2-57
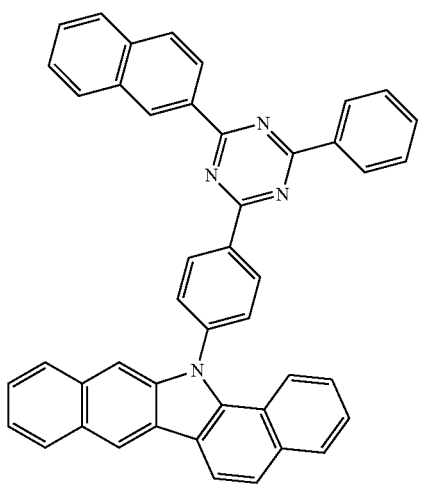
C2-58
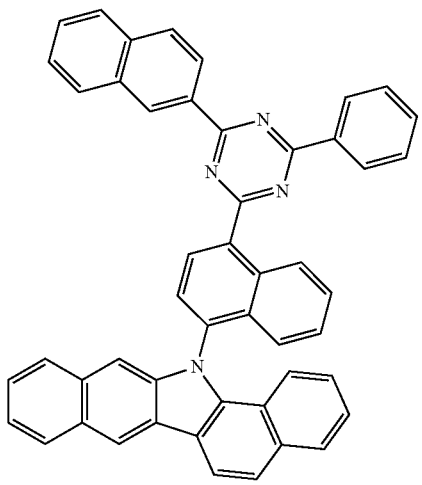
C2-59
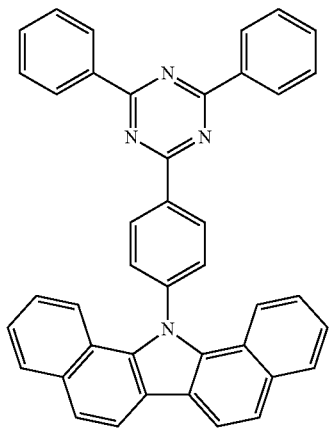

C2-60
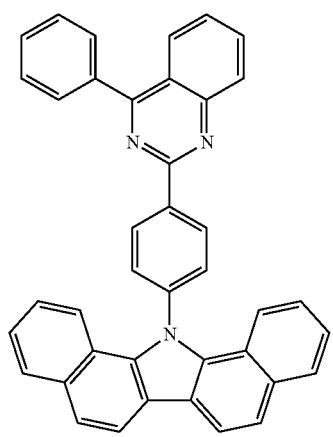
C2-61
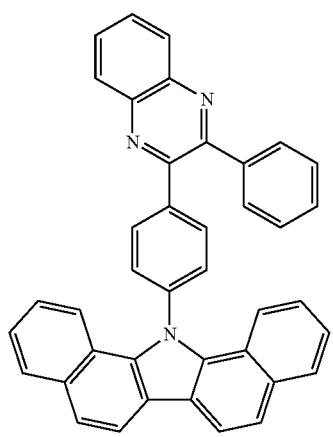
C2-62
C2-63
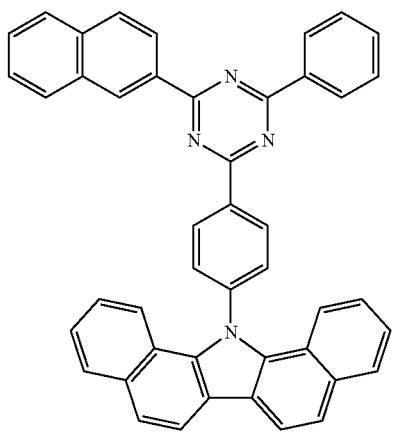
C2-64
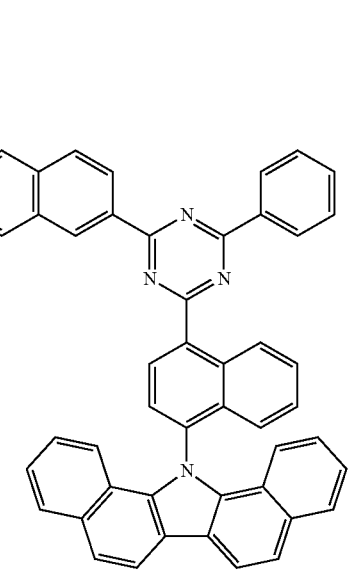
C2-65
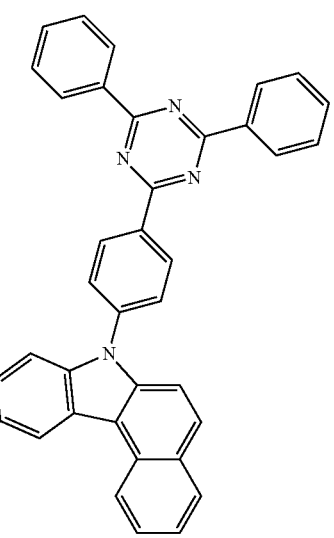

C2-66
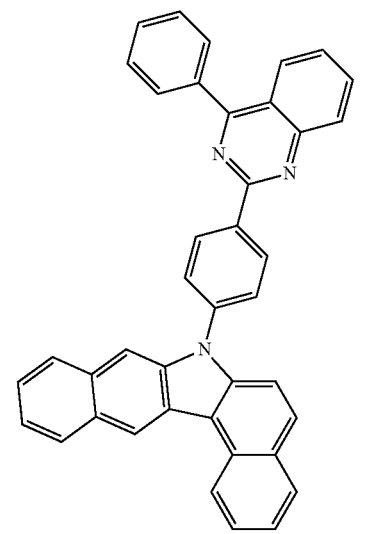
C2-67
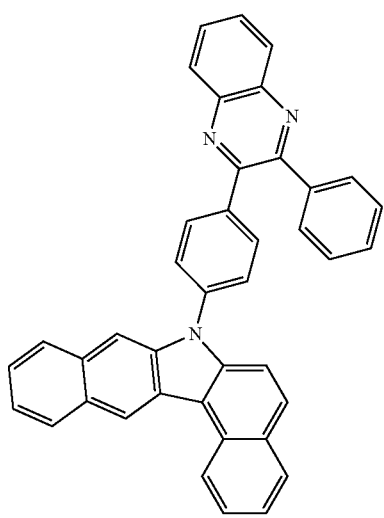
C2-68
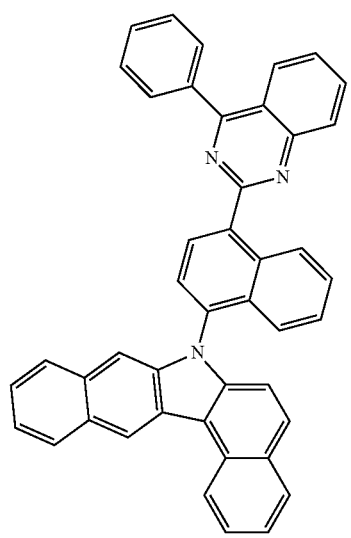
C2-69
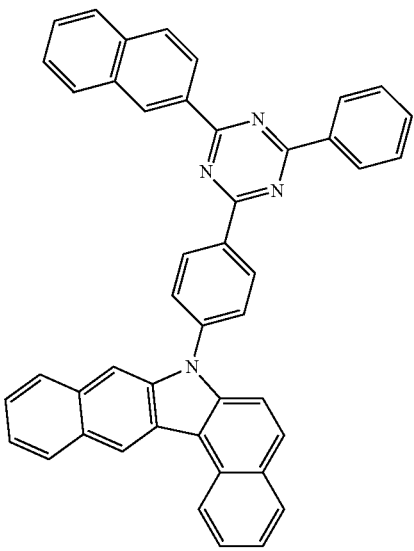
C2-70
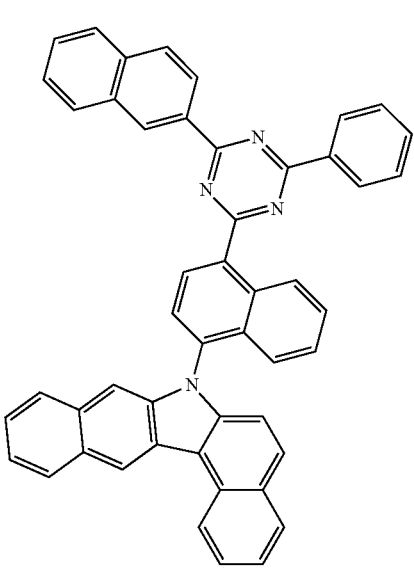
C2-71
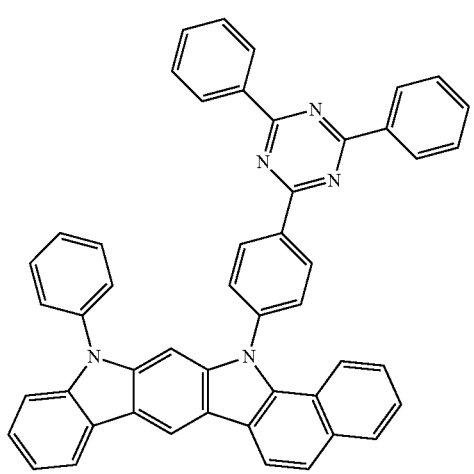

-continued
C2-72
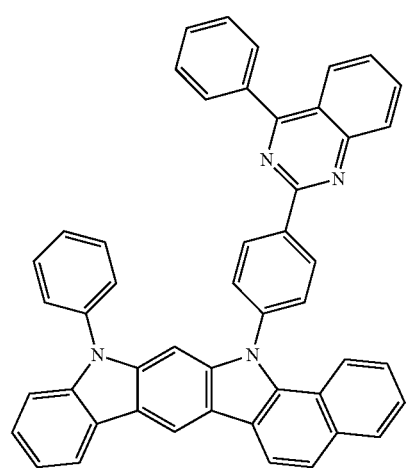
C2-73
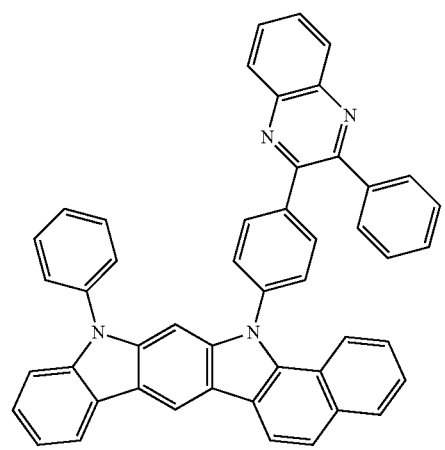
C2-74
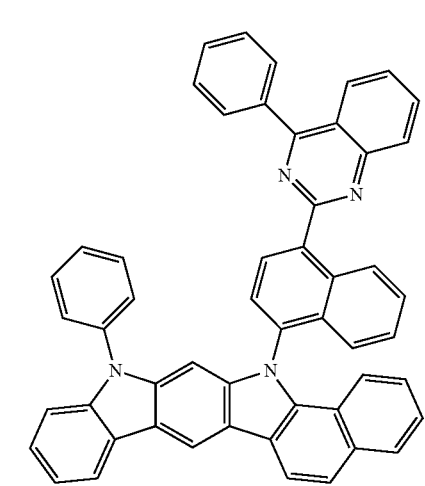
-continued
C2-75
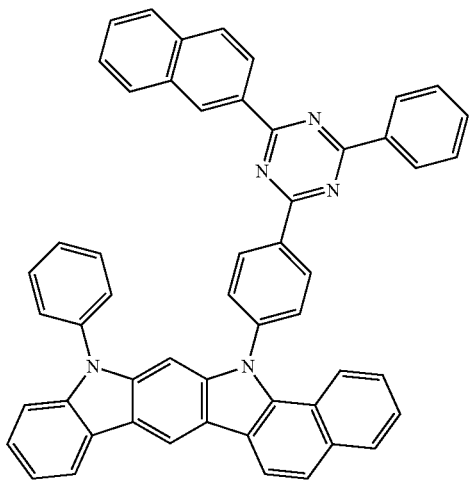
C2-76
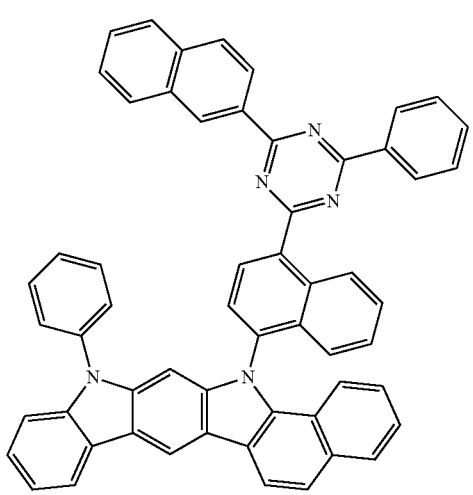
C2-77
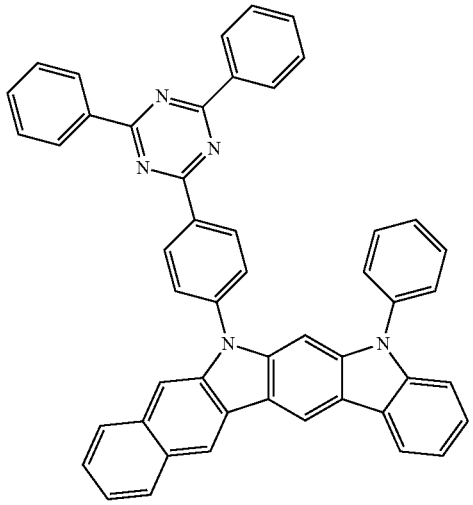

C2-78
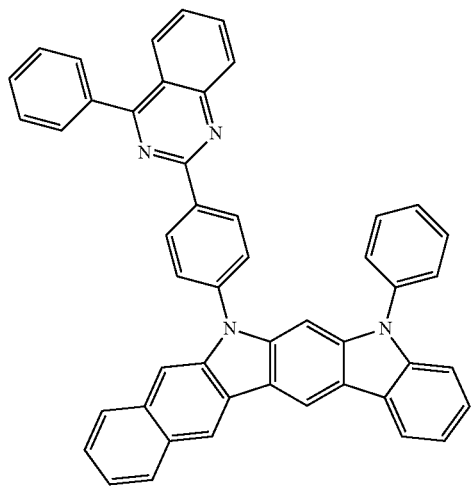
C2-79
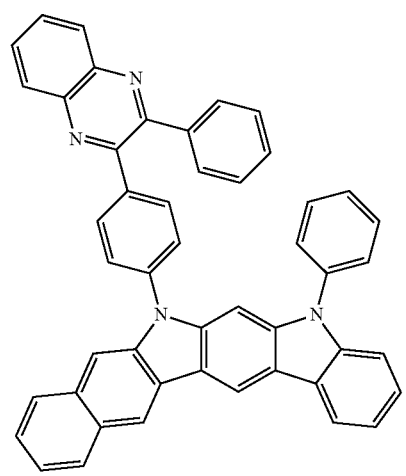
C2-80
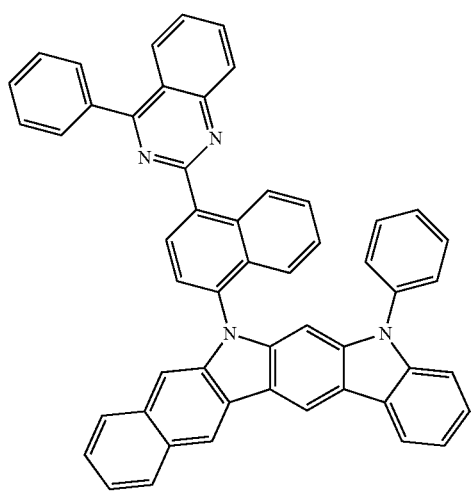
C2-81
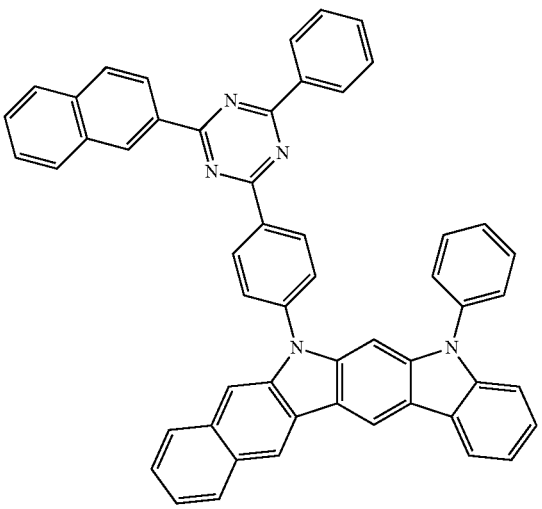
C2-82
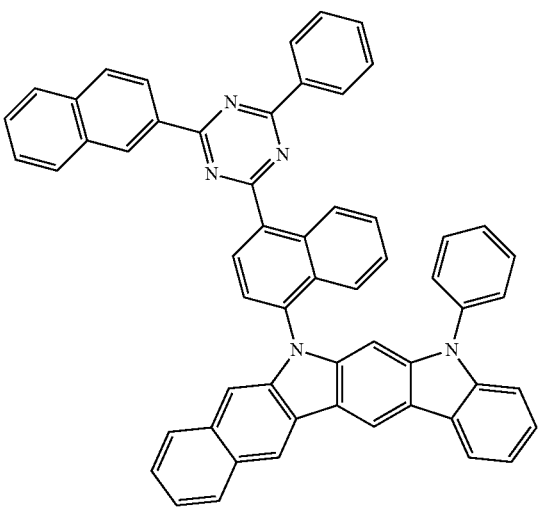
C2-83
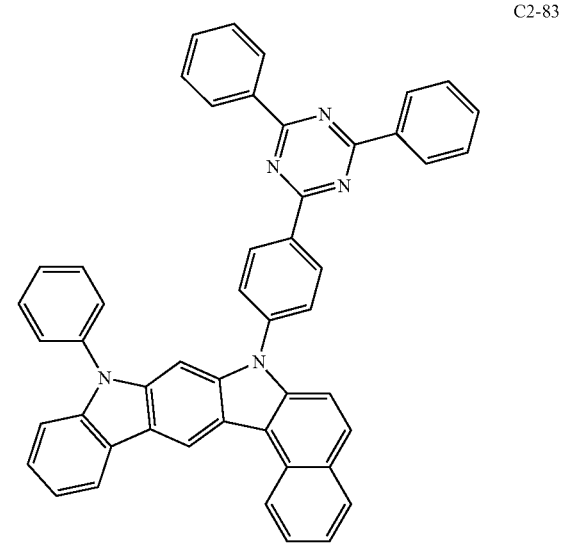

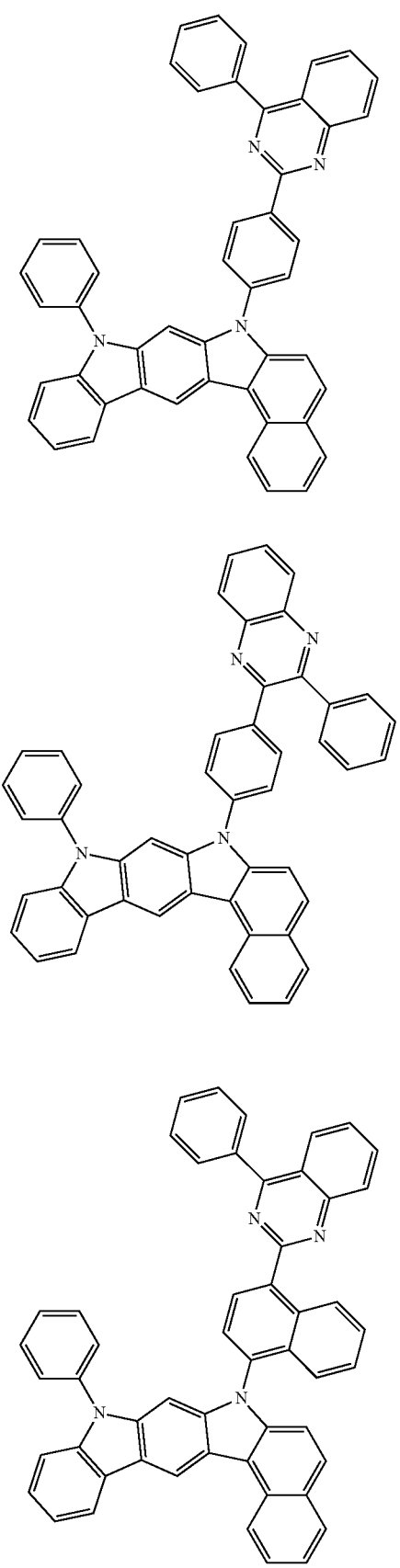
C2-84
C2-85
C2-86
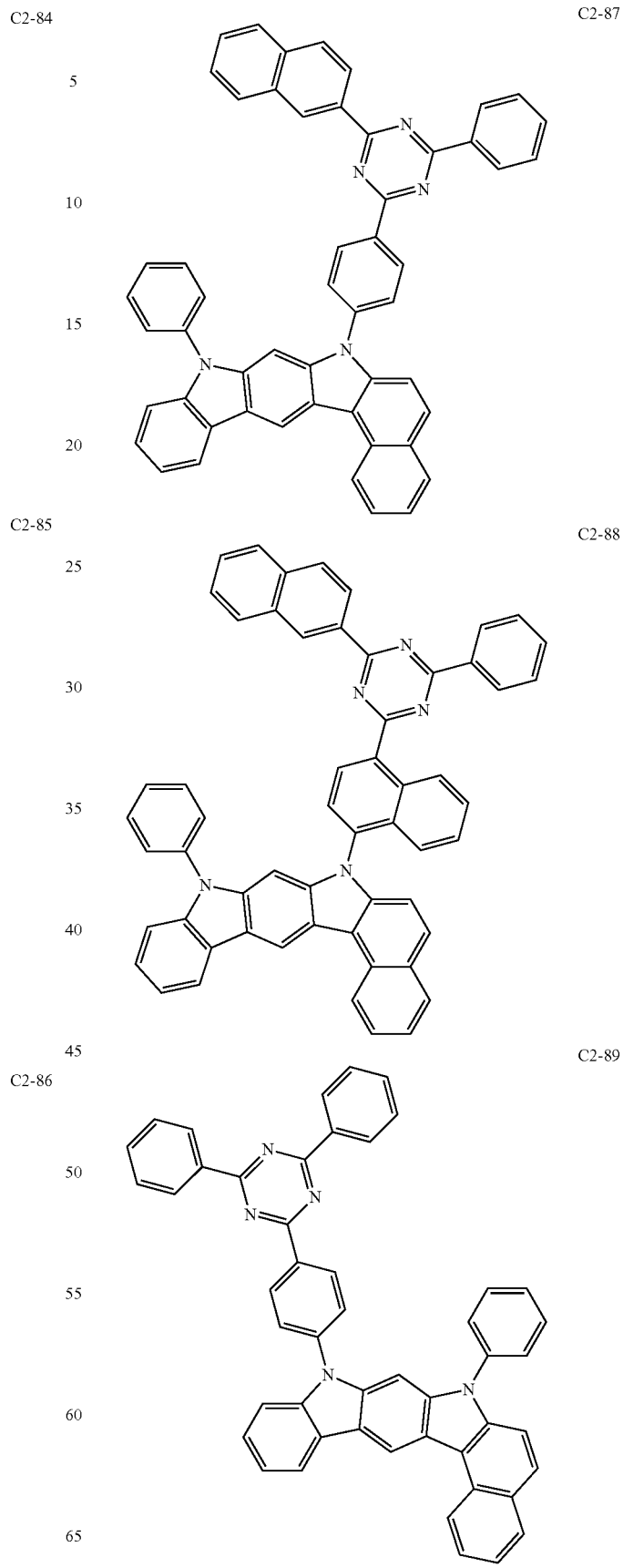
C2-87
C2-88
C2-89

C2-90
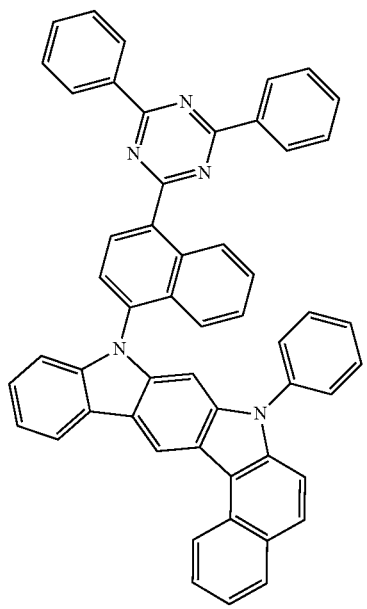
C2-91
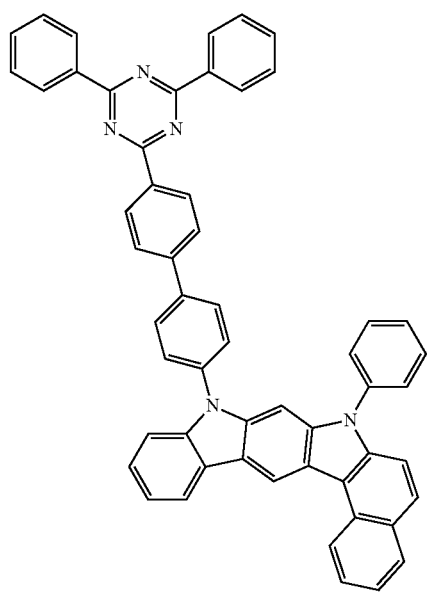
C2-92
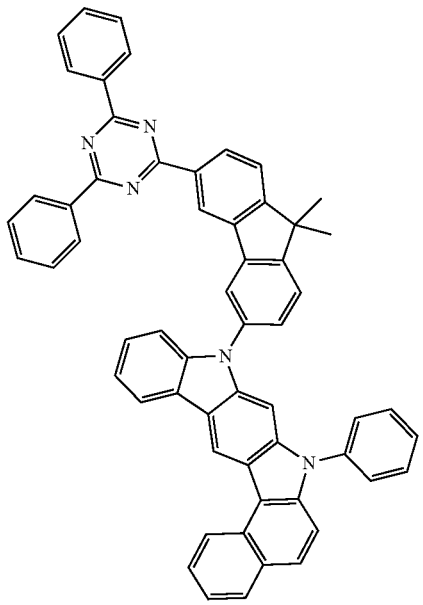
C2-93
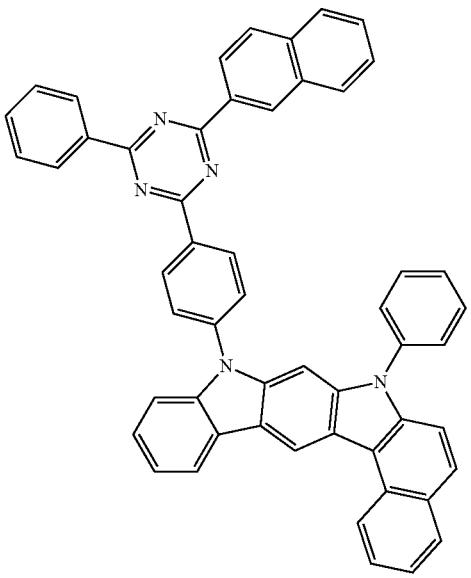

C2-94
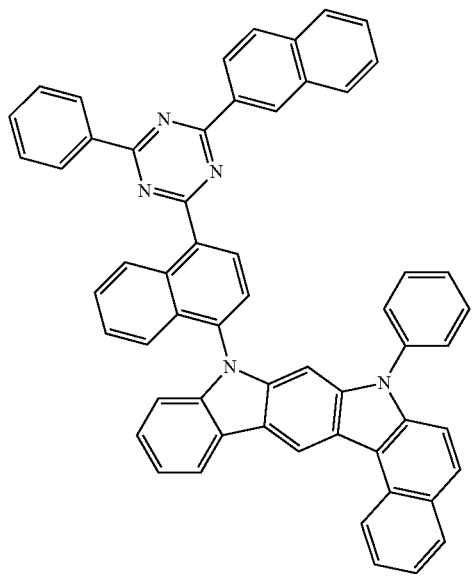
C2-96
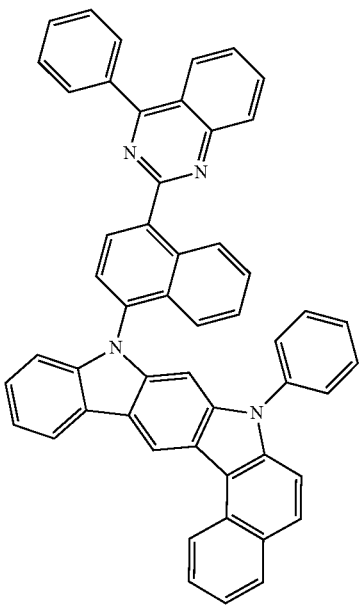
C2-95
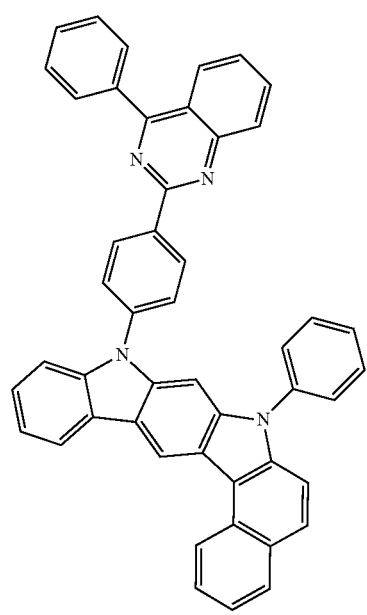
C2-97
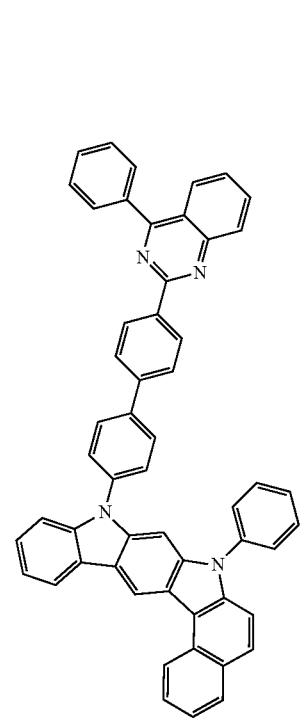

C2-98
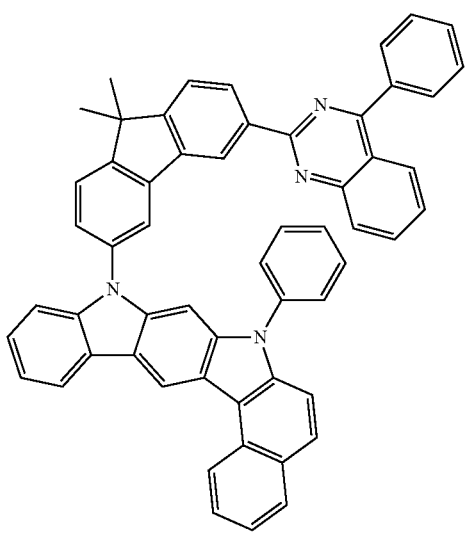
C2-100
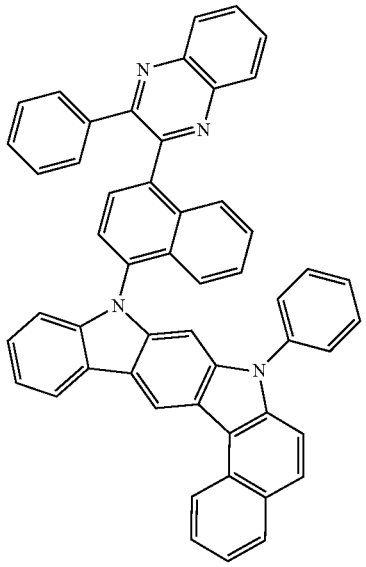
C2-99
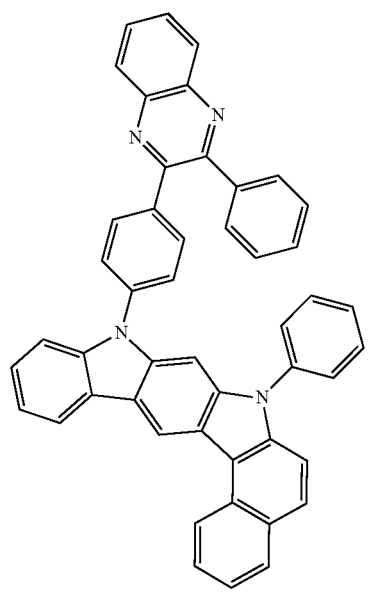
C2-101
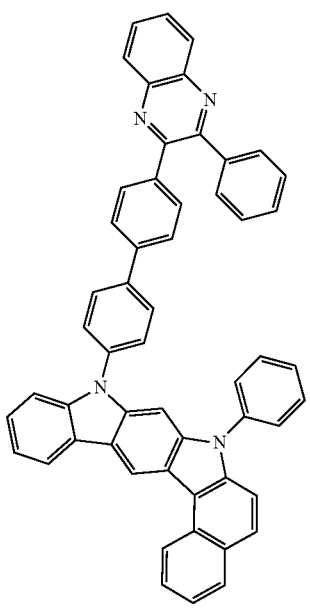

C2-102
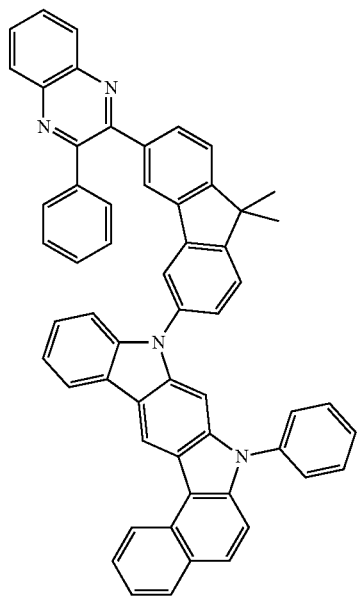
C2-103
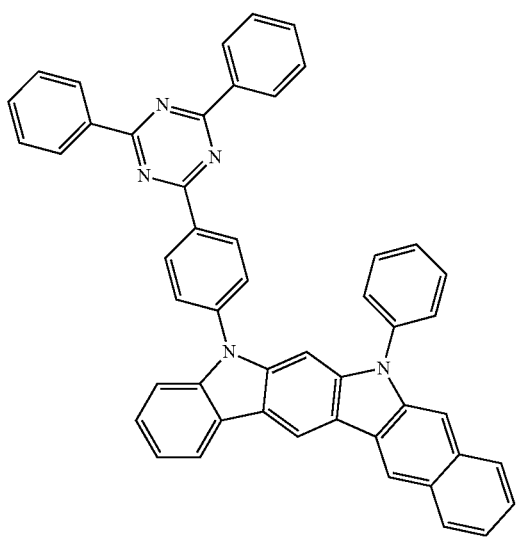
C2-104
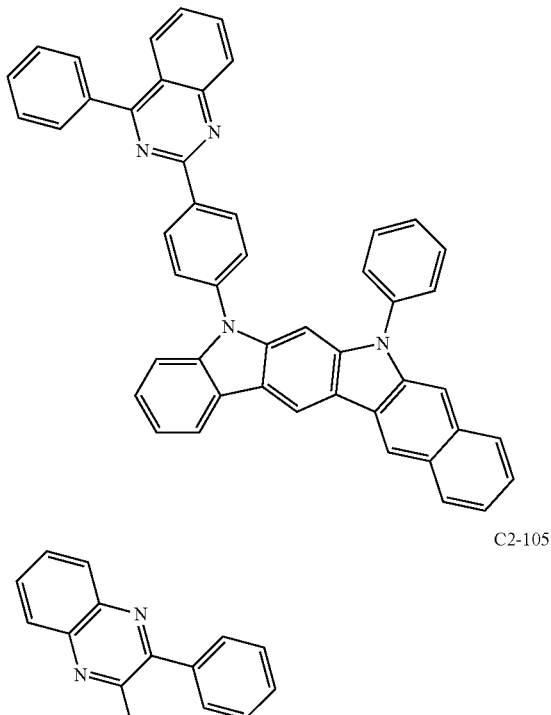
C2-105
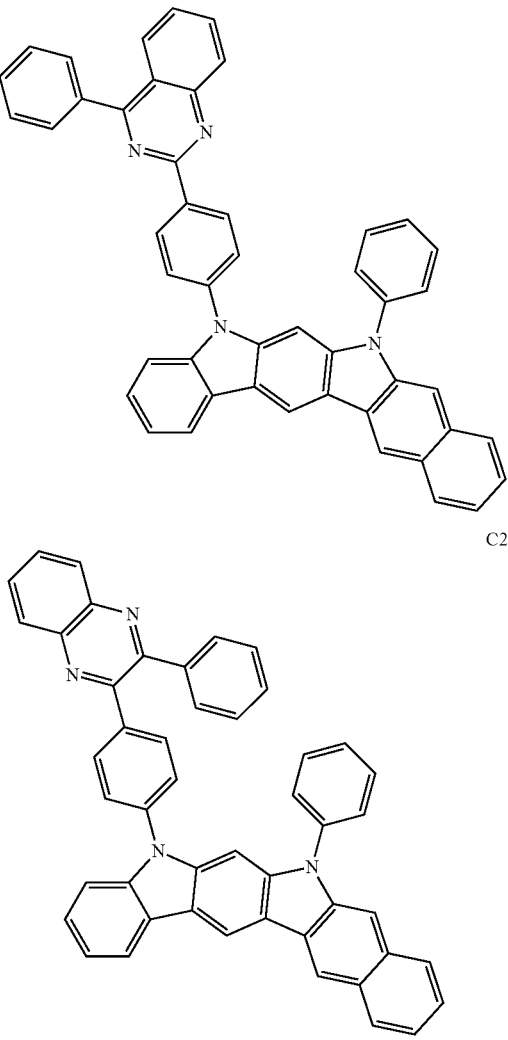
C2-106
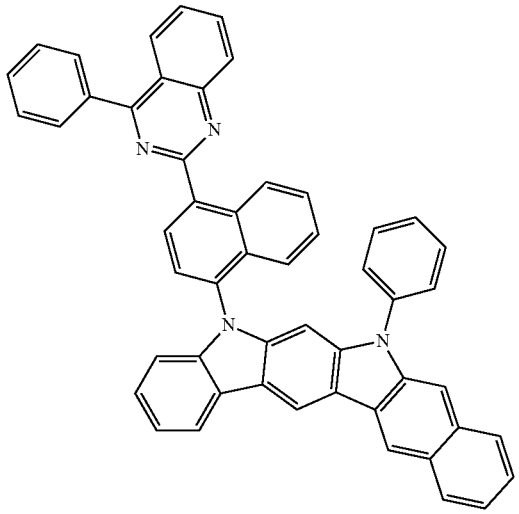

C2-107
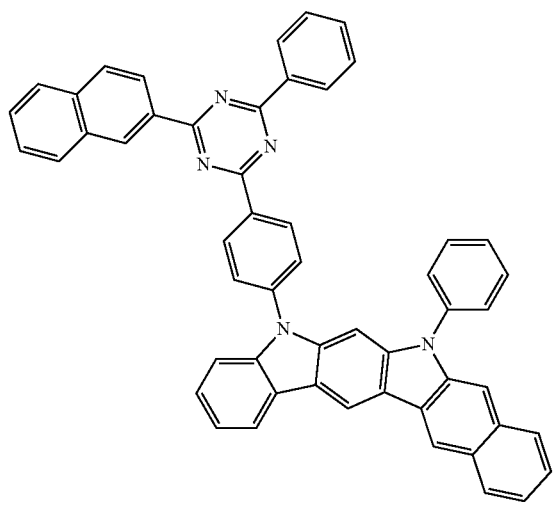
C2-108
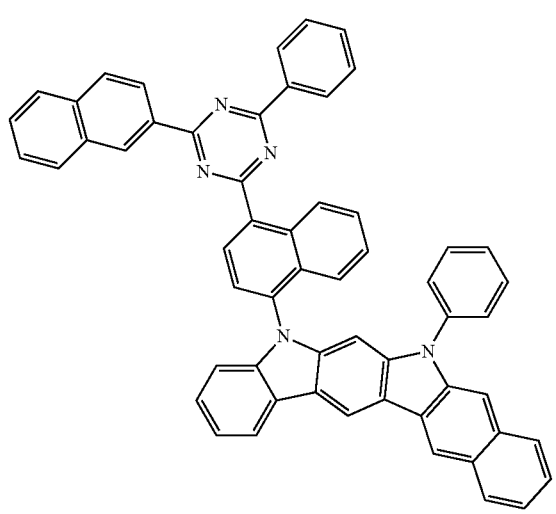
C2-109
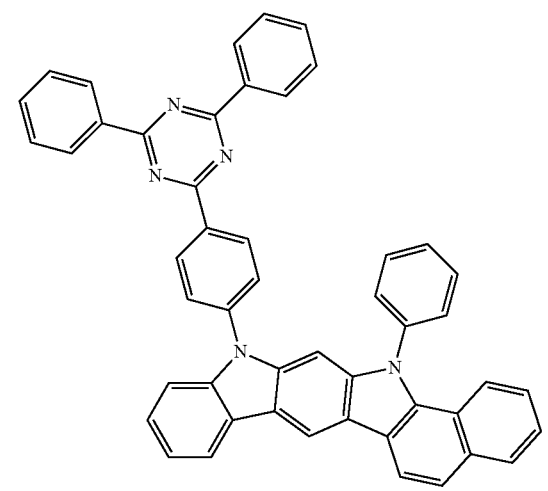
C2-110
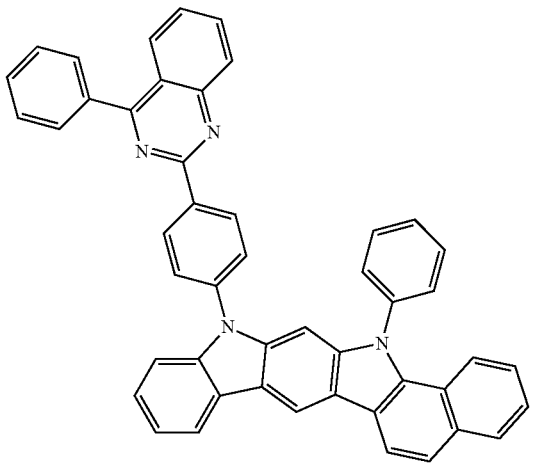
C2-111
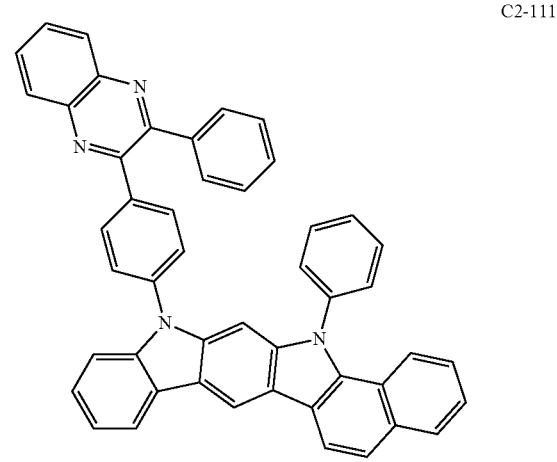
C2-112
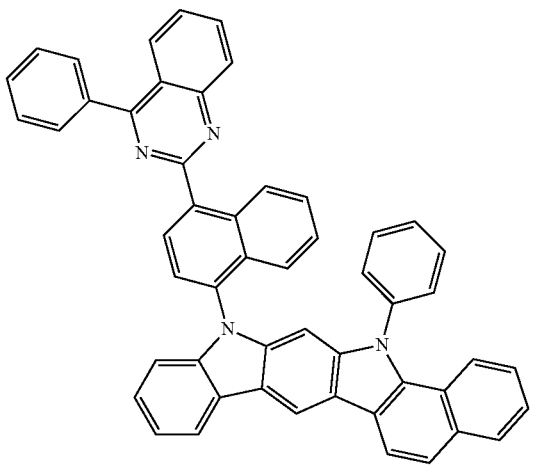

-continued
C2-113
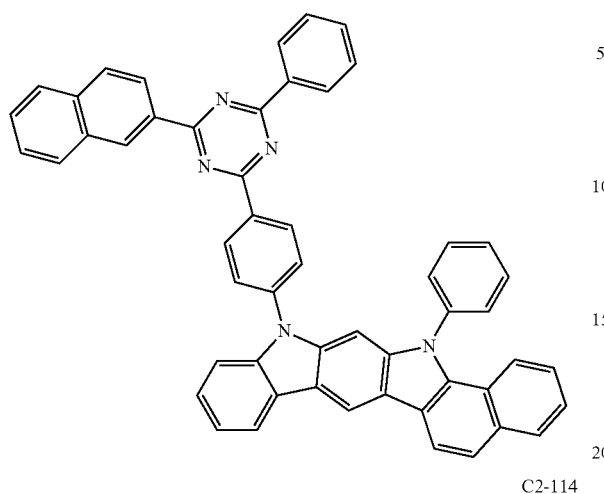
C2-114
C2-115
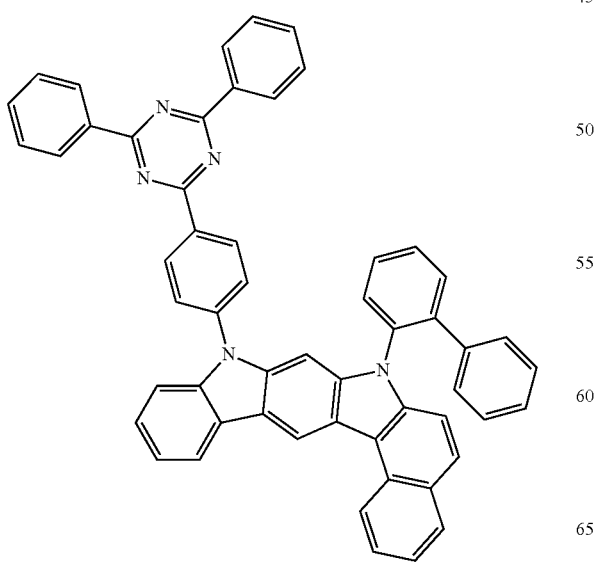
-continued
C2-116
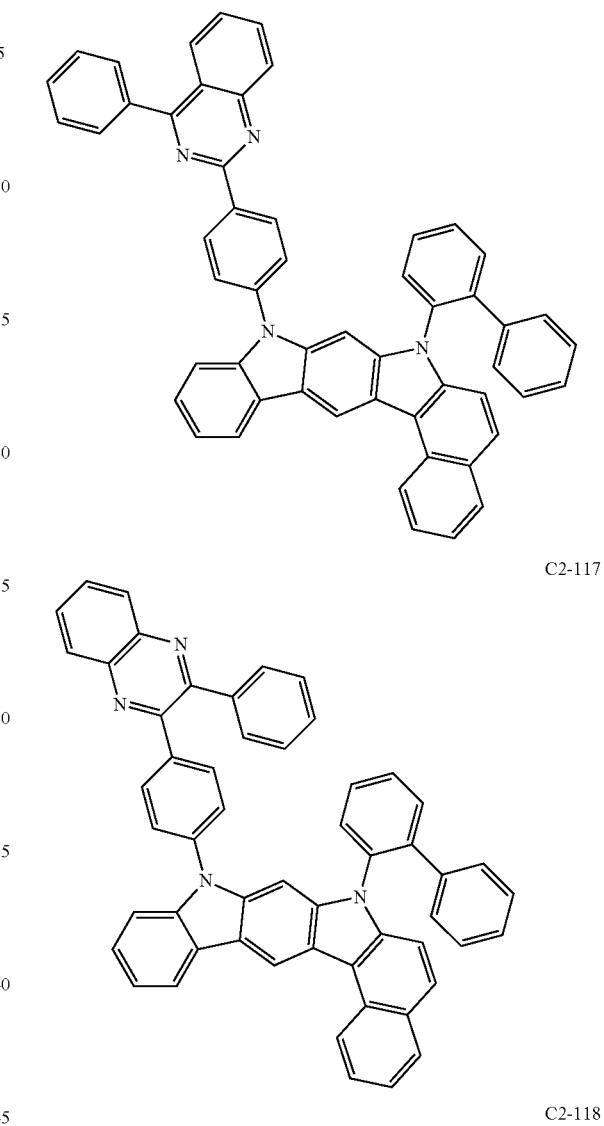
C2-117
C2-118

C2-119
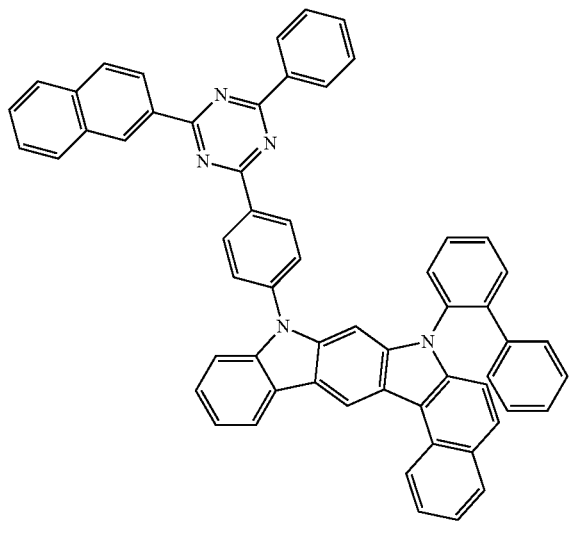
C2-122
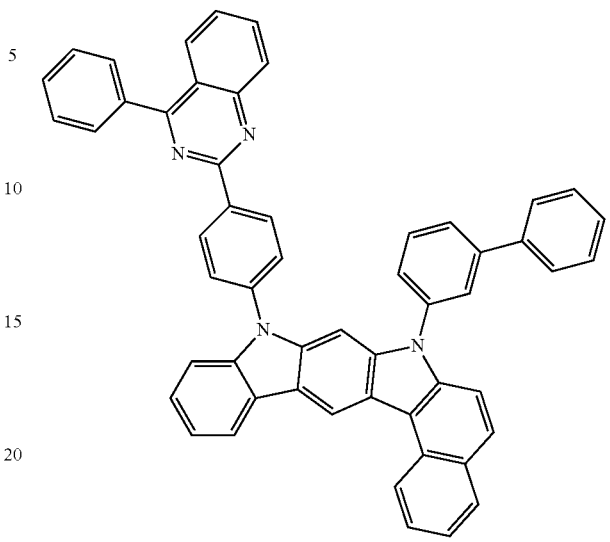
C2-120
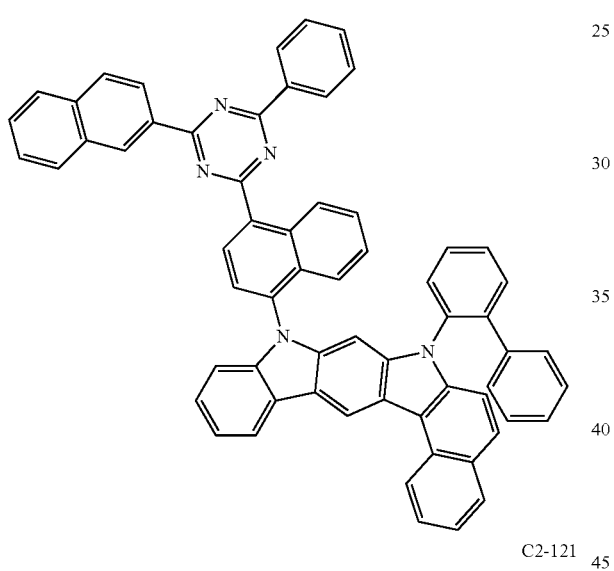
C2-123
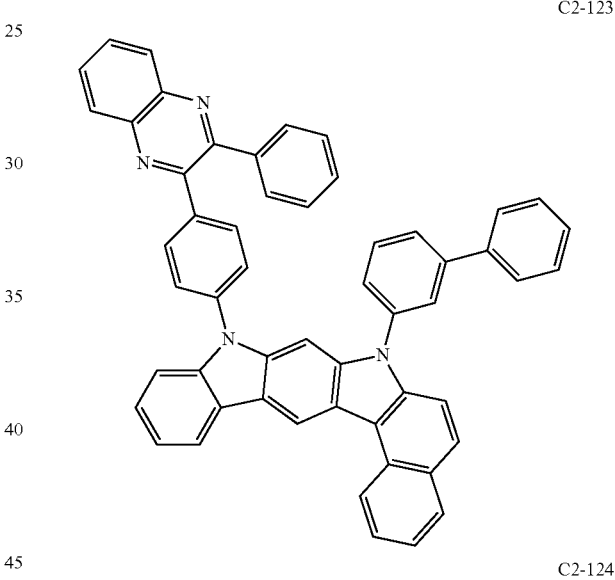
C2-121
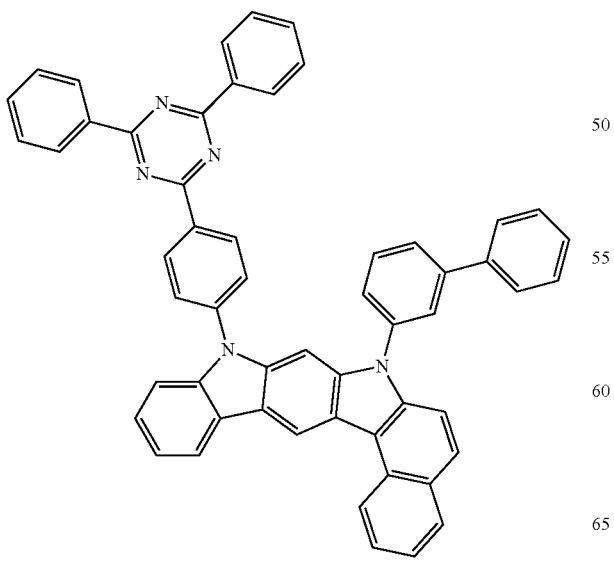
C2-124
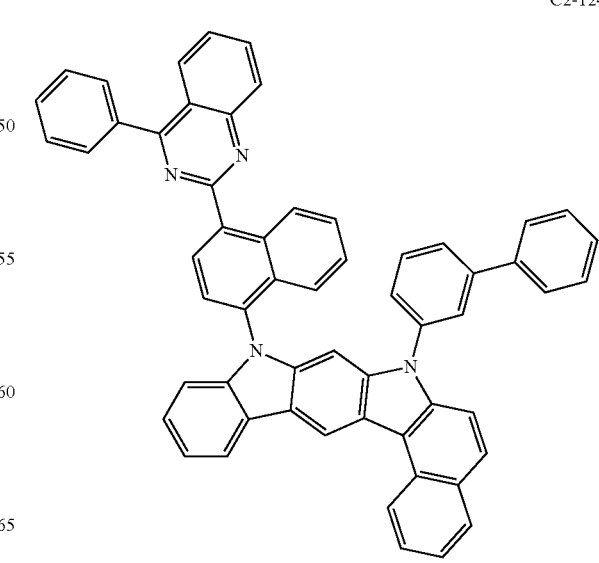

-continued
C2-125
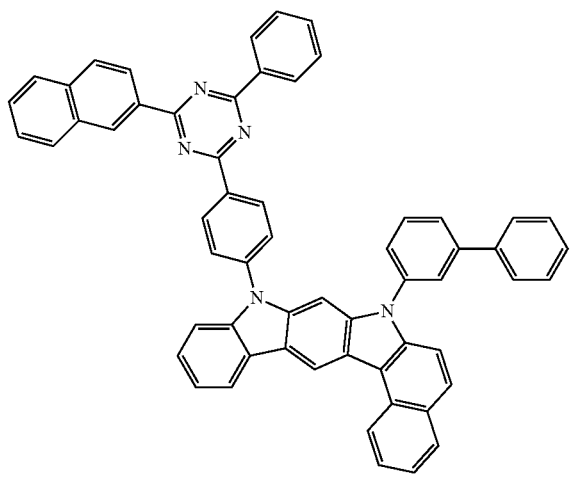
C2-126
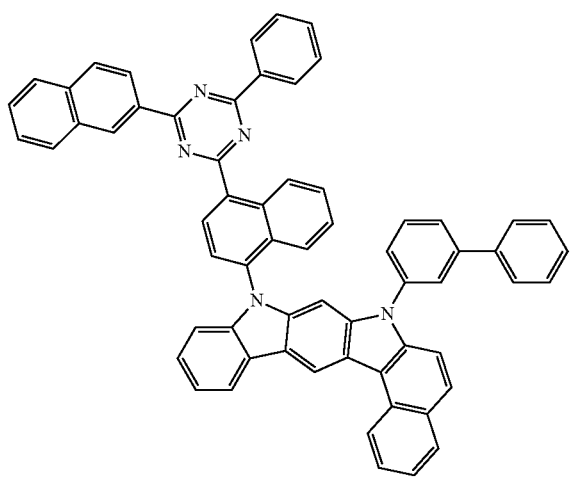
C2-127
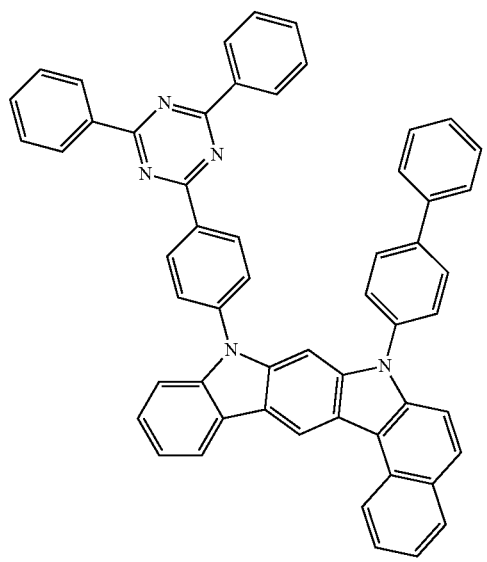
-continued
C2-128
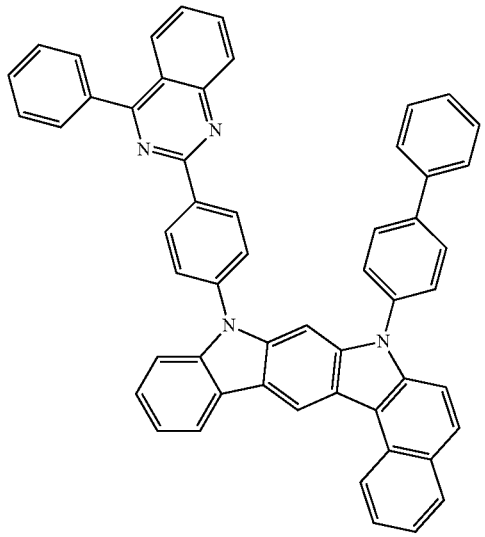
C2-129
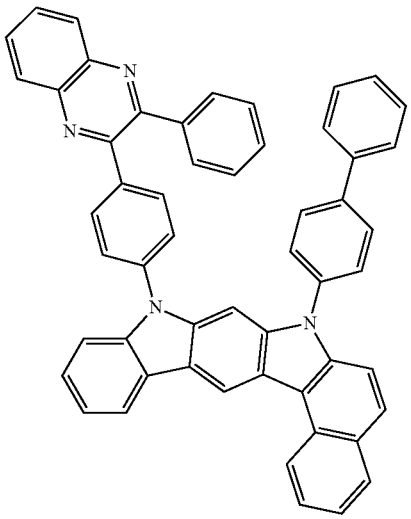
C2-130
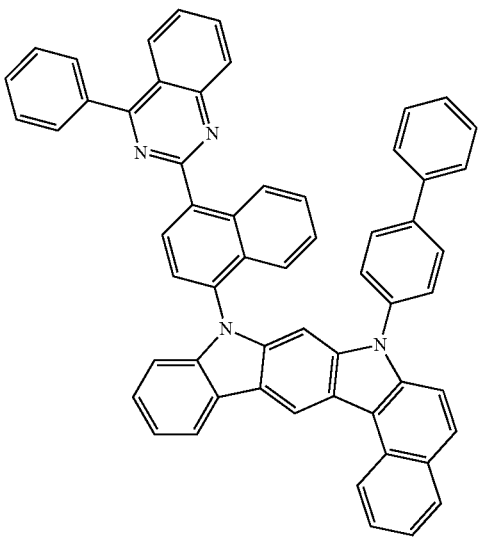

C2-131
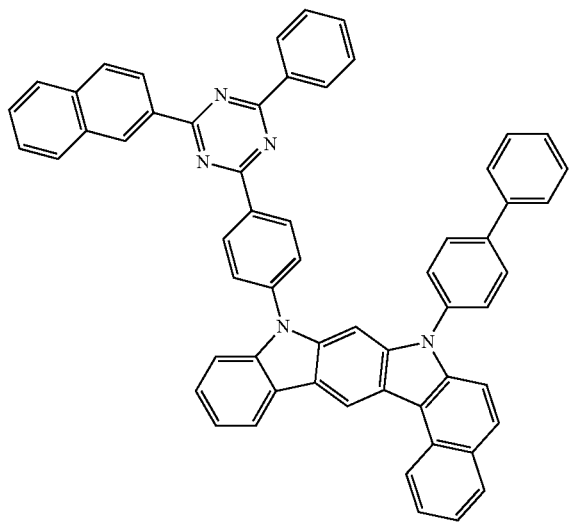
C2-132
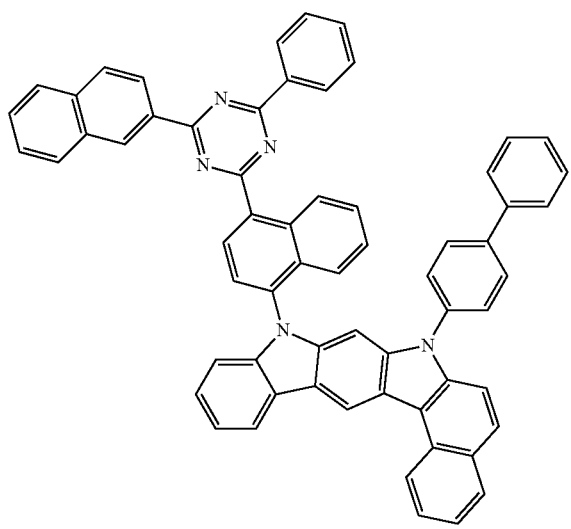
C2-133
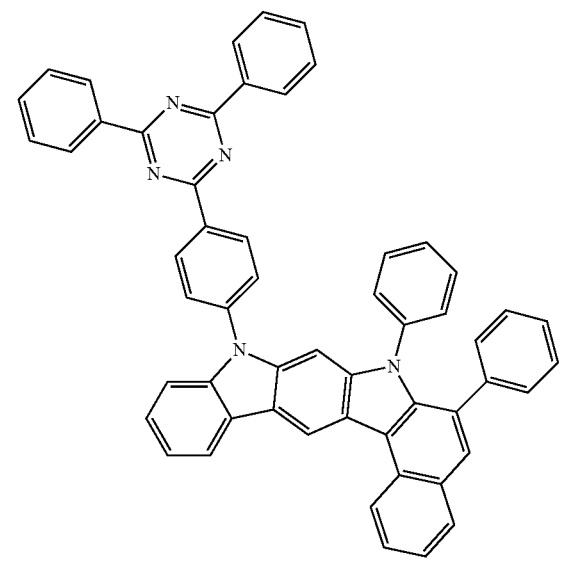
C2-134
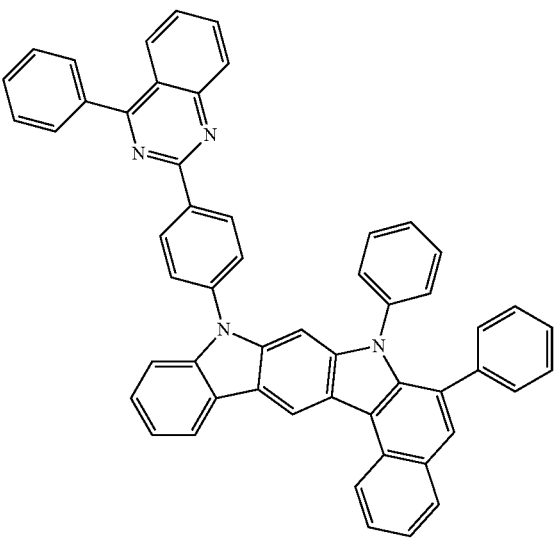
C2-135
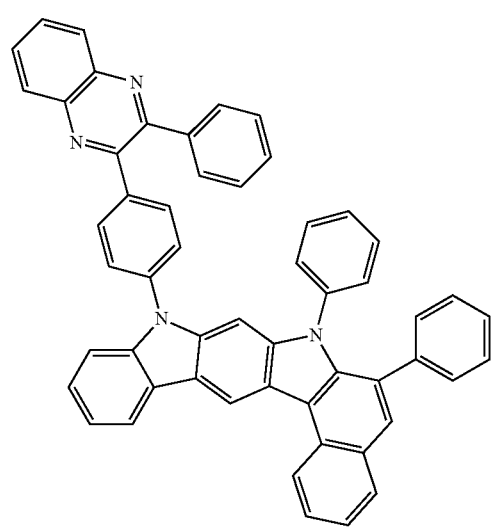
C2-136
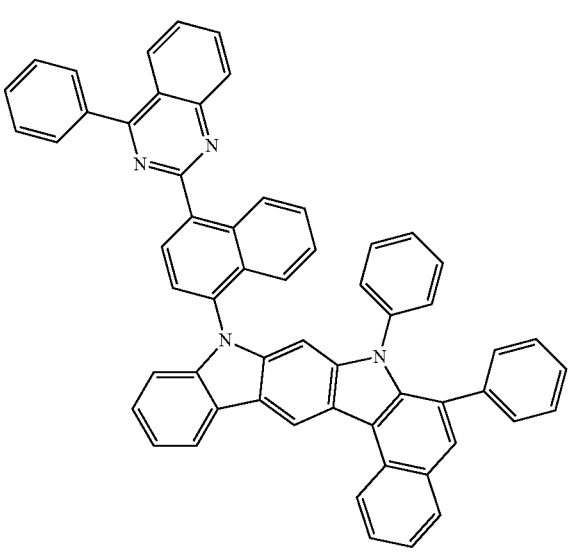

-continued
C2-137
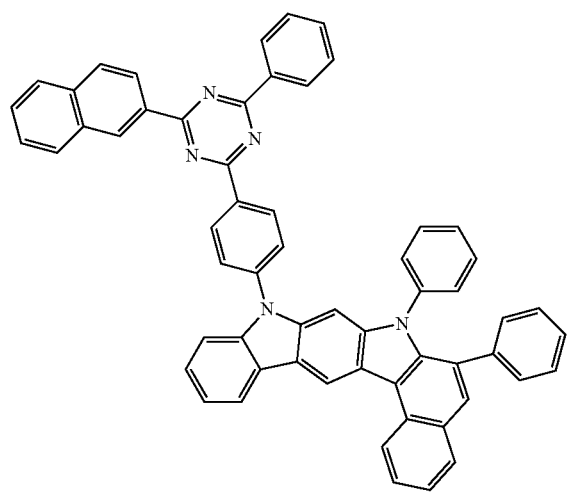
C2-140
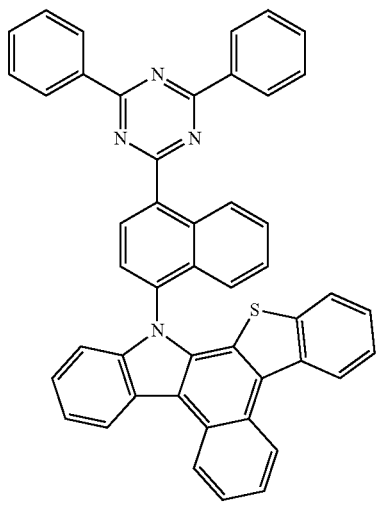
C2-138
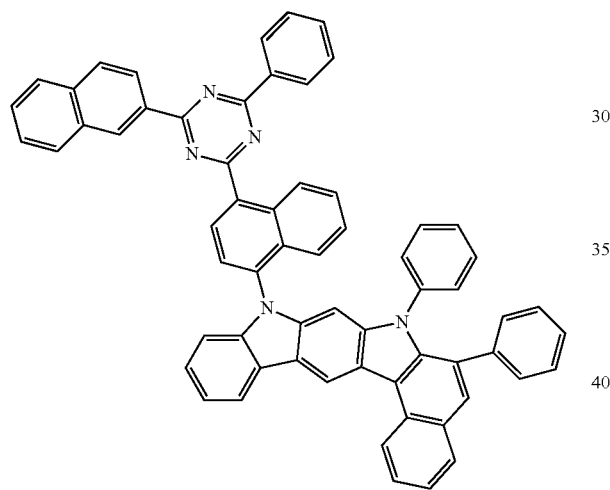
C2-141
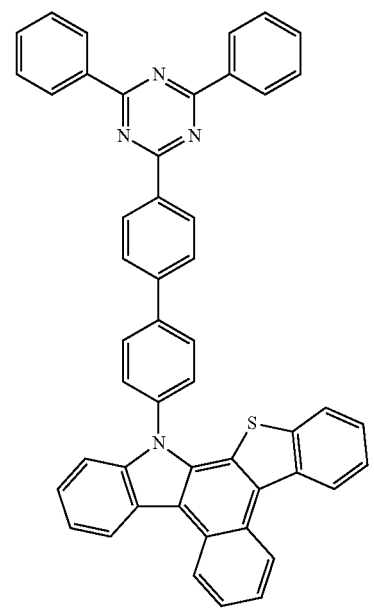
C2-139
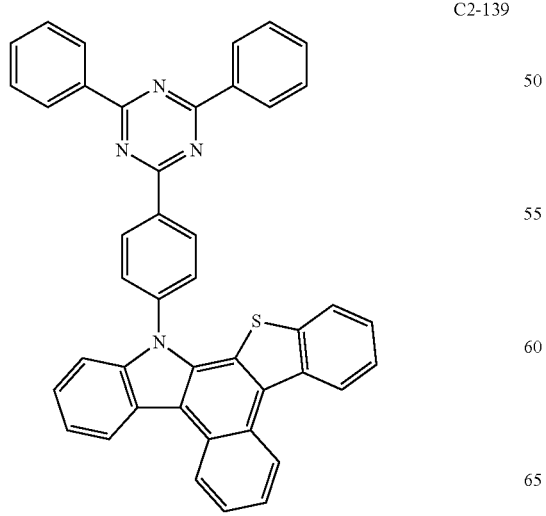
C2-142
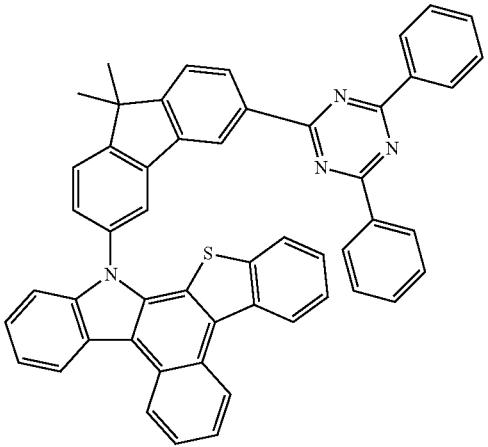

-continued
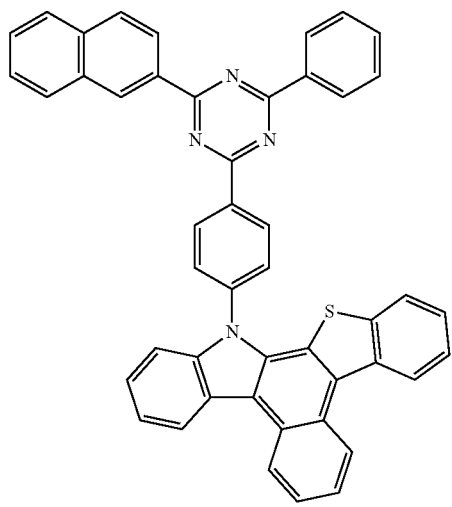
C2-143
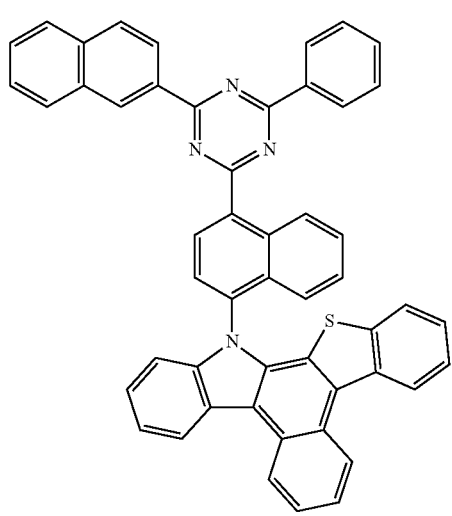
C2-144
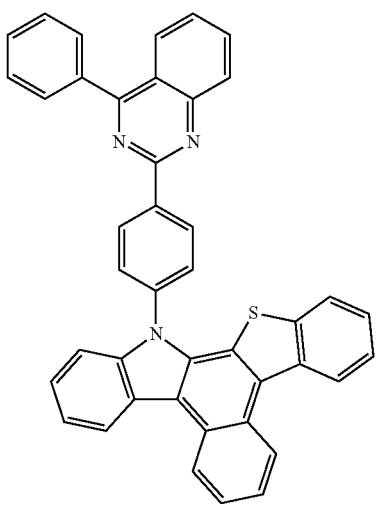
C2-145
-continued
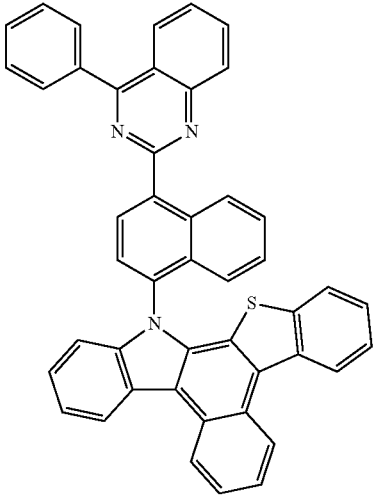
C2-146
C2-147
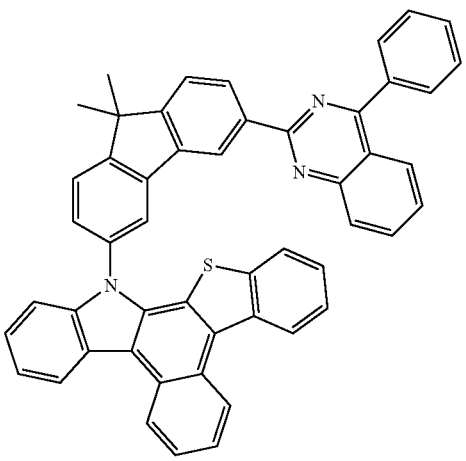
C2-148

C2-149
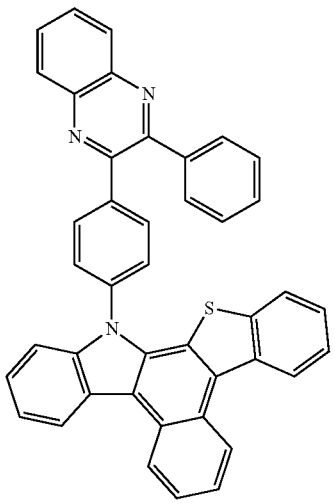
C2-150
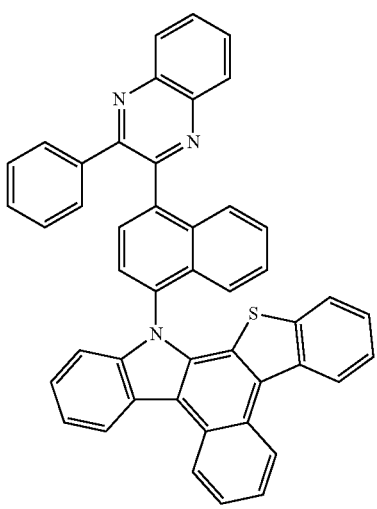
C2-151
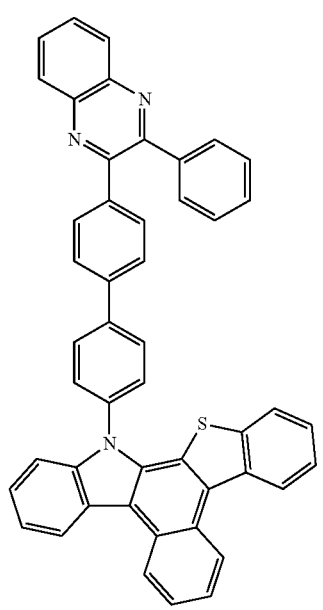
C2-152
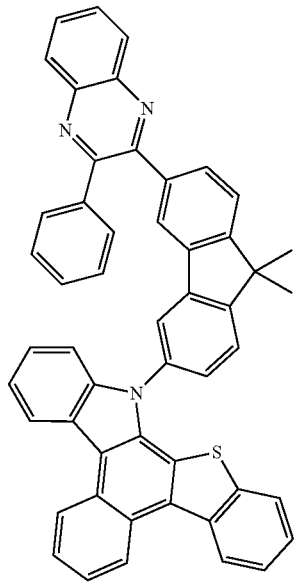
C2-153
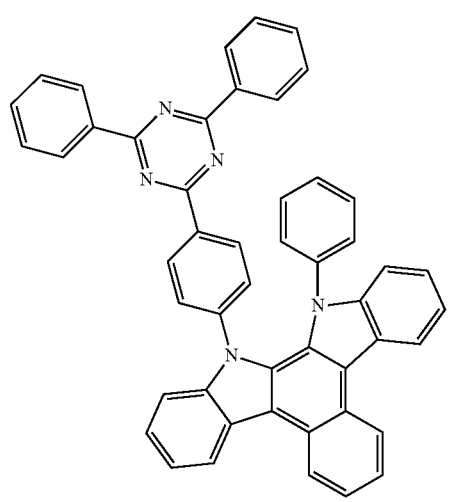
C2-154
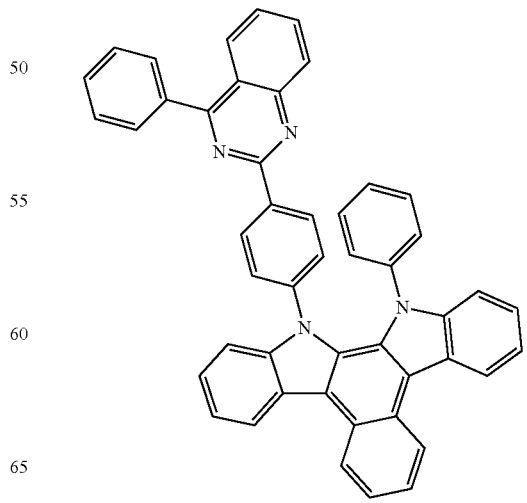

-continued
C2-155
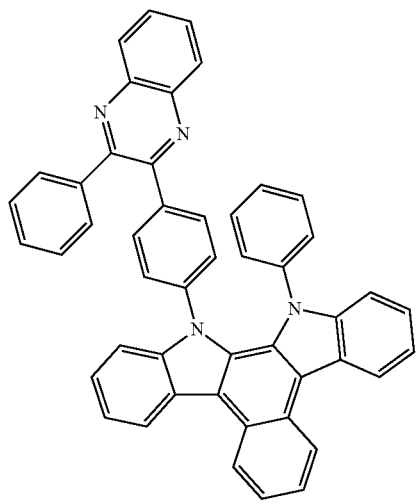
C2-156
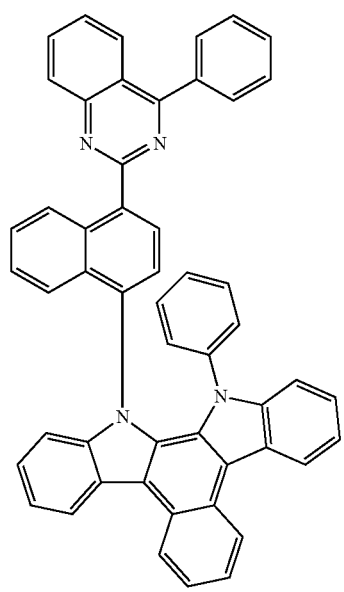
C2-157
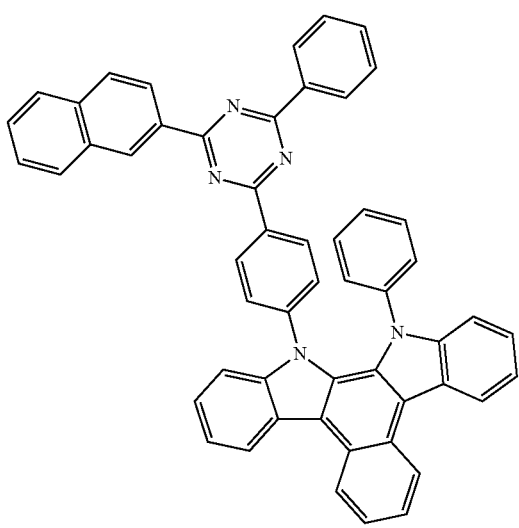
-continued
C2-158
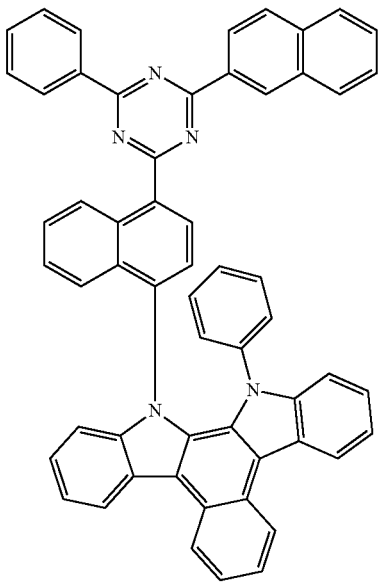
C2-159
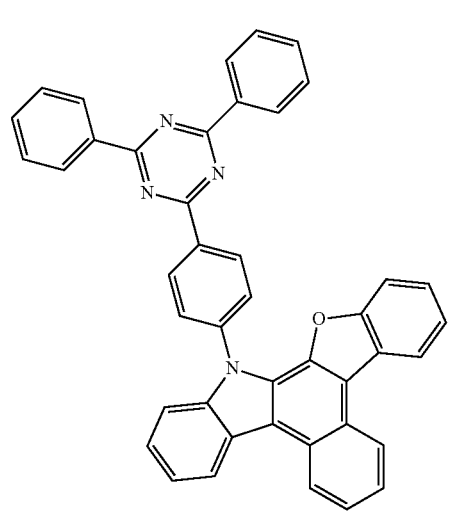
C2-160
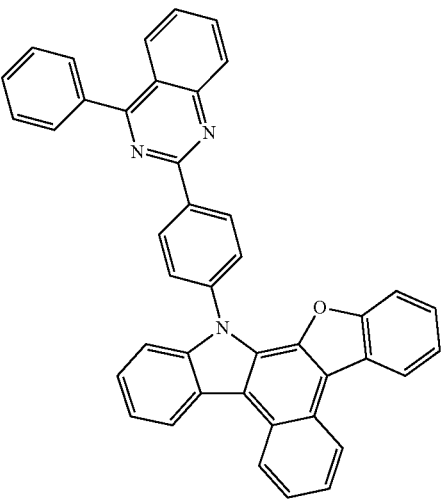

C2-161
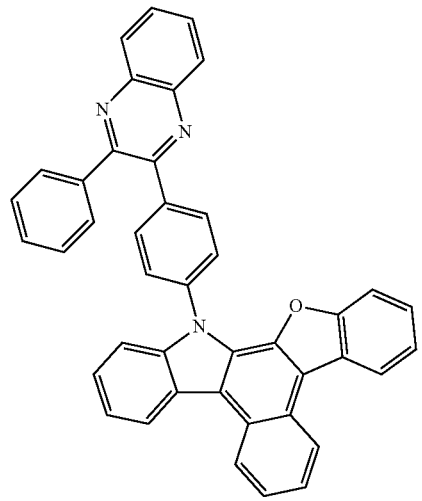
C2-162
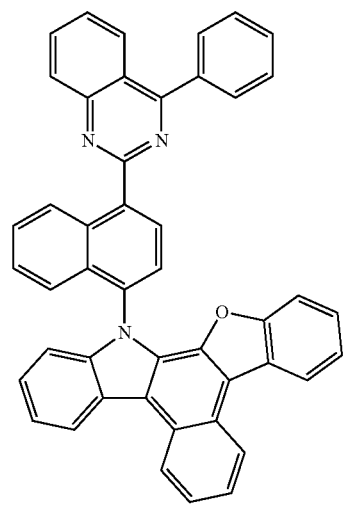
C2-163
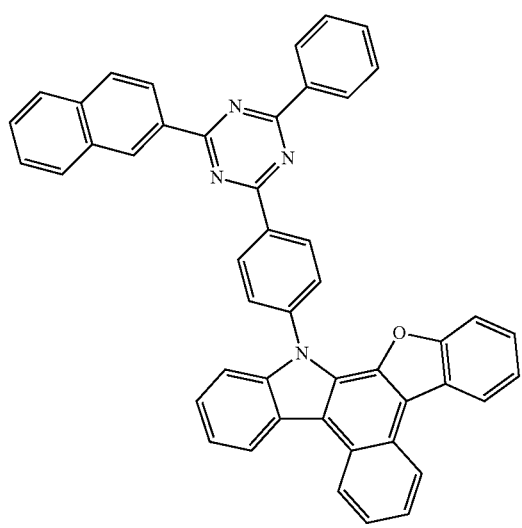
C2-164
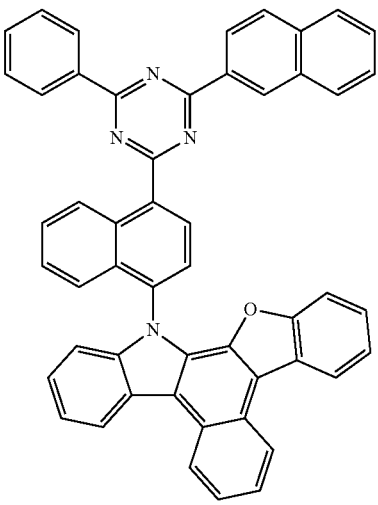
C2-165
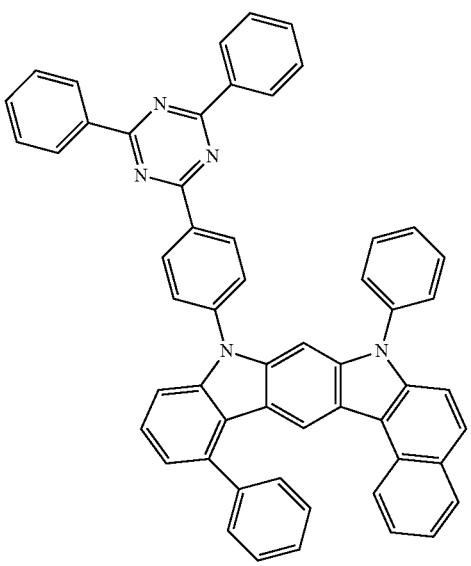
C2-166
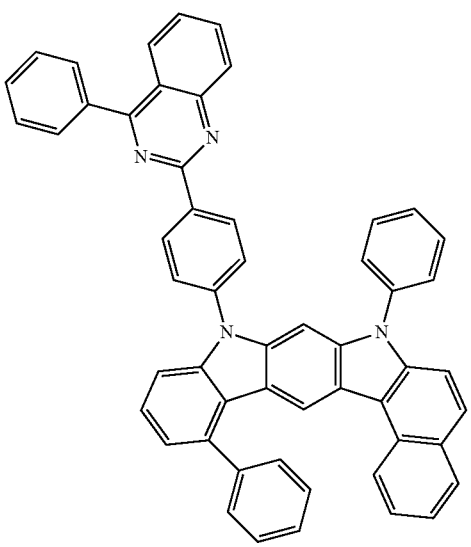

C2-167
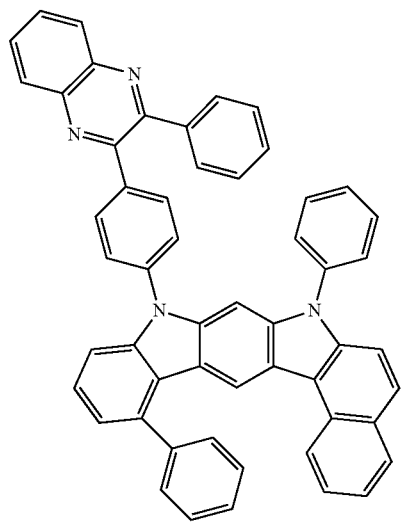
C2-168
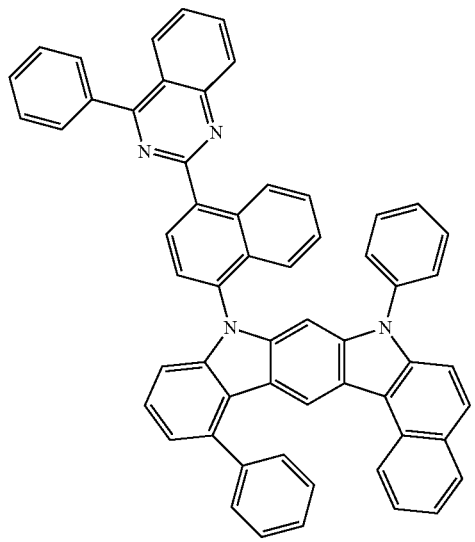
C2-169
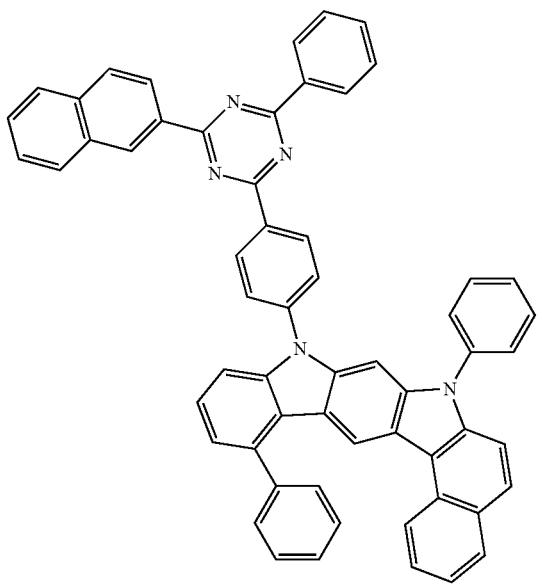
C2-170
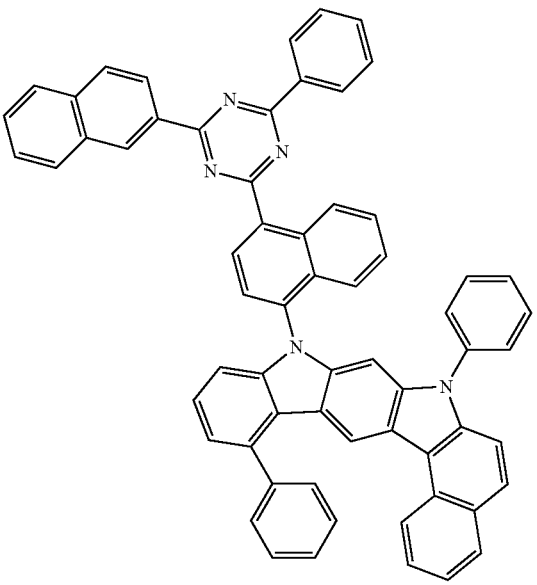
C2-171
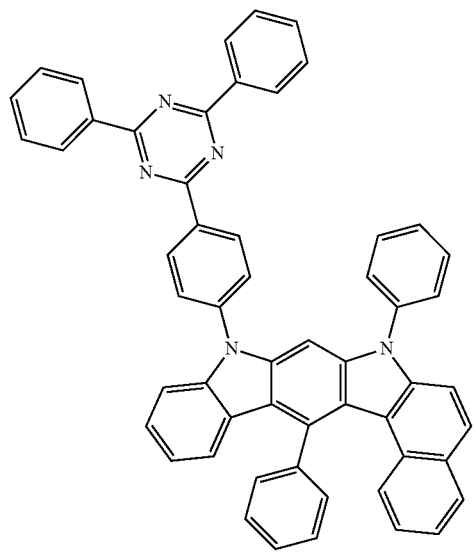

C2-172
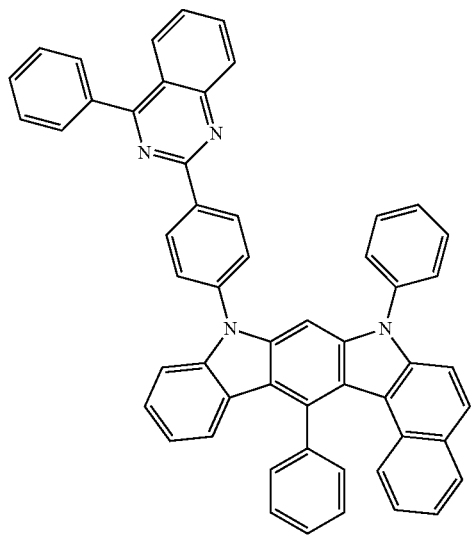
C2-173
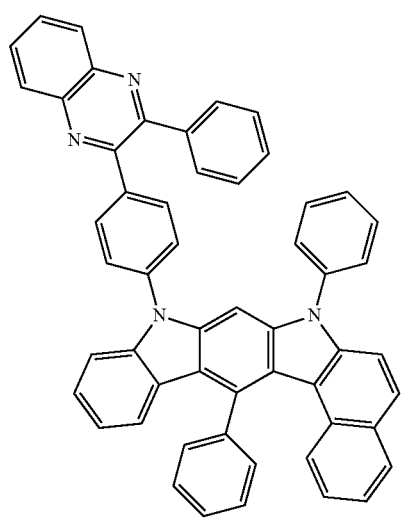
C2-174
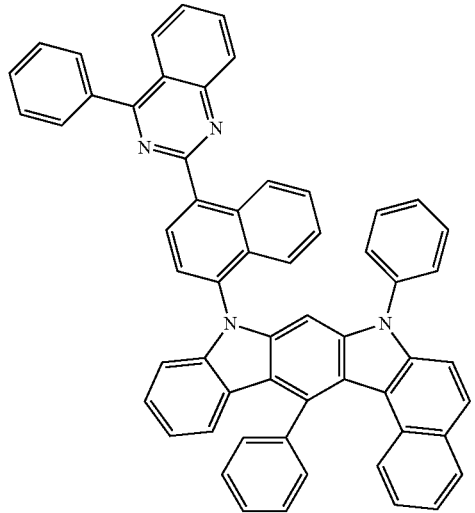
C2-175
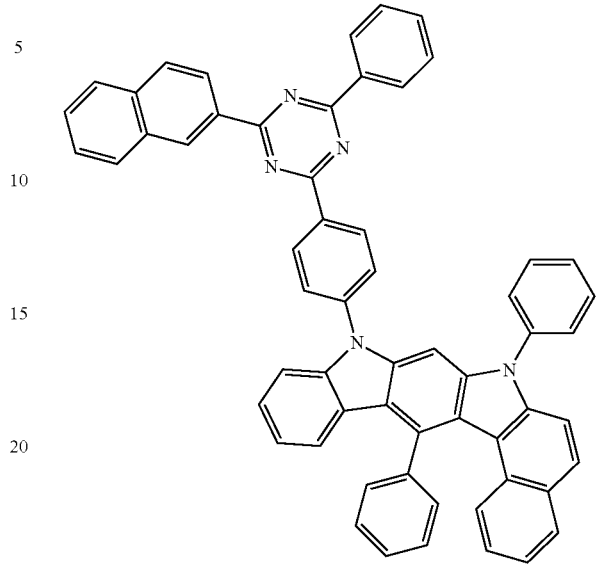
C2-176
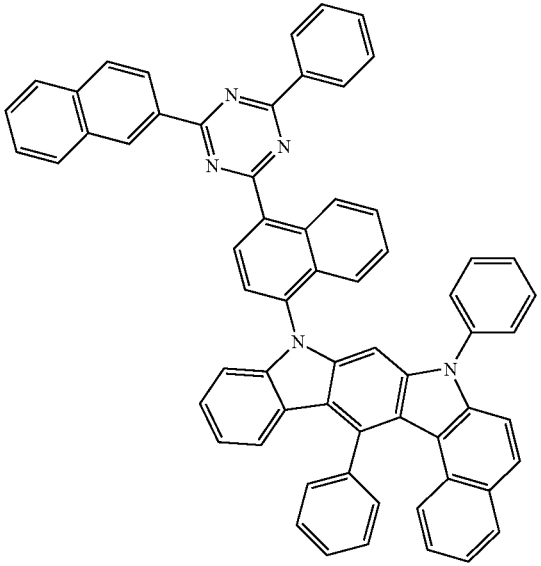

C2-177
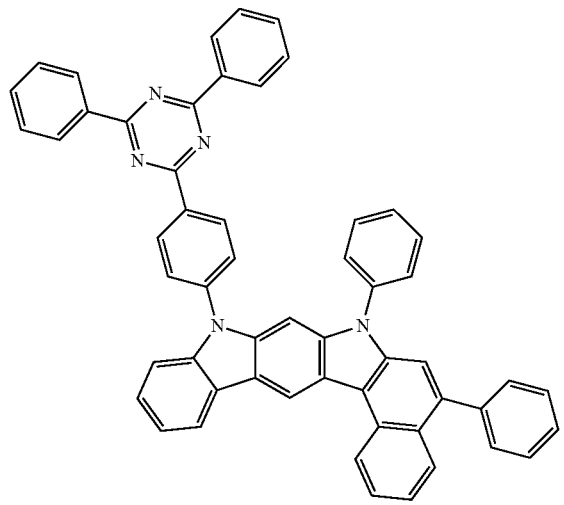
C2-178
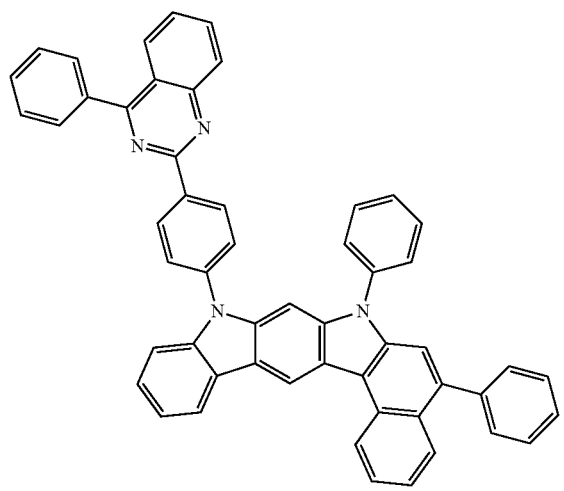
C2-179
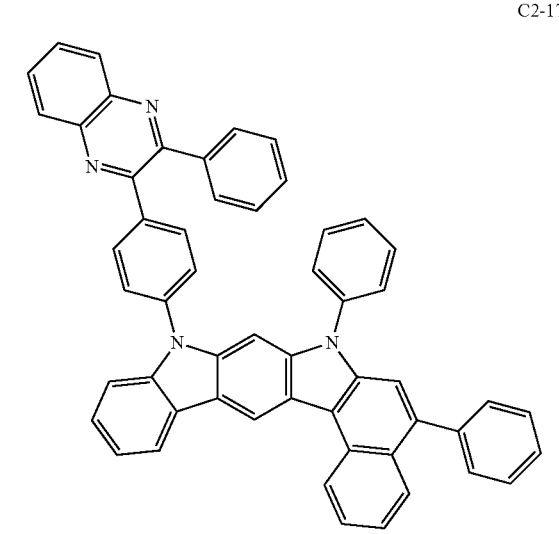
C2-180
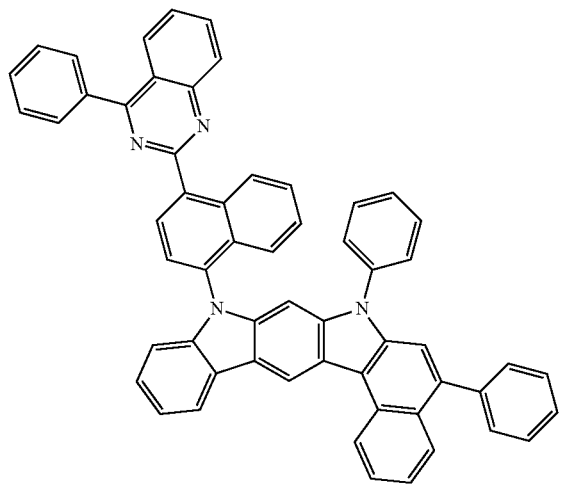
C2-181
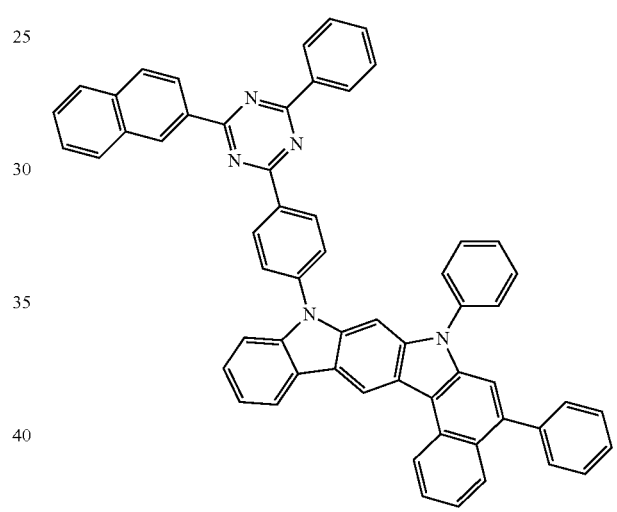
C2-182
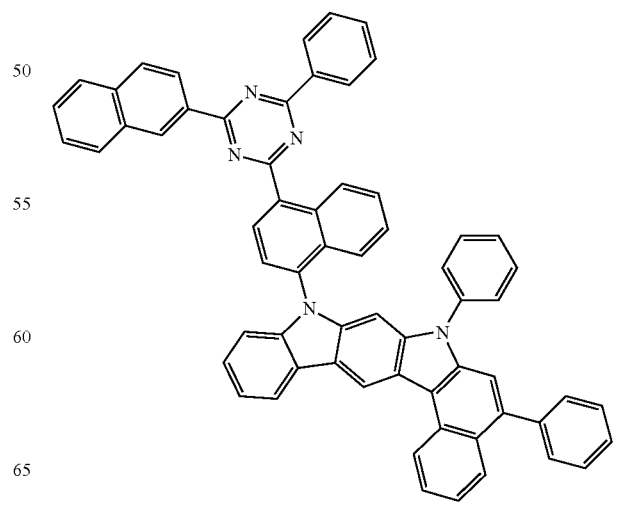

-continued
C2-183
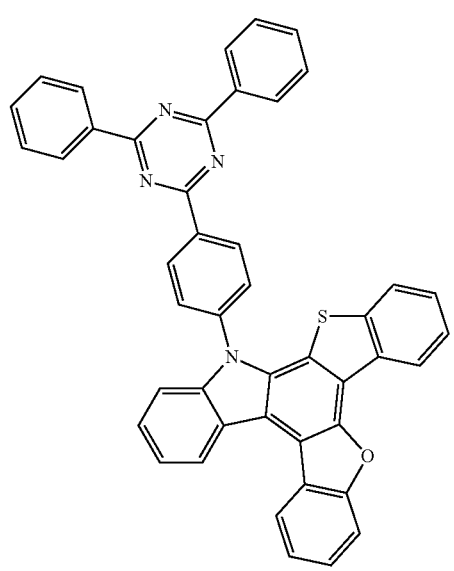
C2-184
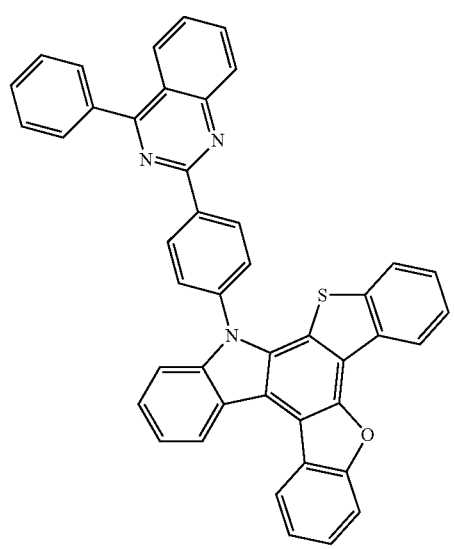
C2-185
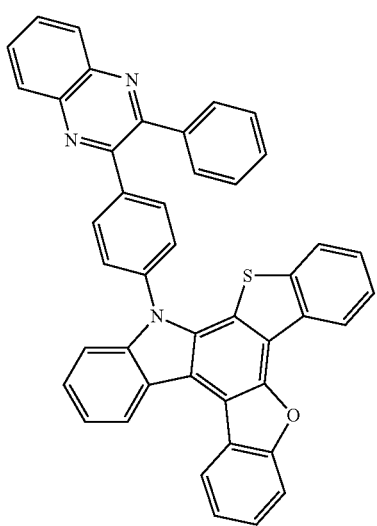
-continued
C2-186
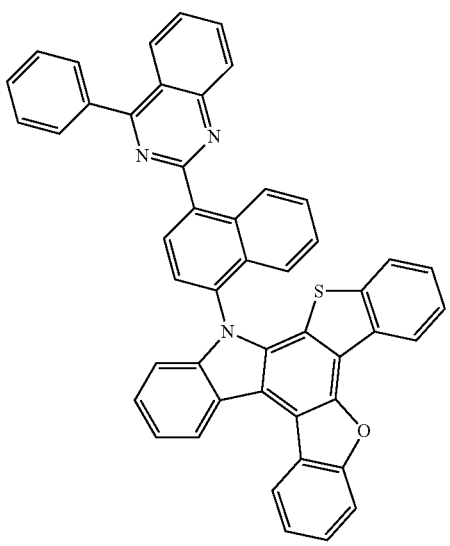
C2-187
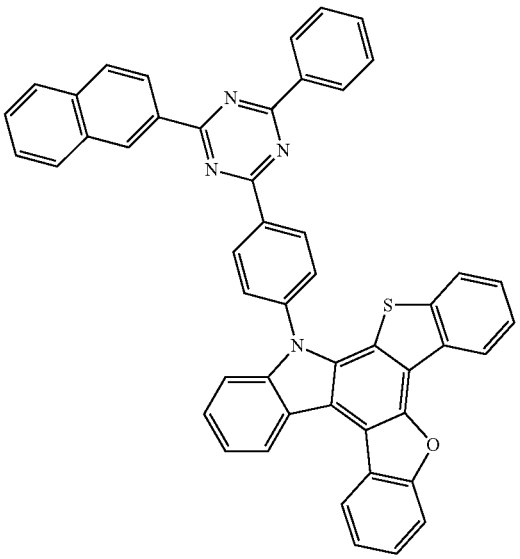

C2-188
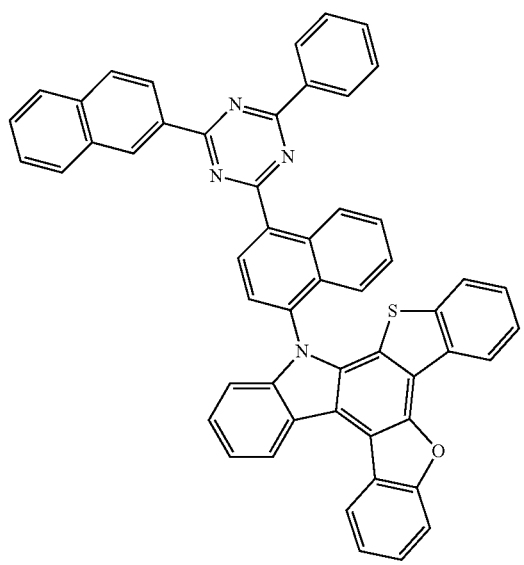
C2-190
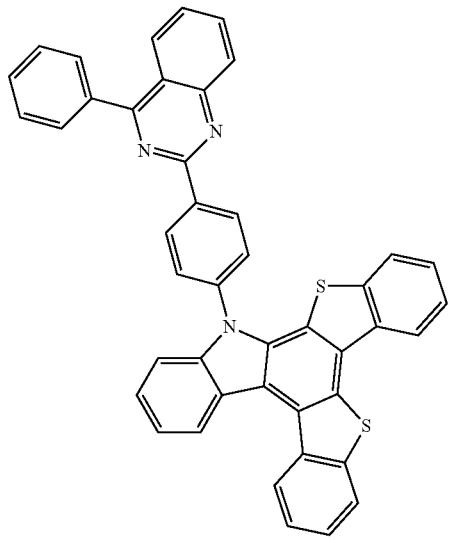
C2-191
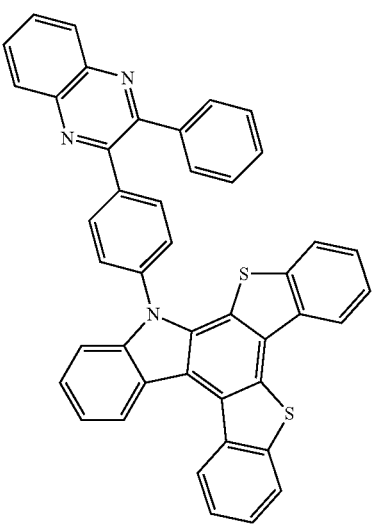
C2-189
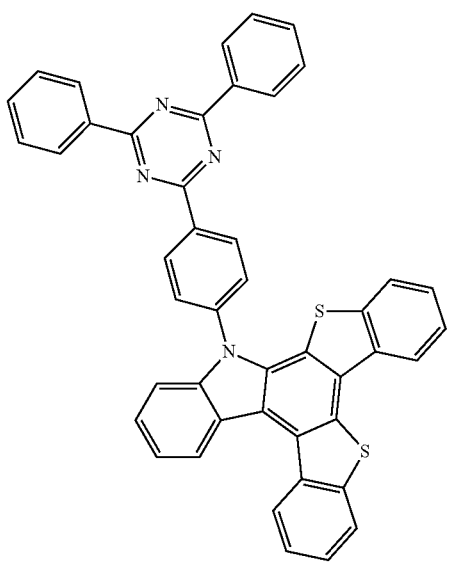
C2-192
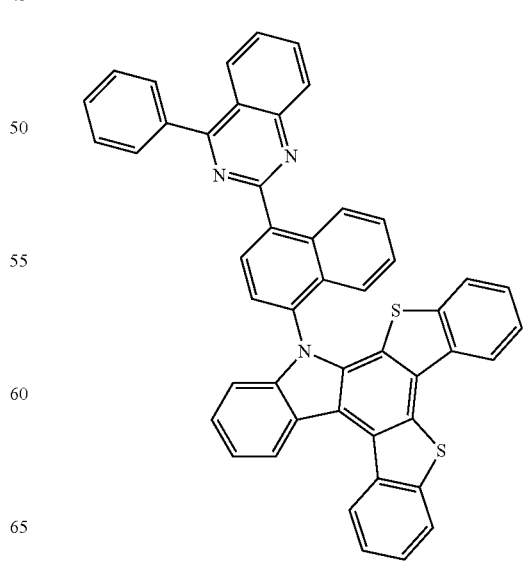

C2-193
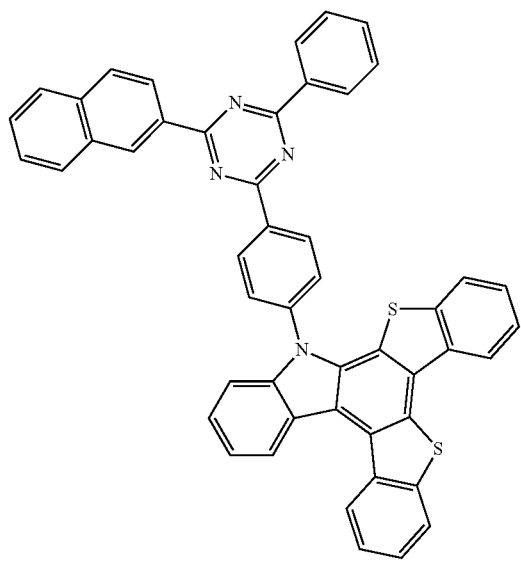
C2-194
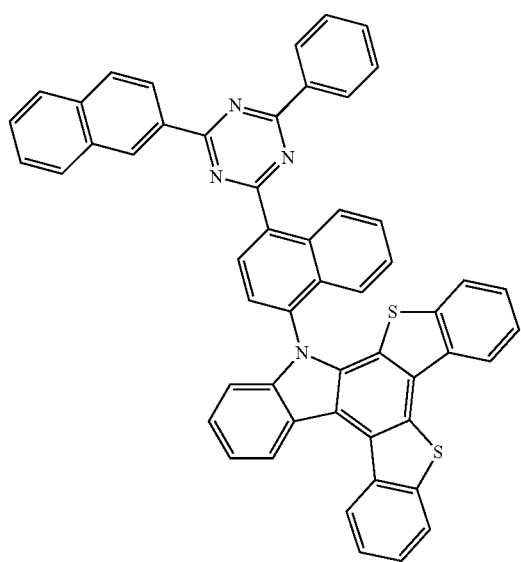
C2-195
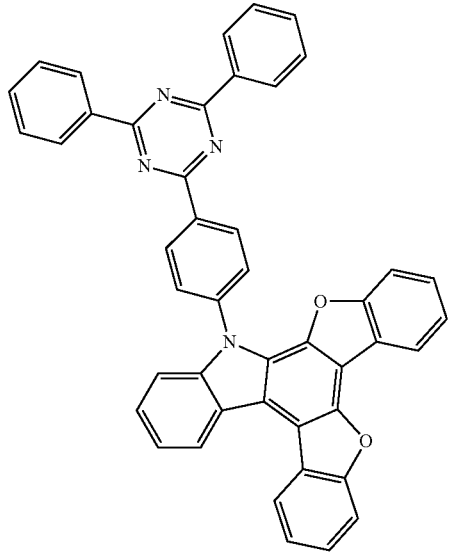
C2-196
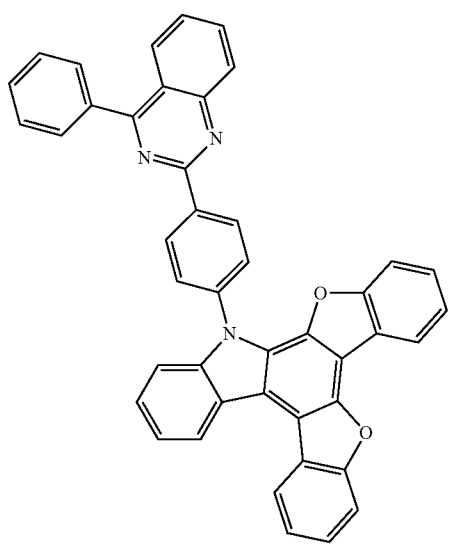
C2-197
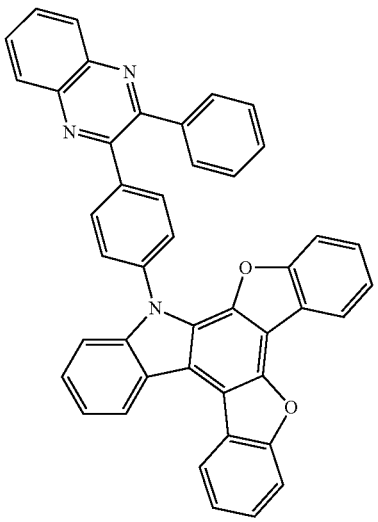

C2-198
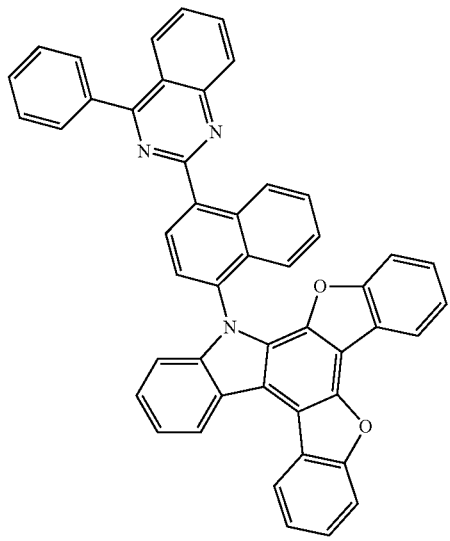
C2-200
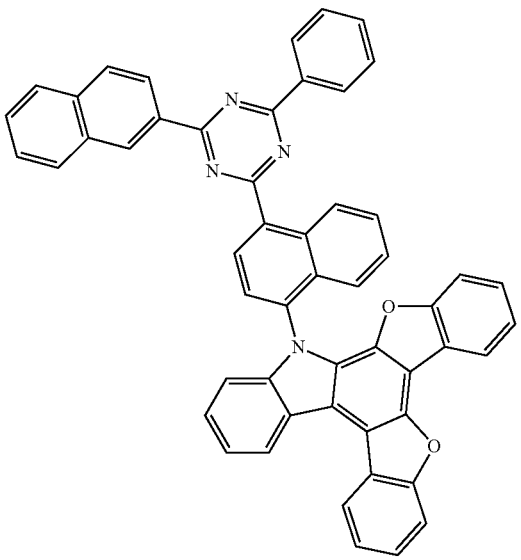
C2-201
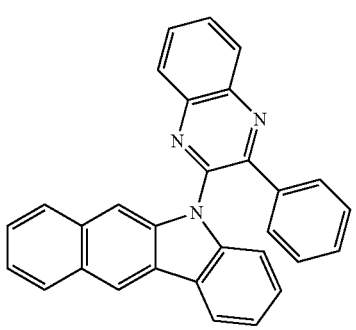
C2-202
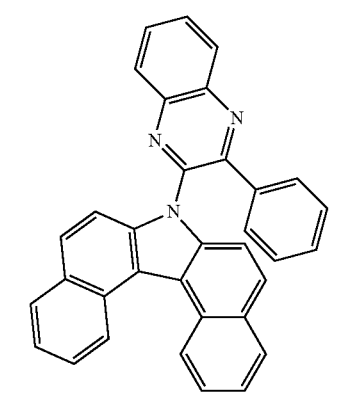
C2-199
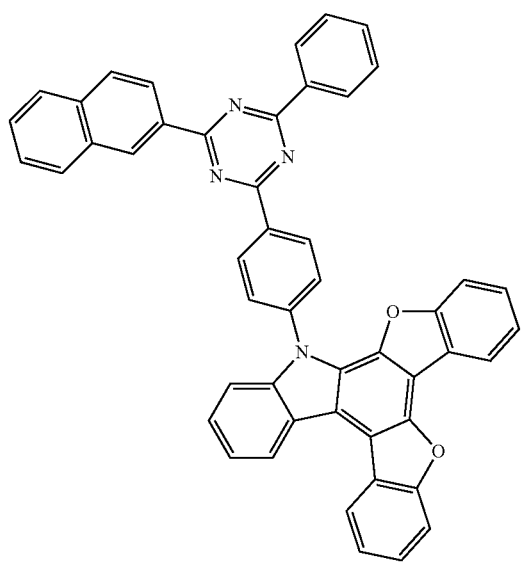
C2-203
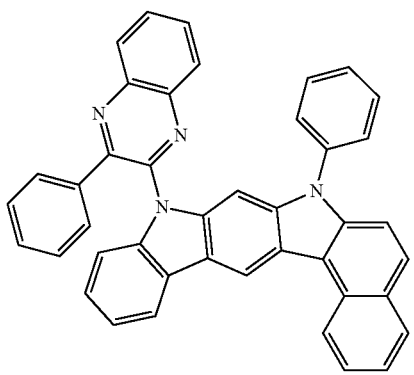

C2-204
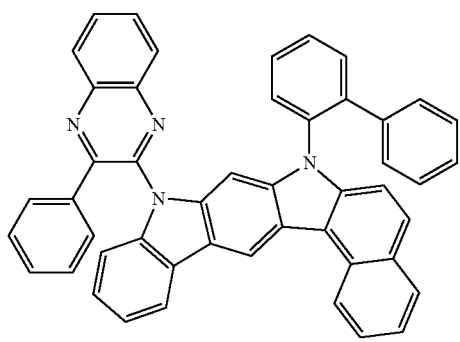
C2-206
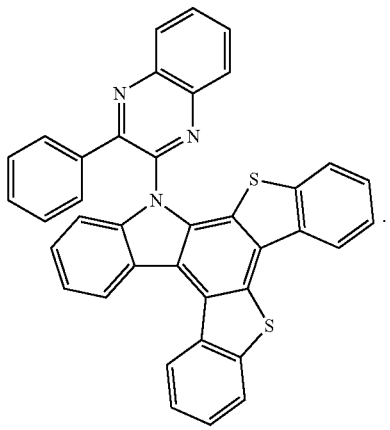
C2-205
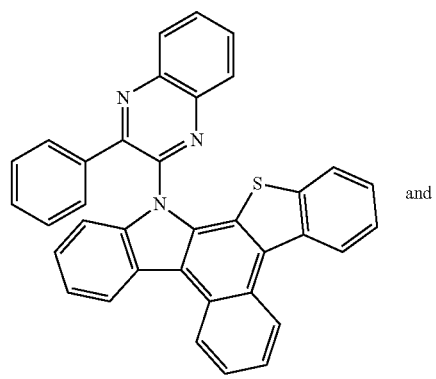
and
10. An organic electroluminescent device comprising an anode, a cathode, and at least one light-emitting layer between the anode and the cathode, wherein at least one layer of the light-emitting layers comprises the plurality of host materials according to claim 1.
* * * * *